US009062052B2

(12) United States Patent
Yu et al.

(10) Patent No.: US 9,062,052 B2
(45) Date of Patent: *Jun. 23, 2015

(54) CARBOXAMIDE COMPOUNDS AND METHODS FOR USING THE SAME

(71) Applicant: Rigel Pharmaceuticals, Inc., South San Francisco, CA (US)

(72) Inventors: Jiaxin Yu, San Carlos, CA (US); Hui Hong, Palo Alto, CA (US); Ihab S. Darwish, San Carlos, CA (US); Xiang Xu, Foster City, CA (US); Rajinder Singh, Belmont, CA (US)

(73) Assignee: Rigel Pharmaceuticals, Inc., South San Francisco, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 14/493,050

(22) Filed: Sep. 22, 2014

(65) Prior Publication Data

US 2015/0011582 A1    Jan. 8, 2015

Related U.S. Application Data

(63) Continuation of application No. 14/171,624, filed on Feb. 3, 2014, now Pat. No. 8,871,770, which is a continuation of application No. 13/622,078, filed on Sep. 18, 2012, now Pat. No. 8,785,449, which is a continuation of application No. 12/428,334, filed on Apr. 22, 2009, now Pat. No. 8,314,107.

(60) Provisional application No. 61/047,399, filed on Apr. 23, 2008, provisional application No. 61/048,997, filed on Apr. 30, 2008, provisional application No. 61/054,035, filed on May 16, 2008, provisional application No. 61/054,934, filed on May 21, 2008, provisional application No. 61/058,854, filed on Jun. 4, 2008, provisional application No. 61/078,166, filed on Jul. 3, 2008, provisional application No. 61/078,180, filed on Jul. 3, 2008, provisional application No. 61/078,209, filed on Jul. 3, 2008.

(51) Int. Cl.
| | |
|---|---|
| A61K 31/437 | (2006.01) |
| C07D 471/04 | (2006.01) |
| C07D 211/58 | (2006.01) |
| C07D 401/12 | (2006.01) |
| C07D 401/14 | (2006.01) |
| C07D 413/12 | (2006.01) |
| C07D 413/14 | (2006.01) |
| C07D 417/14 | (2006.01) |
| C07D 487/08 | (2006.01) |

(52) U.S. Cl.
CPC ............ *C07D 471/04* (2013.01); *A61K 31/437* (2013.01); *C07D 211/58* (2013.01); *C07D 401/12* (2013.01); *C07D 401/14* (2013.01); *C07D 413/12* (2013.01); *C07D 413/14* (2013.01); *C07D 417/14* (2013.01); *C07D 487/08* (2013.01)

(58) Field of Classification Search
USPC .......................... 514/121, 300; 546/300, 121
See application file for complete search history.

(56) References Cited

U.S. PATENT DOCUMENTS

| | | | |
|---|---|---|---|
| 3,035,047 | A | 5/1962 | Perron et al. |
| 4,559,346 | A | 12/1985 | King |
| 4,569,940 | A | 2/1986 | Watts |
| 4,694,016 | A | 9/1987 | Lu et al. |
| 5,965,261 | A | 10/1999 | Webster |
| 6,063,843 | A | 5/2000 | Sidqi et al. |
| 6,080,742 | A | 6/2000 | Germann et al. |
| 6,172,232 | B1 | 1/2001 | Stahrfeldt |
| 6,472,405 | B1 | 10/2002 | Fisher et al. |
| 7,001,900 | B2 | 2/2006 | Jacobsen et al. |
| 7,208,491 | B2 | 4/2007 | Fertig et al. |
| 7,253,286 | B2 | 8/2007 | Funahashi et al. |
| 7,273,868 | B2 | 9/2007 | Yamada et al. |

(Continued)

FOREIGN PATENT DOCUMENTS

| | | |
|---|---|---|
| EP | 1813613 | 8/2007 |
| GB | 914419 | 1/1963 |

(Continued)

OTHER PUBLICATIONS

International Search Report and Written Opinion in PCT/US2009/041448.

(Continued)

*Primary Examiner* — Kristin Vajda
(74) *Attorney, Agent, or Firm* — Travis Young; McDonnell Boehnen Hulbert & Berghoff LLP

(57) ABSTRACT

Disclosed are carboxamide compounds, as well as pharmaceutical compositions and methods of use. One embodiment is a compound having the structure

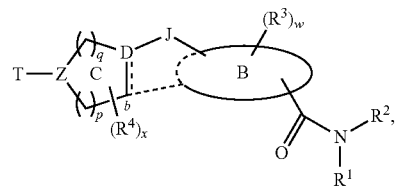

in which $R^1$, $R^2$, $R^3$, $R^4$, D, J, Z, T, p, q, w and x are as described herein. In certain embodiments, a compound disclosed herein activates the AMPK pathway, and can be used to treat metabolism-related disorders and conditions.

43 Claims, No Drawings

(56) References Cited

U.S. PATENT DOCUMENTS

| | | |
|---|---|---|
| 8,012,955 B2 | 9/2011 | Singh et al. |
| 8,119,809 B2 | 2/2012 | Hong et al. |
| 8,129,390 B2 | 3/2012 | Darwish et al. |
| 8,314,107 B2 | 11/2012 | Yu et al. |
| 8,785,449 B2 | 7/2014 | Darwish et al. |
| 2002/0183327 A1 | 12/2002 | Gerlach et al. |
| 2004/0002513 A1 | 1/2004 | Mazurov et al. |
| 2004/0023972 A1 | 2/2004 | Sundermann et al. |
| 2005/0165049 A1 | 7/2005 | Hulme et al. |
| 2005/0282864 A1 | 12/2005 | McArthur et al. |
| 2006/0205772 A1 | 9/2006 | Coppola et al. |
| 2007/0123515 A1 | 5/2007 | Nettekoven et al. |
| 2007/0123525 A1 | 5/2007 | Nettekoven et al. |
| 2007/0123526 A1 | 5/2007 | Nettekoven et al. |
| 2009/0163511 A1 | 6/2009 | Darwish et al. |
| 2009/0170829 A1 | 7/2009 | Hong et al. |
| 2009/0275609 A1 | 11/2009 | Yu et al. |
| 2010/0190802 A1 | 7/2010 | Darwish et al. |

FOREIGN PATENT DOCUMENTS

| | | |
|---|---|---|
| GB | 2 327 675 | 3/1999 |
| WO | WO9736903 | 10/1997 |
| WO | WO9821208 | 5/1998 |
| WO | WO0012074 | 3/2000 |
| WO | WO0059904 | 10/2000 |
| WO | WO0164639 | 9/2001 |
| WO | WO0200651 | 1/2002 |
| WO | WO0218335 | 3/2002 |
| WO | WO03015774 | 2/2003 |
| WO | WO03018586 | 3/2003 |
| WO | WO03022856 | 3/2003 |
| WO | WO03070732 | 8/2003 |
| WO | WO03072578 | 9/2003 |
| WO | WO04000820 | 12/2003 |
| WO | WO2004054974 | 7/2004 |
| WO | WO2004085409 | 10/2004 |
| WO | WO2004111003 | 12/2004 |
| WO | WO2005002552 | 1/2005 |
| WO | WO2005020921 | 3/2005 |
| WO | WO2005040144 | 5/2005 |
| WO | WO2005061442 | 7/2005 |
| WO | WO2005116000 | 12/2005 |
| WO | WO2005117865 | 12/2005 |
| WO | WO2006002004 | 1/2006 |
| WO | WO2006045416 | 5/2006 |
| WO | WO2006058905 | 6/2006 |
| WO | WO2006064355 | 6/2006 |
| WO | WO2006067462 | 6/2006 |
| WO | WO2006076131 | 7/2006 |
| WO | WO2006094235 | 9/2006 |
| WO | WO2006099379 | 9/2006 |
| WO | WO2006101434 | 9/2006 |
| WO | WO2006114313 | 11/2006 |
| WO | WO2007005951 | 1/2007 |
| WO | WO2007075688 | 7/2007 |
| WO | WO2007087548 | 8/2007 |
| WO | WO2007087549 | 8/2007 |
| WO | WO2007098086 | 8/2007 |
| WO | WO2007099423 | 9/2007 |
| WO | WO2007104162 | 9/2007 |
| WO | WO2007122482 | 11/2007 |
| WO | WO2007143823 | 12/2007 |
| WO | WO2007143824 | 12/2007 |
| WO | WO2008007979 | 1/2008 |
| WO | WO2008017685 | 2/2008 |
| WO | WO2008083124 | 7/2008 |
| WO | WO2008133975 | 11/2008 |

OTHER PUBLICATIONS

Boger et al., "Solution Phase Combinatorial Synthesis of Biaryl Libraries Employing Heterogeneous Conditions for Catalysis and Isolation with Size Exclusion Chromatography for Purification", J. Org. Chem., 1999, vol. 64, 2422-2427.

Wolff, Burger's Medicinal Chemistry and Drug Discovery, vol. I: Principles and Practice, 5th Edition, 1994, 975-977.

Testa, "Prodrug Research: Futile or Fertile?", Biochemical Pharmacology, 2004, vol. 68, 2097-2106.

CAS Registry Nos. 896885-08-8; 896884-87-0; 896870-69-2; and 896870-65-8, report generated Dec. 10, 2007.

CAS Registry Nos. 894782-16-2; 894780-97-3; 894780-86-0; 894780-85-9; 894780-83-7; and 894779-82-9, report generated Dec. 10, 2007.

CAS Registry Nos. 197893-73-5; 197893-70-2; 197893-61-1; 197892-93-6; 197890-89-4; 197890-86-1; 197890-77-0, report generated Dec. 10, 2007.

CAS Registry Nos. 197893-74-6 and 197890-90-7, report generated Dec. 10, 2007.

Copending U.S. Appl. No. 14/171,624, filed Feb. 3, 2014.

CARBOXAMIDE COMPOUNDS AND METHODS FOR USING THE SAME

CROSS-REFERENCE TO RELATED APPLICATIONS

This application is a continuation of U.S. patent application Ser. No. 14/171,624, filed Feb. 3, 2014, which is a continuation of U.S. patent application Ser. No. 13/622,078, now U.S. Pat. No. 8,785,449, filed Sep. 18, 2012, which is a continuation of U.S. patent application Ser. No. 12/428,334, now U.S. Pat. No. 8,314,107, filed Apr. 22, 2009, and claims the benefit of the earlier filing dates of U.S. Provisional Patent Applications Ser. No. 61/047,399, filed Apr. 23, 2008; Ser. No. 61/048,997, filed Apr. 30, 2008; Ser. No. 61/054,035, filed May 16, 2008; Ser. No. 61/054,934, filed May 21, 2008; Ser. No. 61/058,854, filed Jun. 4, 2008; Ser. No. 61/078,166, filed Jul. 3, 2008; Ser. No. 61/078,180, filed Jul. 3, 2008; and Ser. No. 61/078,209, filed Jul. 3, 2008, each of which is hereby incorporated herein by reference in its entirety.

BACKGROUND

1. Field

This disclosure relates generally to compounds, pharmaceutical compositions and methods of use of the compounds and compositions containing them. This disclosure relates more particularly to certain carboxamide compounds and pharmaceutical compositions thereof, and to methods of treating and preventing metabolic disorders such as type II diabetes, atherosclerosis and cardiovascular disease using certain carboxamide compounds.

2. Technical Background

Adiponectin is a protein hormone exclusively expressed in and secreted from adipose tissue and is the most abundant adipose-specific protein. Adiponectin has been implicated in the modulation of glucose and lipid metabolism in insulin-sensitive tissues. Decreased circulating adiponectin levels have been demonstrated in some insulin-resistant states, such as obesity and type 2 diabetes mellitus and also in patients with coronary artery disease, atherosclerosis and hypertension. Adiponectin levels are positively correlated with insulin sensitivity, HDL (high density lipoprotein) levels and insulin stimulated glucose disposal and inversely correlated with adiposity and glucose, insulin and triglyceride levels. Thiazolidinedione drugs, which enhance insulin sensitivity through activation of the peroxisome proliferator-activated receptor-γ, increase endogenous adiponectin production in humans.

Adiponectin binds its receptors in liver and skeletal muscle and thereby activates the 5'-AMP-activated protein kinase (AMPK) pathway. Adiponectin receptors 1 and 2 are membrane-bound proteins found in skeletal muscle and liver tissue. Being a multi-substrate enzyme, AMPK regulates a variety of metabolic processes, such as glucose transport, glycolysis and lipid metabolism. It acts as a sensor of cellular energy homeostasis and is activated in response to certain hormones and muscle contraction as well as to intracellular metabolic stress signals such as exercise, ischemia, hypoxia and nutrient deprivation. Once activated, AMPK switches on catabolic pathways (such as fatty acid oxidation and glycolysis) and switches off ATP-consuming pathways (such as lipogenesis). Adiponectin improves insulin sensitivity by directly stimulating glucose uptake in adipocytes and muscle and by increasing fatty acid oxidation in liver and muscle, resulting in reduced circulating fatty acid levels and reduced intracellular triglyceride contents. Moreover, adiponectin decreases glycogen concentration by reducing the activity of glycogen synthase. Adiponectin also plays a protective role against inflammation and atherosclerosis. It suppresses the expression of adhesion molecules in vascular endothelial cells and cytokine production from macrophages, thus inhibiting the inflammatory processes that occur during the early phases of atherosclerosis.

SUMMARY

What is needed are compounds, pharmaceutical compositions and methods of using them to treat disease states associated with circulating adiponectin levels, such as type II diabetes, atherosclerosis and cardiovascular disease.

Disclosed herein are compounds having structural formula (I)

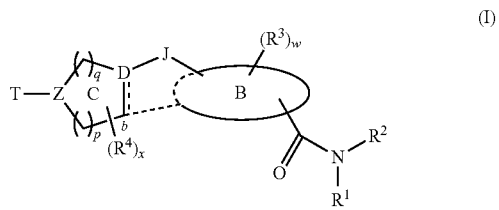

and pharmaceutically acceptable salts, prodrugs and N-oxides thereof (and solvates and hydrates thereof), wherein $R^1$, $R^2$, $R^3$, $R^4$, D, J, Z, T, p, q, w and x are as described herein.

Also disclosed herein are pharmaceutical compositions. Examples of such compositions include those having at least one pharmaceutically acceptable carrier, diluent or excipient; and a compound, pharmaceutically acceptable salt, prodrug or N-oxide (or solvate or hydrate) as described herein.

Another aspect of the present disclosure includes methods for modulating metabolism in subjects. Accordingly, also disclosed are methods for treating metabolic disorders using the presently disclosed compounds and pharmaceutical compositions.

DETAILED DESCRIPTION

One aspect of the disclosure provides compounds having structural formula (I):

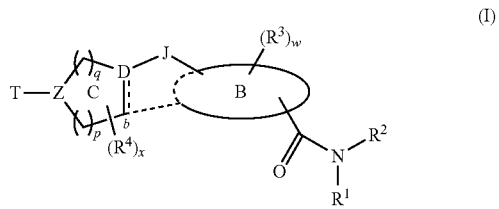

and pharmaceutically acceptable salts, prodrugs and N-oxides thereof (and solvates and hydrates thereof), wherein
  ring system "B" is -(aryl or heteroaryl)-;
  ring system "C" is an azacycloalkyl ring in which
    D is C, CH, $CR^4$, or N,
    Z is CH, $CR^4$ or N, provided that at least one of D and Z is N, and
    the bond between D and the carbon at the position denoted by "b" is a single bond or a double bond;

J is —O—, —N(R$^{38}$)—C(O)—, —C(O)— or absent, provided that:
- (a) when J is —O— or —N(R$^{38}$)—C(O)—, D is CH or CR$^4$, Z is N, J links ring systems "B" and "C", the dotted line connecting ring system "B" to the carbon denoted by "b" in ring system "C" is absent, and the bond between D and the carbon atom at the position denoted by "b" is a single bond,
- (b) when J is —C(O)—, J links ring systems "B" and "C", the dotted line connecting ring "B" to the carbon denoted by "b" in ring system "C" is absent, and the bond between D and the carbon atom at the position denoted by "b" is a single bond,
- (c) when J is absent, the dotted line connecting ring system "B" to the carbon denoted by "b" in ring system "C" signifies that ring systems "B" and "C" are fused through the bond connecting D and the carbon atom denoted by "b" in ring system "C", and
- (d) when J is —O—, the ring system denoted by "B" is other than phenyl, that is, the compound does not have the formula

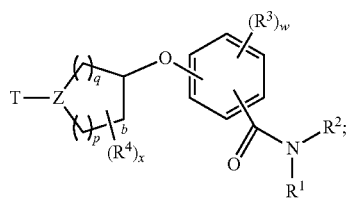

$R^1$ is H, —($C_1$-$C_4$ alkyl), —C(O)—($C_1$-$C_4$ alkyl) or —C(O)O—($C_1$-$C_4$ alkyl), and $R^2$ is -Hca, -Cak-N($R^9$)-G-$R^{22}$ or —($C_2$-$C_8$ alkyl)-N($R^9$)—$R^{24}$ in which one or two (e.g., non-adjacent) carbons of the ($C_2$-$C_8$ alkyl) are optionally replaced by —O—, —S— or —N($R^9$)—, and $R^{24}$ is —$R^{23}$, -G-$R^{23}$ or —C(O)O—($C_1$-$C_6$ alkyl), provided that two consecutive carbons of the ($C_2$-$C_8$ alkyl) are not replaced by —O—, or $R^1$ and $R^2$ together with the nitrogen to which they are attached come together to form -Hca;

each $R^3$ is independently selected from —($C_1$-$C_6$ alkyl), —($C_1$-$C_6$ haloalkyl), —($C_0$-$C_6$ alkyl)-Ar, —($C_0$-$C_6$ alkyl)-Het, —($C_0$-$C_6$ alkyl)-Cak, —($C_0$-$C_6$ alkyl)-Hca, —($C_0$-$C_6$ alkyl)-L-$R^7$, —($C_0$-$C_6$ alkyl)-N$R^8R^9$, —($C_0$-$C_6$ alkyl)-O$R^{10}$, —($C_0$-$C_6$ alkyl)-C(O)$R^{10}$, —($C_0$-$C_6$ alkyl)-S(O)$_{0-2}R^{10}$, -halogen, —NO$_2$ and —CN;

w is 0, 1, 2, 3 or 4;

each $R^4$ is independently selected from —($C_1$-$C_6$ alkyl), —($C_1$-$C_6$ haloalkyl), —($C_0$-$C_6$ alkyl)-Ar, —($C_0$-$C_6$ alkyl)-Het, —($C_0$-$C_6$ alkyl)-Cak, —($C_0$-$C_6$ alkyl)-Hca, —($C_0$-$C_6$ alkyl)-L-$R^7$, —($C_0$-$C_6$ alkyl)-N$R^8R^9$, —($C_0$-$C_6$ alkyl)-O$R^{10}$, —($C_0$-$C_6$ alkyl)-C(O)$R^{10}$, —($C_0$-$C_6$ alkyl)-S(O)$_{0-2}R^{10}$, -halogen, —NO$_2$ and —CN, and two $R^4$ on the same carbon optionally combine to form oxo;

p is 0, 1, 2, 3 or 4;

q is 0, 1, 2, 3 or 4, provided that the sum of p and q is 1, 2, 3 or 4;

x is 0 or an integer ≤p+q, wherein when D or Z is CR$^4$, the $R^4$ of D or Z is one of the x $R^4$ groups on ring system "C";

T is —($C_0$-$C_6$ alkyl)-L-$R^7$, —($C_0$-$C_6$ alkyl)-N$R^8R^9$, —($C_0$-$C_6$ alkyl)-O$R^{10}$, —($C_0$-$C_6$ alkyl)-C(O)$R^{10}$, —($C_0$-$C_6$ alkyl)-S(O)$_{0-2}R^{10}$ or

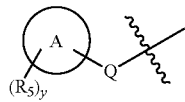

in which

Q is —S(O)$_2$—, L, or ($C_0$-$C_3$ alkyl)-, in which each carbon of the —($C_0$-$C_3$ alkyl)- is optionally and independently substituted with one or two $R^{16}$;

the ring denoted by "A" is heteroaryl, aryl, cycloalkyl or heterocycloalkyl;

each $R^5$ is independently selected from —($C_1$-$C_6$ alkyl), —($C_1$-$C_6$ haloalkyl), —($C_0$-$C_6$ alkyl)-Ar, —($C_0$-$C_6$ alkyl)-Het, —($C_0$-$C_6$ alkyl)-Cak, —($C_0$-$C_6$ alkyl)-Hca, —($C_0$-$C_6$ alkyl)-L-$R^7$, —($C_0$-$C_6$ alkyl)-N$R^8R^9$, —($C_0$-$C_6$ alkyl)-O$R^{10}$, —($C_0$-$C_6$ alkyl)-C(O)$R^{10}$, —($C_0$-$C_6$ alkyl)-S(O)$_{0-2}R^{10}$, -halogen, —NO$_2$ and —CN; and y is 0, 1, 2, 3 or 4;

in which each L is independently selected from —N$R^9$C(O)O—, —OC(O)N$R^9$—, —N$R^9$C(O)—N$R^9$—, —N$R^9$C(O)S—, —SC(O)N$R^9$—, —N$R^9$C(O)—, —C(O)N$R^9$—, —N$R^9$C(S)O—, —OC(S)N$R^9$—, —N$R^9$C(S)—N$R^9$—, —N$R^9$C(S)S—, —SC(S)N$R^9$—, —N$R^9$C(S)—, —C(S)N$R^9$—, —SC(O)N$R^9$—, —N$R^9$C(S)—, —S(O)$_{0-2}$—, —C(O)O—, —OC(O)—, —C(S)O—, —OC(S)—, —C(O)S—, —SC(O)—, —C(S)S—, —SC(S)—, —OC(O)O—, —SC(O)O—, —OC(O)S—, —SC(S)O—, —OC(S)S—, —N$R^9$C(N$R^2$)N$R^9$—, —N$R^9$SO$_2$—, —SO$_2$N$R^9$— and —N$R^9$SO$_2$N$R^9$—, each $R^6$, $R^7$, $R^8$ and $R^{10}$ is independently selected from H, —($C_1$-$C_6$ alkyl), —($C_1$-$C_6$ haloalkyl), —($C_0$-$C_6$ alkyl)-Ar, —($C_0$-$C_6$ alkyl)-Het, —($C_0$-$C_6$ alkyl)-Cak, —($C_0$-$C_6$ alkyl)-Hca, —($C_0$-$C_6$ alkyl)-L-($C_0$-$C_6$ alkyl), —($C_0$-$C_6$ alkyl)-N$R^9$—($C_0$-$C_6$ alkyl), —($C_0$-$C_6$ alkyl)-O—($C_0$-$C_6$ alkyl), —($C_0$-$C_6$ alkyl)-C(O)—($C_0$-$C_6$ alkyl) and —($C_0$-$C_6$ alkyl)-S(O)$_{0-2}$—($C_0$-$C_6$ alkyl), each $R^9$ is independently selected from —H, —($C_1$-$C_4$ alkyl), —C(O)—($C_1$-$C_4$ alkyl) and —C(O)O—($C_1$-$C_4$ alkyl), each G is independently —S(O)$_2$—, L, or —($C_0$-$C_3$ alkyl)-, in which each carbon of the —($C_0$-$C_3$ alkyl)- is optionally and independently substituted with one or two $R^{16}$, each $R^{16}$ is independently selected from —($C_1$-$C_6$ alkyl), —($C_1$-$C_6$ haloalkyl), —($C_0$-$C_6$ alkyl)-Ar, —($C_0$-$C_6$ alkyl)-Het, —($C_0$-$C_6$ alkyl)-Cak, —($C_0$-$C_6$ alkyl)-Hca, —($C_0$-$C_6$ alkyl)-L-$R^7$, —($C_0$-$C_6$ alkyl)-N$R^8R^9$, —($C_0$-$C_6$ alkyl)-O$R^{10}$, —($C_0$-$C_6$ alkyl)-C(O)$R^{10}$, —($C_0$-$C_6$ alkyl)-S(O)$_{0-2}R^{10}$, -halogen, —NO$_2$ and —CN, or two $R^{16}$ on the same carbon combine to form oxo, $R^{38}$ is independently selected from —H, —($C_1$-$C_4$ alkyl), —C(O)—($C_1$-$C_4$ alkyl) and —C(O)O—($C_1$-$C_4$ alkyl), $R^{22}$ and $R^{23}$ are each independently Ar or Het, each Ar is an optionally substituted aryl, each Het is an optionally substituted heteroaryl, each Cak is an optionally substituted cycloalkyl, each Hca is an optionally substituted heterocycloalkyl, and each alkyl is optionally substituted.

In certain embodiments of the presently disclosed compounds of structural formula (I), J is —O— or —N(R$^{38}$)—C(O)— and D is CH or C— substituted with one of the x R$^4$ groups. In other embodiments of the presently disclosed compounds of structural formula (I), J is —C(O)—. In certain such embodiments, D is N.

In certain embodiments of the presently disclosed compounds of structural formula (I), Z is N and D is C, CH or C— substituted with one of the x R$^4$ groups. In other embodiments, D is N and Z is CH or C— substituted with one of the x R$^4$ groups. In further embodiments, D is N and Z is N.

In certain embodiments of the presently disclosed compounds of structural formula (I), R$^{38}$ is —H. In other embodiments, R$^{38}$ is —(C$_1$-C$_4$ alkyl), for example methyl, ethyl or propyl. In other embodiments, R$^{38}$ is —C(O)—(C$_1$-C$_4$ alkyl), for example acetyl. In other embodiments, R$^{38}$ is —C(O)—O—(C$_1$-C$_4$ alkyl)-, for example —C(O)—O-t-butyl. In certain embodiments, no alkyl of R$^{38}$ is substituted with an aryl-, heteroaryl-, cycloalkyl- or heterocycloalkyl-containing group.

In certain embodiments of the presently disclosed compounds of structural formula (I) as described above, ring system "B" is not fused to ring system "C" at the position denoted by "b," so that the compounds have structural formula (II):

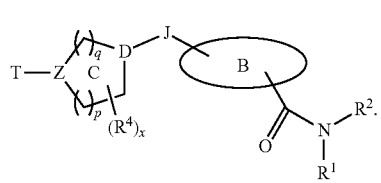
(II)

In other embodiments, ring system "B" is fused to ring system "C" at the position denoted by "b"; for example, the compounds can have structural formula (III):

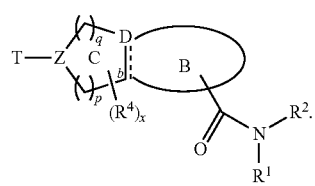
(III)

In certain embodiments of the presently disclosed compounds of structural formula (I), "B" represents

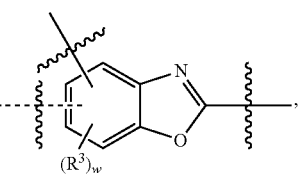

in which the benzo ring is linked or fused to ring system "C" and the dotted line is not a bond but merely indicates that the benzo ring is fused to ring system "C" or not. Examples of such compounds wherein ring system "B" is not fused to ring system "C" are represented by the formula

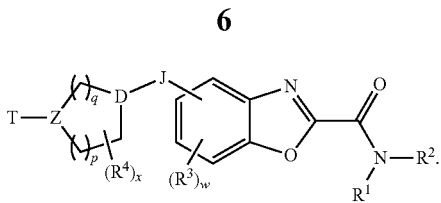

In certain such embodiments, J is —O—, Z is N and D is CH or C— substituted by one of the x R$^4$.

In other embodiments of the presently disclosed compounds of structural formula (I), "B" represents

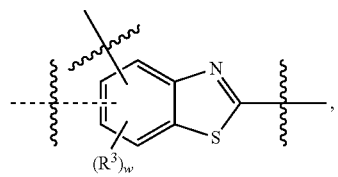

in which the benzo ring is linked or fused to ring system "C" and the dotted line is not a bond but merely indicates that the benzo ring is fused to ring system "C" or not. Examples of such compounds wherein ring system "B" is not fused to ring system "C" are represented by the formula

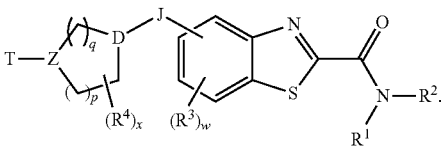

In certain such embodiments, J is —O—, Z is N and D is CH or C— substituted by one of the x R$^4$.

In other embodiments of the presently disclosed compounds of structural formula (I), "B" represents

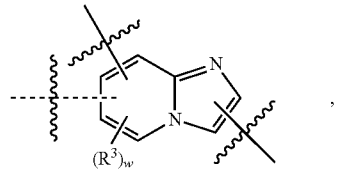

in which the pyrido ring is linked or fused to ring system "C" and the dotted line is not a bond but merely indicates that the pyrido ring is fused to ring system "C" or not. Examples of such compounds wherein ring system "B" is not fused to ring system "C" are represented by the formula

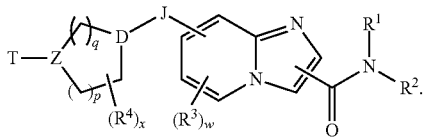

In certain such embodiments, J is —O—, Z is N and D is CH or C— substituted by one of the x R$^4$. Floating bonds indicate attachment on any carbon of the imidazo[1,2-a]pyridine ring system. In some embodiments, for example, the J moiety is on the pyridine ring of the imidazo[1,2-a]pyridine ring system, and the carboxamide (i.e., —C(O)—NR$^1$R$^2$) moiety is on the imidazo ring of the imidazo[1,2-a]pyridine ring system, and any R$^3$ groups can be on either ring of the imidazo[1,2-a]pyridine ring system.

In other embodiments of the presently disclosed compounds of structural formula (I), "B" represents

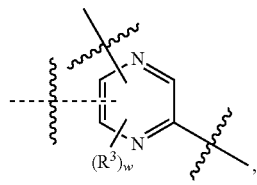

in which the pyrazine ring is linked or fused to ring system "C" and the dotted line is not a bond but merely indicates that the pyrazine ring is fused to ring system "C" or not. Examples of such compounds wherein ring system "B" is not fused to ring system "C" are represented by the formula

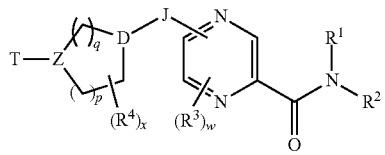

In certain such embodiments, J is —O—, Z is N and D is CH or C— substituted by one of the x R$^4$.

In other embodiments of the presently disclosed compounds of structural formula (I), "B" represents

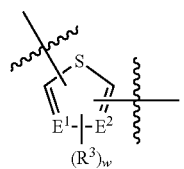

and is not fused to ring system "C", one of E$^1$ and E$^2$ is N and the other is CH, C substituted with the R$^3$, C substituted with the -J-(ring system "C"), or C substituted with the —C(O)—NR$^1$R$^2$), w is 0 or 1. In certain such embodiments, J is —O—, Z is N and D is CH or C— substituted by one of the x R$^4$.

In other embodiments of the presently disclosed compounds of structural formula (I), ring system "B" is

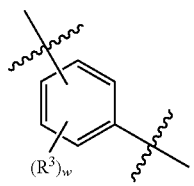

and is not fused to ring system "C". In such embodiments, J is other than O. In certain such embodiments, J is —C(O)—, Z is N, CH or C— substituted by one of the x R$^4$ and D is N. In other such embodiments, J is —N(R$^{38}$)—C(O)—, Z is N and D is CH or C— substituted by one of the x R$^4$.

In certain embodiments according to structural formulae (I)-(III), the sum of p and q is 2 or 3. For example, in one embodiment, the sum of p and q is 2 (e.g., p is 1 and q is 1). In another embodiment, the sum of p and q is 3 (e.g., p is 1 and q is 2).

In other embodiments of the presently disclosed compounds of structural formula (I), ring system "B" is a phenyl and is fused to ring system "C" (i.e., J is absent), Z is N, D is C, q is 2 and p is 1, such that the compound has structural formula (IV):

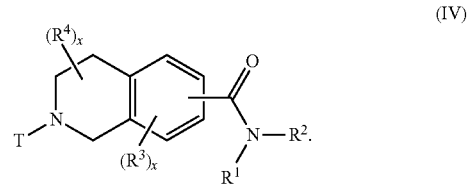

(IV)

In certain embodiments of the presently disclosed compounds of structural formulae (I)-(IV), T is

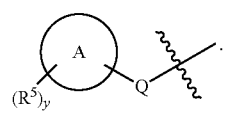

In such embodiments, Q is —S(O)$_2$—, L or —(C$_0$-C$_3$ alkyl)- in which each carbon of the (C$_0$-C$_3$ alkyl) is optionally and independently substituted with one or two R$^{16}$, in which each R$^{16}$ is independently selected from —(C$_1$-C$_6$ alkyl), —(C$_1$-C$_6$ haloalkyl), —(C$_0$-C$_6$ alkyl)-Ar, —(C$_0$-C$_6$ alkyl)-Het, —(C$_0$-C$_6$ alkyl)-Cak, —(C$_0$-C$_6$ alkyl)-Hca, —(C$_0$-C$_6$ alkyl)-L-R$^7$, —(C$_0$-C$_6$ alkyl)-NR$^8$R$^9$, —(C$_0$-C$_6$ alkyl)-OR$^{10}$, —(C$_0$-C$_6$ alkyl)-C(O)R$^{10}$, —(C$_0$-C$_6$ alkyl)-S(O)$_{0-2}$R$^{10}$, -halogen, —NO$_2$ and —CN, and optionally two of R$^{16}$ on the same carbon combine to form oxo. In certain embodiments, each R$^{16}$ is independently selected from —(C$_1$-C$_6$ alkyl), —(C$_1$-C$_6$ haloalkyl) (e.g., difluoromethyl, trifluoromethyl and the like), —(C$_0$-C$_6$ alkyl)-L-R$^7$, —(C$_0$-C$_6$ alkyl)-NR$^8$R$^9$, —(C$_0$-C$_6$ alkyl)-OR$^{10}$, —(C$_0$-C$_6$ alkyl)-C(O)R$^{10}$, —(C$_0$-C$_6$ alkyl)-S(O)$_{0-2}$R$^{10}$, -halogen, —NO$_2$ and —CN, and two R$^{16}$ on the same carbon optionally combine to form an oxo, in which each R$^7$, R$^8$ and R$^{10}$ is independently selected from H, —(C$_1$-C$_6$ alkyl), —(C$_1$-C$_6$ haloalkyl), —(C$_0$-C$_6$ alkyl)-L-(C$_0$-C$_6$ alkyl), —(C$_0$-C$_6$ alkyl)-NR$^9$(C$_0$-C$_6$ alkyl), —(C$_0$-C$_6$ alkyl)-O—(C$_0$-C$_6$ alkyl), —(C$_0$-C$_6$ alkyl)-C(O)—(C$_0$-C$_6$ alkyl), and —(C$_0$-C$_6$ alkyl)-S(O)$_{0-2}$—(C$_0$-C$_6$ alkyl), and in which no alkyl or haloalkyl is substituted with an aryl-, heteroaryl-, cycloalkyl- or heterocycloalkyl-containing group. For example, in particular compounds, each R$^{16}$ is —(C$_1$-C$_3$ alkyl), —(C$_1$-C$_3$ haloalkyl), —(C$_0$-C$_3$ alkyl)-L-R$^7$, —(C$_0$-C$_3$ alkyl)-NR$^8$R$^9$, —(C$_0$-C$_3$ alkyl)-OR$^{10}$, —(C$_0$-C$_3$ alkyl)-C(O)R$^{10}$, —(C$_0$-C$_3$ alkyl)-S(O)$_{0-2}$R$^{10}$, -halogen, —NO$_2$ and —CN, and two R$^{16}$ on the same carbon optionally combine to form an oxo, in which each R$^7$, R$^8$ and R$^{10}$ is independently selected from H, —(C$_1$-C$_2$ alkyl), —(C$_1$-C$_2$ haloalkyl), —(C$_0$-C$_2$ alkyl)-L-(C$_0$-C$_2$ alkyl), —(C$_0$-C$_2$ alkyl)-NR$^9$(C$_0$-C$_2$ alkyl), —(C$_0$-C$_2$ alkyl)-O—(C$_0$-C$_2$ alkyl), —(C$_0$-C$_2$ alkyl)-C(O)—(C$_0$-C$_2$ alkyl) and —(C$_0$-C$_2$ alkyl)-S(O)$_{0-2}$—(C$_0$-C$_2$ alkyl), and in which no alkyl or haloalkyl is substituted with an aryl-, heteroaryl-, cycloalkyl- or heterocycloalkyl-containing group. In certain embodiments, Q has at most one R$^{16}$ or oxo substituted thereon. Q can be, for example, an unsubstituted —($C_0$-$C_3$ alkyl)-. In other embodiments, Q is a ($C_1$-$C_3$ alkyl) having as its only substitution a single oxo group. For example, in certain embodiments, Q is —$CH_2$—a single bond; —$S(O)_2$——$C(O)$— or —$CH(CH_3)$—.

In certain embodiments of the compounds of structural formulae (I)-(IV), the

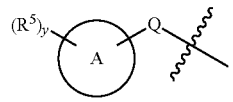

moiety is

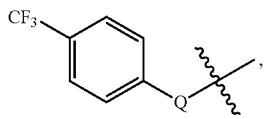

for example, p-(trifluoromethyl)phenyl. In other embodiments, the

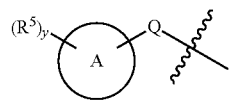

moiety is

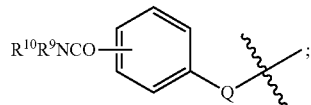

in one such embodiment, Q is a single bond.

The number of substituents on the ring system denoted by "A", y, is 0, 1, 2, 3 or 4. For example, in some embodiments of the presently disclosed compounds of structural formulae (I)-(IV), y is 0, 1, 2 or 3, such as 1. In one embodiment, y is not zero and at least one $R^5$ is halo, cyano, —($C_1$-$C_4$ haloalkyl), —O—($C_1$-$C_4$ haloalkyl), —($C_1$-$C_4$ alkyl), —O—($C_1$-$C_4$ alkyl), —C(O)—($C_0$-$C_4$ alkyl), —C(O)O—($C_0$-$C_4$ alkyl), —C(O)N($C_0$-$C_4$ alkyl)($C_0$-$C_4$ alkyl), $NO_2$ or —C(O)-Hca wherein the Hca contains a ring nitrogen atom through which it is bound to the —C(O)—, and wherein no alkyl, haloalkyl or heterocycloalkyl is substituted by an aryl, heteroaryl, cycloalkyl or heterocycloalkyl-containing group.

In certain embodiments of the presently disclosed compounds of structural formulae (I)-(IV), each $R^5$ is independently selected from —($C_1$-$C_6$ alkyl), —($C_1$-$C_6$ haloalkyl) (e.g., difluoromethyl, trifluoromethyl and the like), —($C_0$-$C_6$ alkyl)-L-$R^7$, —($C_0$-$C_6$ alkyl)-$NR^8R^9$, —($C_0$-$C_6$ alkyl)-$OR^{10}$, —($C_0$-$C_6$ alkyl)-C(O)$R^{10}$—($C_0$-$C_6$ alkyl)-$S(O)_{0-2}R^{10}$, -halogen, —$NO_2$ and —CN, in which each $R^7$, $R^8$ and $R^{10}$ is independently selected from H, —($C_1$-$C_6$ alkyl), —($C_1$-$C_6$ haloalkyl) (e.g., difluoromethyl, trifluoromethyl and the like), —($C_0$-$C_6$ alkyl)-L-($C_0$-$C_6$ alkyl), —($C_0$-$C_6$ alkyl)-$NR^9$($C_0$-$C_6$ alkyl), —($C_0$-$C_6$ alkyl)-O—($C_0$-$C_6$ alkyl), —($C_0$-$C_6$ alkyl)-C(O)—($C_0$-$C_6$ alkyl) and —($C_0$-$C_6$ alkyl)-$S(O)_{0-2}$—($C_0$-$C_6$ alkyl), and in which no alkyl or haloalkyl is substituted with an aryl-, heteroaryl-, cycloalkyl- or heterocycloalkyl-containing group. For example, in one embodiment, each $R^5$ is —($C_1$-$C_3$ alkyl), —($C_1$-$C_3$ haloalkyl), —($C_0$-$C_3$ alkyl)-L-$R^7$, —($C_0$-$C_3$ alkyl)-$NR^8R^9$, —($C_0$-$C_3$ alkyl)-$OR^{10}$, —($C_0$-$C_3$ alkyl)-C(O)$R^{10}$, —($C_0$-$C_3$ alkyl)-$S(O)_{0-2}R^{10}$, -halogen, —$NO_2$ and —CN, in which each $R^7$, $R^8$ and $R^{10}$ is independently selected from H, —($C_1$-$C_2$ alkyl), —($C_1$-$C_2$ haloalkyl), —($C_0$-$C_2$ alkyl)-L-($C_0$-$C_2$ alkyl), —($C_0$-$C_2$ alkyl)-$NR^9$($C_0$-$C_2$ alkyl), —($C_0$-$C_2$ alkyl)-O—($C_0$-$C_2$ alkyl), —($C_0$-$C_2$ alkyl)-C(O)—($C_0$-$C_2$ alkyl) and —($C_0$-$C_2$ alkyl)-$S(O)_{0-2}$—($C_0$-$C_2$ alkyl), and in which no alkyl or haloalkyl is substituted with an aryl-, heteroaryl-, cycloalkyl- or heterocycloalkyl-containing group.

In one embodiment of the compounds of structural formulae (I)-(IV), y is 0.

In the presently disclosed compounds of structural formulae (I)-(IV), the ring system denoted by "A" is heteroaryl, aryl, cycloalkyl or heterocycloalkyl. For example, in one embodiment, the ring system denoted by "A" is an aryl or a heteroaryl. The ring system denoted by "A" can be, for example, a monocyclic aryl or heteroaryl. In one embodiment, when the "A" ring system is aryl, Q is a —($C_0$-$C_3$ alkyl)- optionally substituted with oxo, and optionally substituted with one or more $R^{16}$. For example, Q can be a —($C_1$-$C_3$ alkyl)- having its only substitution a single oxo, or an unsubstituted —($C_0$-$C_3$ alkyl)-. For example, in certain embodiments, Q is —$CH_2$—; a single bond; —$S(O)_2$—; —C(O)—; or —$CH(CH_3)$—.

For example, in certain embodiments of the presently disclosed compounds of structural formulae (I)-(IV), the ring system denoted by "A" is a phenyl. In one embodiment, y is 1 and $R^5$ is attached to the phenyl in the para position relative to Q. In another embodiment, y is 1 and $R^5$ is selected from the group consisting of halo, cyano, —($C_1$-$C_4$ haloalkyl), —O—($C_1$-$C_4$ haloalkyl), —($C_1$-$C_4$ alkyl), —O—($C_1$-$C_4$ alkyl), —C(O)—($C_0$-$C_4$ alkyl), —C(O)O—($C_0$-$C_4$ alkyl), —C(O)N($C_0$-$C_4$ alkyl)($C_0$-$C_4$ alkyl), $NO_2$ and —C(O)-Hca in which the Hca contains a ring nitrogen atom through which it is bound to the —C(O)—, and in which no ($C_0$-$C_4$ alkyl) or ($C_1$-$C_4$ alkyl) is substituted by an aryl, heteroaryl, cycloalkyl or heterocycloalkyl-containing group. $R^5$ can be, for example, —Cl, —F, cyano, —C(O)$CH_3$, —C(O)OH, —C(O)$NH_2$, trifluoromethyl, difluoromethyl, difluoromethoxy or trifluoromethoxy. In another embodiment, the

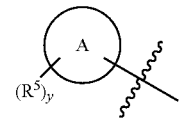

moiety is a 3,4-dihalophenyl.

In another embodiment of the presently disclosed compounds of structural formulae (I)-(IV), the ring system denoted by "A" is a heteroaryl. For example, in certain embodiments, the ring system denoted by "A" is a pyridyl, a thienyl, or a furanyl. In one embodiment, when the "A" ring system is heteroaryl, Q is a —($C_0$-$C_3$ alkyl)- optionally substituted with oxo, and optionally substituted with one or more $R^{16}$. For example, Q can be a —($C_1$-$C_3$ alkyl)- having its only substitution a single oxo, or an unsubstituted —($C_0$-$C_3$ alkyl)-. In certain embodiments, Q is —$CH_2$—; a single bond; —$S(O)_2$—; —C(O)—; or —$CH(CH_3)$—.

In certain embodiments (e.g., when ring system "B" is a phenyl and is fused to ring system "C", J is absent, Z is N, D is carbon, q is 2 and p is 1), T is not —C(O)O—($C_0$-$C_6$ alkyl).

In certain embodiments (e.g., when ring system "B" is a phenyl and is fused to ring system "C", J is absent, Z is N, D is carbon, q is 2 and p is 1), T is not is not —CH₂C(O)OH; —NH—CH₂—C(O)OH; —O—CH₂—C(O)OH; —CH₂—CH₂—C(O)OH; —CH=CH—C(O)OH; —N(C(O)CH₃)—CH₂—C(O)OH; =CH—C(O)OH or =CH—CH₂—CH₂—C(O)OH.

In one embodiment of the presently disclosed compounds, the compound has structural formula (V):

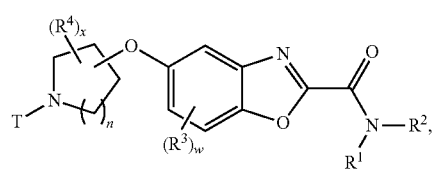

(V)

in which n is 1, 2, 3 or 4, and all other variables are defined as described above with reference to structural formulae (I)-(IV).

In one embodiment of the presently disclosed compounds, the compound has structural formula (VI):

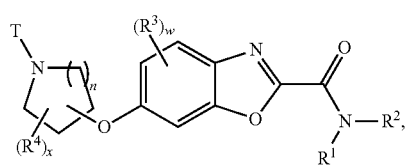

(VI)

in which n is 1, 2, 3 or 4, and all other variables are defined as described above with reference to structural formulae (I)-(IV).

In one embodiment of the presently disclosed compounds, the compound has structural formula (VII):

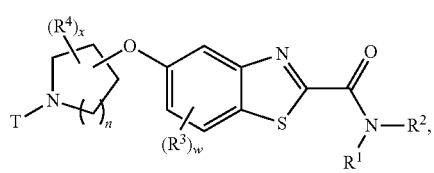

(VII)

in which n is 1, 2, 3 or 4, and all other variables are defined as described above with reference to structural formulae (I)-(IV).

In one embodiment of the presently disclosed compounds, the compound has structural formula (VIII):

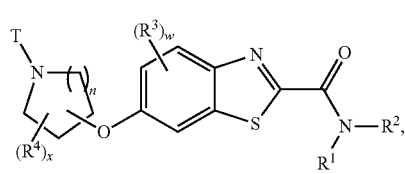

(VIII)

in which n is 1, 2, 3 or 4, and all other variables are defined as described above with reference to structural formulae (I)-(IV).

In one embodiment of the presently disclosed compounds, the compound has structural formula (IX):

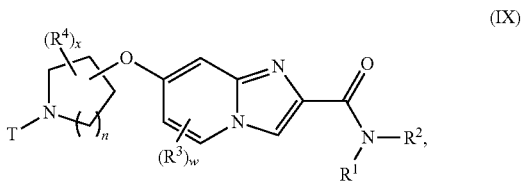

(IX)

in which n is 1, 2, 3 or 4, and all other variables are defined as described above with reference to structural formulae (I)-(IV).

In one embodiment of the presently disclosed compounds, the compound has structural formula (X):

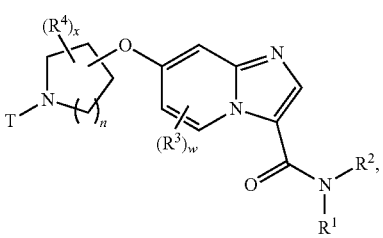

(X)

in which n is 1, 2, 3 or 4, and all other variables are defined as described above with reference to structural formulae (I)-(IV).

In one embodiment of the presently disclosed compounds, the compound has structural formula (XI):

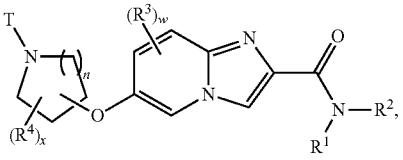

(XI)

in which n is 1, 2, 3 or 4, and all other variables are defined as described above with reference to structural formulae (I)-(IV).

In one embodiment of the presently disclosed compounds, the compound has structural formula (XII):

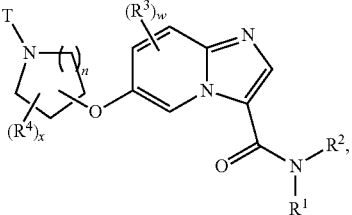

(XII)

in which n is 1, 2, 3 or 4, and all other variables are defined as described above with reference to structural formulae (I)-(IV).

In one embodiment of the presently disclosed compounds, the compound has structural formula (XIII):

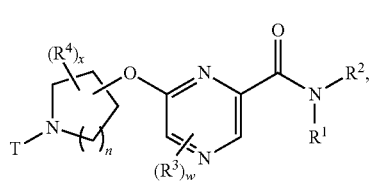

(XIII)

in which n is 1, 2, 3 or 4, and all other variables are defined as described above with reference to structural formulae (I)-(IV).

In one embodiment of the presently disclosed compounds, the compound has structural formula (XIV):

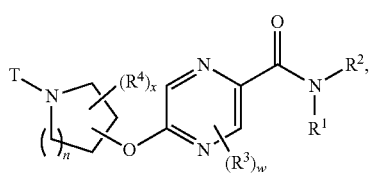

(XIV)

in which n is 1, 2, 3 or 4, and all other variables are defined as described above with reference to structural formulae (I)-(IV).

In one embodiment of the presently disclosed compounds, the compound has structural formula (XV):

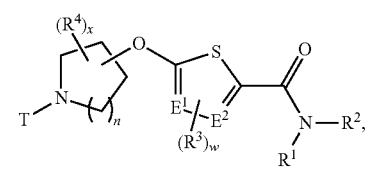

(XV)

in which n is 1, 2, 3 or 4, w is 0 or 1, and all other variables are defined as described above with reference to structural formulae (I)-(IV). For example, in one embodiment, $E^1$ is N and $E^2$ is —CH— or —$CR^3$—. In another embodiment, $E^1$ is —CH— or —$CR^3$— and $E^2$ is N.

In one embodiment of the presently disclosed compounds, the compound has structural formula (XVI):

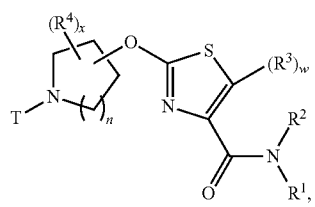

(XVI)

in which n is 1, 2, 3 or 4, w is 0 or 1, and all other variables are defined as described above with reference to structural formulae (I)-(IV). When w is 0, the ring position shown occupied by $R^3$ bears a hydrogen atom.

In one embodiment of the presently disclosed compounds, the compound has structural formula (XVII):

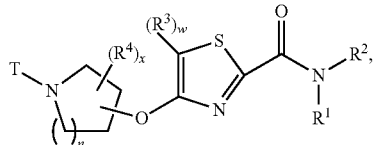

(XVII)

in which n is 1, 2, 3 or 4, w is 0 or 1, and all other variables are defined as described above with reference to structural formulae (I)-(IV). When w is 0, the ring position shown occupied by $R^3$ bears a hydrogen atom.

In certain embodiments of the compounds disclosed with reference to structural formulae (V)-(XVII), n is 1 or 2. For example, in one embodiment, n is 2. In another embodiment, n is 1.

For example, in one embodiment of the presently disclosed compounds, the compound has structural formula (XVIII):

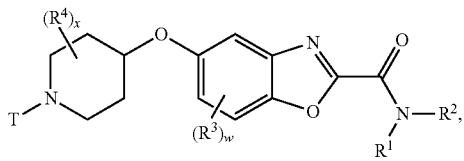

(XVIII)

in which all variables are defined as described above with reference to structural formulae (I)-(IV).

In another embodiment of the presently disclosed compounds, the compound has structural formula (XIX):

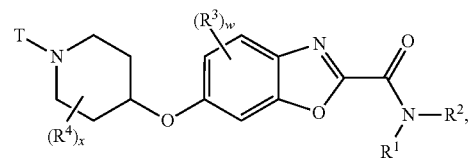

(XIX)

in which all variables are defined as described above with reference to structural formulae (I)-(IV).

In another embodiment of the presently disclosed compounds, the compound has structural formula (XX):

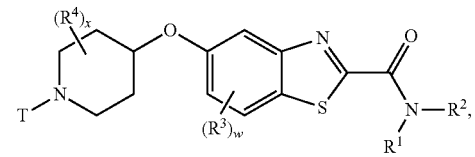

(XX)

in which all variables are defined as described above with reference to structural formulae (I)-(IV).

In another embodiment of the presently disclosed compounds, the compound has structural formula (XXI):

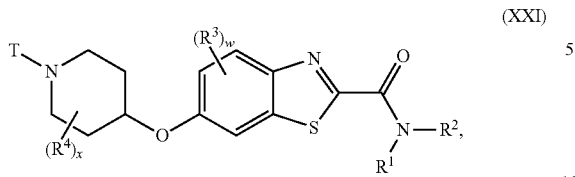
(XXI)

in which all variables are defined as described above with reference to structural formulae (I)-(IV).

In another embodiment of the presently disclosed compounds, the compound has structural formula (XXII):

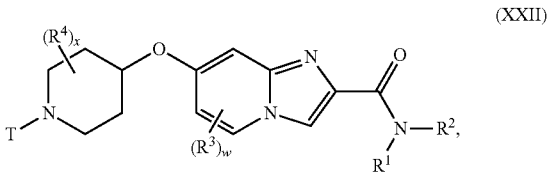
(XXII)

in which all variables are defined as described above with reference to structural formulae (I)-(IV).

In another embodiment of the presently disclosed compounds, the compound has structural formula (XXIII):

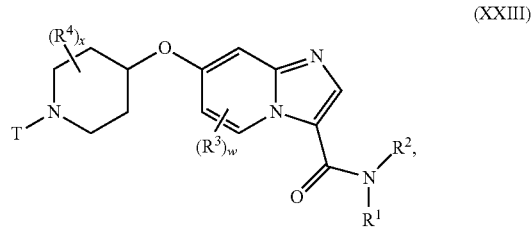
(XXIII)

in which all variables are defined as described above with reference to structural formulae (I)-(IV).

In another embodiment of the presently disclosed compounds, the compound has structural formula (XXIV):

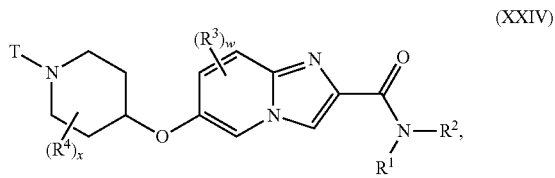
(XXIV)

in which all variables are defined as described above with reference to structural formulae (I)-(IV).

In another embodiment of the presently disclosed compounds, the compound has structural formula (XXV):

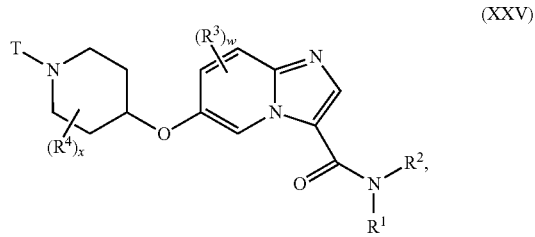
(XXV)

in which all variables are defined as described above with reference to structural formulae (I)-(IV).

In another embodiment of the presently disclosed compounds, the compound has structural formula (XXVI):

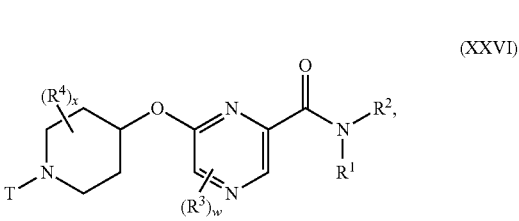
(XXVI)

in which all variables are defined as described above with reference to structural formulae (I)-(IV).

In another embodiment of the presently disclosed compounds, the compound has structural formula (XXVII):

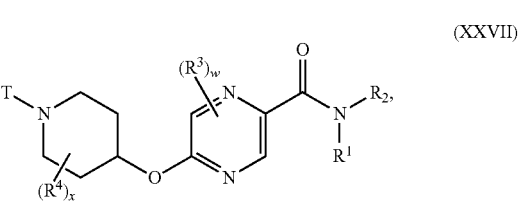
(XXVII)

in which all variables are defined as described above with reference to structural formulae (I)-(IV).

In another embodiment of the presently disclosed compounds, the compound has structural formula (XXVIII):

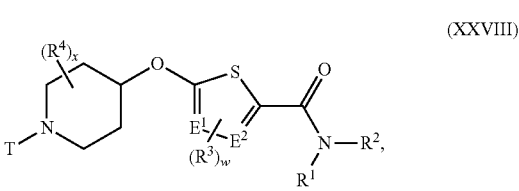
(XXVIII)

in which w is 0 or 1 and all other variables are defined as described above with reference to structural formulae (I)-(IV). When w is 0, the ring position shown occupied by $R^3$ bears a hydrogen atom. In one embodiment, $E^1$ is —CH— or —CR$^3$— and $E^2$ is N. In another embodiment, $E^1$ is N and $E^2$ is —CH— or —CR$^3$—.

In another embodiment of the presently disclosed compounds, the compound has structural formula (XXIX):

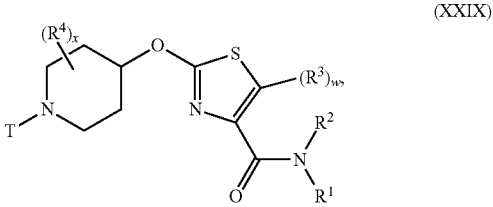
(XXIX)

in which w is 0 or 1 and all other variables are defined as described above with reference to structural formulae (I)-(IV). When w is 0, the ring position shown occupied by $R^3$ bears a hydrogen atom.

In another embodiment of the presently disclosed compounds, the compound has structural formula (XXX):

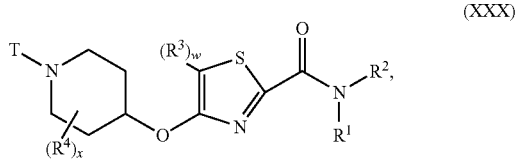

(XXX)

in which w is 0 or 1 and all other variables are defined as described above with reference to structural formulae (I)-(IV). When w is 0, the ring position shown occupied by $R^3$ bears a hydrogen atom.

In one embodiment of the presently disclosed compounds, the compound has structural formula (XXXI):

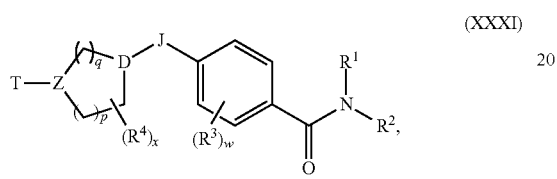

(XXXI)

in which all variables are defined as described above with reference to structural formulae (I)-(IV). In one such embodiment, J is —C(O)—, Z is CH or C substituted with one of the x $R^4$ and D is N. In another such embodiment, J is —C(O)—, Z is N and D is N. In a further such embodiment, J is —N($R^{38}$)—C(O)— (e.g., —NH—C(O)—), Z is N and D is CH or C substituted with one of the x $R^4$.

In another embodiment of the presently disclosed compounds, the compound has structural formula (XXXII):

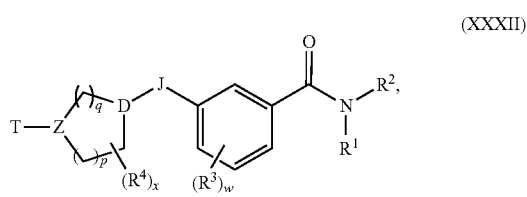

(XXXII)

in which all variables are defined as described above with reference to structural formulae (I)-(IV). In one such embodiment, J is —C(O)—, Z is CH or C substituted with one of the x $R^4$ and D is N. In another such embodiment, J is —C(O)—, Z is N and D is N. In a further such embodiment, J is —N($R^{38}$)—C(O)— (e.g., —NH—C(O)—), Z is N and D is CH or C substituted with one of the x $R^4$.

In another embodiment of the presently disclosed compounds, the compound has structural formula (XOCH):

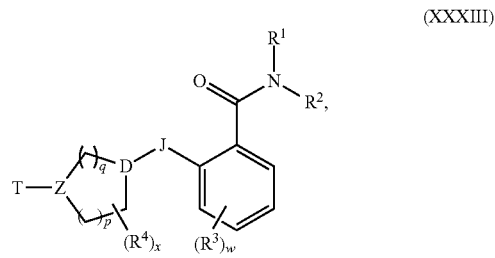

(XXXIII)

in which all variables are defined as described above with reference to structural formulae (I)-(IV). In one such embodiment, J is —C(O)—, Z is CH or C substituted with one of the x $R^4$ and D is N. In another such embodiment, J is —C(O)—, Z is N and D is N. In a further such embodiment, J is —N($R^{38}$)—C(O)— (e.g., —NH—C(O)—), Z is N and D is CH or C substituted with one of the x $R^4$.

In certain embodiments according to structural formulae (XXXI)-(XXXIII), the sum of p and q is 2 or 3. For example, in one embodiment, the sum of p and q is 2 (e.g., p is 1 and q is 1). In another embodiment, the sum of p and q is 3 (e.g., p is 1 and q is 2).

For example, in one embodiment of the presently disclosed compounds, the compound has structural formula (XXXIV):

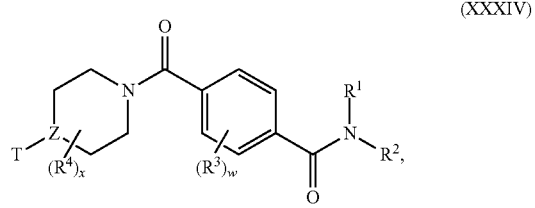

(XXXIV)

in which all variables are defined as described above with reference to structural formulae (I)-(IV). In one such embodiment, Z is N. In another such embodiment, Z is CH or C substituted with one of the x $R^4$.

In another embodiment of the presently disclosed compounds, the compound has structural formula (XXXV):

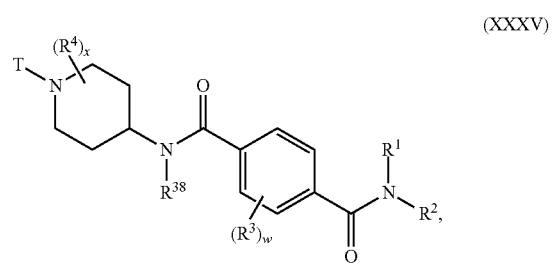

(XXXV)

in which all variables are defined as described above with reference to structural formulae (I)-(IV).

In another embodiment of the presently disclosed compounds, the compound has structural formula (XXXVI):

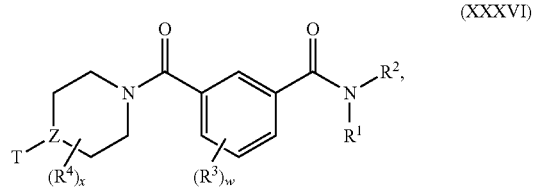

(XXXVI)

in which all variables are defined as described above with reference to structural formulae (I)-(IV). In one such embodiment, Z is N. In another such embodiment, Z is CH or C substituted with one of the x $R^4$.

For example, in one embodiment of the presently disclosed compounds, the compound has structural formula (XXXVII):

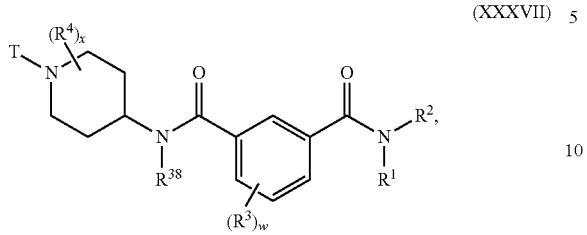
(XXXVII)

in which all variables are defined as described above with reference to structural formulae (I)-(IV).

For example, in one embodiment of the presently disclosed compounds, the compound has structural formula (XXXVIII):

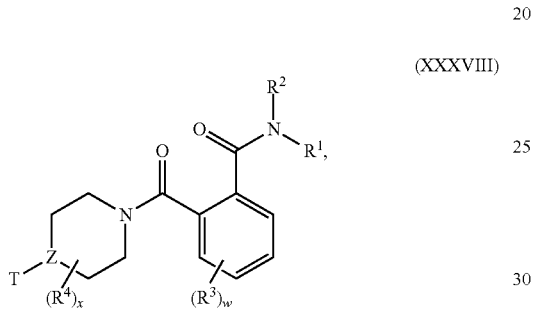
(XXXVIII)

in which all variables are defined as described above with reference to structural formulae (I)-(IV). In one such embodiment, Z is N. In another such embodiment, Z is CH or C substituted with one of the x $R^4$.

In another embodiment of the presently disclosed compounds, the compound has structural formula (XXXIX):

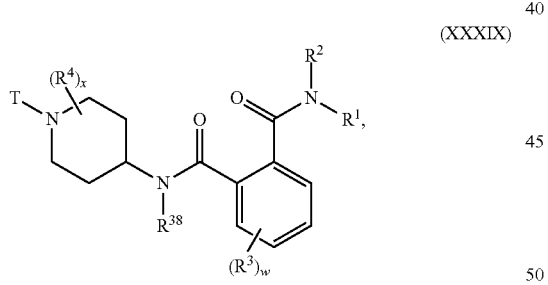
(XXXIX)

in which all variables are defined as described above with reference to structural formulae (I)-(IV).

In one embodiment of the presently disclosed compounds, the compound has structural formula (XL):

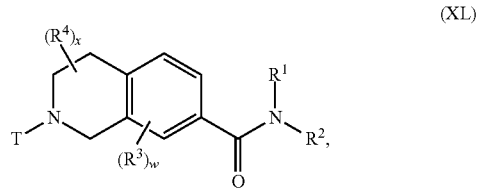
(XL)

in which all variables are defined as described above with reference to structural formulae (I)-(IV).

In one embodiment of the presently disclosed compounds, the compound has structural formula (XLI):

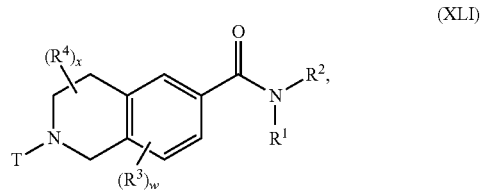
(XLI)

in which all variables are defined as described above with reference to structural formulae (I)-(IV).

In one embodiment of the presently disclosed compounds, the compound has structural formula (XLII):

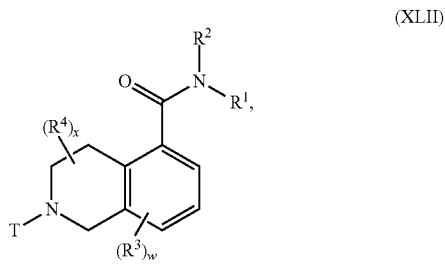
(XLII)

in which all variables are defined as described above with reference to structural formulae (I)-(IV).

In one embodiment of the presently disclosed compounds, the compound has structural formula (XLIII):

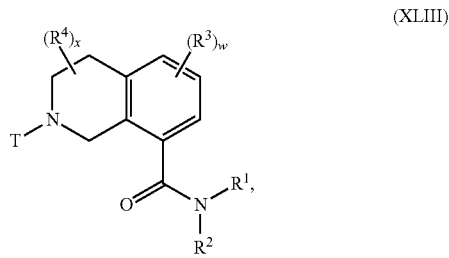
(XLIII)

in which all variables are defined as described above with reference to structural formulae (I)-(IV).

In certain embodiments of the presently disclosed compounds of structural formulae (I)-(XLIII), $R^1$ is H, —($C_1$-$C_4$ alkyl), —C(O)—($C_1$-$C_4$ alkyl) or —C(O)O—($C_1$-$C_4$ alkyl), and $R^2$ is -Hca, -Cak-N($R^9$)-G-$R^{22}$ or —($C_2$-$C_8$ alkyl)-N($R^9$)—$R^{24}$ in which one or two (for example, non-adjacent) carbons of the ($C_2$-$C_8$ alkyl) are optionally replaced by —O—, —S— or —N($R^9$)—, and $R^{24}$ is —$R^{23}$, -G-$R^{23}$ or —C(O)O—($C_1$-$C_6$ alkyl), provided that two consecutive carbons of the ($C_2$-$C_8$ alkyl) are not replaced by —O—. For example, in one embodiment, $R^1$ is H, —($C_1$-$C_4$ alkyl), —C(O)—($C_1$-$C_4$ alkyl) or —C(O)O—($C_1$-$C_4$ alkyl), and $R^2$ is -Hca.

In certain embodiments of the presently disclosed compounds of any of structural formulae (I)-(XLIII), $R^1$ is —H. In other embodiments, $R^1$ is ($C_1$-$C_4$ alkyl), for example methyl, ethyl, n-propyl or isopropyl.

In certain embodiments of the presently disclosed compounds of any structural formulae (I)-(XLIII), $R^2$ is -Hca. In certain embodiments, $R^2$ is an optionally-substituted monocyclic heterocycloalkyl.

In certain of the presently disclosed compounds of any structural formulae (I)-(XLIII), $R^2$ is -(optionally-substituted azetidinyl), -(optionally-substituted pyrrolidinyl), -(optionally-substituted piperidinyl) or -(optionally-substituted azepanyl). For example, $R^2$ can be -(optionally substituted piperidinyl) or -(optionally substituted pyrrolidinyl). In one embodiment, $R^2$ is -(optionally substituted piperidinyl). In another embodiment, $R^2$ is -(optionally substituted pyrrolidinyl).

In certain particular embodiments of the presently disclosed compounds of any of structural formulae (I)-(XLIII), $R^2$ is -(optionally-substituted azetidin-3-yl), -(optionally substituted piperidin-4-yl), -(optionally substituted pyrrolidin-3-yl) or -(optionally-substituted azepan-4-yl). For example, in one embodiment, $R^2$ is -(optionally substituted piperidin-4-yl). In another embodiment, $R^2$ is -(optionally substituted pyrrolidin-3-yl).

In certain embodiments of the presently disclosed compounds of any of structural formulae (I)-(XLIII), the azetidinyl, pyrrolidinyl, piperidinyl and azepanyl $R^2$ moieties described above are substituted at their 1-positions. For example, in one embodiment, $R^2$ is substituted at its 1-position with —$(C_0$-$C_3$ alkyl)-Ar or —$(C_0$-$C_3$ alkyl)-Het, for example -(unsubstituted $C_0$-$C_3$ alkyl)-Ar or -(unsubstituted $C_0$-$C_3$ alkyl)-Het. For example, in one particular embodiment, the azetidinyl, pyrrolidinyl, piperidinyl or azepanyl $R^2$ moiety is substituted at its 1-position with an optionally substituted benzyl or an optionally substituted phenyl. In another embodiment, the azetidinyl, pyrrolidinyl, piperidinyl or azepanyl $R^2$ moiety is substituted at its 1-position with a benzyl substituted with an electron withdrawing group; or with a pyridinylmethyl optionally substituted with an electron withdrawing group. For example, the benzyl or pyridinylmethyl can be substituted with an electron withdrawing group selected from the group consisting of halo, cyano, —$(C_1$-$C_4$ fluoroalkyl), —O—$(C_1$-$C_4$ fluoroalkyl), —C(O)—$(C_0$-$C_4$ alkyl), —C(O)O—$(C_0$-$C_4$ alkyl), —C(O)N$(C_0$-$C_4$ alkyl)$(C_0$-$C_4$ alkyl), —S(O)$_2$O—$(C_0$-$C_4$ alkyl), $NO_2$ and —C(O)-Hca in which the Hca includes a nitrogen atom to which the —C(O)— is bound, in which no alkyl, fluoroalkyl or heterocycloalkyl is substituted with an aryl, heteroaryl, cycloalkyl or heterocycloalkyl-containing group. In other embodiments, the azetidinyl, pyrrolidinyl, piperidinyl or azepanyl $R^2$ moiety is substituted at its 1-position with an unsubstituted benzyl or an unsubstituted phenyl.

In other embodiments of the compounds disclosed herein having any of structural formulae (I)-(XLIII), the azetidinyl, pyrrolidinyl, piperidinyl or azepanyl $R^2$ moiety is substituted at its 1-position with an optionally substituted pyridinylmethyl, an optionally substituted furanylmethyl, an optionally substituted thienylmethyl, an optionally substituted oxazolylmethyl, or an optionally substituted imidazolylmethyl. For example, the azetidinyl, pyrrolidinyl, piperidinyl or azepanyl $R^2$ moiety can be substituted with an unsubstituted pyridinylmethyl, an unsubstituted furanylmethyl, an unsubstituted thienylmethyl, an unsubstituted oxazolylmethyl, or an unsubstituted imidazolylmethyl. In other embodiments, the azetidinyl, pyrrolidinyl, piperidinyl or azepanyl $R^2$ moiety can be substituted with an pyridinylmethyl, furanylmethyl, thienylmethyl, oxazolylmethyl or imidazolylmethyl substituted with an electron withdrawing group as described above.

In certain embodiments of the compounds disclosed herein having any of structural formulae (I)-(XLIII), the azetidinyl, pyrrolidinyl, piperidinyl or azepanyl $R^2$ moiety is substituted at its 1-position with -L-Ar or -L-Het, in which Ar and Het can be, for example, as described above with reference to —$(C_0$-$C_3$ alkyl)-Ar or —$(C_0$-$C_3$ alkyl)-Het. In one such embodiment, L is —C(O)—$NR^9$—, such as —C(O)—NH—.

In other embodiments of the presently disclosed compounds of any of structural formulae (I)-(XLIII), the azetidinyl, pyrrolidinyl, piperidinyl or azepanyl $R^2$ moiety is substituted at its 1-position with —C(O)—O$(C_0$-$C_6$ alkyl), —C(O)-Het, —C(O)—Ar, —S(O)$_2$-Het, —S(O)$_2$—Ar or —S(O)$_2$—O$(C_0$-$C_6$ alkyl), in which Ar and Het can be, for example, as described above with reference to —$(C_0$-$C_3$ alkyl)-Ar or —$(C_0$-$C_3$ alkyl)-Het. In one embodiment, the azetidinyl, pyrrolidinyl, piperidinyl or azepanyl $R^2$ moiety is substituted at its 1-position with —C(O)-Het or —C(O)—Ar; in another embodiment, it is substituted at its 1-position with —S(O)$_2$-Het or —S(O)$_2$—Ar. For example, in certain embodiments, the azetidinyl, pyrrolidinyl, piperidinyl or azepanyl $R^2$ moiety is substituted at its 1-position with an optionally-substituted benzoyl (e.g., substituted with an electron withdrawing group as described above); or with an optionally-substituted nicotinyl, isonicotinyl or picolinyl (e.g., optionally substituted with an electron withdrawing group as described above). In other embodiments, the azetidinyl, pyrrolidinyl, piperidinyl or azepanyl $R^2$ moiety is substituted at its 1-position with an unsubstituted benzoyl; or an unsubstituted nicotinoyl, isonicotinoyl or picolinoyl.

In certain embodiments, $R^2$ is an optionally-substituted bridged azacycloalkyl or diazacycloalkyl, for example, a bridged azabicyclohexyl, a bridged azabicycloheptyl, a bridged azabicyclooctyl, a bridged diazabicyclohexyl, a bridged diazabicycloheptyl or a bridged diazabicyclooctyl. Particular examples of such $R^2$ moieties include optionally substituted azabicyclo[2.2.2]octyl, optionally substituted azabicyclo[3.2.1]octyl, and optionally substituted 2,5-diazabicyclo[2.2.1]heptyl.

When $R^2$ is a bridged azacycloalkyl or diazacycloalkyl, it can be substituted as described above with reference to the azetidinyl, pyrrolidinyl, piperidinyl and azepanyl $R^2$ moieties. For example, a bridged azacycloalkyl or diazacycloalkyl $R^2$ moiety can be substituted (e.g., at a nitrogen) with —$(C_0$-$C_3$ alkyl)-Ar, —$(C_0$-$C_3$ alkyl)-Het, -L-Ar, -L-Het, —C(O)—O$(C_0$-$C_6$ alkyl), —C(O)-Het, —C(O)—Ar, —S(O)$_2$-Het, —S(O)$_2$—Ar or —S(O)$_2$—O$(C_0$-$C_6$ alkyl), as described above.

In certain embodiments of the compounds of any of structural formulae (I)-(XLIII), $R^2$ is -Cak-N$(R^9)$-G-$R^{22}$, as described above. For example, in one embodiment of the disclosed compounds, $R^2$ has the structure

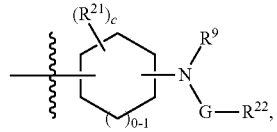

in which c is 0, 1, 2, 3 or 4, and each $R^{21}$ is independently selected from —$(C_1$-$C_6$ alkyl), —$(C_1$-$C_6$ haloalkyl), —$(C_0$-$C_6$ alkyl)-Ar, —$(C_0$-$C_6$ alkyl)-Het, —$(C_0$-$C_6$ alkyl)-Cak, —$(C_0$-$C_6$ alkyl)-Hca, —$(C_0$-$C_6$ alkyl)-L-$R^7$, —$(C_0$-$C_6$ alkyl)-NR$^8$R$^9$, —$(C_0$-$C_6$ alkyl)-OR$^{10}$, —$(C_0$-$C_6$ alkyl)-C(O)R$^{10}$, —$(C_0$-$C_6$ alkyl)-S(O)$_{0-2}$R$^{10}$, -halogen, —$NO_2$ and —CN, and two $R^{21}$ on the same carbon optionally combine to form oxo. In certain embodiments of the presently disclosed compounds, each $R^{21}$ is independently selected from —$(C_1$-$C_6$ alkyl), —$(C_1$-$C_6$ haloalkyl) (e.g., difluoromethyl, trifluoromethyl and the like), —$(C_0$-$C_6$ alkyl)-L-$R^7$, —$(C_0$-$C_6$ alkyl)-NR$^8$R$^9$, —$(C_0$-$C_6$ alkyl)-OR$^{10}$, —$(C_0$-$C_6$ alkyl)-C(O)R$^{10}$, —$(C_0$-$C_6$ alkyl)-S(O)$_{0-2}$R$^{10}$, -halogen, —$NO_2$ and —CN and two $R^{21}$ on the same carbon optionally combine to form oxo, in which each $R^7$, $R^8$ and $R^{10}$ is independently selected from H, —(C$_1$-C$_6$ alkyl), —(C$_1$-C$_6$ haloalkyl), —(C$_0$-C$_6$ alkyl)-L-(C$_0$-C$_6$ alkyl), —(C$_0$-C$_6$ alkyl)-NR$^9$(C$_0$-C$_6$ alkyl), —(C$_0$-C$_6$ alkyl)-O—(C$_0$-C$_6$ alkyl), —(C$_0$-C$_6$ alkyl)-C(O)—(C$_0$-C$_6$ alkyl) and —(C$_0$-C$_6$ alkyl)-S(O)$_{0-2}$—(C$_0$-C$_6$ alkyl), and in which no alkyl or haloalkyl is substituted with an aryl-, heteroaryl-, cycloalkyl- or heterocycloalkyl-containing group. For example, in one embodiment, each R$^{21}$ is —(C$_1$-C$_3$ alkyl), —(C$_1$-C$_3$ haloalkyl), —(C$_0$-C$_3$ alkyl)-L-R$^7$, —(C$_0$-C$_3$ alkyl)-NR$^8$R$^9$, —(C$_0$-C$_3$ alkyl)-OR$^{10}$, —(C$_0$-C$_3$ alkyl)-C(O)R$^{10}$, —(C$_0$-C$_3$ alkyl)-S(O)$_{0-2}$R$^{10}$, -halogen, —NO$_2$ and —CN and two R$^{21}$ on the same carbon optionally combine to form oxo, in which each R$^7$, R$^8$ and R$^{10}$ is independently selected from H, —(C$_1$-C$_2$ alkyl), —(C$_1$-C$_2$ haloalkyl), —(C$_0$-C$_2$ alkyl)-L-(C$_0$-C$_2$ alkyl), —(C$_0$-C$_2$ alkyl)-NR$^9$(C$_0$-C$_2$ alkyl), —(C$_0$-C$_2$ alkyl)-O—(C$_0$-C$_2$ alkyl), —(C$_0$-C$_2$ alkyl)-C(O)—(C$_0$-C$_2$ alkyl) and —(C$_0$-C$_2$ alkyl)-S(O)$_{0-2}$—(C$_0$-C$_2$ alkyl), and in which no alkyl or haloalkyl is substituted with an aryl-, heteroaryl-, cycloalkyl- or heterocycloalkyl-containing group. In certain embodiments, c is 1 or 2. In other embodiments, c is 0. In certain embodiments, R$^9$ is H. In certain embodiments, G is a single bond. In certain embodiments of the presently disclosed compounds, R$^{22}$ is not substituted with an aryl-, heteroaryl-, cycloalkyl- or heterocycloalkyl-containing group. In certain embodiments of the presently disclosed compounds, R$^{23}$ is not substituted with an aryl-, heteroaryl-, cycloalkyl- or heterocycloalkyl-containing group.

In one embodiment of compounds of any of structural formulae (I)-(XLIII), R$^2$ has the structure

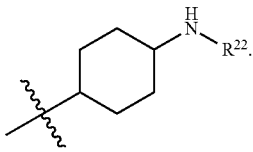

In certain embodiments of the compounds of any of structural formulae (I)-(XLIII), R$^2$ is —(C$_2$-C$_8$ alkyl)-N(R$^9$)—R$^{24}$ in which one or two carbons of the (C$_2$-C$_8$ alkyl) are optionally replaced by —O— or —N(R$^9$)— and R$^{24}$ is —R$^{23}$, -GR$^{23}$ or —C(O)O—(C$_1$-C$_6$ alkyl). In certain embodiments, the (C$_2$-C$_8$ alkyl) is unsubstituted and no carbon is replaced by —O— or —N(R$^9$)—. For example, in one embodiment, R$^2$ is —CH$_2$—CH$_2$—CH$_2$—N(R$^9$)—R$^{24}$ or —CH$_2$—CH$_2$—CH$_2$—CH$_2$—N(R$^9$)—R$^{24}$. In other embodiments, the (C$_2$-C$_8$ alkyl) is substituted and/or one or two carbons are replaced by —O— or —N(R$^9$)—. For example, in one embodiment, R$^2$ is —CH$_2$—CH$_2$—O—CH$_2$—CH$_2$—N(R$^9$)—R$^{24}$; —CH$_2$—CH(CH$_3$)—N(R$^9$)—R$^{24}$; or —CH$_2$—CH$_2$—O—CH$_2$—C(O)—N(R$^9$)—R$^{24}$. In certain embodiments, R$^9$ is H. In certain embodiments, R$^{24}$ is Ar or Het. In certain embodiments, R$^{24}$ is not substituted with an aryl-, heteroaryl-, cycloalkyl- or heterocycloalkyl-containing group. In certain embodiments, the (C$_2$-C$_8$ alkyl) is a (C$_2$-C$_5$ alkyl).

In certain embodiments (e.g., when rings system "B" is

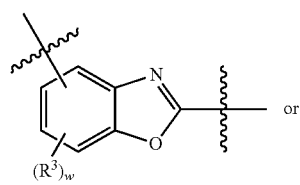 or

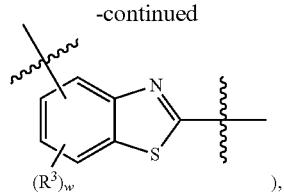), when R$^2$ is an azabicycloalkyl moiety (e.g., a 1-azabicycloheptyl, a 1-azabicyclooctyl, a 1-azabicyclononyl or a 1-azabicyclodecyl), R$^2$ is not vicinally substituted (i.e., at the position next to the amide nitrogen) with —(C$_0$-C$_4$)-Het.

In certain embodiments (e.g., when rings system "B" is

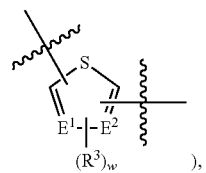),

R$^2$ is not a benzo-, pyrido-, pyrimido-, pyrazino- or pyridazino- fused azacycloalkyl. In other embodiments, R$^2$ is not 7-azabicyclo[2.2.1]hept-2-yl. In other embodiments, R$^2$ is not a quinuclidin-3-yl moiety.

In certain embodiments (e.g., when "B" represents

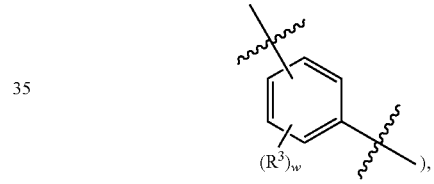),

R$^2$ is not a 4,5-dihydroisoxazol-4-yl moiety or an optionally substituted optionally ring-fused azetidin-2-on-3-yl moiety. In one embodiment, R$^2$ is not an oxo-substituted heterocycloalkyl.

In certain embodiments of the presently disclosed compounds, R$^1$ and R$^2$ together with the nitrogen to which they are attached (i.e., the carboxamide nitrogen) come together to form Hca. R$^1$, R$^2$ and the nitrogen can come together to form, for example, an optionally-substituted monocyclic azacycloalkyl or monocyclic diazacycloalkyl, such as a piperidine, a pyrrolidine, a piperazine or an imidazolidine. In other embodiments, R$^1$ and R$^2$ come together to form an optionally-substituted bridged azacycloalkyl or diazacycloalkyl, for example, a bridged azabicyclohexyl, a bridged azabicycloheptyl, a bridged azabicyclooctyl, a bridged diazabicyclohexyl, a bridged diazabicycloheptyl or a bridged diazabicyclooctyl. Particular examples of such R$^2$ moieties include azabicyclo[2.2.2]octyl, azabicyclo[3.2.1]octyl, and 2,5-diazabicyclo[2.2.1]heptyl.

When R$^1$, R$^2$ and the nitrogen come together to form Hca, the Hca can be substituted as described above with reference to the azetidinyl, pyrrolidinyl, piperidinyl and azepanyl R$^2$ moieties. For example, the heterocycloalkyl can be substituted with —(C$_0$-C$_3$ alkyl)-Ar, —(C$_0$-C$_3$ alkyl)-Het, -L-Ar, -L-Het, —C(O)—O(C$_0$-C$_6$ alkyl), —C(O)-Het, —C(O)—Ar, —S(O)$_2$-Het, —S(O)$_2$—Ar or —S(O)$_2$—O(C$_0$-C$_6$ alkyl), as described above. When $R^1$ and $R^2$ come together to form a diazacycloalkyl, it can be substituted at a nitrogen atom.

For example, in certain embodiments, the —C(O)—$NR^1R^2$ moiety is

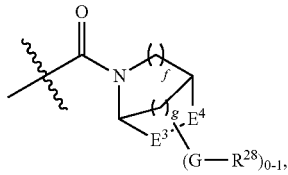

in which f is 0 or 1; g is 0, 1 or 2; c is 0, 1, 2, 3 or 4; $R^{28}$ is Ar or Het; $E^3$ is NH, N substituted by one of the c $R^{21}$, N substituted by the -G-$R^{28}$, $CH_2$, CH substituted by one of the c $R^{21}$, CH substituted by the -G-$R^{28}$, or C substituted by one of the c $R^{21}$ and the -G-$R^{28}$; and $E^4$ is absent, NH, N substituted by one of the c $R^{21}$, N substituted by the -G-$R^{28}$, $CH_2$, CH substituted by one of the c $R^{21}$, CH substituted by the -G-$R^{28}$, or C substituted by one of the c $R^{21}$ and the -G-$R^{28}$, provided that both of $E^3$ and $E^4$ are not N. When g is 0, $R^1$, $R^2$ and the nitrogen come together to form a monocyclic azacycloalkyl or diazacycloalkyl. In other embodiments, when g is 1 or 2, $R^1$, $R^2$ and the nitrogen come together to form a bridged bicyclic azacycloalkyl or diazacycloalkyl. The c $R^{21}$ moieties can be disposed anywhere on the azacycloalkyl or diazacycloalkyl ring system. Each $R^{21}$ is independently selected from —($C_1$-$C_6$ alkyl), —($C_1$-$C_6$ haloalkyl), —($C_0$-$C_6$ alkyl)-Ar, —($C_0$-$C_6$ alkyl)-Het, —($C_0$-$C_6$ alkyl)-Cak, —($C_0$-$C_6$ alkyl)-Hca, —($C_0$-$C_6$ alkyl)-L-$R^7$, —($C_0$-$C_6$ alkyl)-$NR^8R^9$, —($C_0$-$C_6$ alkyl)-$OR^{10}$, —($C_0$-$C_6$ alkyl)-C(O)$R^{10}$, —($C_0$-$C_6$ alkyl)-$S(O)_{0-2}R^{10}$, -halogen, —$NO_2$ and —CN, and two $R^{21}$ on the same carbon optionally combine to form oxo. In certain embodiments of the presently disclosed compounds, each $R^{21}$ is independently selected from —($C_1$-$C_6$ alkyl), —($C_1$-$C_6$ haloalkyl) (e.g., difluoromethyl, trifluoromethyl and the like), —($C_0$-$C_6$ alkyl)-L-$R^7$, —($C_0$-$C_6$ alkyl)-$NR^8R^9$, —($C_0$-$C_6$ alkyl)-$OR^{10}$, —($C_0$-$C_6$ alkyl)-C(O)$R^{10}$, —($C_0$-$C_6$ alkyl)-$S(O)_{0-2}R^{10}$, -halogen, —$NO_2$ and —CN and two $R^{21}$ on the same carbon optionally combine to form oxo, in which each $R^7$, $R^8$ and $R^{10}$ is independently selected from H, —($C_1$-$C_6$ alkyl), —($C_1$-$C_6$ haloalkyl), —($C_0$-$C_6$ alkyl)-L-($C_0$-$C_6$ alkyl), —($C_0$-$C_6$ alkyl)-$NR^9$($C_0$-$C_6$ alkyl), —($C_0$-$C_6$ alkyl)-O—($C_0$-$C_6$ alkyl), —($C_0$-$C_6$ alkyl)-C(O)—($C_0$-$C_6$ alkyl) and —($C_0$-$C_6$ alkyl)-$S(O)_{0-2}$—($C_0$-$C_6$ alkyl), and in which no alkyl or haloalkyl is substituted with an aryl-, heteroaryl-, cycloalkyl- or heterocycloalkyl-containing group. For example, in one embodiment, each $R^{21}$ is —($C_1$-$C_3$ alkyl), —($C_1$-$C_3$ haloalkyl), —($C_0$-$C_3$ alkyl)-L-$R^7$, —($C_0$-$C_3$ alkyl)-$NR^8R^9$, —($C_0$-$C_3$ alkyl)-$OR^{10}$, —($C_0$-$C_3$ alkyl)-C(O)$R^{10}$, —($C_0$-$C_3$ ($C_0$-$C_3$ alkyl)-$S(O)_{0-2}R^{10}$, -halogen, —$NO_2$ and —CN and two $R^{21}$ on the same carbon optionally combine to form oxo, in which each $R^7$, $R^8$ and $R^{10}$ is independently selected from H, —($C_1$-$C_2$ alkyl), —($C_1$-$C_2$ haloalkyl), —($C_0$-$C_2$ alkyl)-L-($C_0$-$C_2$ alkyl), —($C_0$-$C_2$ alkyl)-$NR^9$($C_0$-$C_2$ alkyl), —($C_0$-$C_2$ alkyl)-O—($C_0$-$C_2$ alkyl), —($C_0$-$C_2$ alkyl)-C(O)—($C_0$-$C_2$ alkyl) and —($C_0$-$C_2$ alkyl)-$S(O)_{0-2}$—($C_0$-$C_2$ alkyl), and in which no alkyl or haloalkyl is substituted with an aryl-, heteroaryl-, cycloalkyl- or heterocycloalkyl-containing group. In certain embodiments, c is 1 or 2. In other embodiments, c is 0. In certain embodiments, G is a single bond, $CH_2$, or C(O). In certain embodiments of the presently disclosed compounds, $R^{28}$ is not substituted with an aryl-, heteroaryl-, cycloalkyl- or heterocycloalkyl-containing group. In one embodiment, $R^{28}$ is monocyclic aryl or heteroaryl substituted with 0-3 substitutents selected from halo, cyano, —($C_1$-$C_4$ haloalkyl), —O—($C_1$-$C_4$ haloalkyl), —($C_1$-$C_4$ alkyl), —O—($C_1$-$C_4$ alkyl), —C(O)—($C_0$-$C_4$ alkyl), —C(O)O—($C_0$-$C_4$ alkyl), —C(O)N($C_0$-$C_4$ alkyl)($C_0$-$C_4$ alkyl) and $NO_2$, in which each alkyl is not further substituted. The -G-$R^{28}$ moiety, when present, can in some embodiments be as described below for -G-$R^{17}$.

For example, in certain embodiments, the —C(O)—$NR^1R^2$ moiety is

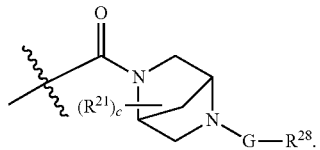

In the compounds of any of structural formulae (I)-(XLIII), the number of substituents on ring system "B", w, is 0, 1, 2 or 3. For example, in one embodiment, w is 0, 1 or 2. In another embodiment, w is 0. In other embodiments, w is at least 1, and at least one $R^3$ is selected from the group consisting of halo, cyano, —($C_1$-$C_4$ fluoroalkyl), —O—($C_1$-$C_4$ fluoroalkyl), —C(O)—($C_0$-$C_4$ alkyl), —C(O)O—($C_0$-$C_4$ alkyl), —C(O)N($C_0$-$C_4$ alkyl)($C_0$-$C_4$ alkyl), —$S(O)_2$O—($C_0$-$C_4$ alkyl), $NO_2$ and —C(O)-Hca in which the Hca includes a nitrogen atom to which the —C(O)— is bound, in which no alkyl, fluoroalkyl or heterocycloalkyl is substituted with an aryl, heteroaryl, cycloalkyl or heterocycloalkyl-containing group. For example, in certain embodiments, at least one $R^3$ is halo (e.g., chloro) or —($C_1$-$C_4$ alkyl) (e.g., methyl, ethyl or propyl). In certain embodiments, an $R^3$ is substituted on the "B" ring system at a 6-membered aromatic ring position in the meta position relative to the J moiety.

In certain embodiments of the compounds of any of structural formulae (I)-(XLIII), each $R^3$ is independently selected from —($C_1$-$C_6$ alkyl), —($C_1$-$C_6$ haloalkyl) (e.g., difluoromethyl, trifluoromethyl and the like), —($C_0$-$C_6$ alkyl)-L-$R^7$, —($C_0$-$C_6$ alkyl)-$NR^8R^9$, —($C_0$-$C_6$ alkyl)-$OR^{10}$, —($C_0$-$C_6$ alkyl)-C(O)$R^{10}$, —($C_0$-$C_6$ alkyl)-$S(O)_{0-2}R^{10}$, -halogen, —$NO_2$ and —CN, in which each $R^7$, $R^8$ and $R^{10}$ is independently selected from H, —($C_1$-$C_6$ alkyl), —($C_1$-$C_6$ haloalkyl), —($C_0$-$C_6$ alkyl)-L-($C_0$-$C_6$ alkyl), —($C_0$-$C_6$ alkyl)-$NR^9$($C_0$-$C_6$ alkyl), —($C_0$-$C_6$ alkyl)-O—($C_0$-$C_6$ alkyl), —($C_0$-$C_6$ alkyl)-C(O)—($C_0$-$C_6$ alkyl), and —($C_0$-$C_6$ alkyl)-$S(O)_{0-2}$—($C_0$-$C_6$ alkyl), and in which no alkyl or haloalkyl is substituted with an aryl-, heteroaryl-, cycloalkyl- or heterocycloalkyl-containing group. For example, in one embodiment, each $R^3$ is —($C_1$-$C_3$ alkyl), —($C_1$-$C_3$ haloalkyl), —($C_0$-$C_3$ alkyl)-L-$R^7$, —($C_0$-$C_3$ alkyl)-$NR^8R^9$, —($C_0$-$C_3$ alkyl)-$OR^{10}$, —($C_0$-$C_3$ alkyl)-C(O)$R^{10}$, —($C_0$-$C_3$ alkyl)-$S(O)_{0-2}R^{10}$, -halogen, —$NO_2$ and —CN, in which each $R^7$, $R^8$ and $R^{10}$ is independently selected from H, —($C_1$-$C_2$ alkyl), —($C_1$-$C_2$ haloalkyl), —($C_0$-$C_2$ alkyl)-L-($C_0$-$C_2$ alkyl), —($C_0$-$C_2$ alkyl)-$NR^9$($C_0$-$C_2$ alkyl), —($C_0$-$C_2$ alkyl)-O—($C_0$-$C_2$ alkyl), —($C_0$-$C_2$ alkyl)-C(O)—($C_0$-$C_2$ alkyl) and —($C_0$-$C_2$ alkyl)-$S(O)_{0-2}$—($C_0$-$C_2$ alkyl), and in which no alkyl or haloalkyl is substituted with an aryl-, heteroaryl-, cycloalkyl- or heterocycloalkyl-containing group. For example, in certain embodiments, each $R^3$ is halo (e.g., chloro) or —($C_1$-$C_4$ alkyl) (e.g., methyl, ethyl or propyl).

In certain embodiments of the compounds of of any of structural formulae (I)-(XLIII), w is at least one, and at least one $R^3$ is —$NR^8R^9$. For example, in one embodiment, w is 1. In certain such embodiments, $R^3$ is substituted on the "B" ring system at a 6-membered aromatic ring position in the meta position relative to the J moiety.

In other embodiments of the compounds of of any of structural formulae (I)-(XLIII), w is at least one, and at least one $R^3$ is —$(C_0-C_3$ alkyl$)-Y^1$—$(C_1-C_3$ alkyl$)-Y^2$—$(C_0-C_3$ alkyl), in which each of $Y^1$ and $Y^2$ is independently L, —O—, —S— or —$NR^9$—. For example, in one embodiment, w is 1. In certain such embodiments, $R^3$ is substituted on the "B" ring system at a 6-membered aromatic ring position in the meta position relative to the J moiety. In one particular embodiment, $R^3$ is —$CH_2$—$N(CH_3)$—$CH_2$—$C(O)$—$OCH_3$.

In certain embodiments in which ring system "B" is

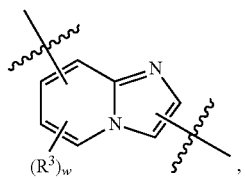

the imidazo portion of the central imidazo[1,2-a]pyridine ring system has no substitutions other than the carboxamide substitution. In another embodiment, no $R^3$ at the 2-position of the imidazo[1,2-a]pyridine core is —$(C_1$ alkyl$)-N(R^8)$-(5,6,7,8-tetrahydroquinolin-8-yl); —$(C_1$ alkyl$)-N(R^8)$-(6,7-dihydro-5H-cyclopenta[b]pyridin-7-yl); —$(C_1$ alkyl$)-N(R^8)$-(6,7,8,9-tetrahydro-5H-cyclohepta[b]pyridin-9-yl); —$(C_1$ alkyl$)-N(R^8)$-(2,3-dihydrofuro[3,2-b]pyridin-3-yl); —$(C_1$ alkyl$)-N(R^8)$-(3,4-dihydro-2H-pyrano[3,2-b]pyridin-4-yl); or —$(C_1$ alkyl$)-N(R^8)$-(6,7,8,9-tetrahydrooxepino[3,2-b]pyridin-9-yl). In another embodiment, the compound does not have two $R^3$ moieties that include Ar or Het as part of each of the moieties' structure. In another embodiment, no $R^3$ at the 3-position of the imidazo[1,2-a]pyridine core is Het.

In certain embodiments in which ring system "B" is

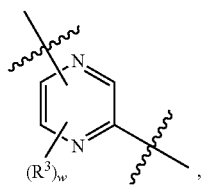

the compound does not have two $R^3$ moieties that include Ar or Het in the moieties' structure. In another embodiment, when an $R^3$ is —$NR^9$—$(C_0-C_6$ alkyl$)$-Ar, —$NR^9$—$(C_0-C_6$ alkyl$)$-Het, —$NR^9$—Hca, —O—$(C_0-C_6$ alkyl$)$-Ar or —O—$(C_0-C_6$ alkyl$)$-Het, it is not substituted on the pyrazine core at a position ortho to (i.e., on the carbon adjacent to) the amide. In another embodiment, when an $R^3$ is —Ar or -Het, it is substituted on the pyrazine core at a position para to (i.e., directly across the ring from) the amide.

In certain embodiments in which ring system "B" is

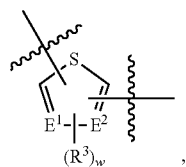

when $R^3$ is $(C_0-C_4$ alkyl$)$-O—$(C_0-C_4$ alkyl$)$-(optionally-substituted phenyl); $(C_0-C_4$ alkyl$)$-S(O)$_{0-2}$—$(C_0-C_4$ alkyl$)$-(optionally-substituted phenyl) or $(C_0-C_4$ alkyl$)$-S(O)$_{0-2}$—$(C_0-C_4$ alkyl$)$-O-(optionally-substituted phenyl), it is not at the 2 position of the thiazole core (i.e., not on the carbon between the N and the S of the thiazole). In one embodiment, the compound does not have two $R^3$ moieties that include Ar or Het in the moieties' structure.

In the presently disclosed compounds of any of structural formulae (I)-(XLIII), the number of substituents on ring system "C", x, is 0 or an integer less than or equal to the sum of p and q. when D or Z is $CR^4$, the $R^4$ of D or Z is one of the x $R^4$ groups on ring system "C". In one embodiment, x is 0, 1, 2 or 3. For example, x can be 0, or can be 1 or 2.

In certain embodiments of the presently disclosed compounds of any of structural formula (I)-(XLIII), two $R^4$ groups combine to form an oxo. The oxo can be bound, for example, at the position alpha to a nitrogen of ring system "C". In other embodiments, no two $R^4$ groups combine to form an oxo.

In certain embodiments of the presently disclosed compounds of any of structural formulae (I)-(XLIII), when x is 4, not all four $R^4$ groups are $(C_1-C_6$ alkyl).

In certain embodiments of the presently disclosed compounds of any of structural formulae (I)-(XLIII), each $R^4$ is independently selected from —$(C_1-C_6$ alkyl), —$(C_1-C_6$ haloalkyl) (e.g., difluoromethyl, trifluoromethyl and the like), —$(C_0-C_6$ alkyl$)$-L-$R^7$, —$(C_0-C_6$ alkyl$)$-$NR^8R^9$, —$(C_0-C_6$ alkyl$)$-$OR^{10}$, —$(C_0-C_6$ alkyl$)$-$C(O)R^{10}$, —$(C_0-C_6$ alkyl$)$-S(O)$_{0-2}R^{10}$, -halogen, —$NO_2$ and —CN, in which each $R^7$, $R^8$ and $R^{10}$ is independently selected from H, —$(C_1-C_6$ alkyl), —$(C_1-C_6$ haloalkyl), —$(C_0-C_6$ alkyl$)$-L-$(C_0-C_6$ alkyl), —$(C_0-C_6$ alkyl$)$-$NR^9(C_0-C_6$ alkyl), —$(C_0-C_6$ alkyl$)$-O—$(C_0-C_6$ alkyl), —$(C_0-C_6$ alkyl$)$-$C(O)$—$(C_0-C_6$ alkyl) and —$(C_0-C_6$ alkyl$)$-S(O)$_{0-2}$—$(C_0-C_6$ alkyl), and in which no alkyl or haloalkyl is substituted with an aryl-, heteroaryl-, cycloalkyl- or heterocycloalkyl-containing group. For example, in one embodiment, each $R^4$ is —$(C_1-C_3$ alkyl), —$(C_1-C_3$ haloalkyl), —$(C_0-C_3$ alkyl$)$-L-$R^7$, —$(C_0-C_3$ alkyl$)$-$NR^8R^9$, —$(C_0-C_3$ alkyl$)$-$OR^{10}$, —$(C_0-C_3$ alkyl$)$-$C(O)R^{10}$, —$(C_0-C_3$ alkyl$)$-S(O)$_{0-2}R^{10}$, -halogen, —$NO_2$ and —CN, in which each $R^7$, $R^8$ and $R^{10}$ is independently selected from H, —$(C_1-C_2$ alkyl), —$(C_1-C_2$ haloalkyl), —$(C_0-C_2$ alkyl$)$-L-$(C_0-C_2$ alkyl), —$(C_0-C_2$ alkyl$)$-$NR^9(C_0-C_2$ alkyl), —$(C_0-C_2$ alkyl$)$-O—$(C_0-C_2$ alkyl), —$(C_0-C_2$ alkyl$)$-$C(O)$—$(C_0-C_2$ alkyl) and —$(C_0-C_2$ alkyl$)$-S(O)$_{0-2}$—$(C_0-C_2$ alkyl), and in which no alkyl or haloalkyl is substituted with an aryl-, heteroaryl-, cycloalkyl- or heterocycloalkyl-containing group.

In certain embodiments, the presently disclosed compounds have the structural formula (XLIV):

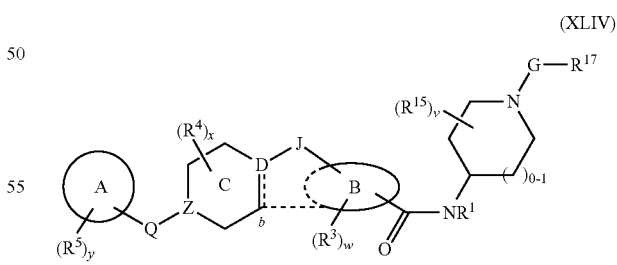

(XLIV)

in which Q and G are each independently a bond, —$CH_2$—, —$C(H)(R^{16})$—, —$C(R^{16})_2$—, L (e.g., —$C(O)$—$NR^9$— or —$NR^9$—$C(O)$—) or —$S(O)_2$— v is 0, 1, 2, 3 or 4; each $R^{15}$ is independently selected from —$(C_1-C_6$ alkyl), —$(C_1-C_6$ haloalkyl), —$(C_0-C_6$ alkyl$)$-Ar, —$(C_0-C_6$ alkyl$)$-Het, —$(C_0-C_6$ alkyl$)$-Cak, —$(C_0-C_6$ alkyl$)$-Hca, —$(C_0-C_6$ alkyl$)$-L-$R^7$, —$(C_0-C_6$ alkyl$)$-$NR^8R^9$, —$(C_0-C_6$ alkyl$)$-$OR^{10}$, —$(C_0-C_6$ alkyl$)$-$C(O)R^{10}$—$(C_0-C_6$ alkyl$)$-S(O)$_{0-2}R^{10}$, -halogen, —NO$_2$ and —CN, and two R$^{15}$ on the same carbon optionally combine to form oxo; R$^{17}$ is Het or Ar, and all other variables are defined as described above with reference to any of structural formula (I)-(XLIII). In one embodiment, Q is a single bond. In another embodiment, Q is —CH$_2$—. In other embodiments, Q is —C(O)— or —S(O)$_2$—. In certain embodiments, G is —CH$_2$—. In other embodiments, G is —C(O)— or —S(O)$_2$—. In other embodiments, G is —CH (CH$_3$)—. In other embodiments, G is —C(O)—NH—. The above-recited Q and G moieties can be combined in any possible combination. For example, in one embodiment, Q is a single bond and G is —CH$_2$— or —C(O)—. As described above, in certain embodiments, the ring system denoted by "A" is aryl or heteroaryl. In one embodiment, the ring system denoted by "A" is substituted with one or more electron-withdrawing groups as described above. In another embodiment, R$^{17}$ is substituted with one or more electron-withdrawing groups as described above. In certain embodiments, the ring system denoted by "A", R$^{17}$ or both are not substituted with an aryl, heteroaryl, cycloalkyl or heterocycloalkyl-containing group. In certain embodiments, the azacycloalkyl to which -G-R$^{17}$ is bound is a piperidinyl; in other embodiments, it is a pyrrolidinyl.

In the presently disclosed compounds of structural formula (XLIV), v is 0, 1, 2, 3 or 4. In one embodiment, v is 0, 1, 2 or 3. For example, v can be 0, or can be 1 or 2.

In certain embodiments of the presently disclosed compounds of structural formula (XLIV), two R$^{15}$ groups combine to form an oxo. The oxo can be bound, for example, at the position alpha relative to the nitrogen of the azacycloalkyl ring. In other embodiments, no two R$^{15}$ groups combine to form an oxo.

In certain embodiments of the presently disclosed compounds of structural formula (XLIV), when v is 4, not all four R$^{15}$ moieties are (C$_1$-C$_6$ alkyl).

In certain embodiments of the presently disclosed compounds of structural formula (XLIV), each R$^{15}$ is independently selected from —(C$_1$-C$_6$ alkyl), —(C$_1$-C$_6$ haloalkyl) (e.g., difluoromethyl, trifluoromethyl and the like), —(C$_0$-C$_6$ alkyl)-L-R$^7$, —(C$_0$-C$_6$ alkyl)-NR$^8$R$^9$, —(C$_0$-C$_6$ alkyl)-OR$^{10}$, —(C$_0$-C$_6$ alkyl)-C(O)R$^{10}$, —(C$_0$-C$_6$ alkyl)-S(O)$_{0-2}$R$^{10}$, -halogen, —NO$_2$ and —CN and two R$^{15}$ on the same carbon optionally combine to form oxo, in which each R$^7$, R$^8$ and R$^{10}$ is independently selected from H, —(C$_1$-C$_6$ alkyl), —(C$_1$-C$_6$ haloalkyl), —(C$_0$-C$_6$ alkyl)-L-(C$_0$-C$_6$ alkyl), —(C$_0$-C$_6$ alkyl)-NR$^9$(C$_0$-C$_6$ alkyl), —(C$_0$-C$_6$ alkyl)-O—(C$_0$-C$_6$ alkyl), —(C$_0$-C$_6$ alkyl)-C(O)—(C$_0$-C$_6$ alkyl) and —(C$_0$-C$_6$ alkyl)-S(O)$_{0-2}$—(C$_0$-C$_6$ alkyl), and in which no alkyl or haloalkyl is substituted with an aryl-, heteroaryl-, cycloalkyl- or heterocycloalkyl-containing group. For example, in one embodiment, each R$^{15}$ is —(C$_1$-C$_3$ alkyl), —(C$_1$-C$_3$ haloalkyl), —(C$_0$-C$_3$ alkyl)-L-R$^7$, —(C$_0$-C$_3$ alkyl)-NR$^8$R$^9$, —(C$_0$-C$_3$ alkyl)-OR$^{10}$, —(C$_0$-C$_3$ alkyl)-C(O)R$^{10}$, —(C$_0$-C$_3$ alkyl)-S(O)$_{0-2}$R$^{10}$, -halogen, —NO$_2$ and —CN and two R$^{15}$ on the same carbon optionally combine to form oxo, in which each R$^7$, R$^8$ and R$^{10}$ is independently selected from H, —(C$_1$-C$_2$ alkyl), —(C$_1$-C$_2$ haloalkyl), —(C$_0$-C$_2$ alkyl)-L-(C$_0$-C$_2$ alkyl), —(C$_0$-C$_2$ alkyl)-NR$^9$(C$_0$-C$_2$ alkyl), —(C$_0$-C$_2$ alkyl)-O—(C$_0$-C$_2$ alkyl), —(C$_0$-C$_2$ alkyl)-C(O)—(C$_0$-C$_2$ alkyl) and —(C$_0$-C$_2$ alkyl)-S(O)$_{0-2}$—(C$_0$-C$_2$ alkyl), and in which no alkyl or haloalkyl is substituted with an aryl-, heteroaryl-, cycloalkyl- or heterocycloalkyl-containing group. In some embodiments, one R$^{15}$ is —C(O)NR$^9$R$^7$, which can be bound, for example, at a position alpha relative to the piperidine nitrogen, or at the position linked to the —N(R$^1$)—.

In certain embodiments of the presently disclosed compounds of structural formula (XLIV), R$^{17}$ is an unsubstituted aryl or heteroaryl. In other embodiments, the R$^{17}$ Ar or Het is substituted with 1, 2 or 3 substituents independently selected from —(C$_1$-C$_6$ alkyl), —(C$_1$-C$_6$ haloalkyl) (e.g., difluoromethyl, trifluoromethyl and the like), —(C$_0$-C$_6$ alkyl)-L-R$^7$, —(C$_0$-C$_6$ alkyl)-NR$^8$R$^9$, —(C$_0$-C$_6$ alkyl)-OR$^{10}$, —(C$_0$-C$_6$ alkyl)-C(O)R$^{10}$, —(C$_0$-C$_6$ alkyl)-S(O)$_{0-2}$R$^{10}$, -halogen, —NO$_2$ and —CN, in which each R$^7$, R$^8$ and R$^{10}$ is independently selected from H, —(C$_1$-C$_6$ alkyl), —(C$_1$-C$_6$ haloalkyl), —(C$_0$-C$_6$ alkyl)-L-(C$_0$-C$_6$ alkyl), —(C$_0$-C$_6$ alkyl)-NR$^9$(C$_0$-C$_6$ alkyl), —(C$_0$-C$_6$ alkyl)-O—(C$_0$-C$_6$ alkyl), —(C$_0$-C$_6$ alkyl)-C(O)—(C$_0$-C$_6$ alkyl) and —(C$_0$-C$_6$ alkyl)-S(O)$_{0-2}$—(C$_0$-C$_6$ alkyl), and in which no alkyl or haloalkyl is substituted with an aryl-, heteroaryl-, cycloalkyl- or heterocycloalkyl-containing group. For example, in one embodiment, the R$^{17}$ Ar or Het is substituted with 1, 2 or 3 substituents independently selected from —(C$_1$-C$_3$ alkyl), —(C$_1$-C$_3$ haloalkyl), —(C$_0$-C$_3$ alkyl)-L-R$^7$, —(C$_0$-C$_3$ alkyl)-NR$^8$R$^9$, —(C$_0$-C$_3$ alkyl)-OR$^{10}$, —(C$_0$-C$_3$ alkyl)-C(O)R$^{10}$, —(C$_0$-C$_3$ alkyl)-S(O)$_{0-2}$R$^{10}$, -halogen, —NO$_2$ and —CN, in which each R$^7$, R$^8$ and R$^{10}$ is independently selected from H, —(C$_1$-C$_2$ alkyl), —(C$_1$-C$_2$ haloalkyl), —(C$_0$-C$_2$ alkyl)-L-(C$_0$-C$_2$ alkyl), —(C$_0$-C$_2$ alkyl)-NR$^9$(C$_0$-C$_2$ alkyl), —(C$_0$-C$_2$ alkyl)-O—(C$_0$-C$_2$ alkyl), —(C$_0$-C$_2$ alkyl)-C(O)—(C$_0$-C$_2$ alkyl) and —(C$_0$-C$_2$ alkyl)-S(O)$_{0-2}$—(C$_0$-C$_2$ alkyl), and in which no alkyl or haloalkyl is substituted with an aryl-, heteroaryl-, cycloalkyl- or heterocycloalkyl-containing group. In certain embodiments, R$^{17}$ is substituted with 1, 2 or 3 substituents selected from halo, cyano, —(C$_1$-C$_4$ haloalkyl), —O—(C$_1$-C$_4$ haloalkyl), —(C$_1$-C$_4$ alkyl), —O—(C$_1$-C$_4$ alkyl), —C(O)—(C$_0$-C$_4$ alkyl), —C(O)O—(C$_0$-C$_4$ alkyl), —C(O)N(C$_0$-C$_4$ alkyl)(C$_0$-C$_4$ alkyl), NO$_2$ and —C(O)-Hca. R$^{17}$ can be substituted with, for example, one such substituent, or two such substituents.

For example, in certain embodiments, the presently disclosed compounds have the structural formula (XLV):

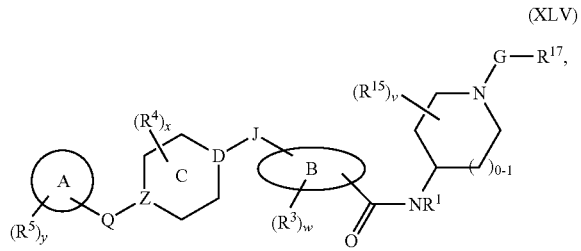

(XLV)

in which all variables are as defined above with reference to any of structural formulae (I)-(XLIV).

In other embodiments, the presently disclosed compounds have structural formula (XLVI):

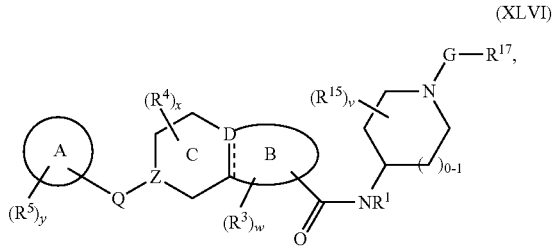

(XLVI)

in which all variables are as defined above with reference to any of structural formulae (I)-(XLIV).

In certain embodiments, the presently disclosed compounds have the structural formula (XLVII):

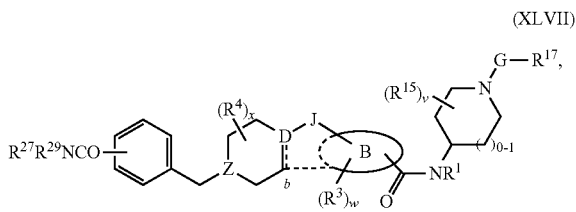

(XLVII)

in which $R^{27}$ is selected from H, —($C_1$-$C_6$ alkyl), —($C_1$-$C_6$ haloalkyl) (e.g., difluoromethyl, trifluoromethyl and the like), —($C_0$-$C_6$ alkyl)-L-($C_0$-$C_6$ alkyl), —($C_0$-$C_6$ alkyl)-$NR^9$($C_0$-$C_6$ alkyl), —($C_0$-$C_6$ alkyl)-O—($C_0$-$C_6$ alkyl), —($C_0$-$C_6$ alkyl)-C(O)—($C_0$-$C_6$ alkyl)-($C_0$-$C_6$ alkyl)-S(O)$_{0-2}$—($C_0$-$C_6$ alkyl), in which no heterocycloalkyl, alkyl or haloalkyl is substituted with an aryl-, heteroaryl-, cycloalkyl- or heterocycloalkyl-containing group, and $R^{29}$ is —H, —($C_1$-$C_4$ alkyl), —C(O)—($C_1$-$C_4$ alkyl) or —C(O)—O—($C_1$-$C_4$ alkyl) in which no ($C_1$-$C_4$ alkyl) is substituted by an aryl, heteroaryl, cycloalkyl or heterocycloalkyl-containing group, or $R^{27}$ and $R^{29}$ together with the nitrogen to which they are bound form Hca, and all other variables are as described above with reference to any of structural formulae (I)-(XLVI). In one embodiment, $R^{27}$ and $R^{29}$ are both H.

In certain embodiments, the presently disclosed compounds have the structural formula (XLVIII):

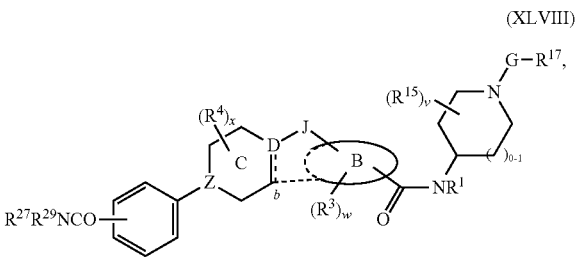

(XLVIII)

in which $R^{27}$ is selected from H, —($C_1$-$C_6$ alkyl), —($C_1$-$C_6$ haloalkyl) (e.g., difluoromethyl, trifluoromethyl and the like), —($C_0$-$C_6$ alkyl)-L-($C_0$-$C_6$ alkyl), —($C_0$-$C_6$ alkyl)-$NR^9$($C_0$-$C_6$ alkyl), —($C_0$-$C_6$ alkyl)-O—($C_0$-$C_6$ alkyl), —($C_0$-$C_6$ alkyl)-C(O)—($C_0$-$C_6$ alkyl)-($C_0$-$C_6$ alkyl)-S(O)$_{0-2}$—($C_0$-$C_6$ alkyl), in which no heterocycloalkyl, alkyl or haloalkyl is substituted with an aryl-, heteroaryl-, cycloalkyl- or heterocycloalkyl-containing group, and $R^{29}$ is —H, —($C_1$-$C_4$ alkyl), —C(O)—($C_1$-$C_4$ alkyl) or —C(O)—O—($C_1$-$C_4$ alkyl) in which no ($C_1$-$C_4$ alkyl) is substituted by an aryl, heteroaryl, cycloalkyl or heterocycloalkyl-containing group, or $R^{27}$ and $R^{29}$ together with the nitrogen to which they are bound form Hca, and all other variables are as described above with reference to any of structural formulae (I)-(XLVI). In one embodiment, $R^{27}$ and $R^{29}$ are both H.

In certain embodiments, the presently disclosed compounds have the structural formula (XLIX):

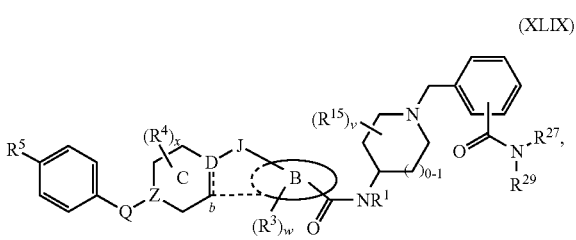

(XLIX)

in which $R^{27}$ is selected from H, —($C_1$-$C_6$ alkyl), —($C_1$-$C_6$ haloalkyl) (e.g., difluoromethyl, trifluoromethyl and the like), —($C_0$-$C_6$ alkyl)-L-($C_0$-$C_6$ alkyl), —($C_0$-$C_6$ alkyl)-$NR^9$($C_0$-$C_6$ alkyl), —($C_0$-$C_6$ alkyl)-O—($C_0$-$C_6$ alkyl), —($C_0$-$C_6$ alkyl)-C(O)—($C_0$-$C_6$ alkyl)-($C_0$-$C_6$ alkyl)-S(O)$_{0-2}$—($C_0$-$C_6$ alkyl), in which no heterocycloalkyl, alkyl or haloalkyl is substituted with an aryl-, heteroaryl-, cycloalkyl- or heterocycloalkyl-containing group, and $R^{29}$ is —H, —($C_1$-$C_4$ alkyl), —C(O)—($C_1$-$C_4$ alkyl) or —C(O)—O—($C_1$-$C_4$ alkyl) in which no ($C_1$-$C_4$ alkyl) is substituted by an aryl, heteroaryl, cycloalkyl or heterocycloalkyl-containing group, or $R^{27}$ and $R^{29}$ together with the nitrogen to which they are bound form Hca, and all other variables are as described above with reference to any of structural formulae (I)-(XLVI). In one embodiment, $R^{27}$ and $R^{29}$ are both H.

In certain embodiments, the presently disclosed compounds have the structural formula (L):

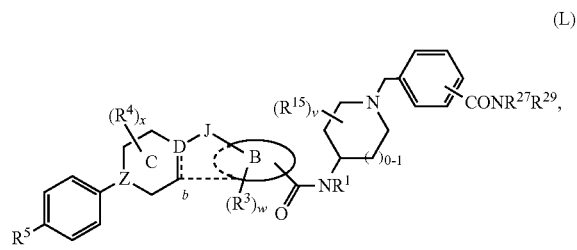

(L)

in which $R^{27}$ is selected from H, —($C_1$-$C_6$ alkyl), —($C_1$-$C_6$ haloalkyl) (e.g., difluoromethyl, trifluoromethyl and the like), —($C_0$-$C_6$ alkyl)-L-($C_0$-$C_6$ alkyl), —($C_0$-$C_6$ alkyl)-$NR^9$($C_0$-$C_6$ alkyl), —($C_0$-$C_6$ alkyl)-O—($C_0$-$C_6$ alkyl), —($C_0$-$C_6$ alkyl)-C(O)—($C_0$-$C_6$ alkyl)-($C_0$-$C_6$ alkyl)-S(O)$_{0-2}$—($C_0$-$C_6$ alkyl), in which no heterocycloalkyl, alkyl or haloalkyl is substituted with an aryl-, heteroaryl-, cycloalkyl- or heterocycloalkyl-containing group, and $R^{29}$ is —H, —($C_1$-$C_4$ alkyl), —C(O)—($C_1$-$C_4$ alkyl) or —C(O)—O—($C_1$-$C_4$ alkyl) in which no ($C_1$-$C_4$ alkyl) is substituted by an aryl, heteroaryl, cycloalkyl or heterocycloalkyl-containing group, or $R^{27}$ and $R^{29}$ together with the nitrogen to which they are bound form Hca, and all other variables are as described above with reference to any of structural formulae (I)-(XLVI). In one embodiment, $R^{27}$ and $R^{29}$ are both H.

In certain embodiments, the presently disclosed compounds have the structural formula (LI):

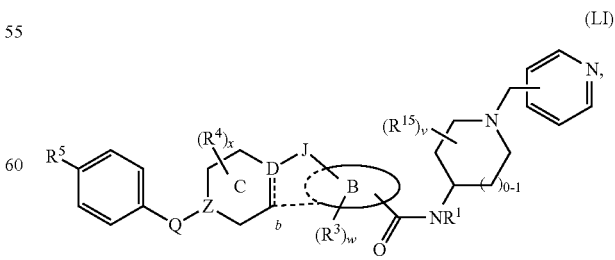

(LI)

in which all variables are as described above with reference to any of structural formulae (I)-(XLVI).

In certain embodiments, the presently disclosed compounds have the structural formula (LII):

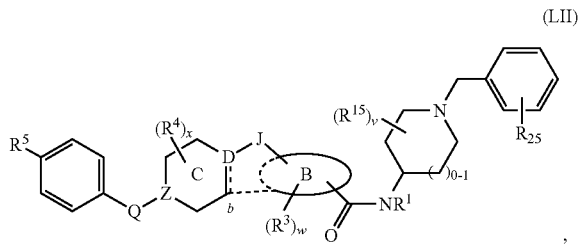

(LII)

in which $R^{25}$ is selected from halo, cyano, —($C_1$-$C_4$ haloalkyl), —O—($C_1$-$C_4$ haloalkyl), —($C_1$-$C_4$ alkyl), —O—($C_1$-$C_4$ alkyl), —C(O)—($C_0$-$C_4$ alkyl), —C(O)O—($C_0$-$C_4$ alkyl), —C(O)N($C_0$-$C_4$ alkyl)($C_0$-$C_4$ alkyl), $NO_2$ and —C(O)-Hca in which the Hca contains a ring nitrogen atom through which it is bound to the —C(O)—, in which no alkyl or haloalkyl is substituted by an aryl, heteroaryl, cycloalkyl or heterocycloalkyl-containing group; and all other variables are as described above with reference to any of structural formulae (I)-(XLVI). $R^{25}$ can be, for example, —Cl, —F, cyano, —C(O)$CH_3$, —C(O)OH, —C(O)$NH_2$, trifluoromethyl, difluoromethyl, difluoromethoxy or trifluoromethoxy.

In certain embodiments, the presently disclosed compounds have the structural formula (LIII):

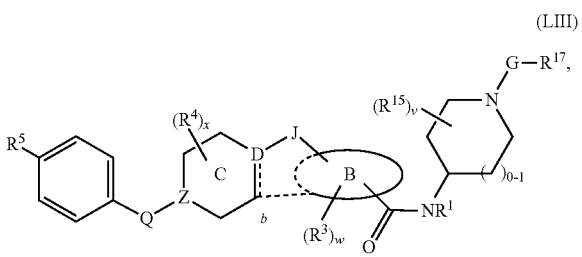

(LIII)

in which G is —C(O)—, —S(O)$_2$— or —C(O)—NH— and all other variables are as described above with reference to any of structural formulae (I)-(XLVI).

In certain embodiments, the presently disclosed compounds have the structural formula (LIV):

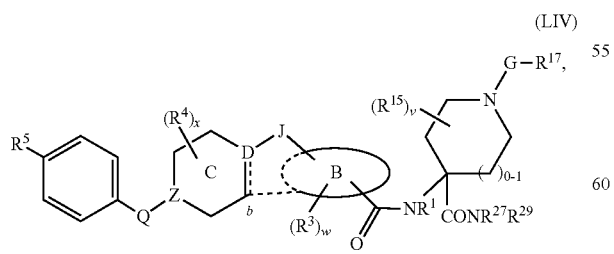

(LIV)

in which $R^{27}$ is selected from H, —($C_1$-$C_6$ alkyl), —($C_1$-$C_6$ haloalkyl) (e.g., difluoromethyl, trifluoromethyl and the like), —($C_0$-$C_6$ alkyl)-L-($C_0$-$C_6$ alkyl), —($C_0$-$C_6$ alkyl)-$NR^9$($C_0$-$C_6$ alkyl), —($C_0$-$C_6$ alkyl)-O—($C_0$-$C_6$ alkyl), —($C_0$-$C_6$ alkyl)-C(O)—($C_0$-$C_6$ alkyl)-($C_0$-$C_6$ alkyl)-S(O)$_{0-2}$—($C_0$-$C_6$ alkyl), in which no heterocycloalkyl, alkyl or haloalkyl is substituted with an aryl-, heteroaryl-, cycloalkyl- or heterocycloalkyl-containing group, and $R^{29}$ is —H, —($C_1$-$C_4$ alkyl), —C(O)—($C_1$-$C_4$ alkyl) or —C(O)—O—($C_1$-$C_4$ alkyl) in which no ($C_1$-$C_4$ alkyl) is substituted by an aryl, heteroaryl, cycloalkyl or heterocycloalkyl-containing group, or $R^{27}$ and $R^{29}$ together with the nitrogen to which they are bound form Hca, and all other variables are as described above with reference to any of structural formulae (I)-(XLVI). In one embodiment, $R^{27}$ and $R^{29}$ are both H. In some embodiments, the compounds of structural formula (LIV) are present as racemic mixtures or scalemic mixtures. In other embodiments, the compounds of structural formula (LIV) are present in an enantiomerically-enriched form, for example as a substantially pure stereoisomer.

In certain embodiments, the presently disclosed compounds have the structural formula (LV):

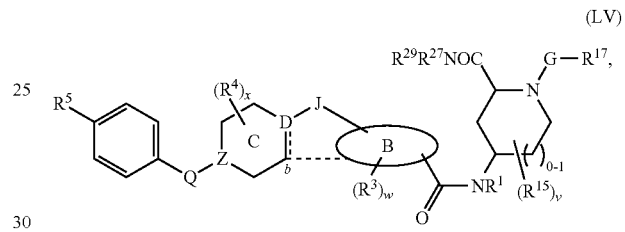

(LV)

in which $R^{27}$ is selected from H, —($C_1$-$C_6$ alkyl), —($C_1$-$C_6$ haloalkyl) (e.g., difluoromethyl, trifluoromethyl and the like), —($C_0$-$C_6$ alkyl)-L-($C_0$-$C_6$ alkyl), —($C_0$-$C_6$ alkyl)-$NR^9$($C_0$-$C_6$ alkyl), —($C_0$-$C_6$ alkyl)-O—($C_0$-$C_6$ alkyl), —($C_0$-$C_6$ alkyl)-C(O)—($C_0$-$C_6$ alkyl)-($C_0$-$C_6$ alkyl)-S(O)$_{0-2}$—($C_0$-$C_6$ alkyl), in which no heterocycloalkyl, alkyl or haloalkyl is substituted with an aryl-, heteroaryl-, cycloalkyl- or heterocycloalkyl-containing group, and $R^{29}$ is —H, —($C_1$-$C_4$ alkyl), —C(O)—($C_1$-$C_4$ alkyl) or —C(O)—O—($C_1$-$C_4$ alkyl) in which no ($C_1$-$C_4$ alkyl) is substituted by an aryl, heteroaryl, cycloalkyl or heterocycloalkyl-containing group, or $R^{27}$ and $R^{29}$ together with the nitrogen to which they are bound form Hca, and all other variables are as described above with reference to any of structural formulae (I)-(XLVI). In one embodiment, $R^{27}$ and $R^{29}$ are both H. In some embodiments, the compounds of structural formula (LV) are present as racemic mixtures or scalemic mixtures. In other embodiments, the compounds of structural formula (LV) are present in an enantiomerically-enriched form, for example as a substantially pure stereoisomer.

In certain embodiments, the presently disclosed compounds have the structural formula (LVI):

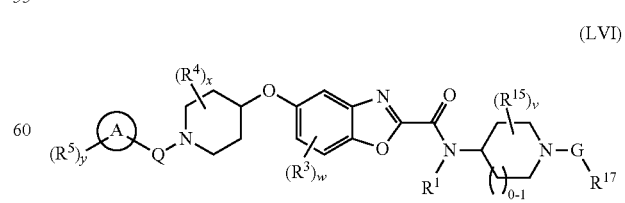

(LVI)

in which G, v, $R^{15}$ and $R^{17}$ are defined as described above with reference to structural formula (XLIV), and all other variables are defined as described above with reference to structural formulae (I)-(IV) and (XVIII). $R^5$, y, v, $R^{15}$, $R^{17}$, Q, G and the ring denoted by "A" can be defined, for example, as described with reference to any of structural formulae (XLVII)-(LV).

In certain embodiments, the presently disclosed compounds have the structural formula (LVII):

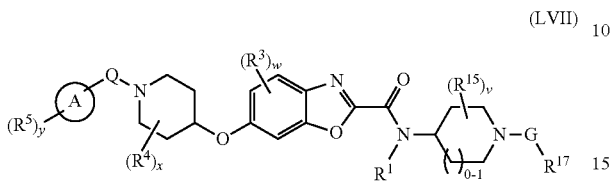
(LVII)

in which G, v, $R^{15}$ and $R^{17}$ are defined as described above with reference to structural formula (XLIV), and all other variables are defined as described above with reference to structural formulae (I)-(IV) and (XIX). $R^5$, y, v, $R^{15}$, $R^{17}$, Q, G and the ring denoted by "A" can be defined, for example, as described with reference to any of structural formulae (XLVII)-(LV).

In certain embodiments, the presently disclosed compounds have the structural formula (LVIII):

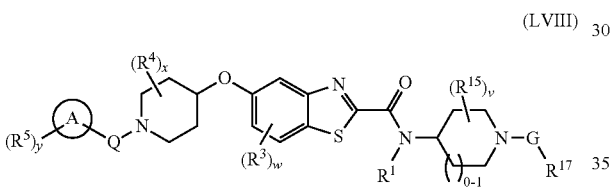
(LVIII)

in which G, v, $R^{15}$ and $R^{17}$ are defined as described above with reference to structural formula (XLIV), and all other variables are defined as described above with reference to structural formulae (I)-(IV) and (XX). $R^5$, y, v, $R^{15}$, $R^{17}$, Q, G and the ring denoted by "A" can be defined, for example, as described with reference to any of structural formulae (XLVII)-(LV).

In certain embodiments, the presently disclosed compounds have the structural formula (LIX):

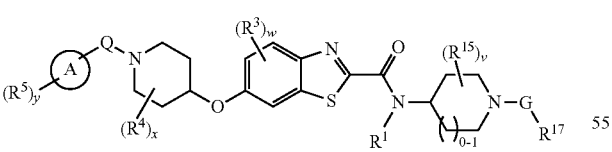
(LIX)

in which G, v, $R^{15}$ and $R^{17}$ are defined as described above with reference to structural formula (XLIV), and all other variables are defined as described above with reference to structural formulae (I)-(IV) and (XXI). $R^5$, y, v, $R^{15}$, $R^{17}$, Q, G and the ring denoted by "A" can be defined, for example, as described with reference to any of structural formulae (XLVII)-(LV).

In certain embodiments, the presently disclosed compounds have the structural formula (LX):

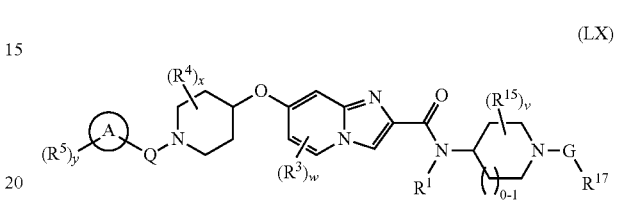
(LX)

in which G, v, $R^{15}$ and $R^{17}$ are defined as described above with reference to structural formula (XLVII), and all other variables are defined as described above with reference to structural formulae (I)-(IV) and (XXII). $R^5$, y, v, $R^{15}$, $R^{17}$, Q, G and the ring denoted by "A" can be defined, for example, as described with reference to any of structural formulae (XLVIII)-(LV).

In certain embodiments, the presently disclosed compounds have the structural formula (LXI):

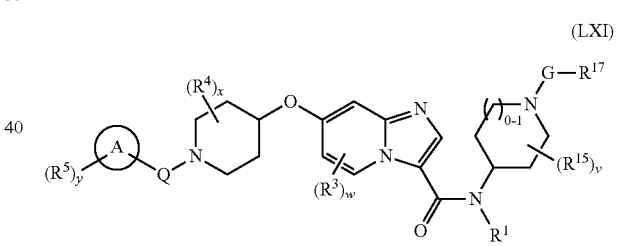
(LXI)

in which G, v, $R^{15}$ and $R^{17}$ are defined as described above with reference to structural formula (XLIV), and all other variables are defined as described above with reference to structural formulae (I)-(IV) and (XOH). $R^5$, y, v, $R^{15}$, $R^{17}$, Q, G and the ring denoted by "A" can be defined, for example, as described with reference to any of structural formulae (XLVII)-(LV).

In certain embodiments, the presently disclosed compounds have the structural formula (LXII):

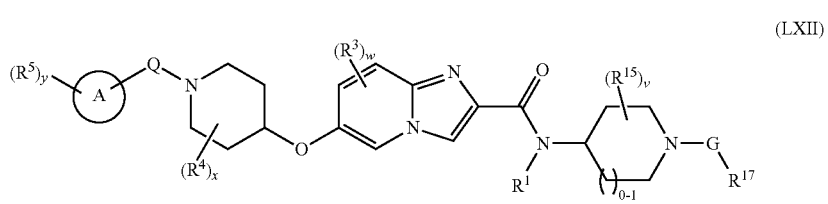
(LXII)

in which G, v, $R^{15}$ and $R^{17}$ are defined as described above with reference to structural formula (XLIV), and all other variables are defined as described above with reference to structural formulae (I)-(IV) and (XXIV). $R^5$, y, v, $R^{15}$, $R^{17}$, Q, G and the ring denoted by "A" can be defined, for example, as described with reference to any of structural formulae (XLVII)-(LV).

In certain embodiments, the presently disclosed compounds have the structural formula (LXIII):

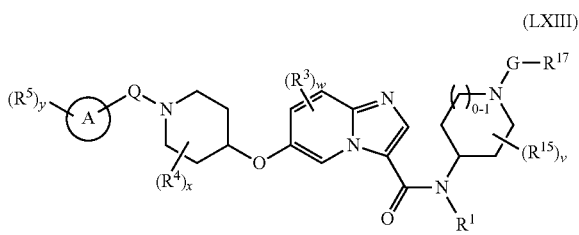

(LXIII)

in which G, v, $R^{15}$ and $R^{17}$ are defined as described above with reference to structural formula (XLIV), and all other variables are defined as described above with reference to structural formulae (I)-(IV) and (XXV). $R^5$, y, v, $R^{15}$, $R^{17}$, Q, G and the ring denoted by "A" can be defined, for example, as described with reference to any of structural formulae (XLVII)-(LV).

In certain embodiments, the presently disclosed compounds have the structural formula (LXIV):

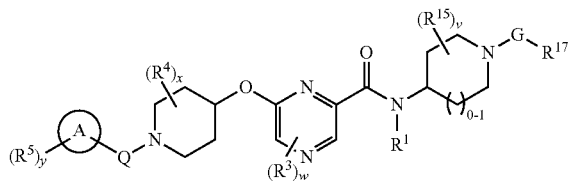

(LXIV)

in which G, v, $R^{15}$ and $R^{17}$ are defined as described above with reference to structural formula (XLIV), and all other variables are defined as described above with reference to structural formulae (I)-(IV) and (XXVI). $R^5$, y, v, $R^{15}$, $R^{17}$, Q, G and the ring denoted by "A" can be defined, for example, as described with reference to any of structural formulae (XLVII)-(LV).

In certain embodiments, the presently disclosed compounds have the structural formula (LXV):

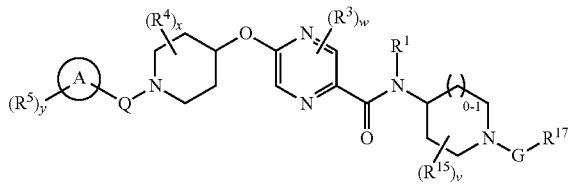

(LXV)

in which G, v, $R^{15}$ and $R^{17}$ are defined as described above with reference to structural formula (XLIV), and all other variables are defined as described above with reference to structural formulae (I)-(IV) and (XXVII). $R^5$, y, v, $R^{15}$, $R^{17}$, Q, G and the ring denoted by "A" can be defined, for example, as described with reference to any of structural formulae (XLVII)-(LV).

In certain embodiments, the presently disclosed compounds have the structural formula (LXVI):

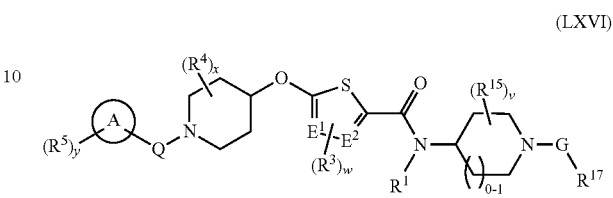

(LXVI)

in which G, v, $R^{15}$ and $R^{17}$ are defined as described above with reference to structural formula (XLIV), and all other variables are defined as described above with reference to structural formulae (I)-(IV) and (XXVIII). $R^5$, y, v, $R^{15}$, $R^{17}$, Q, G and the ring denoted by "A" can be defined, for example, as described with reference to any of structural formulae (XLVII)-(LV). In one embodiment, $E^1$ is carbon and $E^2$ is N. In another embodiment, $E^1$ is N and $E^2$ is carbon.

In certain embodiments, the presently disclosed compounds have the structural formula (LXVII):

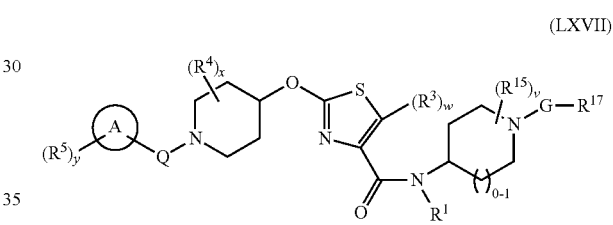

(LXVII)

in which G, v, $R^{15}$ and $R^{17}$ are defined as described above with reference to structural formula (XLIV), and all other variables are defined as described above with reference to structural formulae (I)-(IV) or (XXIX). $R^5$, y, v, $R^{15}$, $R^{17}$, Q, G and the ring denoted by "A" can be defined, for example, as described with reference to any of structural formulae (XLVII)-(LV). When w is 0, the ring position shown occupied by $R^3$ bears a hydrogen atom.

In certain embodiments, the presently disclosed compounds have the structural formula (LXVIII):

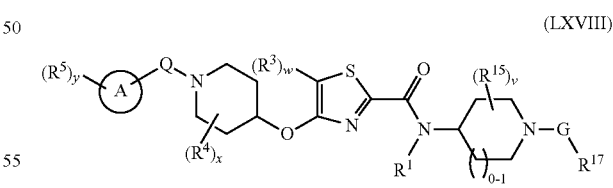

(LXVIII)

in which G, v, $R^{15}$ and $R^{17}$ are defined as described above with reference to structural formula (XLIV), and all other variables are defined as described above with reference to structural formulae (I)-(IV) and (XXX). $R^5$, y, v, $R^{15}$, $R^{17}$, Q, G and the ring denoted by "A" can be defined, for example, as described with reference to any of structural formulae (XLVII)-(LV). When w is 0, the ring position shown occupied by $R^3$ bears a hydrogen atom.

In certain embodiments, the presently disclosed compounds have the structural formula (LXIX):

(LXIX)

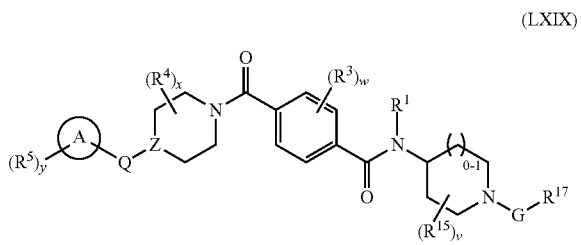

in which G, v, $R^{15}$ and $R^{17}$ are defined as described above with reference to structural formula (XLIV), and all other variables are defined as described above with reference to structural formulae (I)-(IV) and (XXXIV). $R^5$, y, v, $R^{15}$, $R^{17}$, Q, G and the ring denoted by "A" can be defined, for example, as described with reference to any of structural formulae (XLVII)-(LV). In certain embodiments, Z is N. In other embodiments, Z is CH or C substituted with one of the x $R^4$.

In certain embodiments, the presently disclosed compounds have the structural formula (LXX):

(LXX)

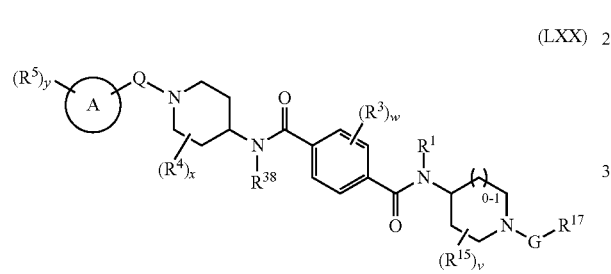

in which G, v, $R^{15}$ and $R^{17}$ are defined as described above with reference to structural formula (XLIV), and all other variables are defined as described above with reference to structural formulae (I)-(IV) and (XXXV). $R^5$, y, v, $R^{15}$, $R^{17}$, Q, G and the ring denoted by "A" can be defined, for example, as described with reference to any of structural formulae (XLVII)-(LV).

In certain embodiments, the presently disclosed compounds have the structural formula (LXXI):

(LXXI)

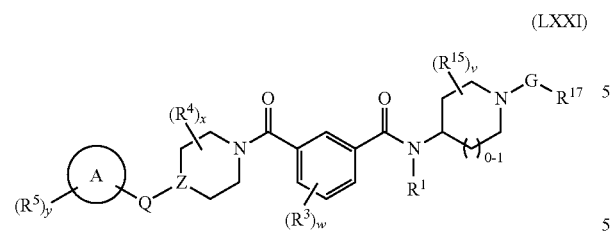

in which G, v, $R^{15}$ and $R^{17}$ are defined as described above with reference to structural formula (XLIV), and all other variables are defined as described above with reference to structural formulae (I)-(IV) and (XXXVI). $R^5$, y, v, $R^{15}$, $R^{17}$, Q, G and the ring denoted by "A" can be defined, for example, as described with reference to any of structural formulae (XLVII)-(LV). In certain embodiments, Z is N. In other embodiments, Z is CH or C substituted with one of the x $R^4$.

In certain embodiments, the presently disclosed compounds have the structural formula (LXXII):

(LXXII)

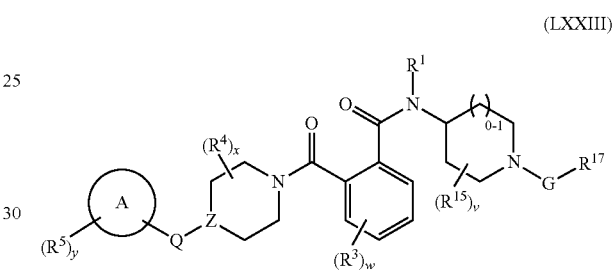

in which G, v, $R^{15}$ and $R^{17}$ are defined as described above with reference to structural formula (XLIV), and all other variables are defined as described above with reference to structural formulae (I)-(IV) and (XXXVII). $R^5$, y, v, $R^{15}$, $R^{17}$, Q, G and the ring denoted by "A" can be defined, for example, as described with reference to any of structural formulae (XLVII)-(LV).

In certain embodiments, the presently disclosed compounds have the structural formula (LXXIII):

(LXXIII)

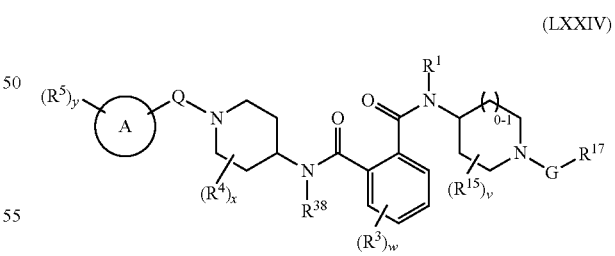

in which G, v, $R^{15}$ and $R^{17}$ are defined as described above with reference to structural formula (XLIV), and all other variables are defined as described above with reference to structural formulae (I)-(IV) and (XXXVIII). $R^5$, y, v, $R^{15}$, $R^{17}$, Q, G and the ring denoted by "A" can be defined, for example, as described with reference to any of structural formulae (XLVII)-(LV). In certain embodiments, Z is N. In other embodiments, Z is carbon (e.g., CH or C substituted with one of the x $R^4$).

In certain embodiments, the presently disclosed compounds have the structural formula (LXXIV):

(LXXIV)

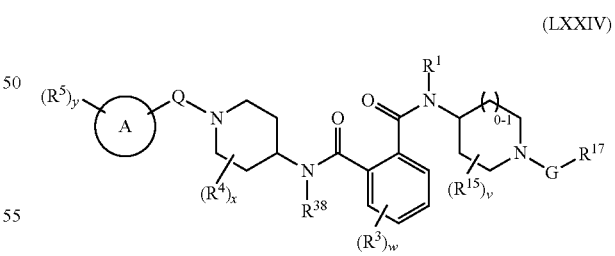

in which G, v, $R^{15}$ and $R^{17}$ are defined as described above with reference to structural formula (XLIV), and all other variables are defined as described above with reference to structural formulae (I)-(IV) and (XXXIX). $R^5$, y, v, $R^{15}$, $R^{17}$, Q, G and the ring denoted by "A" can be defined, for example, as described with reference to any of structural formulae (XLVII)-(LV).

In certain embodiments, the presently disclosed compounds have the structural formula (LXXV):

(LXXV)

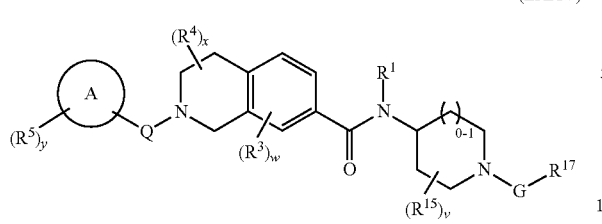

in which G, v, $R^{15}$ and $R^{17}$ are defined as described above with reference to structural formula (XLIV), and all other variables are defined as described above with reference to structural formulae (I)-(IV) and (XL). $R^5$, y, v, $R^{15}$, $R^{17}$, Q, G and the ring denoted by "A" can be defined, for example, as described with reference to any of structural formulae (XLVII)-(LV).

In certain embodiments, the presently disclosed compounds have the structural formula (LXXVI):

(LXXVI)

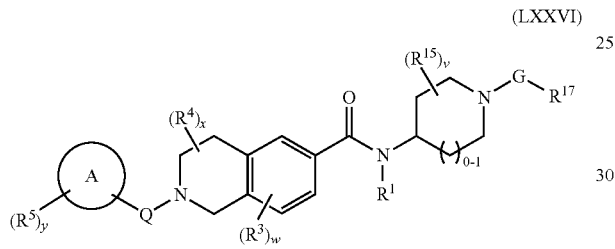

in which G, v, $R^{15}$ and $R^{17}$ are defined as described above with reference to structural formula (XLIV), and all other variables are defined as described above with reference to structural formulae (I)-(IV) and (XLI). $R^5$, y, v, $R^{15}$, $R^{17}$, Q, G and the ring denoted by "A" can be defined, for example, as described with reference to any of structural formulae (XLVII)-(LV).

In certain embodiments, the presently disclosed compounds have the structural formula (LXXVII):

(LXXVII)

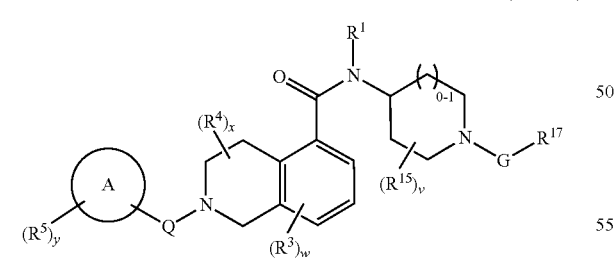

in which G, v, $R^{15}$ and $R^{17}$ are defined as described above with reference to structural formula (XLIV), and all other variables are defined as described above with reference to structural formulae (I)-(IV) and (XLII). $R^5$, y, v, $R^{15}$, $R^{17}$, Q, G and the ring denoted by "A" can be defined, for example, as described with reference to any of structural formulae (XLVII)-(LV).

In certain embodiments, the presently disclosed compounds have the structural formula (LXXVIII):

(LXXVIII)

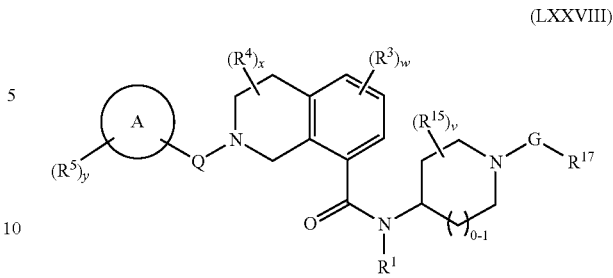

in which G, v, $R^{15}$ and $R^{17}$ are defined as described above with reference to structural formula (XLIV), and all other variables are defined as described above with reference to structural formulae (I)-(IV) and (XLIII). $R^5$, y, v, $R^{15}$, $R^{17}$, Q, G and the ring denoted by "A" can be defined, for example, as described with reference to any of structural formulae (XLVII)-(LV).

In certain embodiments of compounds having structural formulae (XLIV)-(XLVIII), (LIII) and (LVI)-(LXXVIII), the

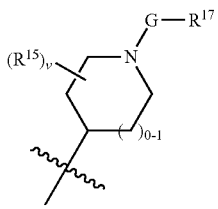

moiety has the structure

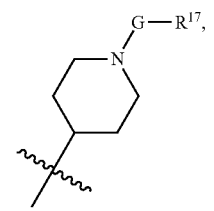

in which G is —$CH_2$—, —$CH(CH_3)$—, —C(O)—, —$S(O)_2$— or —C(O)—NH—. For example, in one embodiment, G is —$CH_2$—. In another embodiment, G is —C(O)— or —$S(O)_2$—. In another embodiment, G is —C(O)—NH—.

In other embodiments of compounds having structural formulae (XLIV)-(XLVIII), (LIII) and (LVI)-(LXXVIII), the

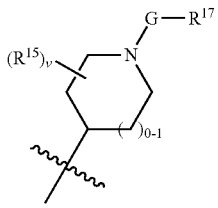

moiety has the structure

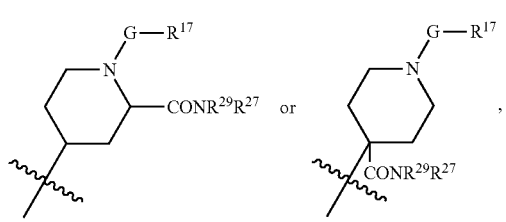

in which G is —$CH_2$—, —C(O)—, —$S(O)_2$— or —C(O)—NH—, $R^{27}$ is selected from H, —($C_1$-$C_6$ alkyl), —($C_1$-$C_6$ haloalkyl) (e.g., difluoromethyl, trifluoromethyl and the like), —($C_0$-$C_6$ alkyl)-L-($C_0$-$C_6$ alkyl), —($C_0$-$C_6$ alkyl)-$NR^9$($C_0$-$C_6$ alkyl), —($C_0$-$C_6$ alkyl)-O—($C_0$-$C_6$ alkyl), —($C_0$-$C_6$ alkyl)-C(O)—($C_0$-$C_6$ alkyl)-($C_0$-$C_6$ alkyl)-S(O)$_{0-2}$—($C_0$-$C_6$ alkyl), in which no heterocycloalkyl, alkyl or haloalkyl is substituted with an aryl-, heteroaryl-, cycloalkyl- or heterocycloalkyl-containing group, and $R^{29}$ is —H, —($C_1$-$C_4$ alkyl), —CO—($C_1$-$C_4$ alkyl) or —CO—O—($C_1$-$C_4$ alkyl) in which no ($C_1$-$C_4$ alkyl) is substituted by an aryl, heteroaryl, cycloalkyl or heterocycloalkyl-containing group, or $R^{27}$ and $R^{29}$ together with the nitrogen to which they are bound form Hca. In such embodiments, the compounds can be present as racemic mixtures or scalemic mixtures, or in an enantiomerically-enriched form, for example as a substantially pure stereoisomer.

In other embodiments of compounds having structural formulae (XLIV)-(XLVIII), (LIII) and (LVI)-(LXXVIII), the

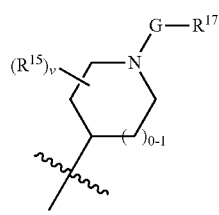

moiety has the structure

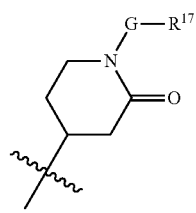

in which G is —CH$_2$—, —C(O)—, —S(O)$_2$— or —C(O)—NH—.

In certain embodiments of compounds having structural formulae (XLIV)-(XLVIII), (LIII) and (LVI)-(LXXVIII), the $R^{17}$ moiety has the structure

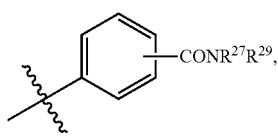

in which $R^{27}$ is selected from H, —($C_1$-$C_6$ alkyl), —($C_1$-$C_6$ haloalkyl) (e.g., difluoromethyl, trifluoromethyl and the like), —($C_0$-$C_6$ alkyl)-L-($C_0$-$C_6$ alkyl), —($C_0$-$C_6$ alkyl)-$NR^9$($C_0$-$C_6$ alkyl), —($C_0$-$C_6$ alkyl)-O—($C_0$-$C_6$ alkyl), —($C_0$-$C_6$ alkyl)-C(O)—($C_0$-$C_6$ alkyl)-($C_0$-$C_6$ alkyl)-S(O)$_{0-2}$—($C_0$-$C_6$ alkyl), in which no heterocycloalkyl, alkyl or haloalkyl is substituted with an aryl-, heteroaryl-, cycloalkyl- or heterocycloalkyl-containing group, and $R^{29}$ is —H, —($C_1$-$C_4$ alkyl), —CO—($C_1$-$C_4$ alkyl) or —CO—O—($C_1$-$C_4$ alkyl) in which no ($C_1$-$C_4$ alkyl) is substituted by an aryl, heteroaryl, cycloalkyl or heterocycloalkyl-containing group, or $R^{27}$ and $R^{29}$ together with the nitrogen to which they are bound form Hca.

In certain embodiments of compounds having structural formulae (XLIV)-(LXXVIII), w is 1, and $R^3$ is —$NR^8R^9$. In certain such embodiments, $R^3$ is substituted at a 6-membered aromatic ring position in the meta position relative to the J moiety.

In other embodiments of compounds having structural formulae (XLIV)-(LXXVIII), w is 1, and $R^3$ is —($C_0$-$C_3$ alkyl)-$Y^1$—($C_1$-$C_3$ alkyl)-$Y^2$—($C_0$-$C_3$ alkyl), in which each of $Y^1$ and $Y^2$ is independently L, —O—, —S— or —$NR^9$—. In certain such embodiments, $R^3$ is substituted at a 6-membered aromatic ring position in the meta position relative to the J moiety.

In certain embodiments described above, each $R^{27}$ is selected from —($C_1$-$C_3$ alkyl), —($C_1$-$C_3$ haloalkyl), —($C_0$-$C_3$ alkyl)-L-$R^7$, —($C_0$-$C_3$ alkyl)-$NR^8R^9$, —($C_0$-$C_3$ alkyl)-$OR^{10}$, —($C_0$-$C_3$ alkyl)-C(O)$R^{10}$, —($C_0$-$C_3$ alkyl)-S(O)$_{0-2}R^{10}$, -halogen, —NO$_2$ and —CN and two $R^{21}$ on the same carbon optionally combine to form oxo, in which each $R^7$, $R^8$ and $R^{10}$ is independently selected from H, —($C_1$-$C_2$ alkyl), —($C_1$-$C_2$ haloalkyl), —($C_0$-$C_2$ alkyl)-L-($C_0$-$C_2$ alkyl), —($C_0$-$C_2$ alkyl)-$NR^9$($C_0$-$C_2$ alkyl), —($C_0$-$C_2$ alkyl)-O—($C_0$-$C_2$ alkyl), —($C_0$-$C_2$ alkyl)-C(O)—($C_0$-$C_2$ alkyl) and —($C_0$-$C_2$ alkyl)-S(O)$_{0-2}$—($C_0$-$C_2$ alkyl), and in which no alkyl or haloalkyl is substituted with an aryl-, heteroaryl-, cycloalkyl- or heterocycloalkyl-containing group, and each $R^{29}$ is H, methyl or ethyl, or $R^{27}$ and $R^{29}$ together with the nitrogen to which they are bound form Hca.

In certain embodiments of compounds having structural formulae (XLIV)-(XLVI) and (XLIX)-(LXXVIII), at least one $R^5$ moiety is a haloalkyl group, and in exemplary embodiments of these formulae the

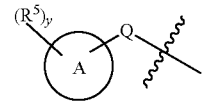

moiety is p-(trifluoromethyl)phenyl.

In one embodiment, the presently disclosed compounds of any of structural formulae (I)-(XLIII) have a T moiety having the structural formula

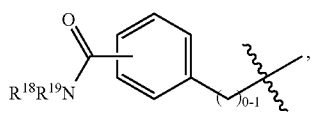

and an $R^2$ moiety having the structural formula

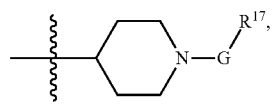

in which G and $R^{17}$ are as described above with reference to any of structural formulae (I)-(LXXVIII), $R^{18}$ is H, —($C_1$-$C_6$ alkyl), —($C_1$-$C_6$ haloalkyl) (e.g., difluoromethyl, trifluoromethyl and the like), —($C_0$-$C_6$ alkyl)-L-($C_0$-$C_6$ alkyl), —($C_0$-$C_6$ alkyl)-$NR^9$($C_0$-$C_6$ alkyl), —($C_0$-$C_6$ alkyl)-O—($C_0$-$C_6$ alkyl), —($C_0$-$C_6$ alkyl)-C(O)—($C_0$-$C_6$ alkyl) and —($C_0$-$C_6$ alkyl)-S(O)$_{0-2}$—($C_0$-$C_6$ alkyl), in which no alkyl or haloalkyl is substituted with an aryl-, heteroaryl-, cycloalkyl- or heterocycloalkyl-containing group and $R^{19}$ is —H, —($C_1$-$C_4$ alkyl), —CO—($C_1$-$C_4$ alkyl) or —CO—O—($C_1$-$C_4$ alkyl) in which no alkyl is substituted by an aryl, heteroaryl, cycloalkyl or heterocycloalkyl-containing group, or $R^{18}$ and $R^{19}$ together with the nitrogen to which they are bound form Hca. In one embodiment, $R^{18}$ and $R^{19}$ are both H.

In another embodiment, the presently disclosed compounds of any of structural formulae (I)-(XLIII) have a T moiety having the structural formula

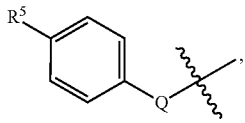

and an $R^2$ moiety having the structural formula

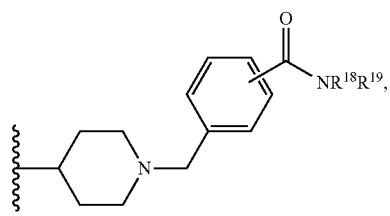

in which Q and $R^5$ are defined as described above with reference to any of structural formulae (I)-(LXXVIII), $R^{18}$ is H, —($C_1$-$C_6$ alkyl), —($C_1$-$C_6$ haloalkyl) (e.g., difluoromethyl, trifluoromethyl and the like), —($C_0$-$C_6$ alkyl)-L-($C_0$-$C_6$ alkyl), —($C_0$-$C_6$ alkyl)-$NR^9$($C_0$-$C_6$ alkyl), —($C_0$-$C_6$ alkyl)-O—($C_0$-$C_6$ alkyl), —($C_0$-$C_6$ alkyl)-C(O)—($C_0$-$C_6$ alkyl) and —($C_0$-$C_6$ alkyl)-S(O)$_{0-2}$—($C_0$-$C_6$ alkyl), in which no alkyl or haloalkyl is substituted with an aryl-, heteroaryl-, cycloalkyl- or heterocycloalkyl-containing group and $R^{19}$ is —H, —($C_1$-$C_4$ alkyl), —CO—($C_1$-$C_4$ alkyl) or —CO—O—($C_1$-$C_4$ alkyl) in which no alkyl is substituted by an aryl, heteroaryl, cycloalkyl or heterocycloalkyl-containing group, or $R^{18}$ and $R^{19}$ together with the nitrogen to which they are bound form Hca. In one embodiment, $R^{18}$ and $R^{19}$ are both H.

In another embodiment, the presently disclosed compounds of any of structural formulae (I)-(XLIII) have a T moiety having the structural formula

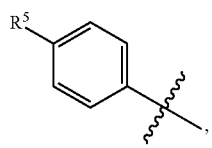

and an $R^2$ moiety having the structural formula

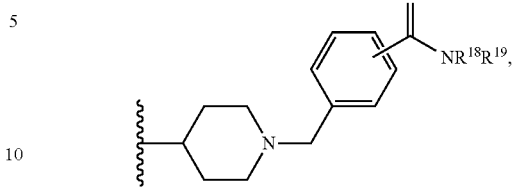

in which Q and $R^5$ are defined as described above with reference to any of structural formulae (I)-(LXXVIII), $R^{18}$ is H, —($C_1$-$C_6$ alkyl), —($C_1$-$C_6$ haloalkyl) (e.g., difluoromethyl, trifluoromethyl and the like), —($C_0$-$C_6$ alkyl)-L-($C_0$-$C_6$ alkyl), —($C_0$-$C_6$ alkyl)-$NR^9$($C_0$-$C_6$ alkyl), —($C_0$-$C_6$ alkyl)-O—($C_0$-$C_6$ alkyl), —($C_0$-$C_6$ alkyl)-C(O)—($C_0$-$C_6$ alkyl) and —($C_0$-$C_6$ alkyl)-S(O)$_{0-2}$—($C_0$-$C_6$ alkyl), in which no alkyl or haloalkyl is substituted with an aryl-, heteroaryl-, cycloalkyl- or heterocycloalkyl-containing group and $R^{19}$ is —H, —($C_1$-$C_4$ alkyl), —CO—($C_1$-$C_4$ alkyl) or —CO—O—($C_1$-$C_4$ alkyl) in which no alkyl is substituted by an aryl, heteroaryl, cycloalkyl or heterocycloalkyl-containing group, or $R^{18}$ and $R^{19}$ together with the nitrogen to which they are bound form Hca. In one embodiment, $R^{18}$ and $R^{19}$ are both H.

In certain embodiments, the presently disclosed compounds have the structural formula (LXXIX):

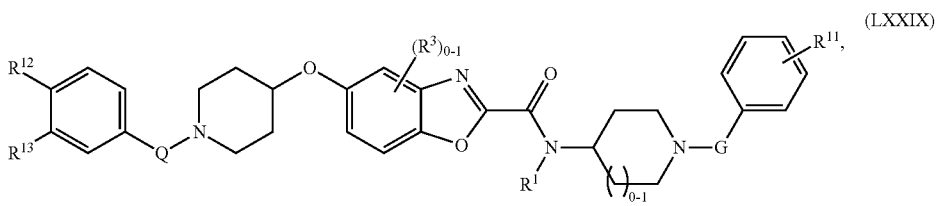

in which Q is —$CH_2$—, —C(O)— or a single bond; G is a single bond, —$CH_2$—, —C(O)—, —S(O)$_2$— or —C(O)—NH—; $R^1$ and $R^3$ are as described above with reference to any of structural formulae (I)-(IV) and (LVI); and $R^{11}$, $R^{12}$ and $R^{13}$ are independently selected from H, halo, cyano, —($C_1$-$C_4$ haloalkyl), —O—($C_1$-$C_4$ haloalkyl), —($C_1$-$C_4$ alkyl), —O—($C_1$-$C_4$ alkyl), —C(O)—($C_0$-$C_4$ alkyl), —C(O)O—($C_0$-$C_4$ alkyl), —C(O)N($C_0$-$C_4$ alkyl)($C_0$-$C_4$ alkyl), $NO_2$ and —C(O)-Hca in which the Hca contains a ring nitrogen atom through which it is bound to the —C(O)—, in which no alkyl, haloalkyl or heterocycloalkyl is substituted by an aryl, heteroaryl, cycloalkyl or heterocycloalkyl-containing group. In one particular such embodiment, at least one of $R^{11}$, $R^{12}$ and $R^{13}$ is not H. In one embodiment, $R^{11}$ is attached in the para position relative to the G moiety; in another embodiment, $R^{11}$ is attached in the meta position relative to the G moiety. In one embodiment, $R^1$ is H. In another embodiment, $R^1$ is methyl, ethyl, propyl or butyl. In one embodiment, no $R^3$ is substituted on the benzo moiety of the central benzo[d]oxazole. In another embodiment, one $R^3$ (e.g., —Cl, —F, —$CH_3$, —$C_2H_5$, —$C_3H_7$) is substituted on the benzo moiety of the central benzo[d]oxazole.

In certain embodiments, the presently disclosed compounds have the structural formula (LXXX):

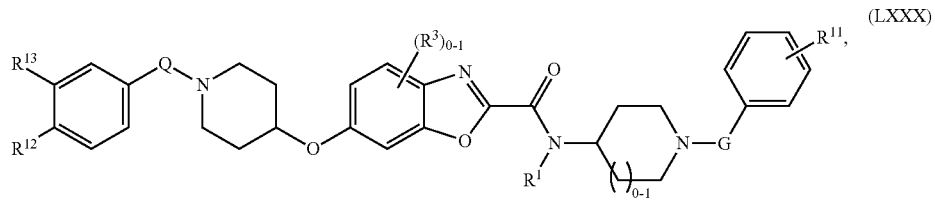
(LXXX)

in which Q is —CH$_2$—, —C(O)— or a single bond; G is a single bond, —CH$_2$—, —C(O)—, —S(O)$_2$— or —C(O)—NH—; R$^1$ and R$^3$ are as described above with reference to any of structural formulae (I)-(IV) and (LVII); and R$^{11}$, R$^{12}$ and R$^{13}$ are independently selected from H, halo, cyano, —(C$_1$-C$_4$ haloalkyl), —O—(C$_1$-C$_4$ haloalkyl), —(C$_1$-C$_4$ alkyl), —O—(C$_1$-C$_4$ alkyl), —C(O)—(C$_0$-C$_4$ alkyl), —C(O)O—(C$_0$-C$_4$ alkyl), —C(O)N(C$_0$-C$_4$ alkyl)(C$_0$-C$_4$ alkyl), NO$_2$ and —C(O)-Hca in which the Hca contains a ring nitrogen atom through which it is bound to the —C(O)—, in which no alkyl, haloalkyl or heterocycloalkyl is substituted by an aryl, heteroaryl, cycloalkyl or heterocycloalkyl-containing group. In one particular such embodiment, at least one of R$^{11}$, R$^{12}$ and R$^{13}$ is not H. In one embodiment, R$^{11}$ is attached in the para position relative to the G moiety; in another embodiment, R$^{11}$ is attached in the meta position relative to the G moiety. In one embodiment, R$^1$ is H. In another embodiment, R$^1$ is methyl, ethyl, propyl or butyl. In one embodiment, no R$^3$ is substituted on the benzo moiety of the central benzo[d]oxazole. In another embodiment, one R$^3$ (e.g., —Cl, —F, —CH$_3$, —C$_2$H$_5$, —C$_3$H$_7$) is substituted on the benzo moiety of the central benzo[d]oxazole.

In certain embodiments, the presently disclosed compounds have the structural formula (LXXXI):

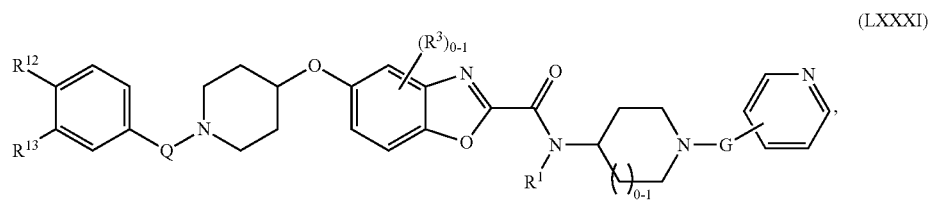
(LXXXI)

in which Q is —CH$_2$—, —C(O)— or a single bond; G is a single bond, —CH$_2$—, —C(O)—, —S(O)$_2$— or —C(O)—NH—; R$^1$ and R$^3$ are as described above with reference to any of structural formulae (I)-(IV) and (LVI); and R$^{12}$ and R$^{13}$ are independently selected from H, halo, cyano, —(C$_1$-C$_4$ haloalkyl), —O—(C$_1$-C$_4$ haloalkyl), —(C$_1$-C$_4$ alkyl), —O—(C$_1$-C$_4$ alkyl), —C(O)—(C$_0$-C$_4$ alkyl), —C(O)O—(C$_0$-C$_4$ alkyl), —C(O)N(C$_0$-C$_4$ alkyl)(C$_0$-C$_4$ alkyl), NO$_2$ and —C(O)-Hca in which the Hca contains a ring nitrogen atom through which it is bound to the —C(O)—, in which no alkyl, haloalkyl or heterocycloalkyl is substituted by an aryl, heteroaryl, cycloalkyl or heterocycloalkyl-containing group. In one particular such embodiment, at least one of R$^{12}$ and R$^{13}$ is not H. In one embodiment, the pyridine nitrogen is positioned in the para position relative to the G moiety; in another embodiment, the pyridine nitrogen is positioned in the meta position relative to the G moiety. In one embodiment, R$^1$ is H. In another embodiment, R$^1$ is methyl, ethyl, propyl or butyl. In one embodiment, no R$^3$ is substituted on the benzo moiety of the central benzo[d]oxazole. In another embodiment, one R$^3$ (e.g., —Cl, —F, —CH$_3$, —C$_2$H$_5$, —C$_3$H$_7$) is substituted on the benzo moiety of the central benzo[d]oxazole.

In certain embodiments, the presently disclosed compounds have the structural formula (LXXXII):

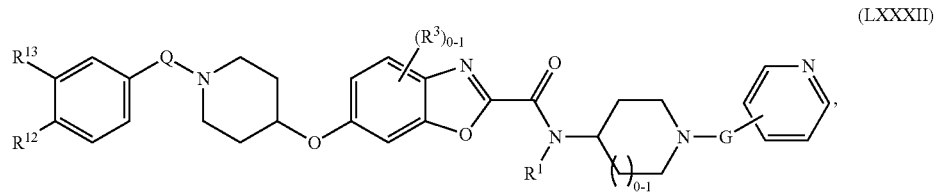
(LXXXII)

in which Q is —CH$_2$—, —C(O)— or a single bond; G is a single bond, —CH$_2$—, —C(O)—, —S(O)$_2$— or —C(O)—NH—; R$^1$ and R$^3$ are as described above with reference to any of structural formulae (I)-(IV) and (LVI); and R$^{12}$ and R$^{13}$ are independently selected from H, halo, cyano, —(C$_1$-C$_4$ haloalkyl), —O—(C$_1$-C$_4$ haloalkyl), —(C$_1$-C$_4$ alkyl), —O—(C$_1$-C$_4$ alkyl), —C(O)—(C$_0$-C$_4$ alkyl), —C(O)O—(C$_0$-C$_4$ alkyl), —C(O)N(C$_0$-C$_4$ alkyl)(C$_0$-C$_4$ alkyl), NO$_2$ and —C(O)-Hca in which the Hca contains a ring nitrogen atom through which it is bound to the —C(O)—, in which no alkyl, haloalkyl or heterocycloalkyl is substituted by an aryl, heteroaryl, cycloalkyl or heterocycloalkyl-containing group. In one particular such embodiment, at least one of R$^{12}$ and R$^{13}$ is not H. In one embodiment, the pyridine nitrogen is positioned in the para position relative to the G moiety; in another embodiment, the pyridine nitrogen is positioned in the meta position relative to the G moiety. In one embodiment, R$^1$ is H. In another embodiment, R$^1$ is methyl, ethyl, propyl or butyl. In one embodiment, no R$^3$ is substituted on the benzo moiety of the central benzo[d]oxazole. In another embodiment, one R$^3$ (e.g., —Cl, —F, —CH$_3$, —C$_2$H$_5$, —C$_3$H$_7$) is substituted on the benzo moiety of the central benzo[d]oxazole.

In certain embodiments, the presently disclosed compounds have the structural formula (LXXXIII):

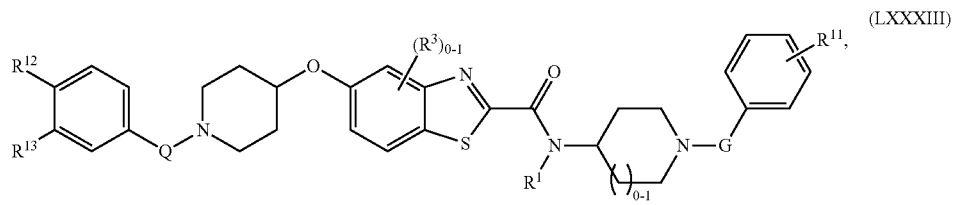

(LXXXIII)

in which Q is —CH$_2$—, —C(O)— or a single bond; G is a single bond, —CH$_2$—, —C(O)—, —S(O)$_2$— or —C(O)—NH—; R$^1$ and R$^3$ are as described above with reference to any of structural formulae (I)-(IV) and (LVIII); and R$^{11}$, R$^{12}$ and R$^{13}$ are independently selected from H, halo, cyano, —(C$_1$-C$_4$ haloalkyl), —O—(C$_1$-C$_4$ haloalkyl), —(C$_1$-C$_4$ alkyl), —O—(C$_1$-C$_4$ alkyl), —C(O)—(C$_0$-C$_4$ alkyl), —C(O)O—(C$_0$-C$_4$ alkyl), —C(O)N(C$_0$-C$_4$ alkyl)(C$_0$-C$_4$ alkyl), NO$_2$ and —C(O)-Hca in which the Hca contains a ring nitrogen atom through which it is bound to the —C(O)—, in which no alkyl, haloalkyl or heterocycloalkyl is substituted by an aryl, heteroaryl, cycloalkyl or heterocycloalkyl-containing group. In one particular such embodiment, at least one of R$^{11}$, R$^{12}$ and R$^{13}$ is not H. In one embodiment, R$^{11}$ is attached in the para position relative to the G moiety; in another embodiment, R$^{11}$ is attached in the meta position relative to the G moiety. In one embodiment, R$^1$ is H. In another embodiment, R$^1$ is methyl, ethyl, propyl or butyl. In one embodiment, no R$^3$ is substituted on the benzo moiety of the central benzo[d]thiazole. In another embodiment, one R$^3$ (e.g., —Cl, —F, —CH$_3$, —C$_2$H$_5$, —C$_3$H$_7$) is substituted on the benzo moiety of the central benzo[d]thiazole.

In certain embodiments, the presently disclosed compounds have the structural formula (LXXXIV):

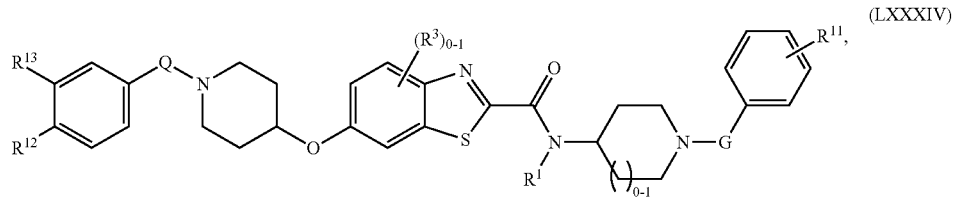

(LXXXIV)

in which Q is —CH$_2$—, —C(O)— or a single bond; G is a single bond, —CH$_2$—, —C(O)—, —S(O)$_2$— or —C(O)—NH—; R$^1$ and R$^3$ are as described above with reference to any of structural formulae (I)-(IV) and (LIX); and R$^{11}$, R$^{12}$ and R$^{13}$ are independently selected from H, halo, cyano, —(C$_1$-C$_4$ haloalkyl), —O—(C$_1$-C$_4$ haloalkyl), —(C$_1$-C$_4$ alkyl), —O—(C$_1$-C$_4$ alkyl), —C(O)—(C$_0$-C$_4$ alkyl), —C(O)O—(C$_0$-C$_4$ alkyl), —C(O)N(C$_0$-C$_4$ alkyl)(C$_0$-C$_4$ alkyl), NO$_2$ and —C(O)-Hca in which the Hca contains a ring nitrogen atom through which it is bound to the —C(O)—, in which no alkyl, haloalkyl or heterocycloalkyl is substituted by an aryl, heteroaryl, cycloalkyl or heterocycloalkyl-containing group. In one particular such embodiment, at least one of R$^{11}$, R$^{12}$ and R$^{13}$ is not H. In one embodiment, R$^{11}$ is attached in the para position relative to the G moiety; in another embodiment, R$^{11}$ is attached in the meta position relative to the G moiety. In one embodiment, R$^1$ is H. In another embodiment, R$^1$ is methyl, ethyl, propyl or butyl. In one embodiment, no R$^3$ is substituted on the benzo moiety of the central benzo[d]thiazole. In another embodiment, one R$^3$ (e.g., —Cl, —F, —CH$_3$, —C$_2$H$_5$, —C$_3$H$_7$) is substituted on the benzo moiety of the central benzo[d]thiazole.

In certain embodiments, the presently disclosed compounds have the structural formula (LXXXV):

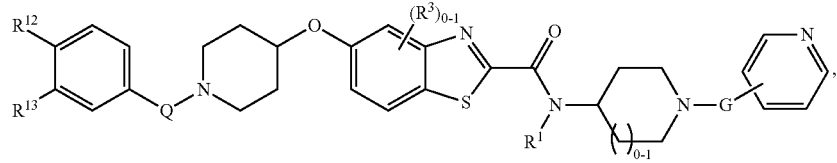

(LXXXV)

in which Q is —CH$_2$—, —C(O)— or a single bond; G is a single bond, —CH$_2$—, —C(O)—, —S(O)$_2$— or —C(O)—NH—; R$^1$ and R$^3$ are as described above with reference to any of structural formulae (I)-(IV) and (LVIII); and R$^{12}$ and R$^{13}$ are independently selected from H, halo, cyano, —(C$_1$-C$_4$ haloalkyl), —O—(C$_1$-C$_4$ haloalkyl), —(C$_1$-C$_4$ alkyl), —O—(C$_1$-C$_4$ alkyl), —C(O)—(C$_0$-C$_4$ alkyl), —C(O)O—(C$_0$-C$_4$ alkyl), —C(O)N(C$_0$-C$_4$ alkyl)(C$_0$-C$_4$ alkyl), NO$_2$ and —C(O)-Hca in which the Hca contains a ring nitrogen atom through which it is bound to the —C(O)—, in which no alkyl, haloalkyl or heterocycloalkyl is substituted by an aryl, heteroaryl, cycloalkyl or heterocycloalkyl-containing group. In one particular such embodiment, at least one of R$^{12}$ and R$^{13}$ is not H. In one embodiment, the pyridine nitrogen is positioned in the para position relative to the G moiety; in another embodiment, the pyridine nitrogen is positioned in the meta position relative to the G moiety. In one embodiment, R$^1$ is H. In another embodiment, R$^1$ is methyl, ethyl, propyl or butyl. In one embodiment, no R$^3$ is substituted on the benzo moiety of the central benzo[d]thiazole. In another embodiment, one R$^3$ (e.g., —Cl, —F, —CH$_3$, —C$_2$H$_5$, —C$_3$H$_7$) is substituted on the benzo moiety of the central benzo[d]thiazole.

In certain embodiments, the presently disclosed compounds have the structural formula (LXXXVI):

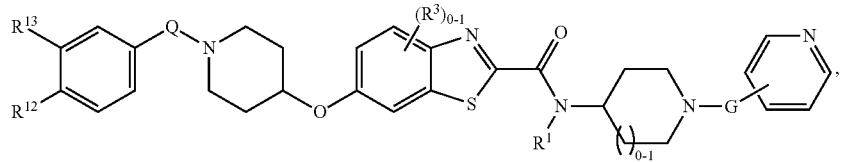

(LXXXVI)

in which Q is —CH$_2$—, —C(O)— or a single bond; G is a single bond, —CH$_2$—, —C(O)—, —S(O)$_2$— or —C(O)—NH—; R$^1$ and R$^3$ are as described above with reference to any of structural formulae (I)-(IV) and (LIX); and R$^{12}$ and R$^{13}$ are independently selected from H, halo, cyano, —(C$_1$-C$_4$ haloalkyl), —O—(C$_1$-C$_4$ haloalkyl), —(C$_1$-C$_4$ alkyl), —O—(C$_1$-C$_4$ alkyl), —C(O)—(C$_0$-C$_4$ alkyl), —C(O)O—(C$_0$-C$_4$ alkyl), —C(O)N(C$_0$-C$_4$ alkyl)(C$_0$-C$_4$ alkyl), NO$_2$ and —C(O)-Hca in which the Hca contains a ring nitrogen atom through which it is bound to the —C(O)—, in which no alkyl, haloalkyl or heterocycloalkyl is substituted by an aryl, heteroaryl, cycloalkyl or heterocycloalkyl-containing group. In one particular such embodiment, at least one of R$^{12}$ and R$^{13}$ is not H. In one embodiment, the pyridine nitrogen is positioned in the para position relative to the G moiety; in another embodiment, the pyridine nitrogen is positioned in the meta position relative to the G moiety. In one embodiment, R$^1$ is H. In another embodiment, R$^1$ is methyl, ethyl, propyl or butyl. In one embodiment, no R$^3$ is substituted on the benzo moiety of the central benzo[d]thiazole. In another embodiment, one R$^3$ (e.g., —Cl, —F, —CH$_3$, —C$_2$H$_5$, —C$_3$H$_7$) is substituted on the benzo moiety of the central benzo[d]thiazole.

In certain embodiments, the presently disclosed compounds have the structural formula (LXXXVII):

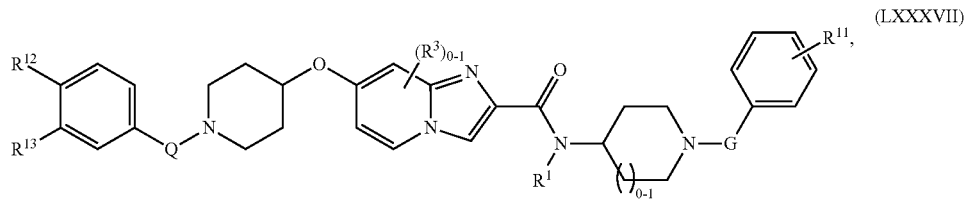

(LXXXVII)

in which Q is —CH$_2$—, —C(O)— or a single bond; G is a single bond, —CH$_2$—, —C(O)—, —S(O)$_2$— or —C(O)—NH—; R$^1$ and R$^3$ are as described above with reference to any of structural formulae (I)-(IV) and (LX); and R$^{11}$, R$^{12}$ and R$^{13}$ are independently selected from H, halo, cyano, —(C$_1$-C$_4$ haloalkyl), —O—(C$_1$-C$_4$ haloalkyl), —(C$_1$-C$_4$ alkyl), —O—(C$_1$-C$_4$ alkyl), —C(O)—(C$_0$-C$_4$ alkyl), —C(O)O—(C$_0$-C$_4$ alkyl), —C(O)N(C$_0$-C$_4$ alkyl)(C$_0$-C$_4$ alkyl), NO$_2$ and —C(O)-Hca in which the Hca contains a ring nitrogen atom through which it is bound to the —C(O)—, in which no alkyl, haloalkyl or heterocycloalkyl is substituted by an aryl, heteroaryl, cycloalkyl or heterocycloalkyl-containing group. In one particular such embodiment, at least one of R$^{11}$, R$^{12}$ and R$^{13}$ is not H. In one embodiment, R$^{11}$ is attached in the para position relative to the G moiety; in another embodiment, R$^{11}$ is attached in the meta position relative to the G moiety. In one embodiment, R$^1$ is H. In another embodiment, R$^1$ is methyl, ethyl, propyl or butyl. In one embodiment, no R$^3$ is substituted on the central imidazo[1,2-a]pyridine. In another embodiment, one R$^3$ (e.g., —Cl, —F, —CH$_3$, —C$_2$H$_5$, —C$_3$H$_7$) is substituted on the central imidazo[1,2-a]pyridine.

In certain embodiments, the presently disclosed compounds have the structural formula (LXXXVIII):

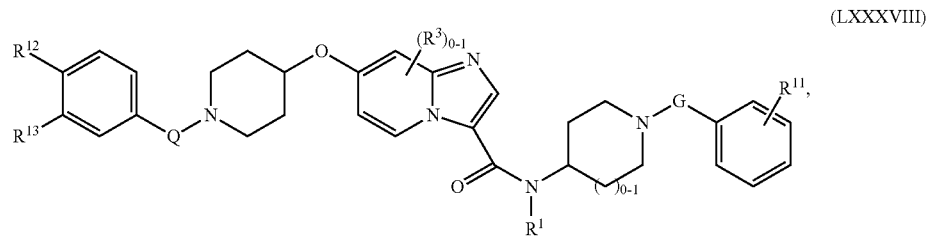

(LXXXVIII)

in which Q is —CH$_2$—, —C(O)— or a single bond; G is a single bond, —CH$_2$—, —C(O)—, —S(O)$_2$— or —C(O)—NH—; R$^1$ and R$^3$ are as described above with reference to any of structural formulae (I)-(IV) and (LXI); and R$^{11}$, R$^{12}$ and R$^{13}$ are independently selected from H, halo, cyano, —(C$_1$-C$_4$ haloalkyl), —O—(C$_1$-C$_4$ haloalkyl), —(C$_1$-C$_4$ alkyl), —O—(C$_1$-C$_4$ alkyl), —C(O)—(C$_0$-C$_4$ alkyl), —C(O)O—(C$_0$-C$_4$ alkyl), —C(O)N(C$_0$-C$_4$ alkyl)(C$_0$-C$_4$ alkyl), NO$_2$ and —C(O)-Hca in which the Hca contains a ring nitrogen atom through which it is bound to the —C(O)—, in which no alkyl, haloalkyl or heterocycloalkyl is substituted by an aryl, heteroaryl, cycloalkyl or heterocycloalkyl-containing group. In one particular such embodiment, at least one of R$^{11}$, R$^{12}$ and R$^{13}$ is not H. In one embodiment, R$^{11}$ is attached in the para position relative to the G moiety; in another embodiment, R$^{11}$ is attached in the meta position relative to the G moiety. In one embodiment, R$^1$ is H. In another embodiment, R$^1$ is methyl, ethyl, propyl or butyl. In one embodiment, no R$^3$ is substituted on the central imidazo[1,2-a]pyridine. In another embodiment, one R$^3$ (e.g., —Cl, —F, —CH$_3$, —C$_2$H$_5$, —C$_3$H$_7$) is substituted on the central imidazo[1,2-a]pyridine.

In certain embodiments, the presently disclosed compounds have the structural formula (LXXXIX):

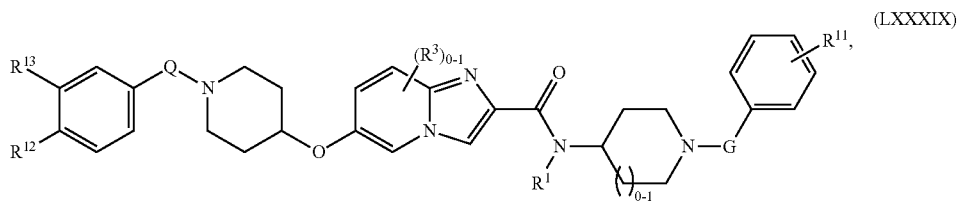

(LXXXIX)

in which Q is —CH$_2$—, —C(O)— or a single bond; G is a single bond, —CH$_2$—, —C(O)—, —S(O)$_2$— or —C(O)—NH—; R$^1$ and R$^3$ are as described above with reference to any of structural formulae (I)-(IV) and (LXII); and R$^{11}$, R$^{12}$ and R$^{13}$ are independently selected from H, halo, cyano, —(C$_1$-C$_4$ haloalkyl), —O—(C$_1$-C$_4$ haloalkyl), —(C$_1$-C$_4$ alkyl), —O—(C$_1$-C$_4$ alkyl), —C(O)—(C$_0$-C$_4$ alkyl), —C(O)O—(C$_0$-C$_4$ alkyl), —C(O)N(C$_0$-C$_4$ alkyl)(C$_0$-C$_4$ alkyl), NO$_2$ and —C(O)-Hca in which the Hca contains a ring nitrogen atom through which it is bound to the —C(O)—, in which no alkyl, haloalkyl or heterocycloalkyl is substituted by an aryl, heteroaryl, cycloalkyl or heterocycloalkyl-containing group. In one particular such embodiment, at least one of R$^{11}$, R$^{12}$ and R$^{13}$ is not H. In one embodiment, R$^{11}$ is attached in the para position relative to the G moiety; in another embodiment, R$^{11}$ is attached in the meta position relative to the G moiety. In one embodiment, R$^1$ is H. In another embodiment, R$^1$ is methyl, ethyl, propyl or butyl. In one embodiment, no R$^3$ is substituted on the central imidazo[1,2-a]pyridine. In another embodiment, one R$^3$ (e.g., —Cl, —F, —CH$_3$, —C$_2$H$_5$, —C$_3$H$_7$) is substituted on the central imidazo[1,2-a]pyridine.

In certain embodiments, the presently disclosed compounds have the structural formula (XC):

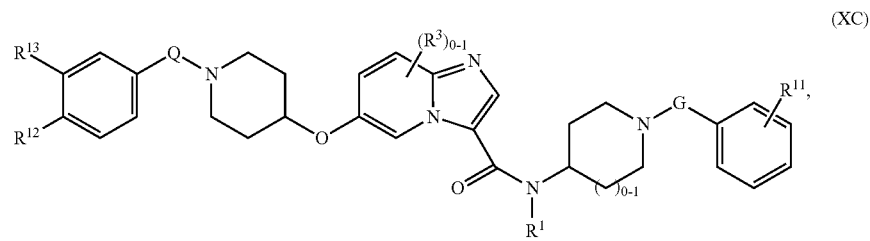

(XC)

in which Q is —CH$_2$—, —C(O)— or a single bond; G is a single bond, —CH$_2$—, —C(O)—, —S(O)$_2$— or —C(O)—NH—; R$^1$ and R$^3$ are as described above with reference to any of structural formulae (I)-(IV) and (LXIII); and R$^{11}$, R$^{12}$ and R$^{13}$ are independently selected from H, halo, cyano, —(C$_1$-C$_4$ haloalkyl), —O—(C$_1$-C$_4$ haloalkyl), —(C$_1$-C$_4$ alkyl), —O—(C$_1$-C$_4$ alkyl), —C(O)—(C$_0$-C$_4$ alkyl), —C(O)O—(C$_0$-C$_4$ alkyl), —C(O)N(C$_0$-C$_4$ alkyl)(C$_0$-C$_4$ alkyl), NO$_2$ and —C(O)-Hca in which the Hca contains a ring nitrogen atom through which it is bound to the —C(O)—, in which no alkyl, haloalkyl or heterocycloalkyl is substituted by an aryl, heteroaryl, cycloalkyl or heterocycloalkyl-containing group. In one particular such embodiment, at least one of R$^{11}$, R$^{12}$ and R$^{13}$ is not H. In one embodiment, R$^{11}$ is attached in the para position relative to the G moiety; in another embodiment, R$^{11}$ is attached in the meta position relative to the G moiety. In one embodiment, R$^1$ is H. In another embodiment, R$^1$ is methyl, ethyl, propyl or butyl. In one embodiment, no R$^3$ is substituted on the central imidazo[1,2-a]pyridine. In another embodiment, one R$^3$ (e.g., —Cl, —F, —CH$_3$, —C$_2$H$_5$, —C$_3$H$_7$) is substituted on the central imidazo[1,2-a]pyridine.

In certain embodiments, the presently disclosed compounds have the structural formula (XCI):

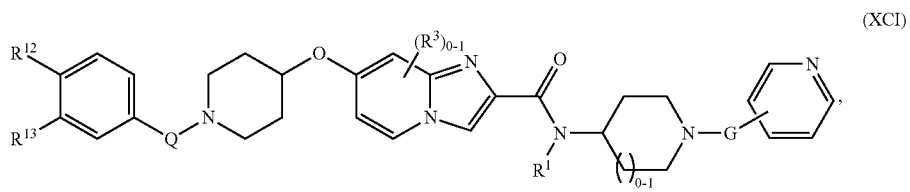

(XCI)

in which Q is —CH$_2$—, —C(O)— or a single bond; G is a single bond, —CH$_2$—, —C(O)—, —S(O)$_2$— or —C(O)—NH—; R$^1$ and R$^3$ are as described above with reference to any of structural formulae (I)-(IV) and (LX); and R$^{12}$ and R$^{13}$ are independently selected from H, halo, cyano, —(C$_1$-C$_4$ haloalkyl), —O—(C$_1$-C$_4$ haloalkyl), —(C$_1$-C$_4$ alkyl), —O—(C$_1$-C$_4$ alkyl), —C(O)—(C$_0$-C$_4$ alkyl), —C(O)O—(C$_0$-C$_4$ alkyl), —C(O)N(C$_0$-C$_4$ alkyl)(C$_0$-C$_4$ alkyl), NO$_2$ and —C(O)-Hca in which the Hca contains a ring nitrogen atom through which it is bound to the —C(O)—, in which no alkyl, haloalkyl or heterocycloalkyl is substituted by an aryl, heteroaryl, cycloalkyl or heterocycloalkyl-containing group. In one particular such embodiment, at least one of R$^{12}$ and R$^{13}$ is not H. In one embodiment, the pyridine nitrogen is positioned in the para position relative to the G moiety; in another embodiment, the pyridine nitrogen is positioned in the meta position relative to the G moiety. In one embodiment, R$^1$ is H. In another embodiment, R$^1$ is methyl, ethyl, propyl or butyl. In one embodiment, no R$^3$ is substituted on the central imidazo[1,2-a]pyridine. In another embodiment, one R$^3$ (e.g., —Cl, —F, —CH$_3$, —C$_2$H$_5$, —C$_3$H$_7$) is substituted on the central imidazo[1,2-a]pyridine.

In certain embodiments, the presently disclosed compounds have the structural formula (XCII):

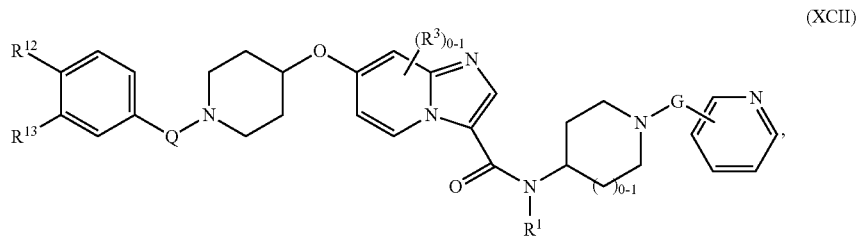

(XCII)

in which Q is —CH$_2$—, —C(O)— or a single bond; G is a single bond, —CH$_2$—, —C(O)—, —S(O)$_2$— or —C(O)—NH—; R$^1$ and R$^3$ are as described above with reference to any of structural formulae (I)-(IV) and (LXI); and R$^{12}$ and R$^{13}$ are independently selected from H, halo, cyano, —(C$_1$-C$_4$ haloalkyl), —O—(C$_1$-C$_4$ haloalkyl), —(C$_1$-C$_4$ alkyl), —O—(C$_1$-C$_4$ alkyl), —C(O)—(C$_0$-C$_4$ alkyl), —C(O)O—(C$_0$-C$_4$ alkyl), —C(O)N(C$_0$-C$_4$ alkyl)(C$_0$-C$_4$ alkyl), NO$_2$ and —C(O)-Hca in which the Hca contains a ring nitrogen atom through which it is bound to the —C(O)—, in which no alkyl, haloalkyl or heterocycloalkyl is substituted by an aryl, heteroaryl, cycloalkyl or heterocycloalkyl-containing group. In one particular such embodiment, at least one of R$^{12}$ and R$^{13}$ is not H. In one embodiment, the pyridine nitrogen is positioned in the para position relative to the G moiety; in another embodiment, the pyridine nitrogen is positioned in the meta position relative to the G moiety. In one embodiment, R$^1$ is H. In another embodiment, R$^1$ is methyl, ethyl, propyl or butyl. In one embodiment, no R$^3$ is substituted on the central imidazo[1,2-a]pyridine. In another embodiment, one R$^3$ (e.g., —Cl, —F, —CH$_3$, —C$_2$H$_5$, —C$_3$H$_7$) is substituted on the central imidazo[1,2-a]pyridine.

In certain embodiments, the presently disclosed compounds have the structural formula (XCIII):

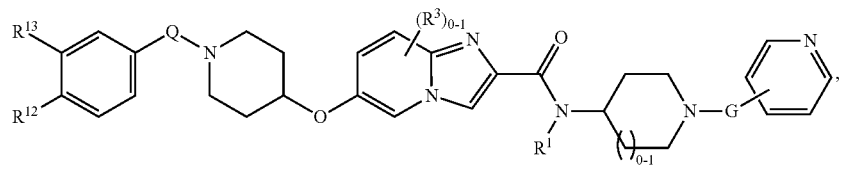

(XCIII)

in which Q is —CH$_2$—, —C(O)— or a single bond; G is a single bond, —CH$_2$—, —C(O)—, —S(O)$_2$— or —C(O)—NH—; R$^1$ and R$^3$ are as described above with reference to any of structural formulae (I)-(IV) and (LXII); and R$^{12}$ and R$^{13}$ are independently selected from H, halo, cyano, —(C$_1$-C$_4$ haloalkyl), —O—(C$_1$-C$_4$ haloalkyl), —(C$_1$-C$_4$ alkyl), —O—(C$_1$-C$_4$ alkyl), —C(O)—(C$_0$-C$_4$ alkyl), —C(O)O—(C$_0$-C$_4$ alkyl), —C(O)N(C$_0$-C$_4$ alkyl)(C$_0$-C$_4$ alkyl), NO$_2$ and —C(O)-Hca in which the Hca contains a ring nitrogen atom through which it is bound to the —C(O)—, in which no alkyl, haloalkyl or heterocycloalkyl is substituted by an aryl, heteroaryl, cycloalkyl or heterocycloalkyl-containing group. In one particular such embodiment, at least one of R$^{12}$ and R$^{13}$ is not H. In one embodiment, the pyridine nitrogen is positioned in the para position relative to the G moiety; in another embodiment, the pyridine nitrogen is positioned in the meta position relative to the G moiety. In one embodiment, R$^1$ is H. In another embodiment, R$^1$ is methyl, ethyl, propyl or butyl. In one embodiment, no R$^3$ is substituted on the central imidazo[1,2-a]pyridine. In another embodiment, one R$^3$ (e.g., —Cl, —F, —CH$_3$, —C$_2$H$_5$, —C$_3$H$_7$) is substituted on the central imidazo[1,2-a]pyridine.

In certain embodiments, the presently disclosed compounds have the structural formula (XCIV):

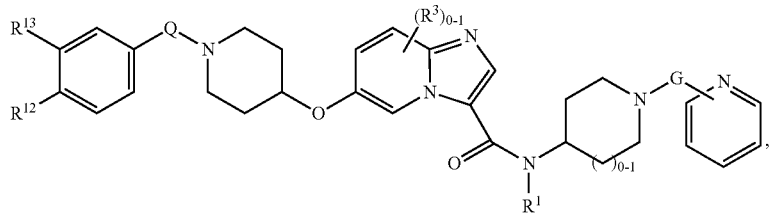

(XCIV)

in which Q is —$CH_2$—, —C(O)— or a single bond; G is a single bond, —$CH_2$—, —C(O)—, —$S(O)_2$— or —C(O)—NH—; $R^1$ and $R^3$ are as described above with reference to any of structural formulae (I)-(IV) and (LXIII); and $R^{12}$ and $R^{13}$ are independently selected from H, halo, cyano, —($C_1$-$C_4$ haloalkyl), —O—($C_1$-$C_4$ haloalkyl), —($C_1$-$C_4$ alkyl), —O—($C_1$-$C_4$ alkyl), —C(O)—($C_0$-$C_4$ alkyl), —C(O)O—($C_0$-$C_4$ alkyl), —C(O)N($C_0$-$C_4$ alkyl)($C_0$-$C_4$ alkyl), $NO_2$ and —C(O)-Hca in which the Hca contains a ring nitrogen atom through which it is bound to the —C(O)—, in which no alkyl, haloalkyl or heterocycloalkyl is substituted by an aryl, heteroaryl, cycloalkyl or heterocycloalkyl-containing group. In one particular such embodiment, at least one of $R^{12}$ and $R^{13}$ is not H. In one embodiment, the pyridine nitrogen is positioned in the para position relative to the G moiety; in another embodiment, the pyridine nitrogen is positioned in the meta position relative to the G moiety. In one embodiment, $R^1$ is H. In another embodiment, $R^1$ is methyl, ethyl, propyl or butyl. In one embodiment, no $R^3$ is substituted on the central imidazo[1,2-a]pyridine. In another embodiment, one $R^3$ (e.g., —Cl, —F, —$CH_3$, —$C_2H_5$, —$C_3H_7$) is substituted on the central imidazo[1,2-a]pyridine.

In certain embodiments, the presently disclosed compounds have the structural formula (XCV):

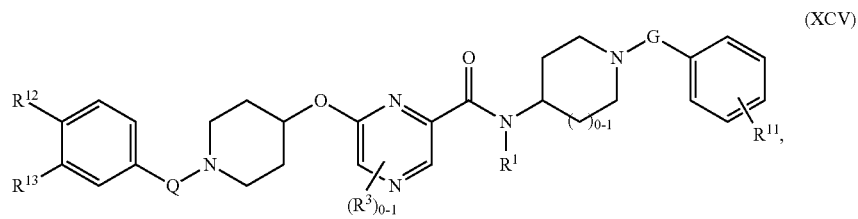

(XCV)

in which Q is —$CH_2$—, —C(O)— or a single bond; G is a single bond, —$CH_2$—, —C(O)—, —$S(O)_2$— or —C(O)—NH—; $R^1$ and $R^3$ are as described above with reference to any of structural formulae (I)-(IV) and (LXIV); and $R^{11}$, $R^{12}$ and $R^{13}$ are independently selected from H, halo, cyano, —($C_1$-$C_4$ haloalkyl), —O—($C_1$-$C_4$ haloalkyl), —($C_1$-$C_4$ alkyl), —O—($C_1$-$C_4$ alkyl), —C(O)—($C_0$-$C_4$ alkyl), —C(O)O—($C_0$-$C_4$ alkyl), —C(O)N($C_0$-$C_4$ alkyl)($C_0$-$C_4$ alkyl), $NO_2$ and —C(O)-Hca in which the Hca contains a ring nitrogen atom through which it is bound to the —C(O)—, in which no alkyl, haloalkyl or heterocycloalkyl is substituted by an aryl, heteroaryl, cycloalkyl or heterocycloalkyl-containing group. In one particular such embodiment, at least one of $R^{11}$, $R^{12}$ and $R^{13}$ is not H. In one embodiment, $R^{11}$ is attached in the para position relative to the G moiety; in another embodiment, $R^{11}$ is attached in the meta position relative to the G moiety. In one embodiment, $R^1$ is H. In another embodiment, $R^1$ is methyl, ethyl, propyl or butyl. In one embodiment, no $R^3$ is substituted on the central pyrazine. In another embodiment, one $R^3$ (e.g., —Cl, —F, —$CH_3$, —$C_2H_5$, —$C_3H_7$) is substituted on the central pyrazine.

In certain embodiments, the presently disclosed compounds have the structural formula (XCVI):

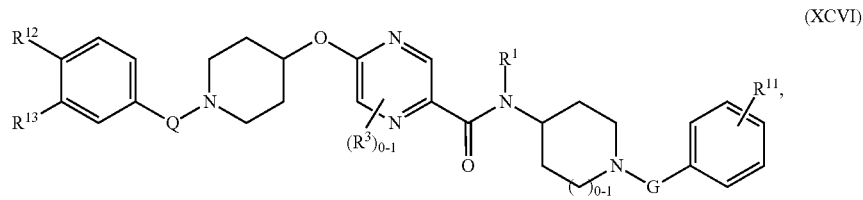

(XCVI)

in which Q is —CH$_2$—, —C(O)— or a single bond; G is a single bond, —CH$_2$—, —C(O)—, —S(O)$_2$— or —C(O)—NH—; R$^1$ and R$^3$ are as described above with reference to any of structural formulae (I)-(IV) and (LXV); and R$^{11}$, R$^{12}$ and R$^{13}$ are independently selected from H, halo, cyano, —(C$_1$-C$_4$ haloalkyl), —O—(C$_1$-C$_4$ haloalkyl), —(C$_1$-C$_4$ alkyl), —O—(C$_1$-C$_4$ alkyl), —C(O)—(C$_0$-C$_4$ alkyl), —C(O)O—(C$_0$-C$_4$ alkyl), —C(O)N(C$_0$-C$_4$ alkyl)(C$_0$-C$_4$ alkyl), NO$_2$ and —C(O)-Hca in which the Hca contains a ring nitrogen atom through which it is bound to the —C(O)—, in which no alkyl, haloalkyl or heterocycloalkyl is substituted by an aryl, heteroaryl, cycloalkyl or heterocycloalkyl-containing group. In one particular such embodiment, at least one of R$^{11}$, R$^{12}$ and R$^{13}$ is not H. In one embodiment, R$^{11}$ is attached in the para position relative to the G moiety; in another embodiment, R$^{11}$ is attached in the meta position relative to the G moiety. In one embodiment, R$^1$ is H. In another embodiment, R$^1$ is methyl, ethyl, propyl or butyl. In one embodiment, no R$^3$ is substituted on the central pyrazine. In another embodiment, one R$^3$ (e.g., —Cl, —F, —CH$_3$, —C$_2$H$_5$, —C$_3$H$_7$) is substituted on the central pyrazine.

In certain embodiments, the presently disclosed compounds have the structural formula (XCVII):

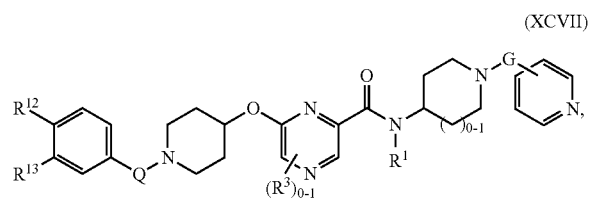

(XCVII)

in which Q is —CH$_2$—, —C(O)— or a single bond; G is a single bond, —CH$_2$—, —C(O)—, —S(O)$_2$— or —C(O)—NH—; R$^1$ and R$^3$ are as described above with reference to any of structural formulae (I) and (LXIV); and R$^{12}$ and R$^{13}$ are independently selected from H, halo, cyano, —(C$_1$-C$_4$ haloalkyl), —O—(C$_1$-C$_4$ haloalkyl), —(C$_1$-C$_4$ alkyl), —O—(C$_1$-C$_4$ alkyl), —C(O)—(C$_0$-C$_4$ alkyl), —C(O)O—(C$_0$-C$_4$ alkyl), —C(O)N(C$_0$-C$_4$ alkyl)(C$_0$-C$_4$ alkyl), NO$_2$ and —C(O)-Hca in which the Hca contains a ring nitrogen atom through which it is bound to the —C(O)—, in which no alkyl, haloalkyl or heterocycloalkyl is substituted by an aryl, heteroaryl, cycloalkyl or heterocycloalkyl-containing group. In one particular such embodiment, at least one of R$^{12}$ and R$^{13}$ is not H. In one embodiment, the pyridine nitrogen is positioned in the para position relative to the G moiety; in another embodiment, the pyridine nitrogen is positioned in the meta position relative to the G moiety. In one embodiment, R$^1$ is H.

In another embodiment, R$^1$ is methyl, ethyl, propyl or butyl. In one embodiment, no R$^3$ is substituted on the central pyrazine. In another embodiment, one R$^3$ (e.g., —Cl, —F, —CH$_3$, —C$_2$H$_5$, —C$_3$H$_7$) is substituted on the central pyrazine.

In certain embodiments, the presently disclosed compounds have the structural formula (XCVIII):

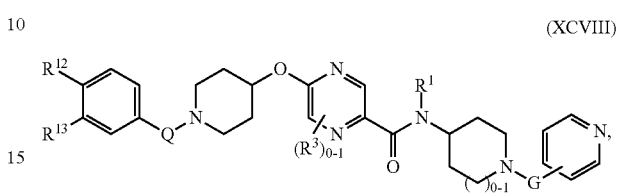

(XCVIII)

in which Q is —CH$_2$—, —C(O)— or a single bond; G is a single bond, —CH$_2$—, —C(O)—, —S(O)$_2$— or —C(O)—NH—; R$^1$ and R$^3$ are as described above with reference to any of structural formulae (I)-(IV) and (LXV); and R$^{12}$ and R$^{13}$ are independently selected from H, halo, cyano, —(C$_1$-C$_4$ haloalkyl), —O—(C$_1$-C$_4$ haloalkyl), —(C$_1$-C$_4$ alkyl), —O—(C$_1$-C$_4$ alkyl), —C(O)—(C$_0$-C$_4$ alkyl), —C(O)O—(C$_0$-C$_4$ alkyl), —C(O)N(C$_0$-C$_4$ alkyl)(C$_0$-C$_4$ alkyl), NO$_2$ and —C(O)-Hca in which the Hca contains a ring nitrogen atom through which it is bound to the —C(O)—, in which no alkyl, haloalkyl or heterocycloalkyl is substituted by an aryl, heteroaryl, cycloalkyl or heterocycloalkyl-containing group. In one particular such embodiment, at least one of R$^{12}$ and R$^{13}$ is not H. In one embodiment, the pyridine nitrogen is positioned in the para position relative to the G moiety; in another embodiment, the pyridine nitrogen is positioned in the meta position relative to the G moiety. In one embodiment, R$^1$ is H. In another embodiment, R$^1$ is methyl, ethyl, propyl or butyl. In one embodiment, no R$^3$ is substituted on the central pyrazine. In another embodiment, one R$^3$ (e.g., —Cl, —F, —CH$_3$, —C$_2$H$_5$, —C$_3$H$_7$) is substituted on the central pyrazine.

In certain embodiments, the presently disclosed compounds have the structural formula (XCIX):

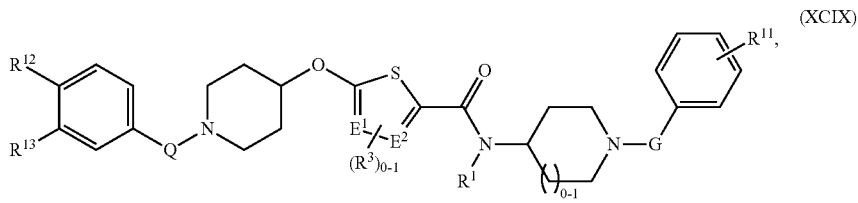

(XCIX)

in which Q is —CH$_2$—, —C(O)— or a single bond; G is a single bond, —CH$_2$—, —C(O)—, —S(O)$_2$— or —C(O)—NH—E$^1$, E$^2$, R$^1$ and R$^3$ are as described above with reference to any of structural formulae (I)-(IV) and (LXVI); and R$^{11}$, R$^{12}$ and R$^{13}$ are independently selected from H, halo, cyano, —(C$_1$-C$_4$ haloalkyl), —O—(C$_1$-C$_4$ haloalkyl), —(C$_1$-C$_4$ alkyl), —O—(C$_1$-C$_4$ alkyl), —C(O)—(C$_0$-C$_4$ alkyl), —C(O)O—(C$_0$-C$_4$ alkyl), —C(O)N(C$_0$-C$_4$ alkyl)(C$_0$-C$_4$ alkyl), NO$_2$ and —C(O)-Hca in which the Hca contains a ring nitrogen atom through which it is bound to the —C(O)—, in which no alkyl, haloalkyl or heterocycloalkyl is substituted by an aryl, heteroaryl, cycloalkyl or heterocycloalkyl-containing group. In one particular such embodiment, at least one of $R^{11}$, $R^{12}$ and $R^{13}$ is not H. In one embodiment, $R^{11}$ is attached in the para position relative to the G moiety; in another embodiment, $R^{11}$ is attached in the meta position relative to the G moiety. In one embodiment, $R^1$ is H. In another embodiment, $R^1$ is methyl, ethyl, propyl or butyl. In one embodiment, no $R^3$ is substituted on the central thiazole. In another embodiment, one $R^3$ (e.g., —Cl, —F, —CH$_3$, —C$_2$H$_5$, —C$_3$H$_7$) is substituted on the central thiazole. In one embodiment, $E^1$ is carbon and $E^2$ is N. In another embodiment, $E^1$ is N and $E^2$ is carbon.

In certain embodiments, the presently disclosed compounds have the structural formula (C):

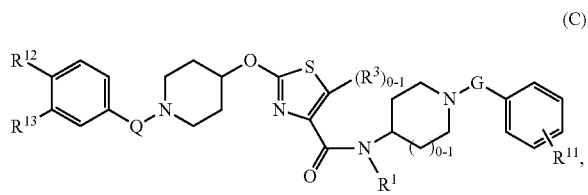

(C)

in which Q is —CH$_2$—, —C(O)— or a single bond; G is a single bond, —CH$_2$—, —C(O)—, —S(O)$_2$— or —C(O)—NH—; $R^1$ and $R^3$ are as described above with reference to any of structural formulae (I)-(IV) and (LXVII); and $R^{11}$, $R^{12}$ and $R^{13}$ are independently selected from H, halo, cyano, —(C$_1$-C$_4$ haloalkyl), —O—(C$_1$-C$_4$ haloalkyl), —(C$_1$-C$_4$ alkyl), —O—(C$_1$-C$_4$ alkyl), —C(O)—(C$_0$-C$_4$ alkyl), —C(O)O—(C$_0$-C$_4$ alkyl), —C(O)N(C$_0$-C$_4$ alkyl)(C$_0$-C$_4$ alkyl), NO$_2$ and —C(O)-Hca in which the Hca contains a ring nitrogen atom through which it is bound to the —C(O)—, in which no alkyl, haloalkyl or heterocycloalkyl is substituted by an aryl, heteroaryl, cycloalkyl or heterocycloalkyl-containing group. In one particular such embodiment, at least one of $R^{11}$, $R^{12}$ and $R^{13}$ is not H. In one embodiment, $R^{11}$ is attached in the para position relative to the G moiety; in another embodiment, $R^{11}$ is attached in the meta position relative to the G moiety. In one embodiment, $R^1$ is H. In another embodiment, $R^1$ is methyl, ethyl, propyl or butyl. In one embodiment, no $R^3$ is substituted on the central thiazole (i.e., the ring position shown occupied by $R^3$ bears a hydrogen atom). In another embodiment, one $R^3$ (e.g., —Cl, —F, —CH$_3$, —C$_2$H$_5$, —C$_3$H$_7$) is substituted on the central thiazole.

In certain embodiments, the presently disclosed compounds have the structural formula (CI):

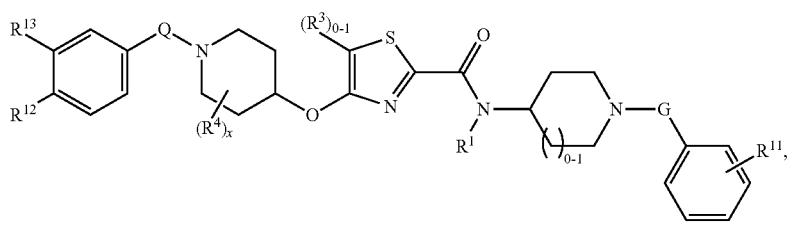

(CI)

in which Q is —CH$_2$—, —C(O)— or a single bond; G is a single bond, —CH$_2$—, —C(O)—, —S(O)$_2$— or —C(O)—NH—; $R^1$ and $R^3$ are as described above with reference to any of structural formulae (I)-(IV) and (LXVIII); and $R^{11}$, $R^{12}$ and $R^{13}$ are independently selected from H, halo, cyano, —(C$_1$-C$_4$ haloalkyl), —O—(C$_1$-C$_4$ haloalkyl), —(C$_1$-C$_4$ alkyl), —O—(C$_1$-C$_4$ alkyl), —C(O)—(C$_0$-C$_4$ alkyl), —C(O)O—(C$_0$-C$_4$ alkyl), —C(O)N(C$_0$-C$_4$ alkyl)(C$_0$-C$_4$ alkyl), NO$_2$ and —C(O)-Hca in which the Hca contains a ring nitrogen atom through which it is bound to the —C(O)—, in which no alkyl, haloalkyl or heterocycloalkyl is substituted by an aryl, heteroaryl, cycloalkyl or heterocycloalkyl-containing group. In one particular such embodiment, at least one of $R^{11}$, $R^{12}$ and $R^{13}$ is not H. In one embodiment, $R^{11}$ is attached in the para position relative to the G moiety; in another embodiment, $R^{11}$ is attached in the meta position relative to the G moiety. In one embodiment, $R^1$ is H. In another embodiment, $R^1$ is methyl, ethyl, propyl or butyl. In one embodiment, no $R^3$ is substituted on the central thiazole (i.e., the ring position shown occupied by $R^3$ bears a hydrogen atom). In another embodiment, one $R^3$ (e.g., —Cl, —F, —CH$_3$, —C$_2$H$_5$, —C$_3$H$_7$) is substituted on the central thiazole.

In certain embodiments, the presently disclosed compounds have the structural formula (CII):

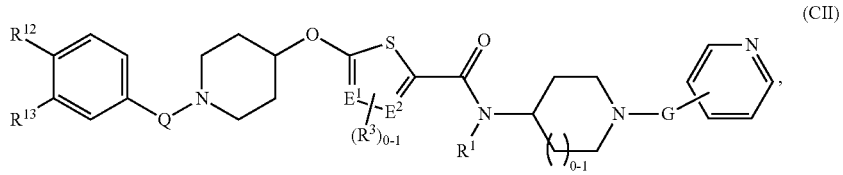

(CII)

in which Q is —CH$_2$—, —C(O)— or a single bond; G is a single bond, —CH$_2$—, —C(O)—, —S(O)$_2$— or —C(O)—NH—E$^1$, E$^2$, R$^1$ and R$^3$ are as described above with reference to any of structural formulae (I)-(IV) and (LXVI); and R$^{11}$, R$^{12}$ and R$^{13}$ are independently selected from H, halo, cyano, —(C$_1$-C$_4$ haloalkyl), —O—(C$_1$-C$_4$ haloalkyl), —(C$_1$-C$_4$ alkyl), —O—(C$_1$-C$_4$ alkyl), —C(O)—(C$_0$-C$_4$ alkyl), —C(O)O—(C$_0$-C$_4$ alkyl), —C(O)N(C$_0$-C$_4$ alkyl)(C$_0$-C$_4$ alkyl), NO$_2$ and —C(O)-Hca in which the Hca contains a ring nitrogen atom through which it is bound to the —C(O)—, in which no alkyl, haloalkyl or heterocycloalkyl is substituted by an aryl, heteroaryl, cycloalkyl or heterocycloalkyl-containing group. In one embodiment, the pyridine nitrogen is positioned in the para position relative to the G moiety; in another embodiment, the pyridine nitrogen is positioned in the meta position relative to the G moiety. In one embodiment, R$^1$ is H. In another embodiment, R$^1$ is methyl, ethyl, propyl or butyl. In one embodiment, no R$^3$ is substituted on the central thiazole.

In another embodiment, one R$^3$ (e.g., —Cl, —F, —CH$_3$, —C$_2$H$_5$, —C$_3$H$_7$) is substituted on the central thiazole. In one embodiment, E$^1$ is carbon and E$^2$ is N. In another embodiment, E$^1$ is N and E$^2$ is carbon.

In certain embodiments, the presently disclosed compounds have the structural formula (CIII):

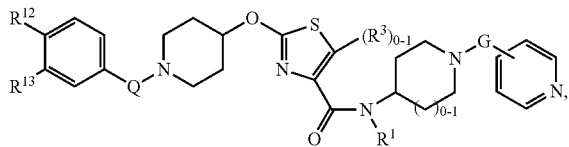

(CIII)

in which Q is —CH$_2$—, —C(O)— or a single bond; G is a single bond, —CH$_2$—, —C(O)—, —S(O)$_2$— or —C(O)—NH—; R$^1$ and R$^3$ are as described above with reference to any of structural formulae (I)-(IV) and (LXVII); and R$^{11}$, R$^{12}$ and R$^{13}$ are independently selected from H, halo, cyano, —(C$_1$-C$_4$ haloalkyl), —O—(C$_1$-C$_4$ haloalkyl), —(C$_1$-C$_4$ alkyl), —O—(C$_1$-C$_4$ alkyl), —C(O)—(C$_0$-C$_4$ alkyl), —C(O)O—(C$_0$-C$_4$ alkyl), —C(O)N(C$_0$-C$_4$ alkyl)(C$_0$-C$_4$ alkyl), NO$_2$ and —C(O)-Hca in which the Hca contains a ring nitrogen atom through which it is bound to the —C(O)—, in which no alkyl, haloalkyl or heterocycloalkyl is substituted by an aryl, heteroaryl, cycloalkyl or heterocycloalkyl-containing group. In one embodiment, the pyridine nitrogen is positioned in the para position relative to the G moiety; in another embodiment, the pyridine nitrogen is positioned in the meta position relative to the G moiety. In one embodiment, R$^1$ is H. In another embodiment, R$^1$ is methyl, ethyl, propyl or butyl. In one embodiment, no R$^3$ is substituted on the central thiazole (i.e., the ring position shown occupied by R$^3$ bears a hydrogen atom). In another embodiment, one R$^3$ (e.g., —Cl, —F, —CH$_3$, —C$_2$H$_5$, —C$_3$H$_7$) is substituted on the central thiazole.

In certain embodiments, the presently disclosed compounds have the structural formula (CIV):

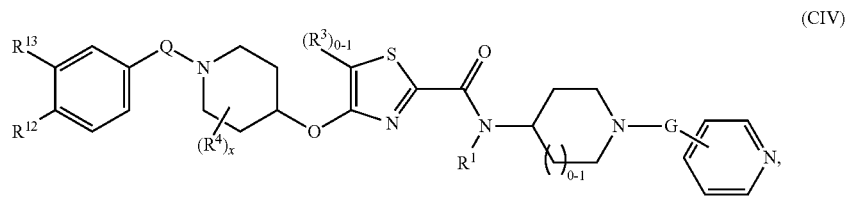

(CIV)

in which Q is —CH$_2$—, —C(O)— or a single bond; G is a single bond, —CH$_2$—, —C(O)—, —S(O)$_2$— or —C(O)—NH—; R$^1$ and R$^3$ are as described above with reference to any of structural formulae (I)-(IV) and (LXVIII); and R$^{11}$, R$^{12}$ and R$^{13}$ are independently selected from H, halo, cyano, —(C$_1$-C$_4$ haloalkyl), —O—(C$_1$-C$_4$ haloalkyl), —(C$_1$-C$_4$ alkyl), —O—(C$_1$-C$_4$ alkyl), —C(O)—(C$_0$-C$_4$ alkyl), —C(O)O—(C$_0$-C$_4$ alkyl), —C(O)N(C$_0$-C$_4$ alkyl)(C$_0$-C$_4$ alkyl), NO$_2$ and —C(O)-Hca in which the Hca contains a ring nitrogen atom through which it is bound to the —C(O)—, in which no alkyl, haloalkyl or heterocycloalkyl is substituted by an aryl, heteroaryl, cycloalkyl or heterocycloalkyl-containing group. In one embodiment, the pyridine nitrogen is positioned in the para position relative to the G moiety; in another embodiment, the pyridine nitrogen is positioned in the meta position relative to the G moiety. In one embodiment, R$^1$ is H. In another embodiment, R$^1$ is methyl, ethyl, propyl or butyl. In one embodiment, no R$^3$ is substituted on the central thiazole (i.e., the ring position shown occupied by R$^3$ bears a hydrogen atom). In another embodiment, one R$^3$ (e.g., —Cl, —F, —CH$_3$, —C$_2$H$_5$, —C$_3$H$_7$) is substituted on the central thiazole.

In certain embodiments, the presently disclosed compounds have the structural formula (CV):

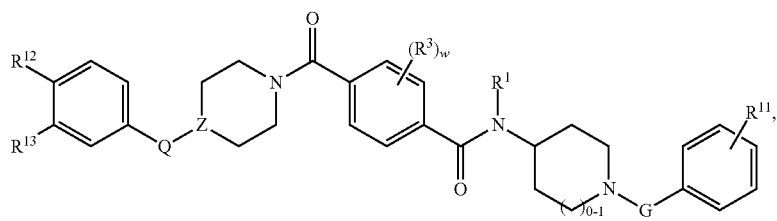

(CV)

in which Q is —CH₂—, —C(O)— or a single bond; G is a single bond, —CH₂—, —C(O)—, —S(O)₂— or —C(O)—NH—; Z, R¹ and R³ are as described above with reference to any of structural formulae (I)-(IV) and (LXIX); and R¹¹, R¹² and R¹³ are independently selected from H, halo, cyano, —(C₁-C₄ haloalkyl), —O—(C₁-C₄ haloalkyl), —(C₁-C₄ alkyl), —O—(C₁-C₄ alkyl), —C(O)—(C₀-C₄ alkyl), —C(O)O—(C₀-C₄ alkyl), —C(O)N(C₀-C₄ alkyl)(C₀-C₄ alkyl), NO₂ and —C(O)-Hca in which the Hca contains a ring nitrogen atom through which it is bound to the —C(O)—, in which no alkyl, haloalkyl or heterocycloalkyl is substituted by an aryl, heteroaryl, cycloalkyl or heterocycloalkyl-containing group.

In one particular such embodiment, at least one of R¹¹, R¹² and R¹³ is not H. In one embodiment, R¹¹ is attached in the para position relative to the G moiety; in another embodiment, R¹¹ is attached in the meta position relative to the G moiety. In one embodiment, R¹ is H. In another embodiment, R¹ is methyl, ethyl, propyl or butyl. In one embodiment, no R³ is substituted on the central phenyl ring. In another embodiment, one R³ (e.g., —Cl, —F, —CH₃, —C₂H₅, —C₃H₇) is substituted on the central phenyl ring. In one embodiment, Z is N. In another embodiment, Z is CH.

In certain embodiments, the presently disclosed compounds have the structural formula (CVI):

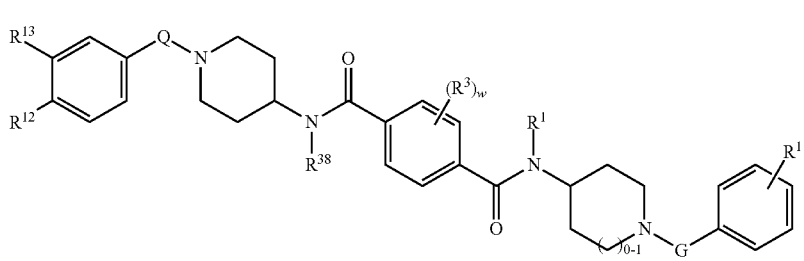

(CVI)

in which Q is —CH₂—, —C(O)— or a single bond; G is a single bond, —CH₂—, —C(O)—, —S(O)₂— or —C(O)—NH—; R¹, R³ and R³⁸ are as described above with reference to any of structural formulae (I)-(IV) and (LXX); and R¹¹, R¹² and R¹³ are independently selected from H, halo, cyano, —(C₁-C₄ haloalkyl), —O—(C₁-C₄ haloalkyl), —(C₁-C₄ alkyl), —O—(C₁-C₄ alkyl), —C(O)—(C₀-C₄ alkyl), —C(O)O—(C₀-C₄ alkyl), —C(O)N(C₀-C₄ alkyl)(C₀-C₄ alkyl), NO₂ and —C(O)-Hca in which the Hca contains a ring nitrogen atom through which it is bound to the —C(O)—, in which no alkyl, haloalkyl or heterocycloalkyl is substituted by an aryl, heteroaryl, cycloalkyl or heterocycloalkyl-containing group. In one particular such embodiment, at least one of R¹¹, R¹² and R¹³ is not H. In one embodiment, R¹¹ is attached in the para position relative to the G moiety; in another embodiment, R¹¹ is attached in the meta position relative to the G moiety. In one embodiment, R¹ is H. In another embodiment, R¹ is methyl, ethyl, propyl or butyl. In one embodiment, no R³ is substituted on the central phenyl ring. In another embodiment, one R³ (e.g., —Cl, —F, —CH₃, —C₂H₅, —C₃H₇) is substituted on the central phenyl ring. In one embodiment, R³⁸ is H. In another embodiment, R³⁸ is methyl, ethyl, propyl or butyl.

In certain embodiments, the presently disclosed compounds have the structural formula (CVII):

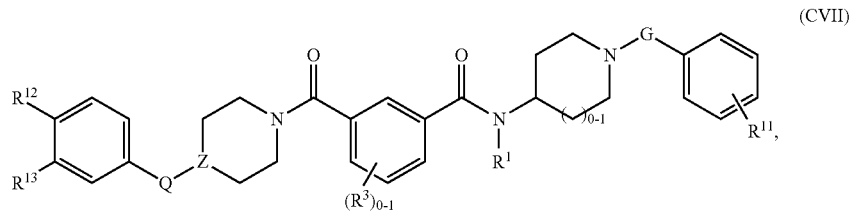

(CVII)

in which Q is —CH$_2$—, —C(O)— or a single bond; G is a single bond, —CH$_2$—, —C(O)—, —S(O)$_2$— or —C(O)—NH—; Z, R$^1$ and R$^3$ are as described above with reference to any of structural formulae (I)-(IV) and (LXXI); and R$^{11}$, R$^{12}$ and R$^{13}$ are independently selected from H, halo, cyano, —(C$_1$-C$_4$ haloalkyl), —O—(C$_1$-C$_4$ haloalkyl), —(C$_1$-C$_4$ alkyl), —O—(C$_1$-C$_4$ alkyl), —C(O)—(C$_0$-C$_4$ alkyl), —C(O)O—(C$_0$-C$_4$ alkyl), —C(O)N(C$_0$-C$_4$ alkyl)(C$_0$-C$_4$ alkyl), NO$_2$ and —C(O)-Hca in which the Hca contains a ring nitrogen atom through which it is bound to the —C(O)—, in which no alkyl, haloalkyl or heterocycloalkyl is substituted by an aryl, heteroaryl, cycloalkyl or heterocycloalkyl-containing group. In one particular such embodiment, at least one of R$^{11}$, R$^{12}$ and R$^{13}$ is not H. In one embodiment, R$^{11}$ is attached in the para position relative to the G moiety; in another embodiment, R$^{11}$ is attached in the meta position relative to the G moiety. In one embodiment, R$^1$ is H. In another embodiment, R$^1$ is methyl, ethyl, propyl or butyl. In one embodiment, no R$^3$ is substituted on the central phenyl ring. In another embodiment, one R$^3$ (e.g., —Cl, —F, —CH$_3$, —C$_2$H$_5$, —C$_3$H$_7$) is substituted on the central phenyl ring. In one embodiment, Z is N. In another embodiment, Z is CH.

In certain embodiments, the presently disclosed compounds have the structural formula (CVIII):

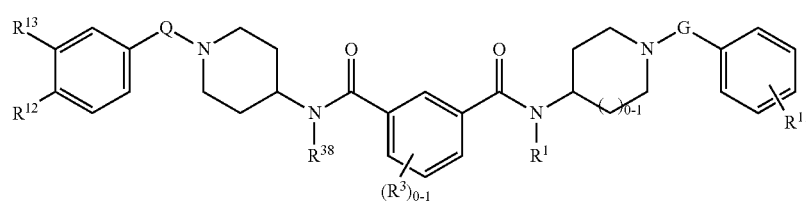

(CVIII)

in which Q is —CH$_2$—, —C(O)— or a single bond; G is a single bond, —CH$_2$—, —C(O)—, —S(O)$_2$— or —C(O)—NH—; R$^1$, R$^3$ and R$^{38}$ are as described above with reference to any of structural formulae (I)-(IV) and (DOM); and R$^{11}$, R$^{12}$ and R$^{13}$ are independently selected from H, halo, cyano, —(C$_1$-C$_4$ haloalkyl), —O—(C$_1$-C$_4$ haloalkyl), —(C$_1$-C$_4$ alkyl), —O—(C$_1$-C$_4$ alkyl), —C(O)—(C$_0$-C$_4$ alkyl), —C(O)O—(C$_0$-C$_4$ alkyl), —C(O)N(C$_0$-C$_4$ alkyl)(C$_0$-C$_4$ alkyl), NO$_2$ and —C(O)-Hca in which the Hca contains a ring nitrogen atom through which it is bound to the —C(O)—, in which no alkyl, haloalkyl or heterocycloalkyl is substituted by an aryl, heteroaryl, cycloalkyl or heterocycloalkyl-containing group. In one particular such embodiment, at least one of R$^{11}$, R$^{12}$ and R$^{13}$ is not H. In one embodiment, R$^{11}$ is attached in the para position relative to the G moiety; in another embodiment, R$^{11}$ is attached in the meta position relative to the G moiety. In one embodiment, R$^1$ is H. In another embodiment, R$^1$ is methyl, ethyl, propyl or butyl. In one embodiment, no R$^3$ is substituted on the central phenyl ring. In another embodiment, one R$^3$ (e.g., —Cl, —F, —CH$_3$, —C$_2$H$_5$, —C$_3$H$_7$) is substituted on the central phenyl ring. In one embodiment, R$^{38}$ is H. In another embodiment, R$^{38}$ is methyl, ethyl, propyl or butyl.

In certain embodiments, the presently disclosed compounds have the structural formula (CIX):

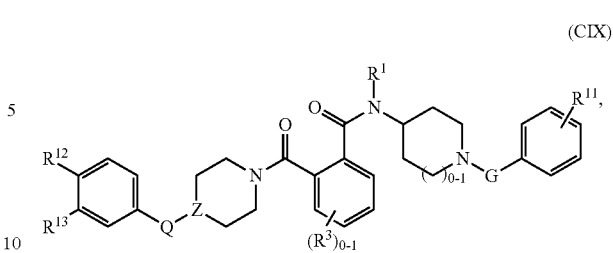

(CIX)

in which Q is —CH$_2$—, —C(O)— or a single bond; G is a single bond, —CH$_2$—, —C(O)—, —S(O)$_2$— or —C(O)—NH—; Z, R$^1$ and R$^3$ are as described above with reference to any of structural formulae (I)-(IV) and (LXXIII); and R$^{11}$, R$^{12}$ and R$^{13}$ are independently selected from H, halo, cyano, —(C$_1$-C$_4$ haloalkyl), —O—(C$_1$-C$_4$ haloalkyl), —(C$_1$-C$_4$ alkyl), —O—(C$_1$-C$_4$ alkyl), —C(O)—(C$_0$-C$_4$ alkyl), —C(O)O—(C$_0$-C$_4$ alkyl), —C(O)N(C$_0$-C$_4$ alkyl)(C$_0$-C$_4$ alkyl), NO$_2$ and —C(O)-Hca in which the Hca contains a ring nitrogen atom through which it is bound to the —C(O)—, in which no alkyl, haloalkyl or heterocycloalkyl is substituted by an aryl, heteroaryl, cycloalkyl or heterocycloalkyl-containing group. In one particular such embodiment, at least one of R$^{11}$, R$^{12}$ and R$^{13}$ is not H. In one embodiment, R$^{11}$ is attached in the para position relative to the G moiety; in another embodiment, R$^{11}$ is attached in the meta position relative to the G moiety. In one embodiment, R$^1$ is H. In another embodiment, R$^1$ is methyl, ethyl, propyl or butyl. In one embodiment, no R$^3$ is substituted on the central phenyl ring. In another embodiment, one R$^3$ (e.g., —Cl, —F, —CH$_3$, —C$_2$H$_5$, —C$_3$H$_7$) is substituted on the central phenyl ring. In one embodiment, Z is N. In another embodiment, Z is CH.

In certain embodiments, the presently disclosed compounds have the structural formula (CX):

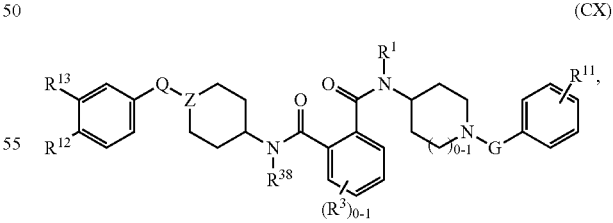

(CX)

in which Q is —CH$_2$—, —C(O)— or a single bond; G is a single bond, —CH$_2$—, —C(O)—, —S(O)$_2$— or —C(O)—NH—; R$^1$, R$^3$ and R$^{38}$ are as described above with reference to any of structural formulae (I)-(IV) and (LXXIV); and R$^{11}$, R$^{12}$ and R$^{13}$ are independently selected from H, halo, cyano, —(C$_1$-C$_4$ haloalkyl), —O—(C$_1$-C$_4$ haloalkyl), —(C$_1$-C$_4$ alkyl), —O—(C$_1$-C$_4$ alkyl), —C(O)—(C$_0$-C$_4$ alkyl), —C(O)O—(C$_0$-C$_4$ alkyl), —C(O)N(C$_0$-C$_4$ alkyl)(C$_0$-C$_4$ alkyl), NO$_2$ and —C(O)-Hca in which the Hca contains a ring nitrogen atom through which it is bound to the —C(O)—, in which no alkyl, haloalkyl or heterocycloalkyl is substituted by an aryl, heteroaryl, cycloalkyl or heterocycloalkyl-containing group. In one particular such embodiment, at least one of $R^{11}$, $R^{12}$ and $R^{13}$ is not H. In one embodiment, $R^{11}$ is attached in the para position relative to the G moiety; in another embodiment, $R^{11}$ is attached in the meta position relative to the G moiety. In one embodiment, $R^1$ is H. In another embodiment, $R^1$ is methyl, ethyl, propyl or butyl. In one embodiment, no $R^3$ is substituted on the central phenyl ring. In another embodiment, one $R^3$ (e.g., —Cl, —F, —CH$_3$, —C$_2$H$_5$, —C$_3$H$_7$) is substituted on the central phenyl ring. In one embodiment, $R^{38}$ is H. In another embodiment, $R^{38}$ is methyl, ethyl, propyl or butyl.

In certain embodiments, the presently disclosed compounds have the structural formula (CXI):

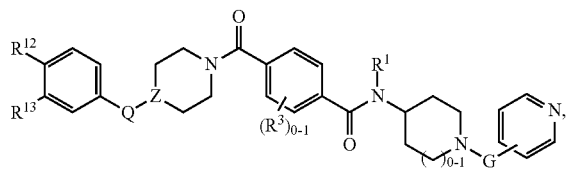

(CXI)

in which Q is —CH$_2$—, —C(O)— or a single bond; G is a single bond, —CH$_2$—, —C(O)—, —S(O)$_2$— or —C(O)—NH—; Z, $R^1$ and $R^3$ are as described above with reference to any of structural formulae (I)-(IV) and (LXIX); and $R^{12}$ and $R^{13}$ are independently selected from H, halo, cyano, —(C$_1$-C$_4$ haloalkyl), —O—(C$_1$-C$_4$ haloalkyl), —(C$_1$-C$_4$ alkyl), —O—(C$_1$-C$_4$ alkyl), —C(O)—(C$_0$-C$_4$ alkyl), —C(O)O—(C$_0$-C$_4$ alkyl), —C(O)N(C$_0$-C$_4$ alkyl)(C$_0$-C$_4$ alkyl), NO$_2$ and —C(O)-Hca in which the Hca contains a ring nitrogen atom through which it is bound to the —C(O)—, in which no alkyl, haloalkyl or heterocycloalkyl is substituted by an aryl, heteroaryl, cycloalkyl or heterocycloalkyl-containing group. In one particular such embodiment, at least one of $R^{12}$ and $R^{13}$ is not H. In one embodiment, the pyridine nitrogen is positioned in the para position relative to the G moiety; in another embodiment, the pyridine nitrogen is positioned in the meta position relative to the G moiety. In one embodiment, $R^1$ is H. In another embodiment, $R^1$ is methyl, ethyl, propyl or butyl. In one embodiment, no $R^3$ is substituted on the central phenyl ring. In another embodiment, one $R^3$ (e.g., —Cl, —F, —CH$_3$, —C$_2$H$_5$, —C$_3$H$_7$) is substituted on the central phenyl ring. In one embodiment, Z is N. In another embodiment, Z is CH.

In certain embodiments, the presently disclosed compounds have the structural formula (CXII):

in which Q is —CH$_2$—, —C(O)— or a single bond; G is a single bond, —CH$_2$—, —C(O)—, —S(O)$_2$— or —C(O)—NH—; $R^1$, $R^3$ and $R^{38}$ are as described above with reference to any of structural formulae (I)-(IV) and (LXX); and $R^{12}$ and $R^{13}$ are independently selected from H, halo, cyano, —(C$_1$-C$_4$ haloalkyl), —O—(C$_1$-C$_4$ haloalkyl), —(C$_1$-C$_4$ alkyl), —O—(C$_1$-C$_4$ alkyl), —C(O)—(C$_0$-C$_4$ alkyl), —C(O)O—(C$_0$-C$_4$ alkyl), —C(O)N(C$_0$-C$_4$ alkyl)(C$_0$-C$_4$ alkyl), NO$_2$ and —C(O)-Hca in which the Hca contains a ring nitrogen atom through which it is bound to the —C(O)—, in which no alkyl, haloalkyl or heterocycloalkyl is substituted by an aryl, heteroaryl, cycloalkyl or heterocycloalkyl-containing group. In one particular such embodiment, at least one of $R^{12}$ and $R^{13}$ is not H. In one embodiment, the pyridine nitrogen is positioned in the para position relative to the G moiety; in another embodiment, the pyridine nitrogen is positioned in the meta position relative to the G moiety. In one embodiment, $R^1$ is H. In another embodiment, $R^1$ is methyl, ethyl, propyl or butyl. In one embodiment, no $R^3$ is substituted on the central phenyl ring. In another embodiment, one $R^3$ (e.g., —Cl, —F, —CH$_3$, —C$_2$H$_5$, —C$_3$H$_7$) is substituted on the central phenyl ring. In one embodiment, $R^{38}$ is H. In another embodiment, $R^{38}$ is methyl, ethyl, propyl or butyl.

In certain embodiments, the presently disclosed compounds have the structural formula (CXIII):

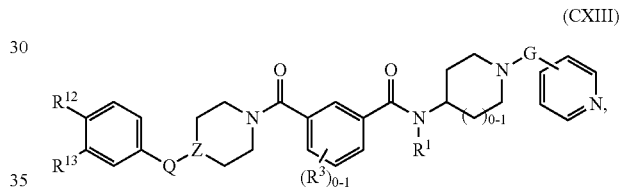

(CXIII)

in which Q is —CH$_2$—, —C(O)— or a single bond; G is a single bond, —CH$_2$—, —C(O)—, —S(O)$_2$— or —C(O)—NH—; Z, $R^1$ and $R^3$ are as described above with reference to any of structural formulae (I)-(IV) and (LXXI); and $R^{12}$ and $R^{13}$ are independently selected from H, halo, cyano, —(C$_1$-C$_4$ haloalkyl), —O—(C$_1$-C$_4$ haloalkyl), —(C$_1$-C$_4$ alkyl), —O—(C$_1$-C$_4$ alkyl), —C(O)—(C$_0$-C$_4$ alkyl), —C(O)O—(C$_0$-C$_4$ alkyl), —C(O)N(C$_0$-C$_4$ alkyl)(C$_0$-C$_4$ alkyl), NO$_2$ and —C(O)-Hca in which the Hca contains a ring nitrogen atom through which it is bound to the —C(O)—, in which no alkyl, haloalkyl or heterocycloalkyl is substituted by an aryl, heteroaryl, cycloalkyl or heterocycloalkyl-containing group. In one particular such embodiment, at least one of $R^{12}$ and $R^{13}$ is not H. In one embodiment, the pyridine nitrogen is positioned in the para position relative to the G moiety; in another embodiment, the pyridine nitrogen is positioned in the meta position relative to the G moiety. In one embodiment, $R^1$ is H.

(CXII)

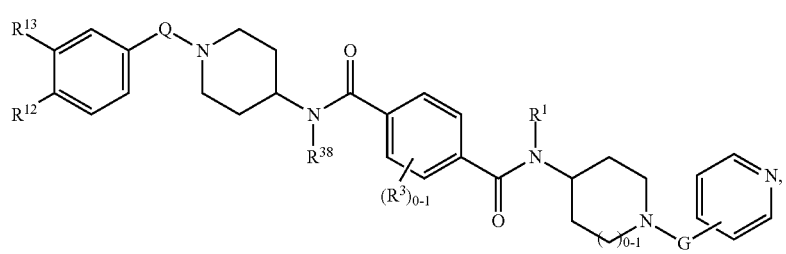

In another embodiment, R¹ is methyl, ethyl, propyl or butyl. In one embodiment, no R³ is substituted on the central phenyl ring. In another embodiment, one R³ (e.g., —Cl, —F, —CH₃, —C₂H₅, —C₃H₇) is substituted on the central phenyl ring. In one embodiment, Z is N. In another embodiment, Z is CH.

In certain embodiments, the presently disclosed compounds have the structural formula (CXIV):

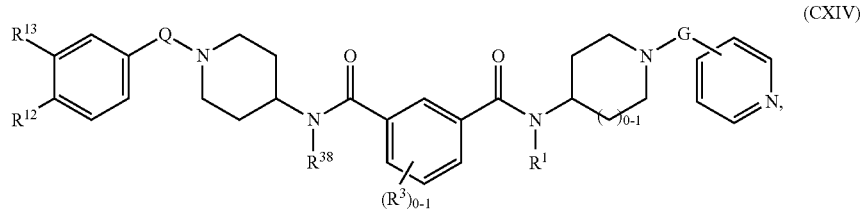

(CXIV)

in which Q is —CH₂—, —C(O)— or a single bond; G is a single bond, —CH₂—, —C(O)—, —S(O)₂— or —C(O)—NH—; R¹, R³ and R³⁸ are as described above with reference to any of structural formulae (I)-(IV) and (DOM); and R¹² and R¹³ are independently selected from H, halo, cyano, —(C₁-C₄ haloalkyl), —O—(C₁-C₄ haloalkyl), —(C₁-C₄ alkyl), —O—(C₁-C₄ alkyl), —C(O)—(C₀-C₄ alkyl), —C(O)O—(C₀-C₄ alkyl), —C(O)N(C₀-C₄ alkyl)(C₀-C₄ alkyl), NO₂ and —C(O)-Hca in which the Hca contains a ring nitrogen atom through which it is bound to the —C(O)—, in which no alkyl, haloalkyl or heterocycloalkyl is substituted by an aryl, heteroaryl, cycloalkyl or heterocycloalkyl-containing group. In one particular such embodiment, at least one of R¹² and R¹³ is not H. In one embodiment, the pyridine nitrogen is positioned in the para position relative to the G moiety; in another embodiment, the pyridine nitrogen is positioned in the meta position relative to the G moiety. In one embodiment, R¹ is H. In another embodiment, R¹ is methyl, ethyl, propyl or butyl. In one embodiment, no R³ is substituted on the central phenyl ring. In another embodiment, one R³ (e.g., —Cl, —F, —CH₃, —C₂H₅, —C₃H₇) is substituted on the central phenyl ring. In one embodiment, R³⁸ is H. In another embodiment, R³⁸ is methyl, ethyl, propyl or butyl.

In certain embodiments, the presently disclosed compounds have the structural formula (CXV):

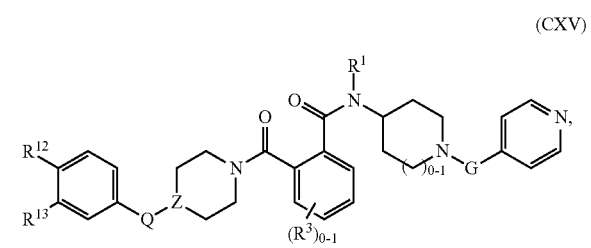

(CXV)

in which Q is —CH₂—, —C(O)— or a single bond; G is a single bond, —CH₂—, —C(O)—, —S(O)₂— or —C(O)—NH—; Z, R¹ and R³ are as described above with reference to any of structural formulae (I)-(IV) and (LXXIII); and R¹² and R¹³ are independently selected from H, halo, cyano, —(C₁-C₄ haloalkyl), —O—(C₁-C₄ haloalkyl), —(C₁-C₄ alkyl), —O—(C₁-C₄ alkyl), —C(O)—(C₀-C₄ alkyl), —C(O)O—(C₀-C₄ alkyl), —C(O)N(C₀-C₄ alkyl)(C₀-C₄ alkyl), NO₂ and —C(O)-Hca in which the Hca contains a ring nitrogen atom through which it is bound to the —C(O)—, in which no alkyl, haloalkyl or heterocycloalkyl is substituted by an aryl, heteroaryl, cycloalkyl or heterocycloalkyl-containing group. In one particular such embodiment, at least one of R¹² and R¹³ is not H. In one embodiment, the pyridine nitrogen is positioned in the para position relative to the G moiety; in another embodiment, the pyridine nitrogen is positioned in the meta position relative to the G moiety. In one embodiment, R¹ is H. In another embodiment, R¹ is methyl, ethyl, propyl or butyl. In one embodiment, no R³ is substituted on the central phenyl ring. In another embodiment, one R³ (e.g., —Cl, —F, —CH₃, —C₂H₅, —C₃H₇) is substituted on the central phenyl ring. In one embodiment, Z is N. In another embodiment, Z is CH.

In certain embodiments, the presently disclosed compounds have the structural formula (CXVI):

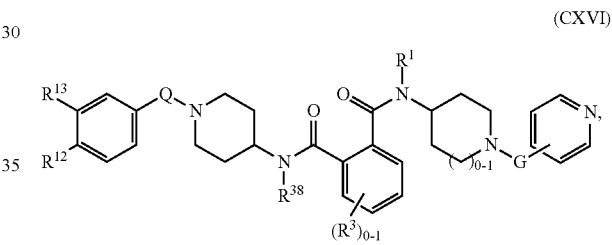

(CXVI)

in which Q is —CH₂—, —C(O)— or a single bond; G is a single bond, —CH₂—, —C(O)—, —S(O)₂— or —C(O)—NH—; R¹, R³ and R³⁸ are as described above with reference to any of structural formulae (I)-(IV) and (LXXIV); and R¹² and R¹³ are independently selected from H, halo, cyano, —(C₁-C₄ haloalkyl), —O—(C₁-C₄ haloalkyl), —(C₁-C₄ alkyl), —O—(C₁-C₄ alkyl), —C(O)—(C₀-C₄ alkyl), —C(O)O—(C₀-C₄ alkyl), —C(O)N(C₀-C₄ alkyl)(C₀-C₄ alkyl), NO₂ and —C(O)-Hca in which the Hca contains a ring nitrogen atom through which it is bound to the —C(O)—, in which no alkyl, haloalkyl or heterocycloalkyl is substituted by an aryl, heteroaryl, cycloalkyl or heterocycloalkyl-containing group. In one particular such embodiment, at least one of R¹² and R¹³ is not H. In one embodiment, the pyridine nitrogen is positioned in the para position relative to the G moiety; in another embodiment, the pyridine nitrogen is positioned in the meta position relative to the G moiety. In one embodiment, R¹ is H. In another embodiment, R¹ is methyl, ethyl, propyl or butyl. In one embodiment, no R³ is substituted on the central phenyl ring. In another embodiment, one R³ (e.g., —Cl, —F, —CH₃, —C₂H₅, —C₃H₇) is substituted on the central phenyl ring. In one embodiment, R³⁸ is H. In another embodiment, R³⁸ is methyl, ethyl, propyl or butyl.

In certain embodiments, the presently disclosed compounds have the structural formula (CXVII):

(CXVII)

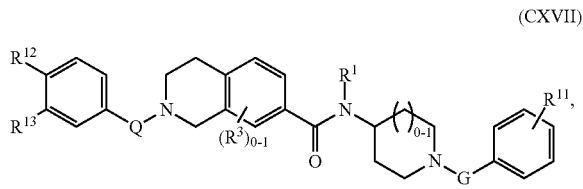

in which Q is —CH$_2$—, —C(O)— or a single bond; G is a single bond, —CH$_2$—, —C(O)—, —S(O)$_2$— or —C(O)—NH—; R$^1$ and R$^3$ are as described above with reference to any of structural formulae (I)-(IV) and (LXXV); and R$^{11}$, R$^{12}$ and R$^{13}$ are independently selected from H, halo, cyano, —(C$_1$-C$_4$ haloalkyl), —O—(C$_1$-C$_4$ haloalkyl), —(C$_1$-C$_4$ alkyl), —O—(C$_1$-C$_4$ alkyl), —C(O)—(C$_0$-C$_4$ alkyl), —C(O)O—(C$_0$-C$_4$ alkyl), —C(O)N(C$_0$-C$_4$ alkyl)(C$_0$-C$_4$ alkyl), NO$_2$ and —C(O)-Hca in which the Hca contains a ring nitrogen atom through which it is bound to the —C(O)—, in which no alkyl, haloalkyl or heterocycloalkyl is substituted by an aryl, heteroaryl, cycloalkyl or heterocycloalkyl-containing group. In one particular such embodiment, at least one of R$^{11}$, R$^{12}$ and R$^{13}$ is not H. In one embodiment, R$^{11}$ is attached in the para position relative to the G moiety; in another embodiment, R$^{11}$ is attached in the meta position relative to the G moiety. In one embodiment, R$^1$ is H. In another embodiment, R$^1$ is methyl, ethyl, propyl or butyl. In one embodiment, no R$^3$ is substituted on the central benzo moiety. In another embodiment, one R$^3$ (e.g., —Cl, —F, —CH$_3$, —C$_2$H$_5$, —C$_3$H$_7$) is substituted on the central benzo moiety.

In certain embodiments, the presently disclosed compounds have the structural formula (CXVIII):

(CXVIII)

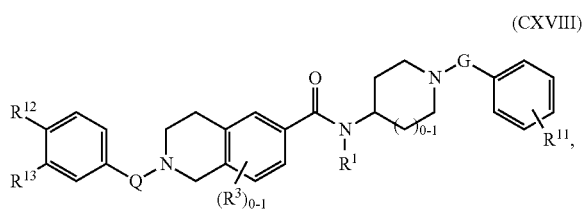

in which Q is —CH$_2$—, —C(O)— or a single bond; G is a single bond, —CH$_2$—, —C(O)—, —S(O)$_2$— or —C(O)—NH—; R$^1$ and R$^3$ are as described above with reference to any of structural formulae (I)-(IV) and (LXXVI); and R$^{11}$, R$^{12}$ and R$^{13}$ are independently selected from H, halo, cyano, —(C$_1$-C$_4$ haloalkyl), —O—(C$_1$-C$_4$ haloalkyl), —(C$_1$-C$_4$ alkyl), —O—(C$_1$-C$_4$ alkyl), —C(O)—(C$_0$-C$_4$ alkyl), —C(O)O—(C$_0$-C$_4$ alkyl), —C(O)N(C$_0$-C$_4$ alkyl)(C$_0$-C$_4$ alkyl), NO$_2$ and —C(O)-Hca in which the Hca contains a ring nitrogen atom through which it is bound to the —C(O)—, in which no alkyl, haloalkyl or heterocycloalkyl is substituted by an aryl, heteroaryl, cycloalkyl or heterocycloalkyl-containing group. In one particular such embodiment, at least one of R$^{11}$, R$^{12}$ and R$^{13}$ is not H. In one embodiment, R$^{11}$ is attached in the para position relative to the G moiety; in another embodiment, R$^{11}$ is attached in the meta position relative to the G moiety. In one embodiment, R$^1$ is H. In another embodiment, R$^1$ is methyl, ethyl, propyl or butyl. In one embodiment, no R$^3$ is substituted on the central benzo moiety. In another embodiment, one R$^3$ (e.g., —Cl, —F, —CH$_3$, —C$_2$H$_5$, —C$_3$H$_7$) is substituted on the central benzo moiety.

In certain embodiments, the presently disclosed compounds have the structural formula (CXIX):

(CXIX)

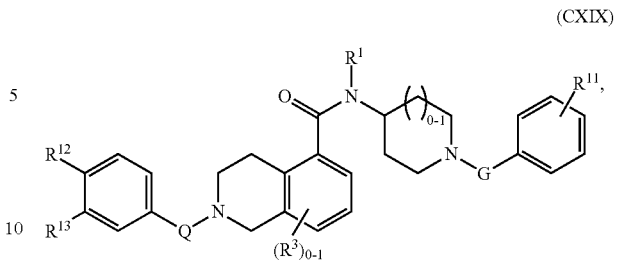

in which Q is —CH$_2$—, —C(O)— or a single bond; G is a single bond, —CH$_2$—, —C(O)—, —S(O)$_2$— or —C(O)—NH—; R$^1$ and R$^3$ are as described above with reference to any of structural formulae (I)-(IV) and (LXXVII); and R$^{11}$, R$^{12}$ and R$^{13}$ are independently selected from H, halo, cyano, —(C$_1$-C$_4$ haloalkyl), —O—(C$_1$-C$_4$ haloalkyl), —(C$_1$-C$_4$ alkyl), —O—(C$_1$-C$_4$ alkyl), —C(O)—(C$_0$-C$_4$ alkyl), —C(O)O—(C$_0$-C$_4$ alkyl), —C(O)N(C$_0$-C$_4$ alkyl)(C$_0$-C$_4$ alkyl), NO$_2$ and —C(O)-Hca in which the Hca contains a ring nitrogen atom through which it is bound to the —C(O)—, in which no alkyl, haloalkyl or heterocycloalkyl is substituted by an aryl, heteroaryl, cycloalkyl or heterocycloalkyl-containing group. In one particular such embodiment, at least one of R$^{11}$, R$^{12}$ and R$^{13}$ is not H. In one embodiment, R$^{11}$ is attached in the para position relative to the G moiety; in another embodiment, R$^{11}$ is attached in the meta position relative to the G moiety. In one embodiment, R$^1$ is H. In another embodiment, R$^1$ is methyl, ethyl, propyl or butyl. In one embodiment, no R$^3$ is substituted on the central benzo moiety. In another embodiment, one R$^3$ (e.g., —Cl, —F, —CH$_3$, —C$_2$H$_5$, —C$_3$H$_7$) is substituted on the central benzo moiety.

In certain embodiments, the presently disclosed compounds have the structural formula (CXX):

(CXX)

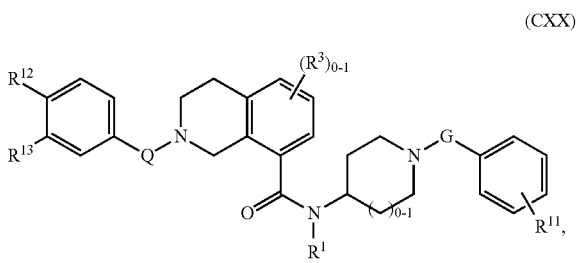

in which Q is —CH$_2$—, —C(O)— or a single bond; G is a single bond, —CH$_2$—, —C(O)—, —S(O)$_2$— or —C(O)—NH—; R$^1$ and R$^3$ are as described above with reference to any of structural formulae (I)-(IV) and (LXXVIII); and R$^{11}$, R$^{12}$ and R$^{13}$ are independently selected from H, halo, cyano, —(C$_1$-C$_4$ haloalkyl), —O—(C$_1$-C$_4$ haloalkyl), —(C$_1$-C$_4$ alkyl), —O—(C$_1$-C$_4$ alkyl), —C(O)—(C$_0$-C$_4$ alkyl), —C(O)O—(C$_0$-C$_4$ alkyl), —C(O)N(C$_0$-C$_4$ alkyl)(C$_0$-C$_4$ alkyl), NO$_2$ and —C(O)-Hca in which the Hca contains a ring nitrogen atom through which it is bound to the —C(O)—, in which no alkyl, haloalkyl or heterocycloalkyl is substituted by an aryl, heteroaryl, cycloalkyl or heterocycloalkyl-containing group. In one particular such embodiment, at least one of R$^{11}$, R$^{12}$ and R$^{13}$ is not H. In one embodiment, R$^{11}$ is attached in the para position relative to the G moiety; in another embodiment, R$^{11}$ is attached in the meta position relative to the G moiety. In one embodiment, R$^1$ is H. In another embodiment, R$^1$ is methyl, ethyl, propyl or butyl. In one embodiment, no R$^3$ is substituted on the central benzo moiety. In another embodiment, one R³ (e.g., —Cl, —F, —CH₃, —C₂H₅, —C₃H₇) is substituted on the central benzo moiety.

In certain embodiments, the presently disclosed compounds have the structural formula (CXXI):

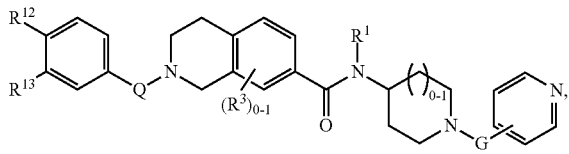

(CXXI)

in which Q is —CH₂—, —C(O)— or a single bond; G is a single bond, —CH₂—, —C(O)—, —S(O)₂— or —C(O)—NH—; R¹ and R³ are as described above with reference to any of structural formulae (I)-(IV) and (LXXV); and R¹² and R¹³ are independently selected from H, halo, cyano, —(C₁-C₄ haloalkyl), —O—(C₁-C₄ haloalkyl), —(C₁-C₄ alkyl), —O—(C₁-C₄ alkyl), —C(O)—(C₀-C₄ alkyl), —C(O)O—(C₀-C₄ alkyl), —C(O)N(C₀-C₄ alkyl)(C₀-C₄ alkyl), NO₂ and —C(O)-Hca in which the Hca contains a ring nitrogen atom through which it is bound to the —C(O)—, in which no alkyl, haloalkyl or heterocycloalkyl is substituted by an aryl, heteroaryl, cycloalkyl or heterocycloalkyl-containing group. In one particular such embodiment, at least one of R¹² and R¹³ is not H. In one embodiment, the pyridine nitrogen is positioned in the para position relative to the G moiety; in another embodiment, the pyridine nitrogen is positioned in the meta position relative to the G moiety. In one embodiment, R¹ is H. In another embodiment, R¹ is methyl, ethyl, propyl or butyl. In one embodiment, no R³ is substituted on the central benzo moiety. In another embodiment, one R³ (e.g., —Cl, —F, —CH₃, —C₂H₅, —C₃H₇) is substituted on the central benzo moiety.

In certain embodiments, the presently disclosed compounds have the structural formula (CXXII):

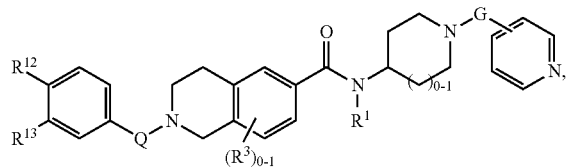

(CXXII)

in which Q is —CH₂—, —C(O)— or a single bond; G is a single bond, —CH₂—, —C(O)—, —S(O)₂— or —C(O)—NH—; R¹ and R³ are as described above with reference to any of structural formulae (I)-(IV) and (LXXVI); and R¹² and R¹³ are independently selected from H, halo, cyano, —(C₁-C₄ haloalkyl), —O—(C₁-C₄ haloalkyl), —(C₁-C₄ alkyl), —O—(C₁-C₄ alkyl), —C(O)—(C₀-C₄ alkyl), —C(O)O—(C₀-C₄ alkyl), —C(O)N(C₀-C₄ alkyl)(C₀-C₄ alkyl), NO₂ and —C(O)-Hca in which the Hca contains a ring nitrogen atom through which it is bound to the —C(O)—, in which no alkyl, haloalkyl or heterocycloalkyl is substituted by an aryl, heteroaryl, cycloalkyl or heterocycloalkyl-containing group. In one particular such embodiment, at least one of R¹² and R¹³ is not H. In one embodiment, the pyridine nitrogen is positioned in the para position relative to the G moiety; in another embodiment, the pyridine nitrogen is positioned in the meta position relative to the G moiety. In one embodiment, R¹ is H. In another embodiment, R¹ is methyl, ethyl, propyl or butyl. In one embodiment, no R³ is substituted on the central benzo moiety. In another embodiment, one R³ (e.g., —Cl, —F, —CH₃, —C₂H₅, —C₃H₇) is substituted on the central benzo moiety.

In certain embodiments, the presently disclosed compounds have the structural formula (CXXIII):

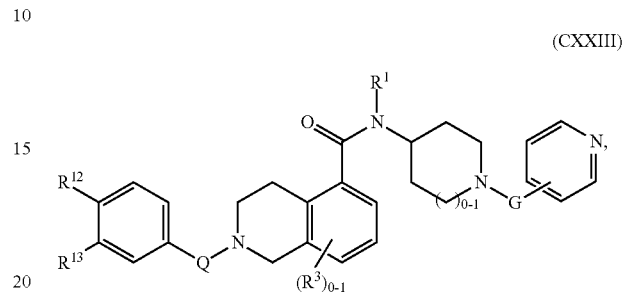

(CXXIII)

in which Q is —CH₂—, —C(O)— or a single bond; G is a single bond, —CH₂—, —C(O)—, —S(O)₂— or —C(O)—NH—; R¹ and R³ are as described above with reference to any of structural formulae (I)-(IV) and (LXXVII); and R¹² and R¹³ are independently selected from H, halo, cyano, —(C₁-C₄ haloalkyl), —O—(C₁-C₄ haloalkyl), —(C₁-C₄ alkyl), —O—(C₁-C₄ alkyl), —C(O)—(C₀-C₄ alkyl), —C(O)O—(C₀-C₄ alkyl), —C(O)N(C₀-C₄ alkyl)(C₀-C₄ alkyl), NO₂ and —C(O)-Hca in which the Hca contains a ring nitrogen atom through which it is bound to the —C(O)—, in which no alkyl, haloalkyl or heterocycloalkyl is substituted by an aryl, heteroaryl, cycloalkyl or heterocycloalkyl-containing group. In one particular such embodiment, at least one of R¹² and R¹³ is not H. In one embodiment, the pyridine nitrogen is positioned in the para position relative to the G moiety; in another embodiment, the pyridine nitrogen is positioned in the meta position relative to the G moiety. In one embodiment, R¹ is H. In another embodiment, R¹ is methyl, ethyl, propyl or butyl. In one embodiment, no R³ is substituted on the central benzo moiety. In another embodiment, one R³ (e.g., —Cl, —F, —CH₃, —C₂H₅, —C₃H₇) is substituted on the central benzo moiety.

In certain embodiments, the presently disclosed compounds have the structural formula (CXXIV):

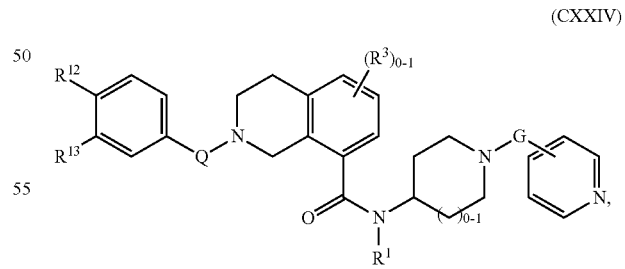

(CXXIV)

in which Q is —CH₂—, —C(O)— or a single bond; G is a single bond, —CH₂—, —C(O)—, —S(O)₂— or —C(O)—NH—; R¹ and R³ are as described above with reference to any of structural formulae (I)-(IV) and (LXXVIII); and R¹² and R¹³ are independently selected from H, halo, cyano, —(C₁-C₄ haloalkyl), —O—(C₁-C₄ haloalkyl), —(C₁-C₄ alkyl), —O—(C₁-C₄ alkyl), —C(O)—(C₀-C₄ alkyl), —C(O)O—(C₀-C₄ alkyl), —C(O)N(C₀-C₄ alkyl)(C₀-C₄ alkyl), NO₂ and —C(O)-Hca in which the Hca contains a ring nitrogen atom through which it is bound to the —C(O)—, in which no alkyl, haloalkyl or heterocycloalkyl is substituted by an aryl, heteroaryl, cycloalkyl or heterocycloalkyl-containing group. In one particular such embodiment, at least one of $R^{12}$ and $R^{13}$ is not H. In one embodiment, the pyridine nitrogen is positioned in the para position relative to the G moiety; in another embodiment, the pyridine nitrogen is positioned in the meta position relative to the G moiety. In one embodiment, $R^1$ is H. In another embodiment, $R^1$ is methyl, ethyl, propyl or butyl. In one embodiment, no $R^3$ is substituted on the central benzo moiety. In another embodiment, one $R^3$ (e.g., —Cl, —F, —CH$_3$, —C$_2$H$_5$, —C$_3$H$_7$) is substituted on the central benzo moiety.

In one embodiment of the presently disclosed compounds, the compound has the structural formula (XLIV), in which the "A" ring system is an aryl or heteroaryl; and in which the compound has a computed low energy three-dimensional conformer in which the oxygen of the carboxamide —C(O)— group is positioned at (0 Å, 0 Å, 0 Å);
the centerpoint of an aromatic ring of the aryl or heteroaryl of the "B" ring system is positioned within 3.5 Å of (−3.1 Å, 0.4 Å, 1.2 Å);
the nitrogen of the right-hand azacycloalkyl (i.e., the ring to which -G-$R^{17}$ is bound) is positioned within 3.5 Å of (0.8 Å, 1.6 Å, −5.3 Å);
the centerpoint of the left-hand azacycloalkyl (i.e., the ring to which -Q-(A ring)-($R^5$)$_y$ is bound) is positioned within 3.5 Å of (−6.2 Å, 0.1 Å, 7.4 Å); and
the centerpoint of an aromatic ring of the aryl or heteroaryl of the "A" ring system is positioned within 3.5 Å of (−7.4 Å, −1.9 Å, 10.7 Å).

In certain embodiments of the presently disclosed compounds of structural formula (XLIV), in a computed low energy three-dimensional conformer:

the oxygen of the carboxamide —C(O)— group is positioned at (0 Å, 0 Å, 0 Å);
the centerpoint of an aromatic ring of the aryl or heteroaryl of the "B" ring system is positioned within 2.5 Å of (−3.1 Å, 0.4 Å, 1.2 Å);
the nitrogen of the right-hand azacycloalkyl is positioned within 1.8 Å of (0.8 Å, 1.6 Å, −5.3 Å);
the centerpoint of the left-hand azacycloalkyl is positioned within 2.5 Å of (−6.2 Å, 0.1 Å, 7.4 Å); and
the centerpoint of an aromatic ring of the aryl or heteroaryl of the "A" ring system is positioned within 2.5 Å of (−7.4 Å, −1.9 Å, 10.7 Å).

In one embodiment of the presently disclosed compounds of structural formula (XLIV), the "A" ring system is an aryl or heteroaryl substituted with a hydrophobic moiety; $R^{17}$ is substituted with an electron acceptor; and the compound has a computed low energy three-dimensional conformer in which the oxygen of the carboxamide —C(O)— group is positioned at (0 Å, 0 Å, 0 Å);
the centerpoint of an aromatic ring of the aryl or heteroaryl of the "B" ring system is positioned within 3.5 Å of (−3.1 Å, 0.4 Å, 1.2 Å);
the nitrogen of the right-hand azacycloalkyl is positioned within 3.5 Å of (0.8 Å, 1.6 Å, −5.3 Å);
the centerpoint of the left-hand azacycloalkyl is positioned within 3.5 Å of (−6.2 Å, 0.1 Å, 7.4 Å); and
the centerpoint of an aromatic ring of the aryl or heteroaryl of the "A" ring system is positioned within 3.5 Å of (−7.4 Å, −1.9 Å, 10.7 Å);

the hydrophobic moiety substituted on the "A" ring system is positioned within 3.5 Å of (−9.0 Å, −3.2 Å, 13.4 Å); and
the electron acceptor substituted on $R^{17}$ is positioned within 3.5 Å of (7.0 Å, −2.7 Å, −7.0 Å).

The hydrophobic moiety can be, for example, any of the following, as defined in SMARTS query format:

```
#INCLUDE
[a]F group(2)
[a]Cl group(2)
[a]Br group(2)
[a]I group(2)
[a]C(F)(F)(F) group(2,3,4,5)
[a][CH2]C(F)(F)(F) group(2,3,4,5,6)
[a]O[CH3] group(2,3)
[a]S[CH3] group(2,3)
[a]OC(F)(F)(F) group(2,3,4,5,6)
C(F)(F)(F) group
F group
Cl group
Br group
I group
default_aromatic_surface group
default_aliphatic_surface group
C[S;X2]C group
[S;X2]CC group
[S;X2]C group.
```

The electron acceptor can be, for example, any of the following, as defined in SMARTS query format:

```
#INCLUDE
[N;X1]#[#6] vector(1)
[N;X1]#CC vector(1)
[N;X2](=C~[C,c])C vector(1)
[N;X2](O)=N[a] vector(1)
[N;X2](=N—O)[a] vector(1)
[n;X2]1ccccc1 vector(1)
[n;X2]([a])([a]) vector(1)
[N;X2](=C~[C,c])(~[*]) vector(1)
[N;X3](C)(C)[N;X3]C vector(1)
[N;X2](=C)(~[*]) vector(1)
[N;X2](~[C,c])=[N;X2] vector(1)
[n;X2]1c[nH]cc1 vector(1)
O=[S;X4](=O)([!#8])([!#8]) vector(1)
[O;X2]C vector(1)
[O;X2]N vector(1)
[O;X1]=[C,c] vector(1)
o vector( 1)
[O;X2](C)C vector(1)
[O;X2]c1nccccc1 vector(1)
[O;X2]~[a] vector(1)
O=PO([!#1]) vector(1)
[O;X2] vector(1)
[S;X2](C)C vector(1)
[S;X2](=C)N vector(1)
#EXCLUDE
O=C[O—,OH] point
[O—,OH]C(=O) point
[nH]([a])[a] point
[#7;X3][*]=[O,S] point
[N;X3](C)(C)[C;X3] point
[N;X3][a] point
N(=N=N)[#6] point
[NH2](C(=O)[NH2]) point
[NH](C=O)(C=O) point
[NH2](S(=O)(=O)[#6])[#6] point
[NH](S(=O)(=O)[#6])[#6] point
n1c([NH2])ccnc1([NH2]) point
o1nccc1 point
o1cncc1 point
o1cccc1 point
[O;X2]C=O point
[O;X2] point.
```

In one embodiment of the presently disclosed compounds of structural formula (XLIV), the "A" ring system is an aryl or heteroaryl substituted with a hydrophobic moiety; $R^{17}$ is substituted with an electron acceptor; and the compound has a computed low energy three-dimensional conformer in which the oxygen of the carboxamide —C(O)— group is positioned at (0 Å, 0 Å, 0 Å);

the centerpoint of an aromatic ring of the aryl or heteroaryl of the "B" ring system is positioned within 2.5 Å of (−3.1 Å, 0.4 Å, 1.2 Å);

the nitrogen of the right-hand azacycloalkyl is positioned within 1.8 Å of (0.8 Å, 1.6 Å, −5.3 Å);

the centerpoint of the left-hand azacycloalkyl is positioned within 2.5 Å of (−6.2 Å, 0.1 Å, 7.4 Å); and the centerpoint of an aromatic ring of the aryl or heteroaryl of the "A" ring system is positioned within 2.5 Å of (−7.4 Å, −1.9 Å, 10.7 Å);

the hydrophobic moiety substituted on the "A" ring system is positioned within 2.5 Å of (−9.0 Å, −3.2 Å, 13.4 Å); and the electron acceptor substituted on $R^{17}$ is positioned within 2 Å of (7.0 Å, −2.7 Å, −7.0 Å).

In certain embodiments of the presently disclosed compounds, the computed low energy three-dimensional conformer has a root mean square deviation from the given points of no greater than 3 Å, and a vector score greater than 0.2.

In certain embodiments of the presently disclosed compounds, the computed low energy three-dimensional conformer has a root mean square deviation from the given points of no greater than 1.5 Å, and a vector score greater than 0.4.

In certain embodiments of the presently disclosed compounds, the computed low energy three-dimensional conformer has a root mean square deviation from the given points of no greater than 1.2 Å, and a vector score greater than 0.5.

A centerpoint of a carbocyclic or heterocyclic ring is the average position of the constituent atoms of the ring (i.e., excluding any substituents) as positioned in the low energy three-dimensional conformer. For example, the centerpoint of the left-hand azacycloalkyl is the average position of its ring carbon and nitrogen atom(s). Similarly, the centerpoint of a phenyl ring is the average position of its six ring carbons. Centerpoints are calculated only on single rings; multi-ring systems have multiple centerpoints, one for each ring. For example, a benzofuran would have two centerpoints, one calculated as the average position of the six carbon rings making up the fused benzene subunit, and the other calculated as the average position of the four carbon atoms and one oxygen atom making up the fused furan subunit.

Low energy three-dimensional conformers can be calculated using the Phase software package version 3.0, available from Schrödinger LLC. Low energy three-dimensional conformers can be generated by a torsion search procedure under OPLS_2005 force field with a distance dependent dielectric constant. As the person of skill in the art will appreciate, the low energy conformer should be translated and rotated so that the the oxygen of the E —C(O)— group is positioned at (0 Å, 0 Å, 0 Å), or one of the oxygens of the E —S(O)$_2$— group is positioned at (0 Å, 0 Å, 0 Å), and so that the root mean square deviation of the rest of the listed features with respect to the given points is minimized.

As the person of skill in the art will recognize, the various embodiments described above can be combined to form other embodiments of the presently disclosed compounds. For example, in one embodiment, Q is —CH$_2$—, as described above, and G is —CH$_2$—, as described above. In another embodiment, the ring system denoted by "A" is a phenyl not fused to the azacycloalkyl, the ring system denoted by "B" is a phenyl, J is —N(R$^{38}$)—, D is a carbon and Z is N.

Examples of compounds according to structural formula (I) include those listed below in Table 1. These compounds can be made according to the general schemes described below, for example using procedures analogous to those described below in the Examples.

TABLE 1

| No. | Name | Structure |
|---|---|---|
| 1 | tert-butyl 4-(6-(1-(4-(trifluoromethyl)phenyl)piperidin-4-yloxy)benzo[d]oxazole-2-carboxamido)piperidine-1-carboxylate | 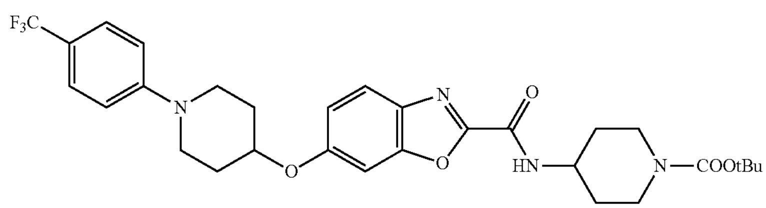 |
| 2 | N-(1-(4-cyanobenzyl)piperidin-4-yl)-6-(1-(4-(trifluoromethyl)phenyl)piperidin-4-yloxy)benzo[d]oxazole-2-carboxamide | 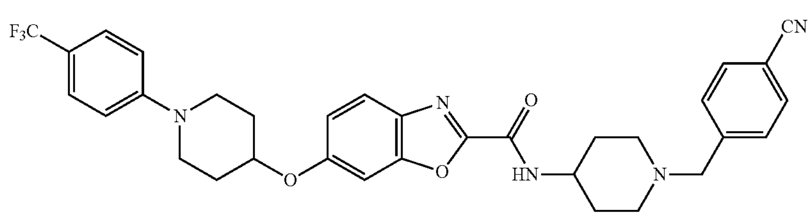 [SMILES: N#Cc1ccc(CN2CCC(NC(=O)c3nc4ccc(OC5CCN(c6ccc(C(F)(F)F)cc6)CC5)cc4o3)CC2)cc1] |
| 3 | N-(1-(pyridin-4-ylmethyl)piperidin-4-yl)-6-(1-(4-(trifluoromethyl)phenyl)piperidin-4-yloxy)benzo[d]oxazole-2-carboxamide | 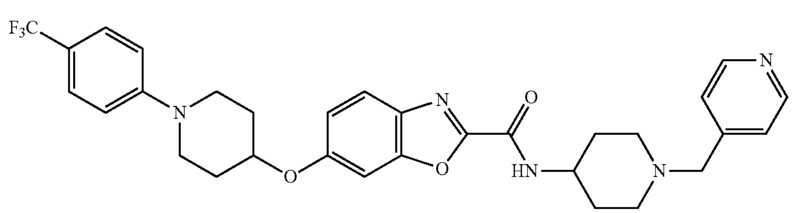 [SMILES: O=C(NC1CCN(Cc2ccncc2)CC1)c1nc2ccc(OC3CCN(c4ccc(C(F)(F)F)cc4)CC3)cc2o1] |

TABLE 1-continued

| No. | Name |
|---|---|
| 4 | N-(1-(4-fluorobenzoyl)piperidin-4-yl)-6-(1-(4-(trifluoromethyl)phenyl)piperidin-4-yloxy)benzo[d]oxazole-2-carboxamide |
| 5 | N-(piperidin-4-yl)-6-(1-(4-(trifluoromethyl)phenyl)piperidin-4-yloxy)benzo[d]oxazole-2-carboxamide |
| 6 | N-(1-(4-cyanobenzoyl)piperidin-4-yl)-6-(1-(4-(trifluoromethyl)phenyl)piperidin-4-yloxy)benzo[d]oxazole-2-carboxamide |
| 7 | N-(4-isonicotinoylcyclohexyl)-6-(1-(4-(trifluoromethyl)phenyl)piperidin-4-yloxy)benzo[d]oxazole-2-carboxamide |
| 8 | (5-(pyridin-4-ylmethyl)-2,5-diazabicyclo[2.2.1]heptan-2-yl)(6-(1-(4-(trifluoromethyl)phenyl)piperidin-4-yloxy)benzo[d]oxazol-2-yl)methanone |
| 9 | 4-((5-(6-(1-(4-(trifluoromethyl)phenyl)piperidin-4-yloxy)benzo[d]oxazole-2-carbonyl)-2,5-diazabicyclo[2.2.1]heptan-2-yl)methyl)benzamide |

TABLE 1-continued

| No. | Name | Structure |
|---|---|---|
| 10 | 4-((5-(6-(1-(4-(trifluoromethyl)phenyl)piperidin-4-yloxy)benzo[d]oxazole-2-carbonyl)-2,5-diazabicyclo[2.2.1]heptan-2-yl)methyl)benzonitrile | 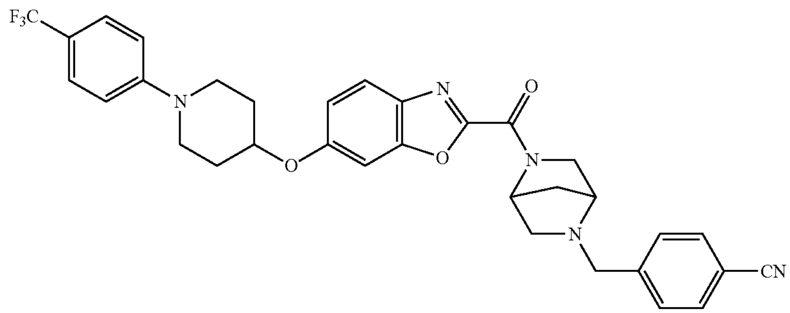 [SMILES: N#Cc1ccc(CN2CC3CC2CN3C(=O)c2nc3ccc(OC4CCN(c5ccc(C(F)(F)F)cc5)CC4)cc3o2)cc1] |
| 11 | (5-isonicotinoyl-2,5-diazabicyclo[2.2.1]heptan-2-yl)(6-(1-(4-(trifluoromethyl)phenyl)piperidin-4-yloxy)benzo[d]oxazol-2-yl)methanone | 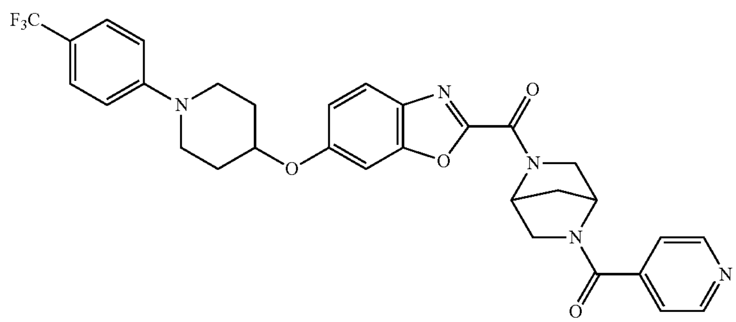 [SMILES: O=C(c1ccncc1)N1CC2CC1CN2C(=O)c1nc2ccc(OC3CCN(c4ccc(C(F)(F)F)cc4)CC3)cc2o1] |
| 12 | 4-(5-(6-(1-(4-(trifluoromethyl)phenyl)piperidin-4-yloxy)benzo[d]oxazole-2-carbonyl)-2,5-diazabicyclo[2.2.1]heptane-2-carbonyl)benzonitrile | 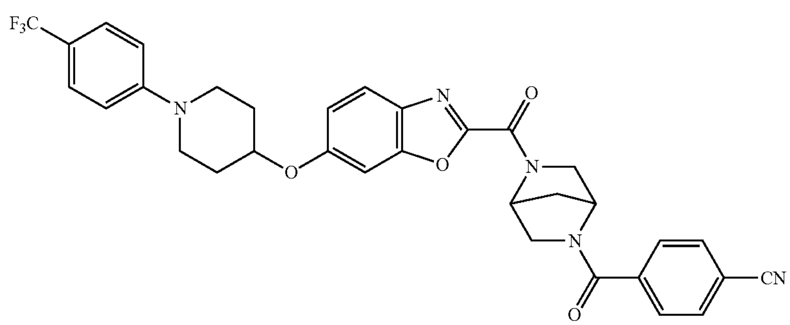 [SMILES: N#Cc1ccc(C(=O)N2CC3CC2CN3C(=O)c2nc3ccc(OC4CCN(c5ccc(C(F)(F)F)cc5)CC4)cc3o2)cc1] |
| 13 | (5-(4-fluorobenzoyl)-2,5-diazabicyclo[2.2.1]heptan-2-yl)(6-(1-(4-(trifluoromethyl)phenyl)piperidin-4-yloxy)benzo[d]oxazol-2-yl)methanone | 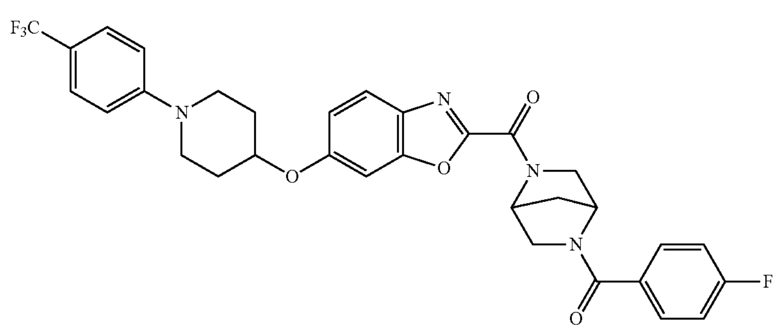 [SMILES: O=C(c1ccc(F)cc1)N1CC2CC1CN2C(=O)c1nc2ccc(OC3CCN(c4ccc(C(F)(F)F)cc4)CC3)cc2o1] |
| 14 | tert-butyl 4-(6-(1-(4-(trifluoromethyl)phenyl)piperidin-4-yloxy)benzo[d]thiazole-2-carboxamido)piperidine-1-carboxylate | 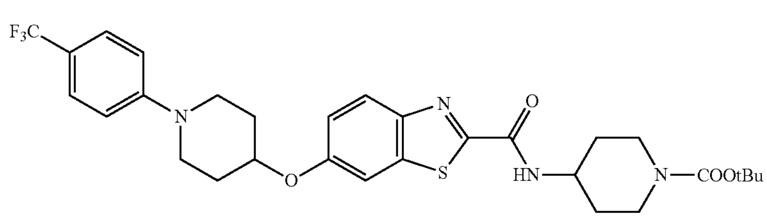 |

TABLE 1-continued

| No. | Name |
|---|---|
| 15 | N-(1-(pyridin-4-ylmethyl)piperidin-4-yl)-6-(1-(4-(trifluoromethyl)phenyl)piperidin-4-yloxy)benzo[d]thiazole-2-carboxamide |
| 16 | N-(1-(4-cyanobenzyl)piperidin-4-yl)-6-(1-(4-(trifluoromethyl)phenyl)piperidin-4-yloxy)benzo[d]thiazole-2-carboxamide |
| 17 | N-(1-(pyridin-4-ylmethyl)piperidin-4-yl)-7-(1-(4-(trifluoromethyl)phenyl)piperidin-4-yloxy)imidazo[1,2-a]pyridine-2-carboxamide |
| 18 | N-(1-(4-cyanobenzyl)piperidin-4-yl)-7-(1-(4-(trifluoromethyl)phenyl)piperidin-4-yloxy)imidazo[1,2-a]pyridine-2-carboxamide |
| 19 | tert-butyl 4-(5-(1-(4-(trifluoromethyl)phenyl)piperidin-4-yloxy)pyrazine-2-carboxamido)piperidine-1-carboxylate |
| 20 | N-(piperidin-4-yl)-5-(1-(4-(trifluoromethyl)phenyl)piperidin-4-yloxy)pyrazine-2-carboxamide |
| 21 | N-(1-(pyridin-4-ylmethyl)piperidin-4-yl)-5-(1-(4-(trifluoromethyl)phenyl)piperidin-4-yloxy)pyrazine-2-carboxamide |

TABLE 1-continued

| No. | Name |
|---|---|
| 22 | N-(1-(4-cyanobenzyl)piperidin-4-yl)-5-(1-(4-(trifluoromethyl)phenyl)piperidin-4-yloxy)pyrazine-2-carboxamide |
| 23 | N-(1-(4-cyanobenzyl)piperidin-4-yl)-2-(1-(4-(trifluoromethyl)phenyl)piperidin-4-yloxy)thiazole-5-carboxamide |
| 24 | N-(1-(4-cyanobenzyl)piperidin-4-yl)-2-(1-(4-cyanophenyl)piperidin-4-yloxy)thiazole-5-carboxamide |
| 25 | N-(1-(4-cyanobenzyl)piperidin-4-yl)-2-(1-(4-(trifluoromethyl)benzyl)piperidin-4-yloxy)thiazole-5-carboxamide |
| 26 | tert-butyl 4-(5-(1-(4-cyanobenzyl)piperidin-4-ylcarbamoyl)thiazol-2-yloxy)piperidine-1-carboxylate |
| 27 | N-(1-(4-cyanobenzyl)piperidin-4-yl)-4-(1-(4-ethoxybenzyl)piperidine-4-carbonyl)benzamide |
| 28 | 4-(4-(4-chlorobenzyl)piperazine-1-carbonyl)-N-(1-(4-cyanobenzyl)piperidin-4-yl)benzamide |

TABLE 1-continued

| No. | Name | Structure |
|-----|------|-----------|
| 29 | 4-(4-(4-chlorophenyl)piperazine-1-carbonyl)-N-(1-(4-cyanobenzyl)piperidin-4-yl)benzamide | 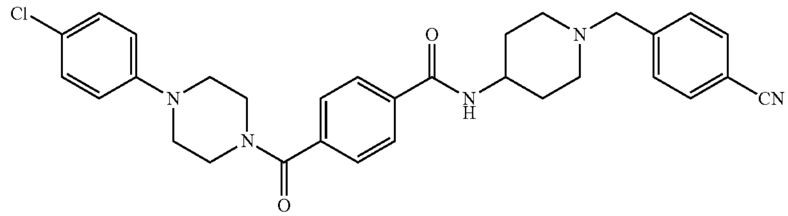 [SMILES: N#Cc1ccc(CN2CCC(NC(=O)c3ccc(C(=O)N4CCN(c5ccc(Cl)cc5)CC4)cc3)CC2)cc1] |
| 30 | N-(1-(4-cyanobenzyl)piperidin-4-yl)-4-(4-(5-(trifluoromethyl)pyridin-2-yl)piperazine-1-carbonyl)benzamide | 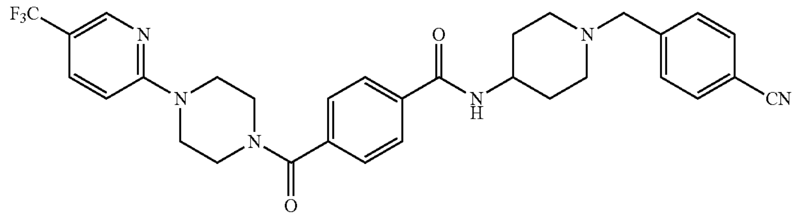 [SMILES: N#Cc1ccc(CN2CCC(NC(=O)c3ccc(C(=O)N4CCN(c5ccc(C(F)(F)F)cn5)CC4)cc3)CC2)cc1] |
| 31 | $N^1$-(1-(4-cyanobenzyl)piperidin-4-yl)-$N^4$-(1-(4-(trifluoromethyl)benzyl)piperidin-4-yl)terephthalamide | 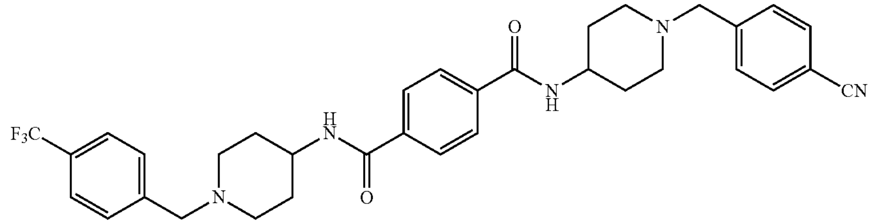 [SMILES: N#Cc1ccc(CN2CCC(NC(=O)c3ccc(C(=O)NC4CCN(Cc5ccc(C(F)(F)F)cc5)CC4)cc3)CC2)cc1] |
| 32 | $N^1$-(1-(4-cyanobenzyl)piperidin-4-yl)-$N^4$-(1-phenylpiperidin-4-yl)terephthalamide | 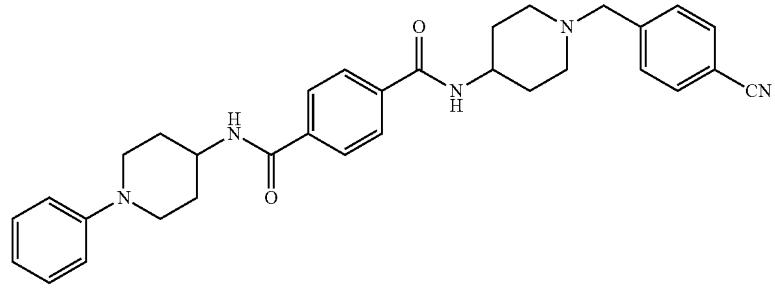 [SMILES: N#Cc1ccc(CN2CCC(NC(=O)c3ccc(C(=O)NC4CCN(c5ccccc5)CC4)cc3)CC2)cc1] |
| 33 | $N^1$-(1-benzylpiperidin-4-yl)-$N^4$-(1-(4-cyanobenzyl)piperidin-4-yl)terephthalamide | 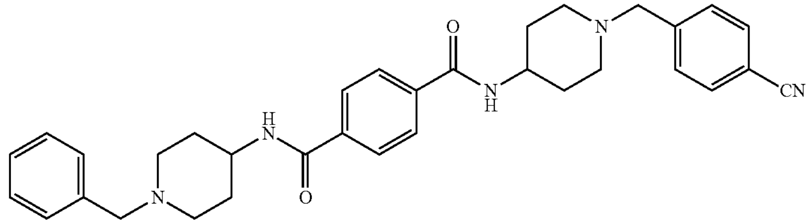 [SMILES: N#Cc1ccc(CN2CCC(NC(=O)c3ccc(C(=O)NC4CCN(Cc5ccccc5)CC4)cc3)CC2)cc1] |
| 34 | N-(1-(4-cyanobenzyl)piperidin-4-yl)-2-(4-fluorobenzyl)-1,2,3,4-tetrahydroisoquinoline-7-carboxamide | 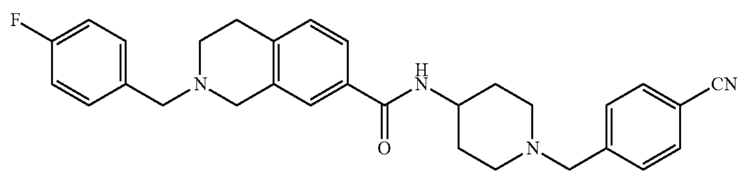 [SMILES: N#Cc1ccc(CN2CCC(NC(=O)c3ccc4c(c3)CN(Cc3ccc(F)cc3)CC4)CC2)cc1] |
| 35 | 2-(4-fluorobenzyl)-N-(1-(pyridin-3-ylmethyl)piperidin-4-yl)-1,2,3,4-tetrahydroisoquinoline-7-carboxamide | 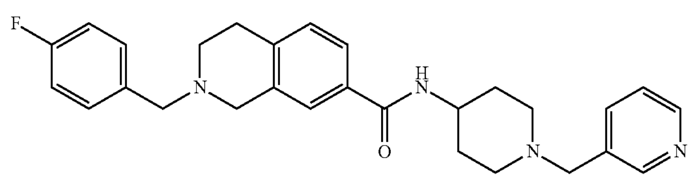 [SMILES: O=C(NC1CCN(Cc2cccnc2)CC1)c1ccc2c(c1)CN(Cc1ccc(F)cc1)CC2] |

TABLE 1-continued

| No. | Name | Structure |
|---|---|---|
| 36 | 2-(4-fluorobenzyl)-N-(1-(4-(trifluoromethyl)benzyl)piperidin-4-yl)-1,2,3,4-tetrahydroisoquinoline-7-carboxamide | 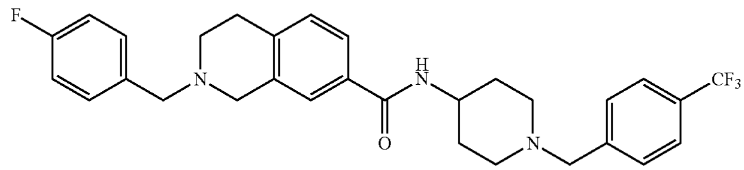 [SMILES: O=C(NC1CCN(Cc2ccc(C(F)(F)F)cc2)CC1)c1ccc2c(c1)CN(Cc1ccc(F)cc1)CC2] |
| 37 | 2-(4-cyanobenzyl)-N-(1-(4-cyanobenzyl)piperidin-4-yl)-1,2,3,4-tetrahydroisoquinoline-7-carboxamide | 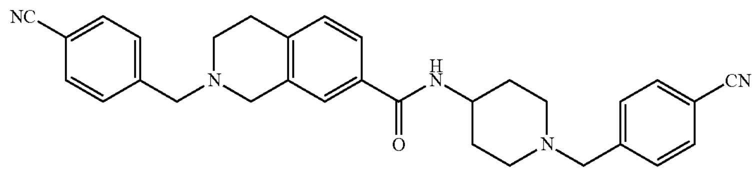 [SMILES: N#Cc1ccc(CN2CCC(NC(=O)c3ccc4c(c3)CN(Cc3ccc(C#N)cc3)CC4)CC2)cc1] |
| 38 | 2-(4-cyanobenzyl)-N-(1-(pyridin-3-ylmethyl)piperidin-4-yl)-1,2,3,4-tetrahydroisoquinoline-7-carboxamide | 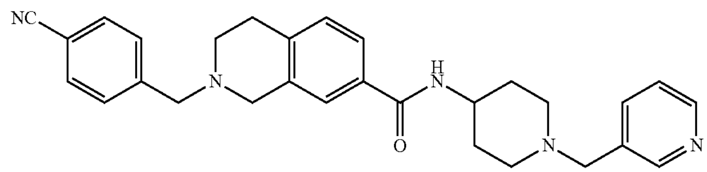 [SMILES: N#Cc1ccc(CN2CCc3ccc(C(=O)NC4CCN(Cc5cccnc5)CC4)cc3C2)cc1] |
| 39 | 2-(4-cyanobenzyl)-N-(1-(4-(trifluoromethyl)benzyl)piperidin-4-yl)-1,2,3,4-tetrahydroisoquinoline-7-carboxamide | 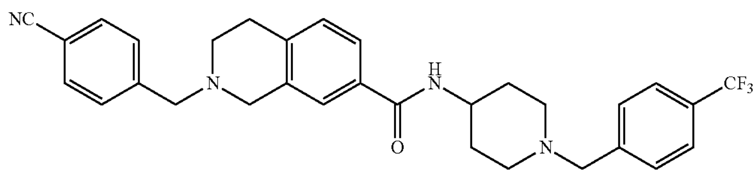 [SMILES: N#Cc1ccc(CN2CCc3ccc(C(=O)NC4CCN(Cc5ccc(C(F)(F)F)cc5)CC4)cc3C2)cc1] |
| 40 | N-(1-(4-cyanobenzyl)piperidin-4-yl)-2-(4-fluorobenzyl)-1,2,3,4-tetrahydroisoquinoline-7-carboxamide | 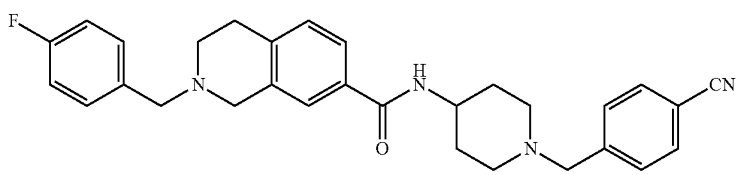 [SMILES: N#Cc1ccc(CN2CCC(NC(=O)c3ccc4c(c3)CN(Cc3ccc(F)cc3)CC4)CC2)cc1] |
| 41 | 2-(4-fluorobenzyl)-N-(1-(pyridine-3-ylmethyl)piperidin-4-yl)-1,2,3,4-tetrahydroisoquinoline-7-carboxamide | 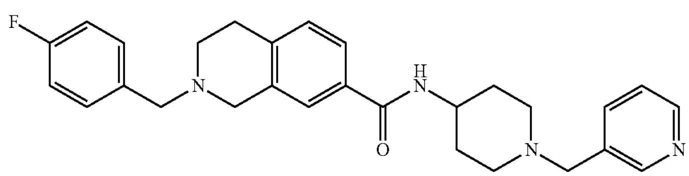 [SMILES: O=C(NC1CCN(Cc2cccnc2)CC1)c1ccc2c(c1)CN(Cc1ccc(F)cc1)CC2] |
| 42 | 2-(4-fluorobenzyl)-N-(1-(4-(trifluoromethyl)benzyl)piperidin-4-yl)-1,2,3,4-tetrahydroisoquinolin-7-carboxamide | 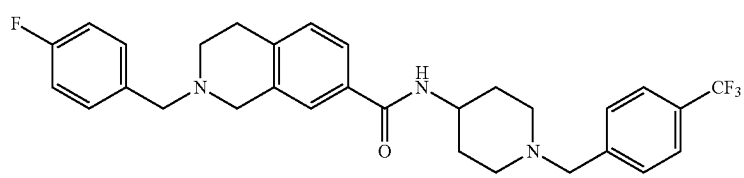 [SMILES: O=C(NC1CCN(Cc2ccc(C(F)(F)F)cc2)CC1)c1ccc2c(c1)CN(Cc1ccc(F)cc1)CC2] |

The present disclosure contemplates combinations of particularly described embodiments. For example, paragraph [0020] discloses certain embodiments of ring system "B" and paragraph [0023] discloses certain embodiments of T; also contemplated are embodiments in which ring system "B" is as described as in paragraph [0020], and T is as described in paragraph [0023]. This disclosure contemplates all such combinations, to the extent the definitions of the various structural features do not conflict with one another.

For simplicity, chemical moieties are defined and referred to throughout primarily as univalent chemical moieties (e.g., alkyl, aryl, etc.). Nevertheless, such terms are also used to convey corresponding multivalent moieties under the appropriate structural circumstances clear to those skilled in the art.

For example, while an "alkyl" moiety can refer to a monovalent radical (e.g. $CH_3$—$CH_2$—), in some circumstances a bivalent linking moiety can be "alkyl," in which case those skilled in the art will understand the alkyl to be a divalent radical (e.g., —$CH_2$—$CH_2$—), which is equivalent to the term "alkylene." (Similarly, in circumstances in which a divalent moiety is required and is stated as being "aryl," those skilled in the art will understand that the term "aryl" refers to the corresponding divalent moiety, arylene). All atoms are understood to have their normal number of valences for bond formation (i.e., 4 for carbon, 3 for N, 2 for O, and 2, 4, or 6 for S, depending on the oxidation state of the S). Nitrogens in the presently disclosed compounds can be hypervalent, e.g., an N-oxide or tetrasubstituted ammonium salt. On occasion a moiety may be defined, for example, as (A).-B-, wherein a is 0 or 1. In such instances, when a is 0 the moiety is B— and when a is 1 the moiety is A-B-.

As used herein, the term "alkyl" includes alkyl, alkenyl and alkynyl groups of a designed number of carbon atoms, desirably from 1 to about 12 carbons (i.e., inclusive of 1 and 12). The term "$C_m$-$C_n$ alkyl" means an alkyl group having from m to n carbon atoms (i.e., inclusive of m and n). The term "$C_m$-$C_n$ alkyl" means an alkyl group having from m to n carbon atoms. For example, "$C_1$-$C_6$ alkyl" is an alkyl group having from one to six carbon atoms. Alkyl and alkyl groups may be straight or branched and depending on context, may be a monovalent radical or a divalent radical (i.e., an alkylene group). In the case of an alkyl or alkyl group having zero carbon atoms (i.e., "$C_0$ alkyl"), the group is simply a single covalent bond if it is a divalent radical or is a hydrogen atom if it is a monovalent radical. For example, the moiety "—($C_0$-$C_6$ alkyl)-Ar" signifies connection of an optionally substituted aryl through a single bond or an alkylene bridge having from 1 to 6 carbons. Examples of "alkyl" include, for example, methyl, ethyl, propyl, isopropyl, butyl, iso-, sec- and tert-butyl, pentyl, hexyl, heptyl, 3-ethylbutyl, 3-hexenyl and propargyl. If the number of carbon atoms is not specified, the subject "alkyl" or "alkyl" moiety has from 1 to 12 carbons.

The term "haloalkyl" is an alkyl group substituted with one or more halogen atoms, e.g. F, Cl, Br and I. A more specific term, e.g., "fluoroalkyl" is an alkyl group substituted with one or more fluorine atoms. Examples of "fluoroalkyl" include fluoromethyl, difluoromethyl, trifluoromethyl, pentafluoroethyl, hexafluoroisopropyl and the like. In certain embodiments of the compounds disclosed herein, each haloalkyl is a fluoroalkyl.

The term "aryl" represents an aromatic ring system having a single ring (e.g., phenyl) which is optionally fused to other aromatic hydrocarbon rings or non-aromatic hydrocarbon rings. "Aryl" includes ring systems having multiple condensed rings and in which at least one is carbocyclic and aromatic, (e.g., 1,2,3,4-tetrahydronaphthyl, naphthyl). Examples of aryl groups include phenyl, 1-naphthyl, 2-naphthyl, indanyl, indenyl, dihydronaphthyl, fluorenyl, tetralinyl, and 6,7,8,9-tetrahydro-5H-benzo[a]cycloheptenyl. In certain examples, aryl groups include those having a first carbocyclic, aromatic ring fused to an aromatic or aliphatic heterocycle, for example, 2,3-dihydrobenzofuranyl. The aryl groups herein are unsubstituted or, when specified as "optionally substituted", can unless stated otherwise be substituted in one or more substitutable positions with various groups, as described below.

The term "heteroaryl" refers to an aromatic ring system containing at least one heteroatom selected from nitrogen, oxygen and sulfur in an aromatic ring. The heteroaryl may be fused to one or more cycloalkyl or heterocycloalkyl rings. Examples of heteroaryl groups include, for example, pyridyl, pyrimidinyl, quinolinyl, benzothienyl, indolyl, indolinyl, pyridazinyl, pyrazinyl, isoindolyl, isoquinolyl, quinazolinyl, quinoxalinyl, phthalazinyl, imidazolyl, isoxazolyl, pyrazolyl, oxazolyl, thiazolyl, indolizinyl, indazolyl, benzothiazolyl, benzimidazolyl, benzofuranyl, furanyl, thienyl, pyrrolyl, oxadiazolyl, thiadiazolyl, benzo[1,4]oxazinyl, triazolyl, tetrazolyl, isothiazolyl, naphthyridinyl, isochromanyl, chromanyl, tetrahydroisoquinolinyl, isoindolinyl, isobenzotetrahydrofuranyl, isobenzotetrahydrothienyl, isobenzothienyl, benzoxazolyl, pyridopyridinyl, benzotetrahydrofuranyl, benzotetrahydrothienyl, purinyl, benzodioxolyl, triazinyl, pteridinyl, benzothiazolyl, imidazopyridinyl, imidazothiazolyl, dihydrobenzisoxazinyl, benzisoxazinyl, benzoxazinyl, dihydrobenzisothiazinyl, benzopyranyl, benzothiopyranyl, chromonyl, chromanonyl, pyridinyl-N-oxide, tetrahydroquinolinyl, dihydroquinolinyl, dihydroquinolinonyl, dihydroisoquinolinonyl, dihydrocoumarinyl, dihydroisocoumarinyl, isoindolinonyl, benzodioxanyl, benzoxazolinonyl, pyrrolyl N-oxide, pyrimidinyl N-oxide, pyridazinyl N-oxide, pyrazinyl N-oxide, quinolinyl N-oxide, indolyl N-oxide, indolinyl N-oxide, isoquinolyl N-oxide, quinazolinyl N-oxide, quinoxalinyl N-oxide, phthalazinyl N-oxide, imidazolyl N-oxide, isoxazolyl N-oxide, oxazolyl N-oxide, thiazolyl N-oxide, indolizinyl N-oxide, indazolyl N-oxide, benzothiazolyl N-oxide, benzimidazolyl N-oxide, pyrrolyl N-oxide, oxadiazolyl N-oxide, thiadiazolyl N-oxide, triazolyl N-oxide, tetrazolyl N-oxide, benzothiopyranyl S-oxide, benzothiopyranyl S,S-dioxide. Preferred heteroaryl groups include pyridyl, pyrimidyl, quinolinyl, indolyl, pyrrolyl, furanyl, thienyl and imidazolyl, pyrazolyl, indazolyl, thiazolyl and benzothiazolyl. In certain embodiments, each heteroaryl is selected from pyridyl, pyrimidinyl, pyridazinyl, pyrazinyl, imidazolyl, isoxazolyl, pyrazolyl, oxazolyl, thiazolyl, furanyl, thienyl, pyrrolyl, oxadiazolyl, thiadiazolyl, triazolyl, tetrazolyl, isothiazolyl, pyridinyl-N-oxide, pyrrolyl N-oxide, pyrimidinyl N-oxide, pyridazinyl N-oxide, pyrazinyl N-oxide, imidazolyl N-oxide, isoxazolyl N-oxide, oxazolyl N-oxide, thiazolyl N-oxide, pyrrolyl N-oxide, oxadiazolyl N-oxide, thiadiazolyl N-oxide, triazolyl N-oxide, and tetrazolyl N-oxide. Preferred heteroaryl groups include pyridyl, pyrimidyl, quinolinyl, indolyl, pyrrolyl, furanyl, thienyl, imidazolyl, pyrazolyl, indazolyl, thiazolyl and benzothiazolyl. The heteroaryl groups herein are unsubstituted or, when specified as "optionally substituted", can unless stated otherwise be substituted in one or more substitutable positions with various groups, as described below.

The term "heterocycloalkyl" refers to a non-aromatic ring or ring system containing at least one heteroatom that is preferably selected from nitrogen, oxygen and sulfur, wherein said heteroatom is in a non-aromatic ring. The heterocycloalkyl may be saturated (i.e., a heterocycloalkyl) or partially unsaturated (i.e., a heterocycloalkenyl). Heterocycloalkyl includes monocyclic groups as well as bicyclic and polycyclic ring systems, including bridged and fused systems. The heterocycloalkyl ring is optionally fused to other heterocycloalkyl rings and/or non-aromatic hydrocarbon rings and/or phenyl rings. In certain embodiments, the heterocycloalkyl groups have from 3 to 7 members in a single ring. In other embodiments, heterocycloalkyl groups have 5 or 6 members in a single ring. Examples of heterocycloalkyl groups include, for example, azabicyclo[2.2.2]octyl (in each case also "quinuclidinyl" or a quinuclidine derivative), azabicyclo[3.2.1]octyl, 2,5-diazabicyclo[2.2.1]heptyl, morpholinyl, thiomorpholinyl, thiomorpholinyl S-oxide, thiomorpholinyl S,S-dioxide, 2-oxazolidonyl, piperazinyl, homopiperazinyl, piperazinonyl, pyrrolidinyl, azepanyl, azetidinyl, pyrrolinyl, tetrahydropyranyl, piperidinyl, tetrahydrofuranyl, tetrahydrothienyl, 3,4-dihydroisoquinolin-2(1H)-yl, isoindolindionyl, homopiperidinyl, homomorpholinyl, homothiomorpholinyl, homothiomorpholinyl S,S-dioxide, oxazolidinonyl, dihydropyrazolyl, dihydropyrrolyl, dihydropyrazinyl, dihydropyridinyl, dihydropyrimidinyl, dihydrofuryl, dihydropyranyl, imidazolidonyl, tetrahydrothienyl S-oxide, tetrahydrothienyl S,S-dioxide and homothiomorpholinyl S-oxide. Especially desirable heterocycloalkyl groups include morpholinyl, 3,4-dihydroisoquinolin-2(1H)-yl, tetrahydropyranyl, piperidinyl, aza-bicyclo[2.2.2]octyl, γ-butyrolactonyl (i.e., an oxo-substituted tetrahydrofuranyl), γ-butyrolactamyl (i.e., an oxo-substituted pyrrolidine), pyrrolidinyl, piperazinyl, azepanyl, azetidinyl, thiomorpholinyl, thiomorpholinyl S,S-dioxide, 2-oxazolidonyl, imidazolidonyl, isoindolindionyl, piperazinonyl. The heterocycloalkyl groups herein are unsubstituted or, when specified as "optionally substituted", can unless stated otherwise be substituted in one or more substitutable positions with various groups, as described below.

The term "cycloalkyl" refers to a non-aromatic carbocyclic ring or ring system, which may be saturated (i.e., a cycloalkyl) or partially unsaturated (i.e., a cycloalkenyl). The cycloalkyl ring optionally fused to or otherwise attached (e.g., bridged systems) to other cycloalkyl rings. Certain examples of cycloalkyl groups present in the disclosed compounds have from 3 to 7 members in a single ring, such as having 5 or 6 members in a single ring. Examples of cycloalkyl groups include, for example, cyclohexyl, cyclopentyl, cyclobutyl, cyclopropyl, tetrahydronaphthyl and bicyclo[2.2.1]heptane. The cycloalkyl groups herein are unsubstituted or, when specified as "optionally substituted", may be substituted in one or more substitutable positions with various groups.

The term "ring system" encompasses monocycles, as well as fused and/or bridged polycycles.

The term "oxa" means a divalent oxygen radical in a chain, sometimes designated as —O—.

The term "oxo" means a doubly bonded oxygen, sometimes designated as =O or for example in describing a carbonyl "C(O)" may be used to show an oxo substituted carbon.

The term "electron withdrawing group" means a group that withdraws electron density from the structure to which it is attached than would a similarly-attached hydrogen atom. For example, electron withdrawing groups can be selected from the group consisting of halo, cyano, —($C_1$-$C_4$ fluoroalkyl), —O—($C_1$-$C_4$ fluoroalkyl), —C(O)—($C_0$-$C_4$ alkyl), —C(O)O—($C_0$-$C_4$ alkyl), —C(O)N($C_0$-$C_4$ alkyl)($C_0$-$C_4$ alkyl), —S(O)$_2$O—($C_0$-$C_4$ alkyl), $NO_2$ and —C(O)-Hca in which the Hca includes a nitrogen atom to which the —C(O)— is bound, in which no alkyl, fluoroalkyl or heterocycloalkyl is substituted with an aryl, heteroaryl, cycloalkyl or heterocycloalkyl-containing group.

The term "substituted," when used to modify a specified group or radical, means that one or more hydrogen atoms of the specified group or radical are each, independently of one another, replaced with the same or different substituent groups as defined below.

Substituent groups for substituting for hydrogens on saturated carbon atoms in the specified group or radical are, unless otherwise specified, —$R^{60}$, halo, —$O^-M^+$, =O, —$OR^{70}$, —$SR^{70}$, —$S^-M^+$, =S, —$NR^{80}R^{80}$, =$NR^{70}$, =N—$OR^{70}$, trihalomethyl, —$CF_3$, —CN, —OCN, —SCN, —NO, —$NO_2$, =$N_2$, —$N_3$, —$SO_2R^{70}$, —$SO_2O^-M^+$, —$SO_2OR^{70}$, —$OSO_2R^{70}$, —$OSO_2O^-M^+$, —$OSO_2OR^{70}$, —P(O)($O^-$)$_2$($M^+$)$_2$, —P(O)($OR^{70}$)$O^-M^+$, —P(O)($OR^{70}$)$_2$, —C(O)$R^{70}$, —C(S)$R^{70}$, —C($NR^{70}$)$R^{70}$, —C(O)$O^-M^+$, —C(O)$OR^{70}$, —C(S)$OR^{70}$, —C(O)$NR^{80}R^{80}$, —C($NR^{70}$)$NR^{80}R^{80}$, —OC(O)$R^{70}$, —OC(S)$R^{70}$, —OC(O)$O^-M^+$, —OC(O)$OR^{70}$, —OC(S)$OR^{70}$, —$NR^{70}$C(O)$R^{70}$, —$NR^{70}$C(S)$R^{70}$, —$NR^{70}CO_2^-M^+$, —$NR^{70}CO_2R^{70}$, —$NR^{70}$C(S)$OR^{70}$, —$NR^{70}$C(O)$NR^{80}R^{80}$, —$NR^{70}$C($NR^{70}$)$R^{70}$ and —$NR^{70}$C($NR^{70}$)$NR^{80}R^{80}$. Each $R^{60}$ is independently selected from the group consisting of alkyl, heteroalkyl, cycloalkyl, heterocycloalkyl, heterocycloalkylalkyl, cycloalkylalkyl, aryl, arylalkyl, heteroaryl and heteroarylalkyl, each of which is optionally substituted with 1, 2, 3, 4 or 5 groups selected from the group consisting of halo, —$O^-M^+$, —$OR^{71}$, —$SR^{71}$, —$S^-M^+$, =S, —$NR^{81}R^{81}$, =$NR^{71}$, =N—$OR^{71}$, trihalomethyl, —$CF_3$, —CN, —OCN, —SCN, —NO, —$NO_2$, =$N_2$, —$N_3$, —$SO_2R^{71}$, —$SO_2O^-M^+$, —$SO_2OR^{71}$, —$OSO_2R^{71}$, —$OSO_2O^-M^+$, —$OSO_2OR^{71}$, —P(O)($O^-$)$_2$($M^+$)$_2$, —P(O)($OR^{71}$)$O^-M^+$, —P(O)($OR^{71}$)$_2$, —C(O)$R^{71}$, —C(S)$R^{71}$, —C($NR^{71}$)$R^{71}$, —C(O)$O^-M^+$, —C(O)$OR^{71}$, —C(S)$OR^{71}$, —C(O)$NR^{81}R^{81}$, —C($NR^{71}$)$NR^{81}R^{81}$, —OC(O)$R^{71}$, —OC(S)$R^{71}$, —OC(O)$R^{71}$, —OC(O)$O^-M^+$, —OC(O)$OR^{71}$, —OC(S)$OR^{71}$, —$NR^{71}$C(O)$R^{71}$, —$NR^{71}$C(S)$R^{71}$, —$NR^{71}CO_2^-M^+$, —$NR^{71}CO_2R^{71}$, —$NR^{71}$C(S)$OR^{71}$, —$NR^{71}$C(O)$NR^{81}R^{81}$, —$NR^{71}$C($NR^{71}$)$R^{71}$ and —$NR^{71}$C($NR^{71}$)$NR^{81}R^{81}$. Each $R^{70}$ is independently hydrogen or $R^{60}$; each $R^{80}$ is independently $R^{70}$ or alternatively, two $R^{80}$'s, taken together with the nitrogen atom to which they are bonded, form a 5-, 6- or 7-membered heterocycloalkyl which may optionally include from 1 to 4 of the same or different additional heteroatoms selected from the group consisting of O, N and S, of which N may have —H or $C_1$-$C_3$ alkyl substitution; and each $M^+$ is a counter ion with a net single positive charge. Each $R^{71}$ is independently hydrogen or $R^{61}$, in which $R^{61}$ is alkyl, heteroalkyl, cycloalkyl, heterocycloalkyl, heterocycloalkylalkyl, cycloalkylalkyl, aryl, arylalkyl, heteroaryl and heteroarylalkyl, each of which is optionally substituted with 1, 2, 3, 4 or 5 groups selected from the group consisting of halo, —$O^-M^+$, =O, —$OR^{72}$, —$SR^{72}$, —$S^-M^+$, =S, —$NR^{82}R^{82}$, =$NR^{72}$, =N—$OR^{72}$, trihalomethyl, —$CF_3$, —CN, —OCN, —SCN, —NO, —$NO_2$, =$N_2$, —$N_3$, —$SO_2R^{71}$, —$SO_2O^-M^+$, —$SO_2OR^{72}$, —$OSO_2R^{72}$, —$OSO_2O^-M^+$, —$OSO_2OR^{72}$, —P(O)($O^-$)$_2$($M^+$)$_2$, —P(O)($OR^{72}$)$O^-M^+$, —P(O)($OR^{72}$)$_2$, —C(O)$R^{72}$, —C(S)$R^{72}$, —C($NR^{72}$)$R^{72}$, —C(O)$O^-M^+$, —C(O)$OR^{72}$, —C(S)$OR^{72}$, —C(O)$NR^{82}R^{82}$, —C($NR^{72}$)$NR^{82}R^{82}$, —OC(O)$R^{72}$, —OC(S)$R^{72}$, —OC(O)$O^-M^+$, —OC(O)$OR^{72}$, —OC(S)$OR^{72}$, —$NR^{72}$C(O)$R^{72}$, —$NR^{72}$C(S)$R^{72}$, —$NR^{72}CO_2^-M^+$, —$NR^{72}CO_2R^{72}$, —$NR^{72}$C(S)$OR^{72}$, —$NR^{72}$C(O)$NR^{82}R^{82}$, —$NR^{72}$C($NR^{72}$)$R^{72}$ and —$NR^{72}$C($NR^{72}$)$NR^{82}R^{82}$; and each $R^{81}$ is independently $R^{71}$ or alternatively, two $R^{81}$s, taken together with the nitrogen atom to which they are bonded, form a 5-, 6- or 7-membered heterocycloalkyl which may optionally include from 1 to 4 of the same or different additional heteroatoms selected from the group consisting of O, N and S, of which N may have —H or $C_1$-$C_3$ alkyl substitution. Each $R^{72}$ is independently hydrogen, ($C_1$-$C_6$ alkyl) or ($C_1$-$C_6$ fluoroalkyl); each $R^{82}$ is independently $R^{72}$ or alternatively, two $R^{82}$s, taken together with the nitrogen atom to which they are bonded, form a 5-, 6- or 7-membered heterocycloalkyl which may optionally include 1, 2, 3 or 4 of the same or different additional heteroatoms selected from the group consisting of O, N and S, of which N may have —H or $C_1$-$C_3$ alkyl substitution. Each M may independently be, for example, an alkali ion, such as $K^+$, $Na^+$, $Li^+$; an ammonium ion, such as $^+N(R^{60})_4$; or an alkaline earth ion, such as $[Ca^{2+}]_{0.5}$, $[Mg^{2+}]_{0.5}$, or $[Ba^{2+}]_{0.5}$ ("subscript 0.5 means e.g. that one of the counter ions for such divalent alkali earth ions can be an ionized form of a presently disclosed compound and the other a typical counter ion such as chloride, or two ionized presently disclosed molecules can serve as counter ions for such divalent alkali earth ions, or a doubly ionized compound can serve as the counter ion for such divalent alkali earth ions). As specific examples, —$NR^{80}R^{80}$ is meant to include —$NH_2$, —NH-alkyl, N-pyrrolidinyl, N-piperazinyl, 4-methyl-piperazin-1-yl and N-morpholinyl.

Substituent groups for hydrogens on unsaturated carbon atoms in "substituted" alkene, alkyne, aryl and heteroaryl groups are, unless otherwise specified, —$R^{60}$, halo, —$O^-M^+$, —$OR^{70}$, —$SR^{70}$, —$S^-M^+$, —$NR^{80}R^{80}$, trihalomethyl, —$CF_3$, —CN, —OCN, —SCN, —NO, —$NO_2$, —$N_3$, —$SO_2R^{70}$, —$SO_3^-M^+$, —$SO_3R^{70}$, —$OSO_2R^{70}$, —$OSO_3^-M^+$, —$OSO_3R^{70}$, —$PO_3^{-2}(M^+)_2$, —P(O)($OR^{70}$)$O^-M^+$, —P(O)($OR^{70}$)$_2$, —C(O)$R^{70}$, —C(S)$R^{70}$, —C($NR^{70}$)$R^{70}$, —$CO_2^-M^+$, —$CO_2R^{70}$, —C(S)$OR^{70}$, —C(O)$NR^{80}R^{80}$, —C(NR$^{70}$)NR$^{80}$R$^{80}$, —OC(O)R$^{70}$, —OC(S)R$^{70}$, —OCO$_2^-$M$^+$, —OCO$_2$R$^{70}$, —OC(S)OR$^{70}$, —NR$^{70}$C(O)R$^{70}$, —NR$^{70}$C(S)R$^{70}$, —NR$^{70}$CO$_2^-$M$^+$, —NR$^{70}$CO$_2$R$^{70}$, —NR$^{70}$C(S)OR$^{70}$, —(NR$^{70}$)C(O)NR$^{80}$R$^{80}$, —NR$^{70}$C(NR$^{70}$)R$^{70}$ and —NR$^{70}$C(NR$^{70}$)NR$^{80}$R$^{80}$, where R$^{60}$, R$^{70}$, R$^{80}$ and M$^+$ are as previously defined.

Substituent groups for hydrogens on nitrogen atoms in "substituted" heteroalkyl and heterocycloalkyl groups are, unless otherwise specified, —R$^{60}$, —O$^-$M$^+$, —OR$^{70}$, —SR$^{70}$, —S$^-$M$^+$, —NR$^{80}$R$^{80}$, trihalomethyl, —CF$_3$, —CN, —NO, —NO$_2$, —S(O)$_2$R$^{70}$, —S(O)$_2$O$^-$M$^+$, —S(O)$_2$OR$^{70}$, —OS(O)$_2$R$^{70}$, —OS(O)$_2$O$^-$M$^+$, —OS(O)$_2$OR$^{70}$, —P(O)(O$^-$)$_2$(M$^+$)$_2$, —P(O)(OR$^{70}$)O$^-$M$^+$, —P(O)(OR$^{70}$)(OR$^{70}$), —C(O)R$^{70}$, —C(S)R$^{70}$, —C(NR$^{70}$)R$^{70}$, —C(O)OR$^{70}$, —C(S)OR$^{70}$, —C(O)NR$^{80}$R$^{80}$, —C(NR$^{70}$)NR$^{80}$R$^{80}$, —OC(O)R$^{70}$, —OC(S)R$^{70}$, —OC(O)OR$^{70}$, —OC(S)OR$^{70}$, —NR$^{70}$C(O)R$^{70}$, —NR$^{70}$C(S)R$^{70}$, —NR$^{70}$C(O)OR$^{70}$, —NR$^{70}$C(S)OR$^{70}$, —NR$^{70}$C(O)NR$^{80}$R$^{80}$, —NR$^{70}$C(NR$^{70}$)R$^{70}$ and —NR$^{70}$C(NR$^{70}$)NR$^{80}$R$^{80}$, where R$^{60}$, R$^{70}$, R$^{80}$ and M$^+$ are as previously defined.

In certain embodiments of the compounds disclosed herein, a group that is substituted has 1, 2, 3, or 4 substituents, 1, 2, or 3 substituents, 1 or 2 substituents, or 1 substituent.

In certain preferred embodiments, substituent groups on "substituted" alkyl, cycloalkyl, heterocycloalkyl, aryl and heteroaryl groups are -halo, —OH, —O—(C$_1$-C$_4$ alkyl), —O—(C$_1$-C$_4$ haloalkyl), —N(C$_0$-C$_4$ alkyl)(C$_0$-C$_4$ alkyl), —SH, —S(O)$_{0-2}$—(C$_1$-C$_4$ alkyl), —(C$_1$-C$_4$ alkyl), —(C$_1$-C$_4$ haloalkyl), —C(O)—(C$_0$-C$_4$ alkyl), —C(O)N(C$_0$-C$_4$ alkyl)(C$_0$-C$_4$ alkyl), —N(C$_0$-C$_4$ alkyl)C(O)(C$_0$-C$_4$ alkyl)(C$_0$-C$_4$ alkyl), —C(O)O—(C$_0$-C$_4$ alkyl), —OC(O)—(C$_0$-C$_4$ alkyl), S(O)$_2$—O(C$_0$-C$_4$ alkyl), and —NO$_2$, in which no alkyl is further substituted.

The compounds disclosed herein can also be provided as pharmaceutically acceptable salts. The term "pharmaceutically acceptable salts" or "a pharmaceutically acceptable salt thereof" refer to salts prepared from pharmaceutically acceptable non-toxic acids or bases including inorganic acids and bases and organic acids and bases. If the compound is basic, salts may be prepared from pharmaceutically acceptable non-toxic acids. Such salts may be, for example, acid addition salts of at least one of the following acids: benzenesulfonic acid, citric acid, α-glucoheptonic acid, D-gluconic acid, glycolic acid, lactic acid, malic acid, malonic acid, mandelic acid, phosphoric acid, propanoic acid, succinic acid, sulfuric acid, tartaric acid (d, l, or dl), tosic acid (toluenesulfonic acid), valeric acid, palmitic acid, pamoic acid, sebacic acid, stearic acid, lauric acid, acetic acid, adipic acid, carbonic acid, 4-chlorobenzenesulfonic acid, ethanedisulfonic acid, ethylsuccinic acid, fumaric acid, galactaric acid (mucic acid), D-glucuronic acid, 2-oxo-glutaric acid, glycerophosphoric acid, hippuric acid, isethionic acid (ethanolsulfonic acid), lactobionic acid, maleic acid, 1,5-naphthalene-disulfonic acid, 2-naphthalene-sulfonic acid, pivalic acid, terephthalic acid, thiocyanic acid, cholic acid, n-dodecyl sulfate, 3-hydroxy-2-naphthoic acid, 1-hydroxy-2-naphthoic acid, oleic acid, undecylenic acid, ascorbic acid, (+)-camphoric acid, d-camphorsulfonic acid, dichloroacetic acid, ethanesulfonic acid, formic acid, hydriodic acid, hydrobromic acid, hydrochloric acid, methanesulfonic acid, nicotinic acid, nitric acid, orotic acid, oxalic acid, picric acid, L-pyroglutamic acid, saccharine, salicylic acid, gentisic acid, and/or 4-acetamidobenzoic acid.

The compounds described herein can also be provided in prodrug form. "Prodrug" refers to a derivative of an active compound (drug) that undergoes a transformation under the conditions of use, such as within the body, to release the active drug. Prodrugs are frequently, but not necessarily, pharmacologically inactive until converted into the active drug. Prodrugs are typically obtained by masking a functional group in the drug believed to be in part required for activity with a progroup (defined below) to form a promoiety which undergoes a transformation, such as cleavage, under the specified conditions of use to release the functional group, and hence the active drug. The cleavage of the promoiety can proceed spontaneously, such as by way of a hydrolysis reaction, or it can be catalyzed or induced by another agent, such as by an enzyme, by light, by acid, or by a change of or exposure to a physical or environmental parameter, such as a change of temperature. The agent can be endogenous to the conditions of use, such as an enzyme present in the cells to which the prodrug is administered or the acidic conditions of the stomach, or it can be supplied exogenously. A wide variety of progroups, as well as the resultant promoieties, suitable for masking functional groups in the active drugs to yield prodrugs are well-known in the art. For example, a hydroxyl functional group can be masked as a sulfonate, ester or carbonate promoiety, which can be hydrolyzed in vivo to provide the hydroxyl group. An amino functional group can be masked as an amide, carbamate, imine, urea, phosphenyl, phosphoryl or sulfenyl promoiety, which can be hydrolyzed in vivo to provide the amino group. A carboxyl group can be masked as an ester (including silyl esters and thioesters), amide or hydrazide promoiety, which can be hydrolyzed in vivo to provide the carboxyl group. Specific examples of suitable progroups and their respective promoieties will be apparent to those of skill in the art.

The compounds disclosed herein can also be provided as N-oxides.

The presently disclosed compounds, salts, prodrugs and N-oxides can be provided, for example, in solvate or hydrate form.

One of ordinary skill in the art of medicinal chemistry also will appreciate that the disclosed structures are intended to include isotopically enriched forms of the present compounds. As used herein "isotopes" includes those atoms having the same atomic number but different mass numbers. As will be apparent to those of skill in the art upon consideration of the present compounds, certain atoms can be enriched an isotope of that atom. For example, compounds having a fluorine atom, may be synthesized in a form enriched in the radioactive fluorine isotope $^{18}$F. Similarly, compounds may be enriched in the heavy isotopes of hydrogen, deuterium and tritium, and can be enriched in a radioactive isotope of carbon, such as $^{13}$C. Such compounds can be useful, for example, in studying the AMPK pathway and its role in metabolism.

Compounds can be assayed for binding to a membrane-bound adiponectin receptor by performing a competitive binding assay with adiponectin. In one such procedure, HEK 293 cellular membrane is coated onto a COSTAR 384 plate, which is then blocked with 1% casein. Polyhistidine-tagged globular adiponectin and a candidate compound is incubated with the membrane in HEPES buffer. Unbound ligands are washed away and the degree of binding of the adiponectin is determined using horseradish peroxidase-conjugated anti-polyhistidine. Compounds that compete with adiponectin binding to the membrane (i.e., give a reduced signal compared to a control performed without a candidate compound) can be chosen as hits and further screened using the below-described functional assays to identify adiponectin receptor agonists.

An in-cell western assay can be performed to demonstrate the activation of AMPK in human liver cells by globular adiponectin using glutathione S-transferase (GST). AMPK activity can be measured by the relative concentration of phosphorylated acetyl Co-A carboxylase, which is one of the products of AMPK. An increase in pACC correlates with an increase in the rate of fatty acid oxidation.

The compounds of structural formulae (I)-(CXXIV) can be administered, for example, orally, topically, parenterally, by inhalation or spray or rectally in dosage unit formulations containing one or more pharmaceutically acceptable carriers, diluents or excipients. The term parenteral as used herein includes percutaneous, subcutaneous, intravascular (e.g., intravenous), intramuscular, or intrathecal injection or infusion techniques and the like.

Pharmaceutical compositions can be made using the presently disclosed compounds. For example, in one embodiment, a pharmaceutical composition includes a pharmaceutically acceptable carrier, diluent or excipient, and compound as described above with reference to structural formulae (I)-(CXXXIV).

In the pharmaceutical compositions disclosed herein, one or more compounds of structural formulae (I)-(CXXIV) may be present in association with one or more pharmaceutically acceptable carriers, diluents or excipients, and, if desired, other active ingredients. The pharmaceutical compositions containing compounds of structural formulae (I)-(CXXIV) may be in a form suitable for oral use, for example, as tablets, troches, lozenges, aqueous or oily suspensions, dispersible powders or granules, emulsion, hard or soft capsules, or syrups or elixirs.

Compositions intended for oral use can be prepared according to any suitable method for the manufacture of pharmaceutical compositions and such compositions may contain one or more agents selected from the group consisting of sweetening agents, flavoring agents, coloring agents and preservative agents in order to provide pharmaceutically elegant and palatable preparations. Tablets contain the active ingredient in admixture with non-toxic pharmaceutically acceptable excipients that are suitable for the manufacture of tablets. These excipients can be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets can be uncoated or they can be coated by known techniques. In some cases such coatings can be prepared by suitable techniques to delay disintegration and absorption in the gastrointestinal tract and thereby provide a sustained action over a longer period. For example, a time delay material such as glyceryl monostearate or glyceryl distearate can be employed.

Formulations for oral use can also be presented as hard gelatin capsules, wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Formulations for oral use can also be presented as lozenges.

Aqueous suspensions contain the active materials in admixture with excipients suitable for the manufacture of aqueous suspensions. Such excipients can be suspending agents, for example sodium carboxymethylcellulose, methylcellulose, hydropropylmethylcellulose, sodium alginate, polyvinylpyrrolidone, gum tragacanth and gum acacia; dispersing or wetting agents such as a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose or saccharin.

Oily suspensions can be formulated by suspending the active ingredients in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents and flavoring agents may be added to provide palatable oral preparations. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents or suspending agents are exemplified by those already mentioned above. Additional excipients, for example sweetening, flavoring and coloring agents, can also be present.

Pharmaceutical compositions can also be in the form of oil-in-water emulsions. The oily phase can be a vegetable oil or a mineral oil or mixtures of these. Suitable emulsifying agents can be naturally-occurring gums, for example gum acacia or gum tragacanth, naturally-occurring phosphatides, for example soy bean, lecithin, and esters or partial esters derived from fatty acids and hexitol, anhydrides, for example sorbitan monooleate, and condensation products of the said partial esters with ethylene oxide, for example polyoxyethylene sorbitan monooleate. The emulsions can also contain sweetening and flavoring agents.

Syrups and elixirs can be formulated with sweetening agents, for example glycerol, propylene glycol, sorbitol, glucose or sucrose. Such formulations can also contain a demulcent, a preservative, flavoring, and coloring agents. The pharmaceutical compositions can be in the form of a sterile injectable aqueous or oleaginous suspension. This suspension can be formulated according to the known art using those suitable dispersing or wetting agents and suspending agents that have been mentioned above. The sterile injectable preparation can also be a sterile injectable solution or suspension in a non-toxic parentally acceptable diluent or solvent, for example as a solution in 1,3-butanediol. Among the acceptable vehicles and solvents that can be employed are water, Ringer's solution and isotonic sodium chloride solution. In addition, sterile, fixed oils can be employed as a solvent or suspending medium. For this purpose any bland fixed oil can be employed including synthetic mono- or diglycerides. In addition, fatty acids such as oleic acid find use in the preparation of injectables.

Compounds of structural formulae (I)-(CXXIV) can also be administered in the form of suppositories, e.g., for rectal administration of the drug. These compositions can be prepared by mixing the compound with a suitable non-irritating excipient that is solid at ordinary temperatures but liquid at the rectal temperature and will therefore melt in the rectum to release the drug. Such materials include cocoa butter and polyethylene glycols.

Compounds of structural formula (I)-(CXXIV) can also be administered parenterally in a sterile medium. The drug, depending on the vehicle and concentration used, can either be suspended or dissolved in the vehicle. Advantageously, adjuvants such as local anesthetics, preservatives and buffering agents can be dissolved in the vehicle.

The compounds disclosed herein can be made using procedures familiar to the person of ordinary skill in the art and as described herein. For example, compounds of structural formulae (V)-(VI) can be prepared according to Scheme 1, below, or analogous synthetic schemes:

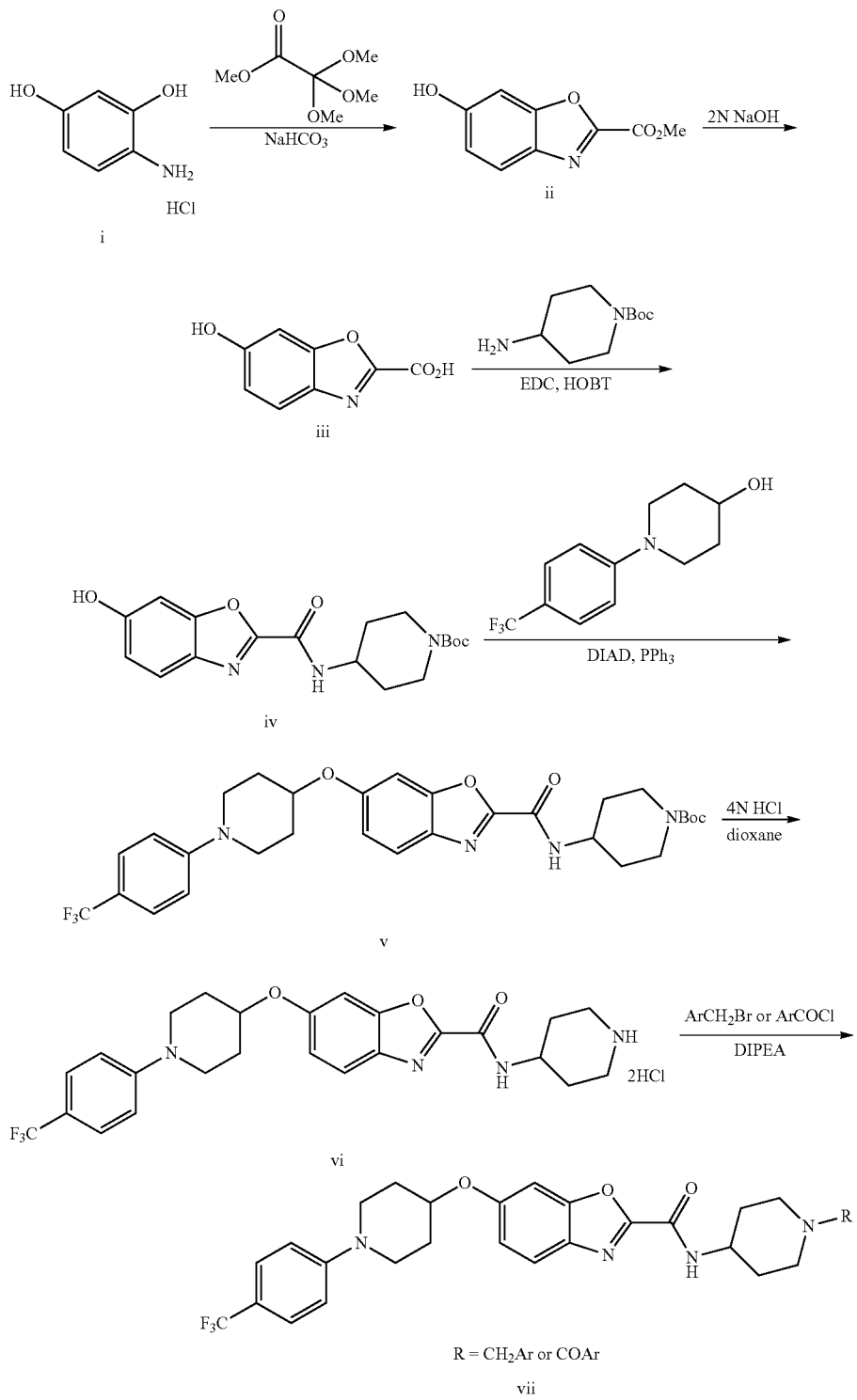

Referring to Scheme 1, a 4-aminoresorcinol i, for example, is reacted with methyl trimethoxyacetate to form a methyl hydroxybenzo[d]oxazolecarboxylate ii, which in turn is saponified then condensed with a heterocycloalkylamine (e.g., a protected 4-aminopiperidine) to form an N-heterocycloalkyl hydroxybenzo[d]oxazolecarboxamide iv. Hydroxybenzo[d]oxazolecarboxamide iv is coupled with, for example, a 1-substituted piperidin-4-ol (e.g., 1-(4-(trifluoromethyl)phenyl)piperidin-4-ol) to form an N-substituted-heterocycloalkyloxybenzo[d]oxazolecarboxamide v. The heterocycloalkyl moiety of the carboxamide can then be further substituted. For example, as shown in Scheme 1, in which the N-substituent of the amide is a 1-protected piperidin-4-yl, the protecting group can be removed and the piperidine nitrogen can be coupled with an aroyl halide or an arylmethyl halide to form compound vii. Of course, in certain situations one of ordinary skill in the art will use different reagents to affect one or more of the individual steps or to use protected versions of certain of the substituents. Synthetic examples are provided below in Example 1.

Compounds of structural formulae (VII)-(VIII) can be prepared according to Scheme 2, below, or analogous synthetic schemes:

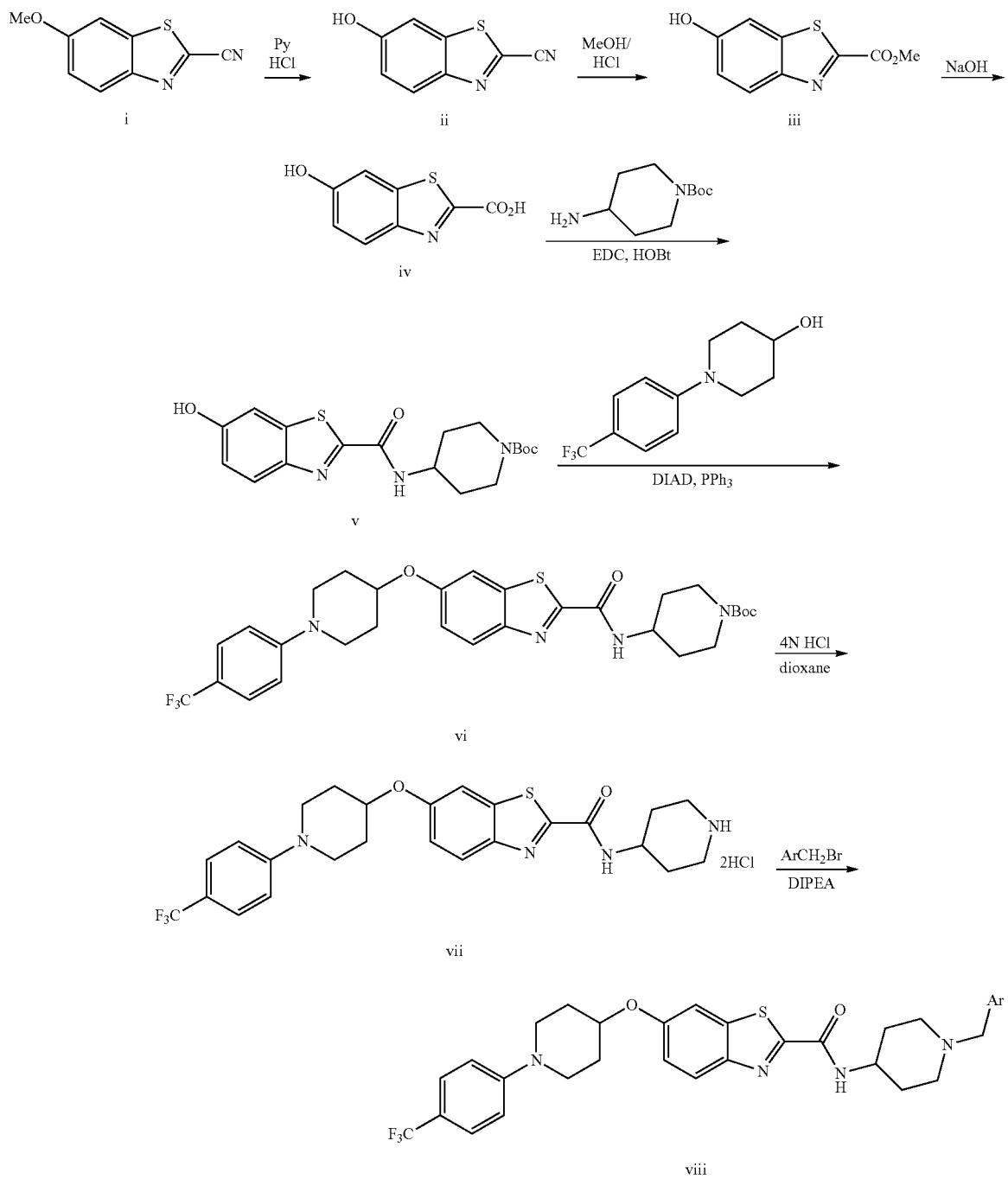

Referring to Scheme 2, a 6-methoxybenzo[d]thiazole-2-carbonitrile i, for example, is reacted with pyridinium hydrochloride, then acidic methanol to form methyl hydroxybenzo[d]thiazolecarboxylate iii, which in turn is saponified and acidified to form acid iv. Acid iv is then condensed with a heterocycloalkylamine (e.g., a protected 4-aminopiperidine) to form an N-heterocycloalkyl hydroxybenzo[d]thiazolecarboxamide v. Hydroxybenzo[d]thiazole carboxamide v is coupled with, for example, a 1-substituted piperidin-4-ol (e.g., 1-(4-trifluoromethylphenyl)piperidin-4-ol) then deprotected to form an N-substituted-heterocycloalkyloxybenzo[d]thiazolecarboxamide vi. The heterocycloalkyl moiety of the carboxamide can then be further substituted. For example, as shown in Scheme 2, in which the N-substituent of the amide is a 1-protected piperidin-4-yl, the protecting group can be removed and the piperidine nitrogen can be coupled with an arylmethyl halide (or e.g. an aroyl halide) to form compound viii. One of ordinary skill in the art would recognize that different reagents can be used to affect one or more of the individual steps or to protect intermediates where appropriate. Specific synthetic examples are provided below in Example 2.

Compounds of structural formulae (IX)-(XII) can be prepared according to Scheme 3, below, or analogous synthetic schemes:

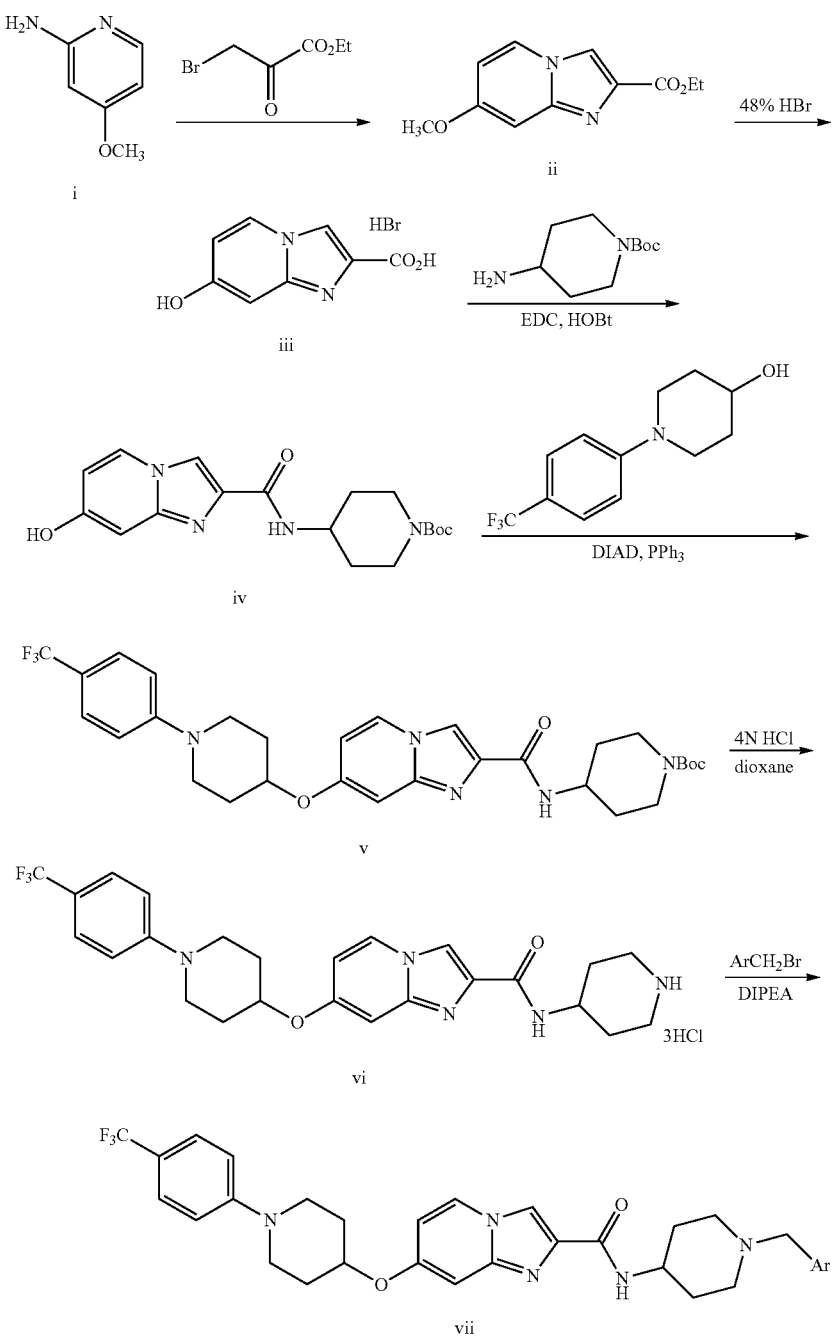

Referring to Scheme 3, a 2-amino-4-methoxypyridine is reacted with ethyl 3-bromo-2-oxopropanoate to form an ethyl 7-methoxyimidazo[1,2-a]pyridine-2-carboxylate ii, which is hydrolyzed, for example, with hydrobromic acid to provide 7-hydroxyimidazo[1,2-a]pyridine-2-carboxylic acid as its hydrobromide salt iii. The 7-hydroxyimidazo[1,2-a]pyridine-2-carboxylic acid iii is then condensed with a heterocycloalkylamine (e.g., a protected 4-aminopiperidine) to form an N-heterocycloalkyl 7-hydroxyimidazo[1,2-a]pyridine-2-carboxamide iv. 7-Hydroxyimidazo[1,2-a]pyridine-2-carboxamide iv is coupled with, for example, a 1-substituted piperidin-4-ol (e.g., 1-(4-trifluoromethylphenyl)piperidin-4-ol) to form an N-substituted-heterocycloalkyloxyimidazo[1,2-a]pyridinecarboxamide v. The heterocycloalkyl moiety of the carboxamide can then be further substituted. For example, as shown in Scheme 3, in which the N-substituent of the amide is a 1-protected piperidin-4-yl, the protecting group can be removed and the piperidine nitrogen can be coupled with an arylmethyl halide (or alternatively an aroyl halide) to form compound vii. Of course, in certain situations one of ordinary skill in the art will use different reagents to affect one or more of the individual steps or to use protected versions of certain of the substituents. Specific synthetic examples are provided below in Example 3.

Compounds of structural formulae (XIII)-(XIV) can be prepared according to Scheme 4, below, or analogous synthetic schemes:

Scheme 4

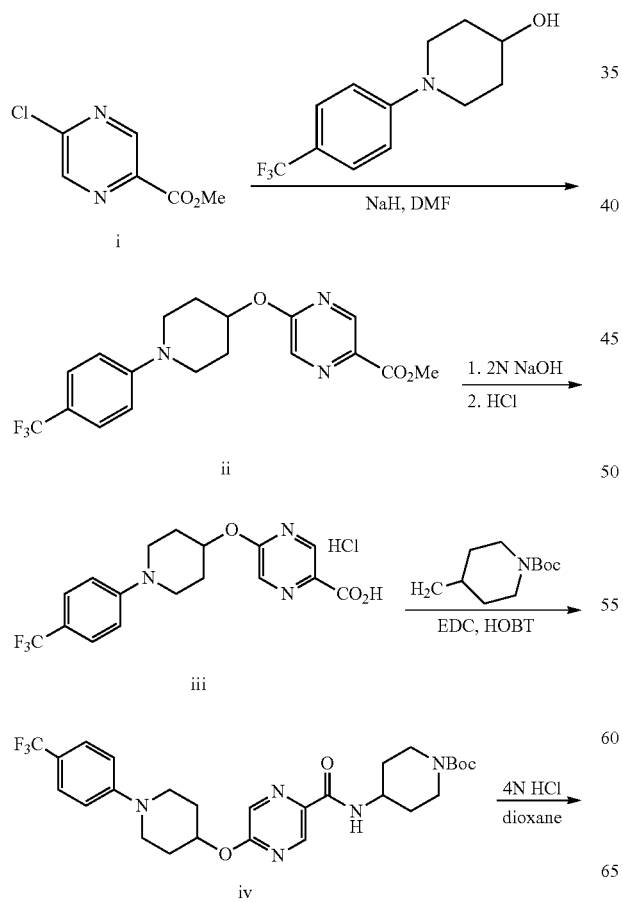

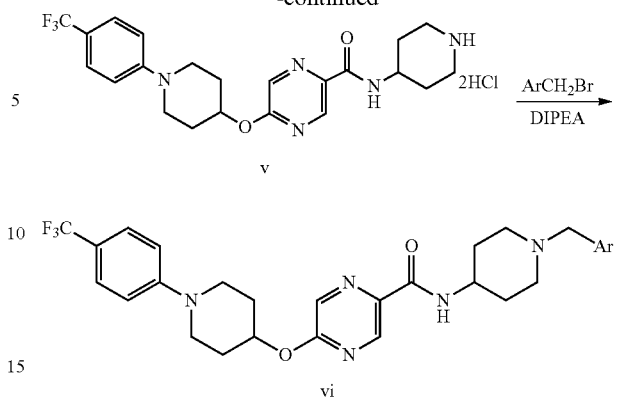

Referring to Scheme 4, a methyl chloropyrazine-2-carboxylate i, for example, is reacted with a 1-substituted piperidin-4-ol (e.g., 1-(4-trifluoromethylphenyl)piperidin-4-ol) to form a methyl (piperidin-4-yloxy)pyrazine-2-carboxylate ii, which in turn is saponified and then acidified to form the corresponding carboxylic acid iii. The (piperidin-4-yloxy)pyrazine-2-carboxylic acid iii is condensed with a heterocycloalkylamine (e.g., a protected 4-aminopiperidine) to form an N-substituted-heterocycloalkyloxypyrazinecarboxamide iv. The heterocycloalkyl moiety of the carboxamide can then be further substituted. For example, as shown in Scheme 4, in which the N-substituent of the amide is a 1-protected piperidin-4-yl, the protecting group can be removed and the piperidine nitrogen can be coupled with an arylmethyl halide (or alternatively an aroyl halide) to form compound vi. Of course, in certain situations one of ordinary skill in the art will use different reagents to affect one or more of the individual steps or to use protected versions of certain of the substituents. Specific synthetic examples are provided below in Example 4.

Compounds of structural formulae (XV)-(XVII) can be prepared according to Scheme 5, below, or analogous synthetic schemes:

Scheme 5

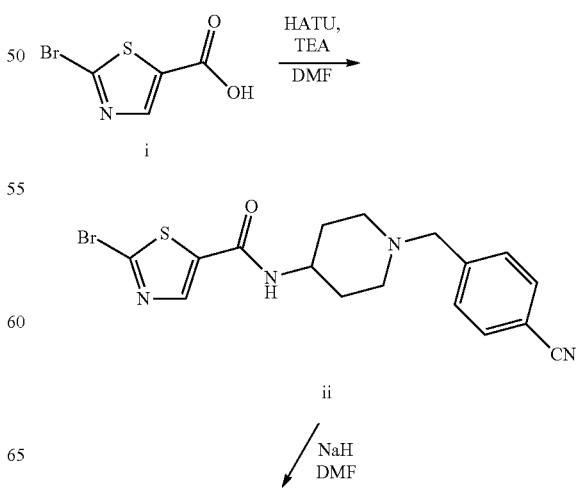

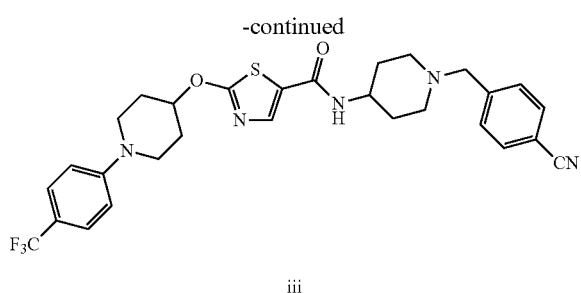

iii

Referring to Scheme 5, a bromothiazolecarboxylic acid i can be condensed with an appropriately substituted heterocycloalkylamine (e.g., 4-((4-aminopiperidin-1-yl)methyl) benzonitrile in the example of Scheme 1) to form the N-heterocycloalkyl bromothiazolecarboxamide ii. Bromothiazolecarboxamide ii can then be coupled with, for example, a 1-substituted piperidin-4-ol (e.g., 1-(4-trifluoromethylphenyl)piperidin-4-ol) to form an N-substituted heterocycloalkyloxybromothiazolecarboxamide iii. Of course, in certain situations one of ordinary skill in the art will use different reagents to affect one or more of the individual steps, use protected versions of certain of the substituents or use alternative synthetic strategies to synthesize the presently disclosed compounds. Specific synthetic examples are provided below in Example 5.

Compounds of structural formulae (XXXI)-(XXXIII) can be prepared according to Scheme 6, below, or analogous synthetic schemes:

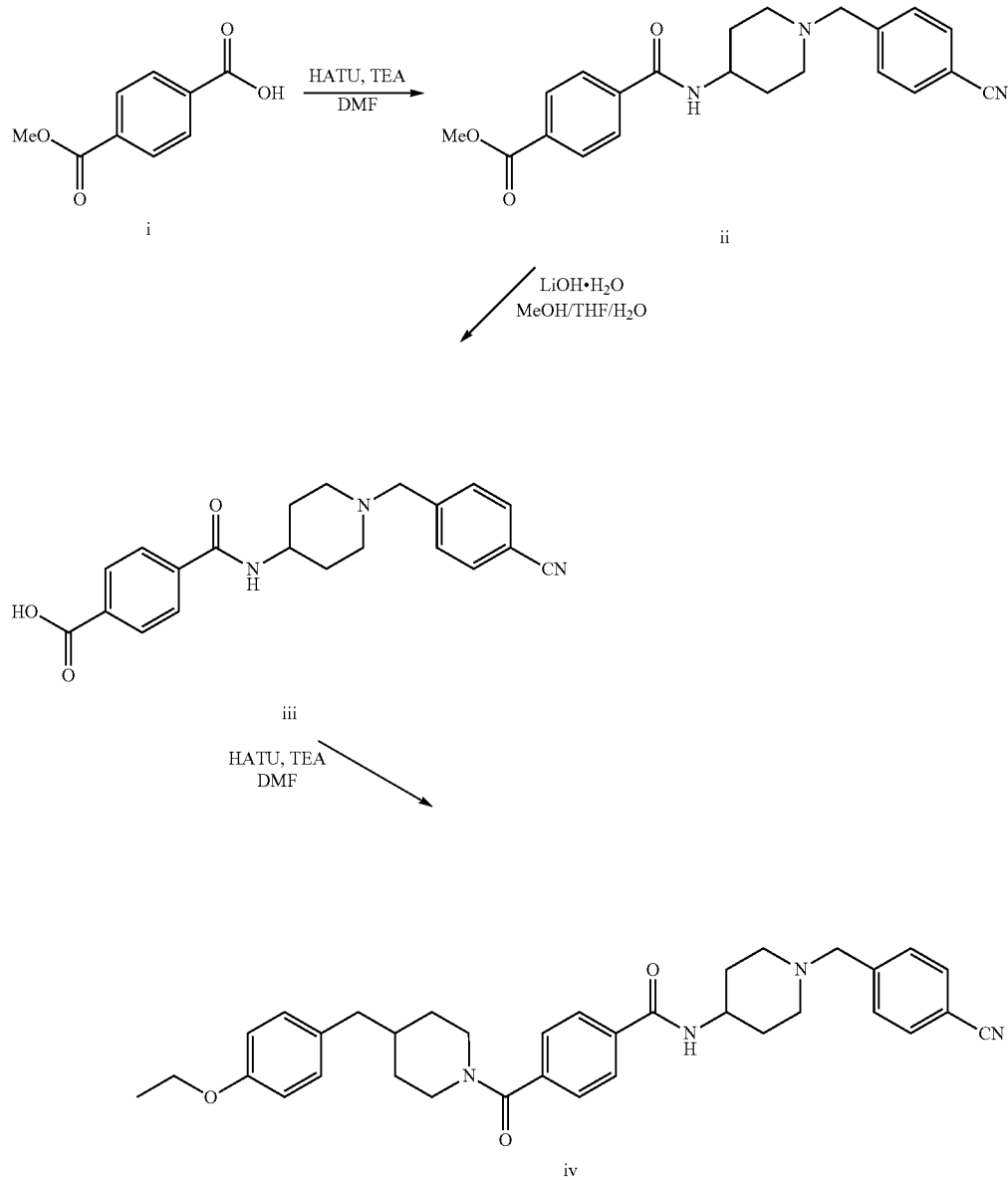

Referring to Scheme 6, carboxylic acid ester i can be condensed with an appropriately substituted heterocycloalkylamine (e.g., 4-((4-aminopiperidin-1-yl)methyl)benzonitrile in the example of Scheme 6) to form the methyl (heterocycloalkylcarbamoyl)benzoate ii. Benzoate ii can then be saponified to form the corresponding benzoic acid iii, which is then coupled with an appropriate amine (e.g., a substituted piperidine as shown in Scheme 6, or alternatively a substituted piperazine, or a substituted piperidinylamine) to form an N-substituted terephthalamide ii. Of course, in certain situations one of ordinary skill in the art will use different reagents to affect one or more of the individual steps or to use protected versions of certain of the substituents. Specific synthetic examples provided below in Example 6.

Compounds of structural formulae (XL)-(XLIII) can be prepared according to Scheme 7, below, or analogous synthetic schemes:

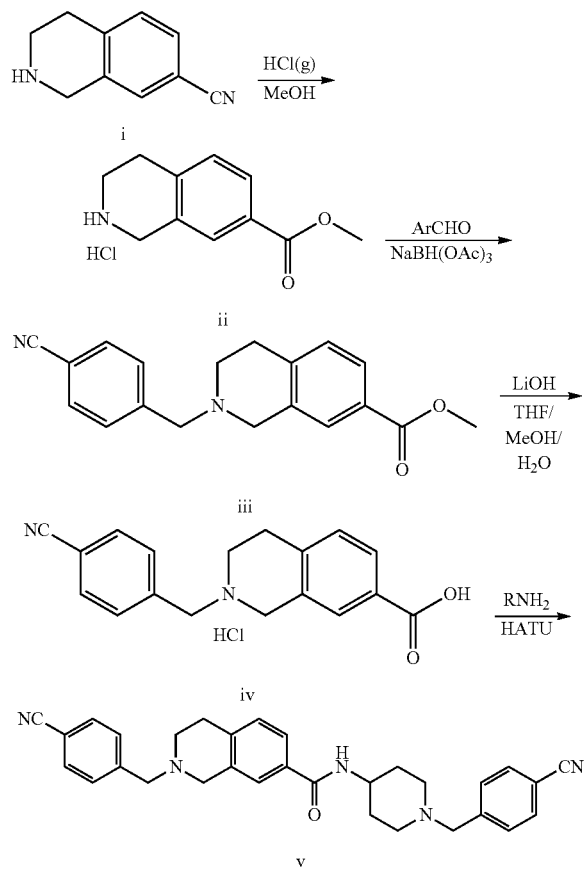

Referring to Scheme 7, a cyano-1,2,3,4-tetrahydroisoquinoline i can be converted to the corresponding methyl ester ii, then reductively coupled with an aryl aldehyde to form a methyl 2-benzyl-1,2,3,4-tetrahydroisoquinoline carboxylate iii. Saponification of iii to its corresponding carboxylic acid iv followed by condensation with a heterocycloalkylamine (in this case, a 1-benzylpiperidin-4-ylamine) can provide carboxamide v. Of course, the person of skill in the art can modify this scheme to provide the desired substitution and regiochemistry of the final compound. Moreover, in certain situations one of ordinary skill in the art will use different reagents to affect one or more of the individual steps or to use protected versions of certain of the substituents. Specific synthetic examples are provided below in Example 7.

One of skill in the art can adapt the reaction sequences of Schemes 1-7 to fit the desired target molecule. Of course, in certain situations one of skill in the art will use different reagents to affect one or more of the individual steps or to use protected versions of certain of the substituents. Additionally, one skilled in the art would recognize that compounds of structural formulae (I)-(CXXIV) can be synthesized using different routes altogether.

Compounds suitable for use in the presently disclosed pharmaceutical compositions include compounds of Table 1, above. These compounds can be made according to the general schemes described above, for example using a procedure similar to that described below in the Examples.

While not intending to be bound by theory, the inventors surmise that compounds of structural formulae (I)-(CXXIV) are mimics of adiponectin which act as adiponectin receptor agonists, thereby activating the AMPK pathway. Activation of the AMPK pathway has the effect of increasing glucose uptake, decreasing glycogen synthesis and increasing fatty acid oxidation, thereby reducing glycogen, intracellular triglyceride and fatty acid concentration and causing an increase in insulin sensitivity. Because they activate the AMPK pathway, compounds of structural formulae (I)-(CXXIV) should also inhibit the inflammatory processes which occur during the early phases of atherosclerosis. Accordingly, compounds of structural formulae (I)-(CXXIV) can be useful in the treatment of type II diabetes and in the treatment and prevention of atherosclerosis, cardiovascular disease, obesity and non-alcoholic fatty liver disease.

Accordingly, another aspect of the present disclosure relates to a method of activating the AMPK pathway. According to this aspect, a method for activating the AMPK pathway in a cell includes contacting the cell with an effective amount of a compound, pharmaceutically acceptable salt, prodrug, N-oxide (or solvate or hydrate thereof) or composition described above.

In one embodiment, a method of increasing fatty acid oxidation in a cell includes contacting the cell with an effective amount of a compound, pharmaceutically acceptable salt, prodrug, N-oxide (or solvate or hydrate thereof) or composition described above. Acetyl Co-A carboxylase (ACC) catalyzes the formation of malonyl Co-A, a potent inhibitor of fatty acid oxidation; phosphorylation of ACC greatly reduces its catalytic activity, thereby reducing the concentration of malonyl Co-A and increasing the rate of fatty acid oxidation. Because the presently disclosed compounds can increase the rate of phosphorylation of ACC, they can reduce the inhibition of fatty acid oxidation and therefore increase its overall rate.

In another embodiment, a method of decreasing glycogen concentration in a cell includes contacting the cell with an effective amount of a compound, pharmaceutically acceptable salt, prodrug, N-oxide (or solvate or hydrate thereof) or composition described above.

In another embodiment, a method of increasing glucose uptake in a cell includes contacting the cell with an effective amount of a compound, pharmaceutically acceptable salt, prodrug, N-oxide (or solvate or hydrate thereof) or composition described above.

In another embodiment, a method of reducing triglyceride levels in a subject includes administering to the subject an effective amount of a compound, pharmaceutically acceptable salt, prodrug, N-oxide (or solvate or hydrate thereof) or composition described above.

In another embodiment, a method of increasing insulin sensitivity of a subject includes administering to the subject an effective amount of a compound, pharmaceutically acceptable salt prodrug, N-oxide (or solvate or hydrate thereof) or composition described above.

Accordingly, the compounds and compositions disclosed herein can be used to treat a variety of metabolic disorders. For example, in one embodiment, a method of treating type II diabetes in a subject in need of such treatment includes administering to the subject an effective amount of a compound, pharmaceutically acceptable salt, prodrug, solvate, hydrate, N-oxide or composition described above. In another embodiment, a method of treating or preventing atherosclerosis or cardiovascular disease in a subject includes administering to the subject an effective amount of a compound, pharmaceutically acceptable salt, prodrug prodrug, N-oxide (or solvate or hydrate thereof) or composition described above.

As described above, the compounds disclosed herein can act as activators of the AMPK pathway. Accordingly, in another embodiment, a method comprises modulating the AMPK pathway (either in vitro or in vivo) by contacting a cell with a compound, pharmaceutically acceptable salt, prodrug, N-oxide (or solvate or hydrate thereof) or composition described above, or administering a compound, pharmaceutically acceptable salt, prodrug, N-oxide (or solvate or hydrate thereof) or composition described above to a mammal (e.g., a human) in an amount sufficient to modulate the AMPK activity and study the effects thereby induced. Such methods are useful for studying the AMPK pathway and its role in biological mechanisms and disease states both in vitro and in vivo.

Another embodiment is the use of a compound, pharmaceutically acceptable salt, prodrug, N-oxide (or solvate or hydrate thereof) or composition as described above in the manufacture of a medicament for any of the therapeutic purposes described above. For example, the medicament can be for the reduction of triglyceride levels in a subject, the treatment of type II diabetes in a subject, or the treatment or prevention of atherosclerosis or cardiovasclular disease in a subject.

The compounds disclosed herein can be linked to labeling agents, for example for use in variety of experiments exploring their receptor binding, efficacy and metabolism. Accordingly, another embodiment is a labeled conjugate comprising a compound as disclosed herein covalently linked to a labeling agent, optionally through a linker. Suitable linker and labeling agents will be readily apparent to those of skill in the art upon consideration of the present disclosure. The labeling agent can be, for example, an affinity label such as biotin or strepavidin, a hapten such as digoxigenin, an enzyme such as a peroxidase, or a fluorophoric or chromophoric tag. Any suitable linker can be used. For example, in some embodiments, an ethylene glycol, oligo(ethylene glycol) or poly(ethylene glycol) linker is used. Other examples of linkers include amino acids, which can be used alone or in combination with other linker groups, such as ethylene glycol, oligo-ethylene glycol or polyethylene glycol. Suitable linkers include, without limitation, single amino acids, as well as di- and tripeptides. In one embodiment, the linker includes a glycine residue. The person of skill in the art will realize, of course, that other linkers and labeling agents can be used. In other embodiments, an alkylene chain is the linker. In other embodiments, the linker has the structure —[($C_0$-$C_3$ alkyl)-$Y^m$-]$_m$—, in which each $Y^m$ is —O—, —N($R^9$)—, or L, and m is in the range of 1-40. For example, in certain embodiments, a labeled conjugate has structural formula (CXXV):

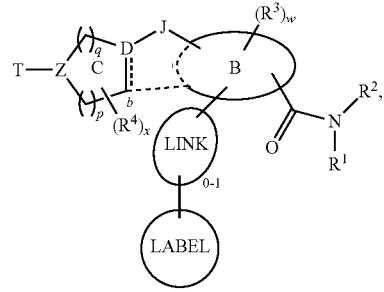

(CXXV)

in which the "LINK" moiety is a linker and is optional, and the "LABEL" moiety is a labeling agent, and all other variables are as described above, for example with reference to structural formula (I). Any of the compounds disclosed with reference to structural formulae (I)-(CXXIV) can be used in the labeled conjugate of structural formula (CXXV).

In certain embodiments, the -(LINK)$_{0-1}$-(LABEL) moiety is attached the "B" ring system at a benzo, pyrido, pyrazino or thieno ring position in the meta position relative to the J moiety. For example, in one embodiment, a labeled conjugate has structural formula (CXXVI):

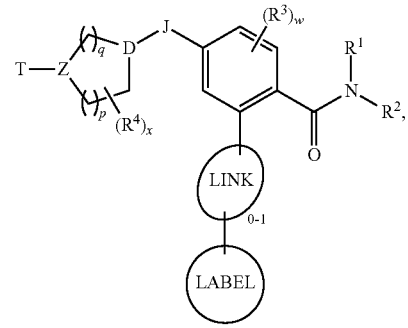

(CXXVI)

in which the "LINK" moiety is a linker and is optional, and the "LABEL" moiety is a labeling agent, and all other variables are as described above, for example with reference to structural formula (I).

For example, in one particular embodiment, a labeled conjugate has structural formula (CXXVII):

(CXXVII)

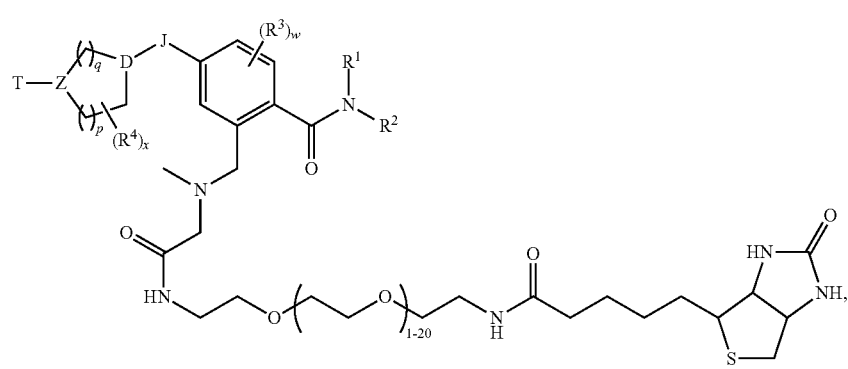

in which all variables are as described above, for example with reference to structural formula (I).

The following examples are intended to further illustrate certain embodiments and are not intended to limit the scope of the presently disclosed compounds.

EXAMPLES

Example 1 a) Synthetic Example: tert-butyl 4-(6-(1-(4-(trifluoromethyl)phenyl)piperidin-4-yloxy)benzo[d]oxazole-2-carboxamido)piperidine-1-carboxylate (compound 1)

Step 1

A mixture of 4-aminobenzene-1,3-diol hydrochloride (i in Scheme 1) (0.50 g, 3.1 mmol) and sodium hydrogen carbonate (2.5 mg) in methyl trimethoxyacetate (2 mL) was stirred at 100° C. overnight and then concentrated under reduced pressure. The residue obtained was purified by flash chromatography (silica gel, methylene chloride/ethyl acetate=9/1) to afford methyl 6-hydroxybenzo[d]oxazole-2-carboxylate as a white solid (0.49 g, 82%). $^1$H-NMR (DMSO-$d_6$, 300 MHz): δ 10.26 (s, 1H), 7.70 (m, 1H), 7.12 (m, 1H), 6.95 (m, 1H), 3.92 (s, 3H) ppm; MS (ESI): 194.3 (M+1).

Step 2

A mixture of methyl 6-hydroxybenzo[d]oxazole-2-carboxylate (0.19 g, 1 mmol) and 1N aqueous sodium hydroxide (2 mL) was stirred at room temperature overnight. The reaction mixture was then acidified with concentrated hydrochloric acid. The precipitate was filtered, washed with water, and dried under reduced pressure to afford 6-hydroxybenzo[d]oxazole-2-carboxylic acid as a white solid (0.16 g, 88%). $^1$H-NMR (DMSO-$d_6$, 300 MHz): δ 10.17 (s, 1H), 7.66 (m, 1H), 7.08 (m, 1H), 6.92 (m, 1H) ppm; MS (ESI): 180.1 (M+1).

Step 3

To a stirred mixture of 6-hydroxybenzo[d]oxazole-2-carboxylic acid (0.15 g, 0.86 mmol) in anhydrous N,N-dimethylformamide (2 mL) was added triethylamine (0.10 g, 0.99 mmol), 1-hydroxybenzotriazole hydrate (0.14 g, 0.99 mmol), 1-(3-dimethylaminopropyl)-3-ethylcarbodiimide hydrochloride (0.20 g, 0.99 mmol), and tert-butyl 4-aminopiperidine-1-carboxylate (0.20 g, 0.99 mmol). The mixture was stirred at room temperature overnight and then concentrated under reduced pressure. The residue obtained was purified by flash chromatography (silica gel, ethyl acetate/hexanes=1/1) to afford tert-butyl 4-(6-hydroxybenzo[d]oxazole-2-carboxamido)piperidine-1-carboxylate as a off-white solid (0.16 g, 52%). $^1$H-NMR (DMSO-$d_6$, 300 MHz): δ 10.10 (s, 1H), 9.04 (m, 1H), 7.63 (m, 1H), 7.10 (m, 1H), 7.27 (m, 5H), 6.91(m, 1H), 3.92 (m, 3H), 2.78 (m, 2H), 1.72 (m, 2H), 1.49 (m, 2H), 1.38 (s, 9H); MS (ESI): 362.1 (M+1).

Step 4

To a stirred solution of tert-butyl 4-(6-hydroxybenzo[d]oxazole-2-carboxamido)piperidine-1-carboxylate (0.15 g, 0.41 mmol) in toluene (4 mL) at room temperature was added diisopropyl azodicarboxylate (0.1 g, 0.49 mmol), 1-(4-(trifluoromethyl)phenyl) piperidin-4-ol (0.1 g, 0.41 mmol), and triphenylphosphine (0.13 g, 0.49 mmol). The mixture was stirred at room temperature overnight and then concentrated under reduced pressure. The residue obtained was purified by flash chromatography (silica gel, ethyl acetate/hexanes=2/3) to afford tert-butyl 4-(6-(1-(4-(trifluoromethyl)phenyl)piperidin-4-yloxy)benzo[d]oxazole-2-carboxamido)piperidine-1-carboxylate (compound 1) as a off-white solid (0.16 g, 66%). $^1$H-NMR (CDCl$_3$, 300 MHz): δ 7.65 (m, 1H), 7.48 (m, 2H), 7.15 (m, 1H), 7.05 (m, 2H), 6.96 (m, 2H), 4.56 (m, 1H), 4.12 (m, 3H), 3.60 (m, 2H), 3.28 (m, 2H), 2.93 (m, 2H), 2.04 (m, 8H), 1.47 (s, 9H) ppm; MS (ESI): 589.6 (M+1).

(b) Synthetic Example: Compounds 2-7

Step 1

A mixture of tert-butyl 4-(6-(1-(4-(trifluoromethyl)phenyl)piperidin-4-yloxy)benzo[d]oxazole-2-carboxamido)piperidine-1-carboxylate (compound 1) (0.16 g, 0.27 mmol) and 4N hydrochloric acid in dioxane (2 mL) was stirred at room temperature for 1 h. The reaction mixture was concentrated and washed with diethyl ether (2×3 mL) and then dried under reduced pressure to afford N-(piperidin-4-yl)-6-(1-(4-(trifluoromethyl)phenyl)piperidin-4-yloxy)benzo[d]oxazole-2-carboxamide dihydrochloride salt as a off-white solid (0.15 g, 99%). $^1$H NMR (CD$_3$OD, 300 MHz) 7.83 (m, 5H), 7.48 (s, 1H), 7.23 (m, 1H), 4.93 (m, 1H), 4.22 (m, 1H), 3.90 (m, 3H), 3.35 (m, 2H), 3.17 (m, 2H), 2.23 (m, 8H), 1.98 (m, 2H) ppm; MS (ES) 489.1 (M+1).

Step 2

To a stirred mixture of N-(piperidin-4-yl)-6-(1-(4-(trifluoromethyl)phenyl)piperidin-4-yloxy)benzo[d]oxazole-2-carboxamide dihydrochloride salt (0.03 g, 0.05 mmol) in anhydrous N,N-dimethylformamide (0.5 mL) or methylene chloride (1 mL) at room temperature was added the appropriately-substituted benzyl halide (0.06 mmol) or benzoyl halide (0.06 mmol) and N,N-diisopropylethylamine (0.03 g, 0.22 mmol). The resulting mixture was stirred at room temperature overnight. After this time the mixture was concentrated under reduced pressure and the resulting residue was purified by flash chromatography (silica gel, methylene chloride/methanol/30% ammonium hydroxide) to afford compounds 2-7 in solid form.

N-(1-(4-Cyanobenzyl)piperidin-4-yl)-6-(1-(4-(trifluoromethyl)phenyl)piperidin-4-yloxy)benzo[d]oxazole-2-carboxamide (compound 2): $^1$H-NMR (CDCl$_3$, 300 MHz): δ 7.63 (m, 2H), 7.46 (m, 4H), 7.18-6.94 (m, 6H), 4.58 (m, 1H), 4.03 (m, 1H), 3.58 (m, 4H), 3.29 (m, 2H), 2.82 (m, 2H), 2.11 (m, 8H), 1.61 (m, 2H) ppm; MS (ESI): 604.7 (M+1).

N-(1-(Pyridin-4-ylmethyl)piperidin-4-yl)-6-(1-(4-(trifluoromethyl)phenyl)piperidin-4-yloxy)benzo[d]oxazole-2-carboxamide (compound 3): $^1$H-NMR (CDC$_3$, 300 MHz): δ 8.55 (m, 2H), 7.65 (m, 1H), 7.48 (m, 2H), 7.28 (m, 2H), 7.08 (m, 3H), 6.94 (m, 2H), 4.56 (m, 1H), 4.04 (m, 1H), 3.62 (m, 2H), 3.56 (s, 2H), 3.28 (m, 2H), 2.89-1.91 (m, 8H), 1.67 (m, 2H) ppm; MS (ESI): 578.5 (M−1).

N-(1-(4-Fluorobenzoyl)piperidin-4-yl)-6-(1-(4-(trifluoromethyl)phenyl)piperidin-4-yloxy)benzo[d]oxazole-2-carboxamide (compound 4): $^1$H-NMR (CDC$_3$, 300 MHz): δ 7.66 (m, 1H), 7.44 (m, 4H), 7.10 (m, 5H), 6.96 (m, 2H), 4.58 (m, 1H), 4.27 (m, 1H), 3.28 (m, 2H), 3.13 (m, 2H), 2.12 (m, 4H), 2.01 (m, 2H), 1.58 (m, 4H) ppm; MS (ESI): 611.6 (M+1).

N-(Piperidin-4-yl)-6-(1-(4-(trifluoromethyl)phenyl)piperidin-4-yloxy)benzo[d]oxazole-2-carboxamide (compound 5): $^1$H NMR (CD$_3$OD, 300 MHz) 7.83 (m, 5H), 7.48 (s, 1H), 7.23 (m, 1H), 4.93 (m, 1H), 4.22 (m, 1H), 3.90 (m, 3H), 3.35 (m, 2H), 3.17 (m, 2H), 2.23 (m, 8H), 1.98 (m, 2H) ppm; MS (ES) 489.1 (M+1).

N-(1-(4-Cyanobenzoyl)piperidin-4-yl)-6-(1-(4-(trifluoromethyl)phenyl)piperidin-4-yloxy)benzo[d]oxazole-2-carboxamide (compound 6): $^1$H-NMR (CDC$_3$, 300 MHz): δ 7.74 (m, 2H), 7.66 (m, 1H), 7.50 (m, 4H), 7.14 (m, 2H), 7.06 (m, 1H), 6.96 (m, 2H), 4.71 (m, 1H), 4.58 (m, 1H), 4.28 (m, 1H), 3.60 (m, 3H), 3.16 (m, 4H), 2.04 (m, 6H), 1.63 (m, 2H) ppm; MS (ESI): 618.5 (M+1).

N-(4-Isonicotinoylcyclohexyl)-6-(1-(4-(trifluoromethyl)phenyl)piperidin-4-yloxy)benzo[d]oxazole-2-carboxamide (compound 7): $^1$H-NMR (CDC$_3$, 300 MHz): δ 8.71 (m, 2H), 7.65 (m, 1H), 7.48 (m, 2H), 7.29 (m, 2H), 7.16 (m, 2H), 7.06 (m, 1H), 6.96 (m, 2H), 4.72 (m, 1H), 4.58 (m, 1H), 4.28 (m, 1H), 3.62 (m, 3H), 3.16 (m, 4H), 2.04 (m, 6H), 1.65 (m, 2H) ppm; MS (ESI): 594.5 (M+1).

(c) Synthetic Example: Compounds 9-11

Compounds 9-11 were prepared using procedures analogous to those described in Example 1(a).

4-((5-(6-(1-(4-(Trifluoromethyl)phenyl)piperidin-4-yloxy)benzo[d]oxazole-2-carbonyl)-2,5-diazabicyclo[2.2.1]heptan-2-yl)methyl)benzamide (compound 9): $^1$H NMR (CDC$_3$, 300 MHz) 8.542 (m, 2H), 7.67 (m, 1H), 7.43 (m, 4H), 7.48 (m, 2H), 7.31 (m, 2H), 7.17 (m, 1H), 7.01 (m, 3H), 4.58 (m, 1H), 3.95 (m, 1H), 3.82 (m, 2H), 3.59 (m, 4H), 3.28 (m, 2H), 2.96 (m, 1H). 2.80 (m, 1H), 2.02 (m. 6H) ppm; MS (ES) 578.6 (M+H).

4-((5-(6-(1-(4-(Trifluoromethyl)phenyl)piperidin-4-yloxy)benzo[d]oxazole-2-carbonyl)-2,5-diazabicyclo[2.2.1]heptan-2-yl)methyl)benzonitrile (compound 10): $^1$H NMR (DMSO-d$_6$, 300 MHz) 7.90 (m, 1H), 7.79 (m, 3H), 7.56 (m, 1H), 7.42 (m, 4H), 7.28 (m, 1H), 7.08 (m, 3H), 4.75 (m, 1H), 3.79 (m, 2H), 3.60 (m, 4H), 3.36 (m, 2H), 2.93 (m, 1H), 2.70 (m, 1H), 2.59 (m, 2H), 1.91 (m, 6H) ppm; MS (ES) 620.6 (M+H).

(5-Isonicotinoyl-2,5-diazabicyclo[2.2.1]heptan-2-yl)(6-(1-(4-(trifluoromethyl)phenyl)piperidin-4-yloxy)benzo[d]oxazol-2-yl)methanone (compound 11): $^1$H NMR (CDC$_3$, 300 MHz) 8.73 (m, 2H), 7.710 (m, 1H), 7.47 (m, 2H), 7.40 (m, 2H), 7.16 (m, 1H), 7.04 (m, 1H), 6.96 (m, 2H), 4.57 (m, 1H), 4.19 (m, 1H), 3.83 (m, 3H), 3.60 (m, 4H), 3.28 (m, 2H), 2.04 (m, 6H) ppm; MS (ES) 592.5 (M+H).

(d) Increase in AMPK Activity

Compounds 1-13 were assayed for their ability to activate AMPK using an enzyme-linked immunosorbent assay. The EC$_{50}$ values for AMPK activation for compounds 1-13 are presented in Table 2 below, in which "A" is less than 0.1 μM; "B" is 0.1-1 μM; "C" is 1-10 μM; and "D" is 10-100 μM:

TABLE 2

| Cpd No. | AMPK EC$_{50}$ |
|---|---|
| 1 | A |
| 2 | A |
| 3 | A |
| 4 | A |
| 5 | D |
| 6 | A |
| 7 | A |
| 8 | B |
| 9 | B |
| 10 | B |
| 11 | B |
| 12 | A |
| 13 | A |

Example 2

(a) Synthetic Example: tert-butyl 4-(6-(1-(4-(trifluoromethyl)phenyl)piperidin-4-yloxy)benzo[d]thiazole-2-carboxamido)piperidine-1-carboxylate (compound 14)

Step 1
A mixture of 6-methoxybenzo[d]thiazole-2-carbonitrile (1.0 g, 5.3 mmol) and dry pyridinium hydrochloride (11.3 g, 98.1 mmol) was stirred at 190° C. for 3 h. After the completion of reaction, it was cooled to room temperature to obtain a yellow solid. This solid was purified by flash chromatography (silica gel, methylene chloride/ethyl acetate=25/1) to afford 6-hydroxybenzo[d]thiazole-2-carbonitrile as a yellow solid (0.42 g, 45%). $^1$H-NMR (DMSO-d$_6$, 300 MHz): δ 10.20 (s, 1H), 8.70 (m, 1H), 8.45 (m, 1H), 8.10 (m, 1H) ppm; MS (ESI): 177.1 (M+1).

Step 2
Dry methanol (30 mL) was bubbled with dry HCl gas for 10 min. To this solution was added 6-hydroxybenzo[d]thiazole-2-carbonitrile (0.42 g, 2.38 mmol) and the resulting mixture was stirred at room temperature for 4 days. The resulting solids were collected by filtration, washed with water and dried under reduced pressure to afford methyl 6-hydroxybenzo[d]thiazole-2-carboxylate as a yellow solid (0.43 g, 86%). $^1$H-NMR (DMSO-d$_6$, 300 MHz): δ 10.28 (s, 1H), 7.99 (m, 1H), 7.46 (m, 1H), 7.08 (m, 1H), 3.93 (s, 3H) ppm; MS (ESI): 210.1 (M+1).

Step 3
A mixture of methyl 6-hydroxybenzo[d]thiazole-2-carboxylate (0.21 g, 1 mmol) and 1N aqueous sodium hydroxide (2 mL) was stirred at room temperature overnight. The reaction mixture was then carefully acidified with concentrated hydrochloric acid. The precipitate formed was filtered, washed with water, and dried under reduced pressure to afford 6-hydroxybenzo[d]thiazole-2-carboxylic acid as a white solid (0.20 g, 99%). $^1$H-NMR (DMSO-d$_6$, 300 MHz): δ 10.20 (s, 1H), 7.96 (m, 1H), 7.44 (m, 1H), 7.06 (m, 1H) ppm; MS (ESI): 196.1 (M+1).

Step 4
To a stirred mixture of 6-hydroxybenzo[d]thiazole-2-carboxylic acid (0.20 g, 1 mmol) in anhydrous N,N-dimethylformamide (2 mL) was added triethylamine (0.12 g, 1.2 mmol), 1-hydroxybenzotriazole hydrate (0.16 g, 1.2 mmol), 1-(3-dimethylaminopropyl)-3-ethylcarbodiimide hydrochloride (0.23 g, 1.2 mmol), and tert-butyl 4-aminopiperidine-1-carboxylate (0.24 g, 1.2 mmol). The mixture was stirred at room temperature overnight and then concentrated under reduced pressure. The residue obtained was purified by flash chromatography (silica gel, ethyl acetate/hexanes=1/1) to afford tert-butyl 4-(6-hydroxybenzo[d]thiazole-2-carboxamido)piperidine-1-carboxylate as a white solid (0.23 g, 62%). $^1$H-NMR (CDC$_3$, 300 MHz): δ 7.90 (m, 1H), 7.38 (m, 1H), 7.28 (m, 2H), 7.11 (m, 1H), 4.12 (m, 3H), 2.95 (m, 2H), 2.04 (m, 2H), 1.58 (m, 2H), 1.48 (s, 9H) ppm; MS (ESI): 379.1 (M+1).

Step 5
To a stirred solution of tert-butyl 4-(6-hydroxybenzo[d]thiazole-2-carboxamido)piperidine-1-carboxylate (0.20 g, 0.54 mmol) in toluene (4 mL) at room temperature was added diisopropyl azodicarboxylate (0.13 g, 0.64 mmol), 1-(4-(trifluoromethyl)phenyl)-piperidin-4-ol (0.13 g, 0.54 mmol), and triphenylphosphine (0.17 g, 0.64 mmol). The mixture was stirred at room temperature overnight and then concentrated under reduced pressure. The residue obtained was purified by flash chromatography (silica gel, ethyl acetate/hexanes=3/7) to afford tert-butyl 4-(6-(1-(4-(trifluoromethyl)phenyl)piperidin-4-yloxy)benzo[d]thiazole-2-carboxamido)piperidine-1-carboxylate (compound 14) as a white solid (0.28 g, 86%). $^1$H-NMR (CDC$_3$, 300 MHz): δ 7.95 (m, 1H), 7.48 (m, 3H), 7.27 (m, 1H), 7.17 (m, 1H), 6.97 (m, 2H), 4.62 (m, 1H), 4.12 (m, 3H), 3.61 (m, 2H), 3.29 (m, 2H), 2.95 (m, 2H), 2.06 (m, 6H), 1.56 (m, 2H), 1.41 (s, 9H) ppm; MS (ESI): 605.5 (M+1).

(b) Synthetic Example: Compounds 15-16

Step 1
A mixture of tert-butyl 4-(6-(1-(4-(trifluoromethyl)phenyl)piperidin-4-yloxy)benzo[d]thiazole-2-carboxamido)piperidine-1-carboxylate (compound 8) (0.16 g, 0.27 mmol) and 4N hydrochloric acid in dioxane (2 mL) was stirred at room temperature for 1 h. The reaction mixture was concentrated and washed with diethyl ether (2×3 mL) and then dried under reduced pressure to afford N-(piperidin-4-yl)-6-(1-(4-(trifluoromethyl)phenyl)piperidin-4-yloxy)benzo[d]thiazole-2-carboxamide as a off-white solid (0.15 g, 99%). $^1$H NMR (CD$_3$OD, 300 MHz) 7.83 (m, 5H), 7.48 (s, 1H), 7.23 (m, 1H), 4.93 (m, 1H), 4.22 (m, 1H), 3.90 (m, 3H), 3.35 (m, 2H), 3.17 (m, 2H), 2.23 (m, 8H), 1.98 (m, 2H) ppm; MS (ES) 489.1 (M+1).

Step 2

To a stirred mixture of N-(piperidin-4-yl)-6-(1-(4-(trifluoromethyl)phenyl)piperidin-4-yloxy)benzo[d]thiazole-2-carboxamide (0.03 g, 0.05 mmol) in anhydrous N,N-dimethylformamide (0.5 mL) at room temperature was added the appropriately-substituted benzyl bromide (0.06 mmol) and N,N-diisopropylethylamine (0.03 g, 0.22 mmol). The resulting mixture was stirred at room temperature overnight. After this time the mixture was concentrated under reduced pressure and the resulting residue was purified by flash chromatography (silica gel, methylene chloride/methanol/30% ammonium hydroxide) to afford compounds 15-16 in solid form.

N-(1-(Pyridin-4-ylmethyl)piperidin-4-yl)-6-(1-(4-(trifluoromethyl)phenyl)piperidin-4-yloxy)benzo[d]thiazole-2-carboxamide (compound 15): $^1$H-NMR (CDC$_3$, 300 MHz): δ 8.56 (m, 2H), 7.95 (m, 1H), 7.46 (m, 3H), 7.27 (m, 3H), 7.17 (m, 1H), 6.97 (m, 2H), 4.62 (m, 1H), 4.01 (m, 1H), 3.62 (m, 2H), 3.53 (s, 2H), 3.29 (m, 2H), 2.84 (m, 2H), 2.13 (m, 8H), 1.68 (m, 2H) ppm; MS (ESI): 596.5 (M+1).

N-(1-(4-Cyanobenzyl)piperidin-4-yl)-6-(1-(4-(trifluoromethyl)phenyl)piperidin-4-yloxy)benzo[d]thiazole-2-carboxamide (compound 16): $^1$H-NMR (CDC$_3$, 300 MHz): δ 7.95 (m, 1H), 7.62 (m, 2H), 7.45 (m, 5H), 7.27 (m, 1H), 7.17 (m, 1H), 6.96 (m, 2H), 4.62 (m, 1H), 4.02 (m, 1H), 3.61 (m, 4H), 3.29 (m, 2H), 2.84 (m, 2H), 2.11 (m, 8H), 1.69 (m, 2H) ppm; MS (ESI): 620.5 (M+1).

(c) Increase in AMPK Activity

Compounds 14-16 were assayed for their ability to activate AMPK using an enzyme-linked immunosorbent assay. The EC$_{50}$ values for AMPK activation for compounds 14-16 are presented in Table 3 below, in which "A" is less than 0.1 μM; "B" is 0.1-1 μM; "C" is 1-10 μM; and "D" is 10-100 μM:

TABLE 3

| Cpd No. | AMPK EC$_{50}$ |
| --- | --- |
| 14 | C |
| 15 | B |
| 16 | B |

Example 3

(a) Synthetic Example: tert-butyl 4-(7-(1-(4-(trifluoromethyl)phenyl)piperidin-4-yloxy)imidazo[1,2-a]yridine-2-carboxamido)piperidine-1-carboxylate Step 1

A mixture of 2-amino-4-methoxypyridine (1.0 g, 8.1 mmol) and ethyl 3-bromo-2-oxopropanoate (1.77 g, 9.1 mmol) in ethanol (10 mL) was refluxed for 6 h. After the reaction was concentrated, ethyl acetate (20 mL) was added to the residue. The mixture was basified by saturated aqueous sodium bicarbonate. The separated organic layer was washed with brine and dried over sodium sulfate. The solvent was evaporated and the residue obtained was purified by flash chromatography (silica gel, methylene chloride/ethyl acetate=1/1) to afford ethyl 7-methoxyimidazo[1,2-a]pyridine-2-carboxylate as a solid (1.04 g, 58%). $^1$H-NMR (DMSO-d$_6$, 300 MHz): δ 8.37 (m, 2H), 6.91 (s, 1H), 6.70 (m, 1H), 4.25 (m, 2H), 3.81 (s, 3H), 1.28 (m, 3H) ppm; MS (ESI): 221.1 (M+1).

Step 2

A mixture of ethyl 7-methoxyimidazo[1,2-a]pyridine-2-carboxylate (0.22 g, 1.0 mmol) and 48% hydrobromic acid (20 mL) was heated at reflux for 3 days. After the completion of reaction, the reaction mixture was concentrated and the residue obtained was washed with diethyl ether and dried under reduced pressure to afford 7-hydroxyimidazo[1,2-c]pyridine-2-carboxylic acid hydrobromide salt as a brown solid (0.24 g, 93%). $^1$H-NMR (CD$_3$OD, 300 MHz): δ 8.57 (m, 1H), 8.44 (s, 1H), 7.07 (m, 1H), 6.95 (m, 1H) ppm; MS (ESI): 178.1 (M+1).

Step 3

To a stirred mixture of 7-hydroxyimidazo[1,2-a]pyridine-2-carboxylic acid hydrobromide salt (0.24 g, 0.93 mmol) in anhydrous N,N-dimethylformamide (2 mL) was added triethylamine (0.22 g, 2.2 mmol), 1-hydroxybenzotriazole hydrate (0.16 g, 1.2 mmol), 1-(3-dimethylaminopropyl)-3-ethylcarbodiimide hydrochloride (0.23 g, 1.2 mmol), and tert-butyl 4-aminopiperidine-1-carboxylate (0.24 g, 1.2 mmol). The mixture was stirred at room temperature overnight and then concentrated under reduced pressure. The residue obtained was purified by flash chromatography (silica gel, ethyl acetate/hexanes=1/1) to afford tert-butyl 4-(7-hydroxyimidazo[1,2-a]pyridine-2-carboxamido)piperidine-1-carboxylate as an off-white solid (0.27 g, 81%). $^1$H-NMR (CDC$_3$, 300 MHz): δ 7.93 (m, 2H), 7.31 (m, 1H), 7.25 (m, 1H), 6.85 (m, 1H), 6.65 (m, 1H), 4.08 (m, 3H), 3.13 (m, 2H), 2.93 (m, 2H), 1.97 (m, 2H), 1.44 (s, 9H) ppm; MS (ESI): 361.1 (M+1).

Step 4

To a stirred solution of tert-butyl 4-(7-hydroxyimidazo[1,2-a]pyridine-2-carboxamido)piperidine-1-carboxylate (0.18 g, 0.50 mmol) in toluene (4 mL) at room temperature was added diisopropyl azodicarboxylate (0.12 g, 0.6 mmol), 1-(4-(trifluoromethyl)phenyl)-piperidin-4-ol (0.12 g, 0.5 mmol), and triphenylphosphine (0.16 g, 0.6 mmol). The mixture was stirred at room temperature overnight and then concentrated under reduced pressure. The residue obtained was purified by flash chromatography (silica gel, methylene chloride/methanol/30% ammonium hydroxide=20/1/0.01) to afford tert-butyl 4-(7-(1-(4-(trifluoromethyl)phenyl)piperidin-4-yloxy)imidazo[1,2-a]pyridine-2-carboxamido)piperidine-1-carboxylate as a off-white solid (0.13 g, 44%). $^1$H-NMR (CDC$_3$, 300 MHz): δ 7.97 (m, 2H), 7.47 (m, 2H), 7.18 (m, 1H), 6.95 (m, 2H), 6.81 (s, 1H), 6.58 (m, 1H), 4.56 (m, 1H), 4.11 (m, 3H), 3.61 (m, 2H), 3.26 (m, 2H), 2.92 (m, 2H), 2.15 (m, 2H), 2.03 (m, 4H), 1.66 (m, 2H), 1.47 (s, 9H) ppm; MS (ESI): 588.4 (M+1).

(b) Synthetic Example: Compounds 17-18

Step 1

A mixture of tert-butyl 4-(7-(1-(4-(trifluoromethyl)phenyl)piperidin-4-yloxy)imidazo[1,2-a]pyridine-2-carboxamido)piperidine-1-carboxylate (0.13 g, 0.22 mmol) and 4N hydrochloric acid in dioxane (2 mL) was stirred at room temperature for 1 h. The reaction mixture was concentrated and washed with diethyl ether (2×3 mL) and then dried under reduced pressure to afford N-(piperidin-4-yl)-7-(1-(4-(trifluoromethyl)phenyl)piperidin-4-yloxy)imidazo[1,2-a]pyridine-2-carboxamide dihydrochloride salt as a brown solid (0.13 g, 98%). $^1$H NMR (CD$_3$OD, 300 MHz) δ 8.72 (m, 1H), 8.56 (m, 1H), 7.64 (m, 2H), 7.45 (m, 2H), 7.31 (m, 1H), 7.26 (m, 1H), 4.97 (m, 1H), 3.64 (m, 5H), 3.01 (m, 2H), 2.14 (m, 10H) ppm; MS (ES) 488.1 (M+1).

Step 2

To a stirred mixture of N-(piperidin-4-yl)-7-(1-(4-(trifluoromethyl)phenyl)piperidin-4-yloxy)imidazo[1,2-a]pyridine-2-carboxamide dihydrochloride salt (0.03 g, 0.05 mmol) in anhydrous N,N-dimethylformamide (0.5 mL) at room temperature was added the appropriately-substituted benzyl bromide (0.06 mmol) and N,N-diisopropylethylamine (0.03 g, 0.22 mmol). The resulting mixture was stirred at room temperature overnight. After this time the mixture was concentrated under reduced pressure and the resulting residue was purified by flash chromatography (silica gel, methylene chloride/methanol/30% ammonium hydroxide) to afford compounds 17-18 in solid form.

N-(1-(Pyridin-4-ylmethyl)piperidin-4-yl)-7-(1-(4-(trifluoromethyl)phenyl)piperidin-4-yloxy)imidazo[1,2-a]pyridine-2-carboxamide (compound 17): $^1$H-NMR (CDC$_3$, 300 MHz): δ 8.55 (m, 2H), 7.97 (m, 2H), 7.48 (m, 2H), 7.30 (m, 2H), 7.20 (m, 1H), 6.96 (m, 2H), 6.82 (m, 1H), 6.57 (m, 1H), 4.56 (m, 1H), 4.02 (m, 1H), 3.60 (m, 4H), 3.26 (m, 2H), 2.88 (m, 2H), 2.20 (m, 4H), 2.02 (m, 4H), 1.68 (m, 2H) ppm; MS (ESI): 579.6 (M+1).

N-(1-(4-Cyanobenzyl)piperidin-4-yl)-7-(1-(4-(trifluoromethyl)phenyl)piperidin-4-yloxy)imidazo[1,2-a]pyridine-2-carboxamide (compound 18): $^1$H-NMR (CDC$_3$, 300 MHz): δ 7.96 (m, 2H), 7.61 (m, 2H), 7.47 (m, 4H), 7.17 (m, 1H), 6.95 (m, 2H), 6.81 (m, 1H), 6.58 (m, 1H), 4.56 (m, 1H), 4.02 (m, 1H), 3.59 (m, 4H), 3.26 (m, 2H), 2.82 (m, 2H), 2.17 (m, 4H), 2.01 (m, 4H), 1.65 (m, 2H) ppm; MS (ESI): 603.6 (M+1).

(c) Increase in AMPK Activity

Compounds 17-18 were assayed for their ability to activate AMPK using an enzyme-linked immunosorbent assay. The EC$_{50}$ values for AMPK activation for compounds 17-18 are presented in Table 4 below, in which "A" is less than 0.1 µM; "B" is 0.1-1 µM; "C" is 1-10 µM; and "D" is 10-100 µM:

TABLE 4

| Cpd No. | AMPK EC$_{50}$ |
|---|---|
| 17 | A |
| 18 | A |

Example 4

(a) Synthetic Example: tert-butyl 4-(5-(1-(4-(trifluoromethyl)phenyl)piperidin-4-yloxy)pyrazine-2-carboxamido)piperidine-1-carboxylate (compound 19)

Step 1

1-(4-(Trifluoromethyl)phenyl)piperidin-4-ol (0.59 g, 2.41 mmol) was dissolved in anhydrous N,N-dimethylformamide (10 mL), cooled in an ice bath and treated with 60% sodium hydride (0.1 g, 2.55 mmol). The mixture was allowed to warm to room temperature over 1 h. A solution of methyl 5-chloropyrazine-2-carboxylate (0.5 g, 2.9 mmol) in anhydrous N,N-dimethylformamide (1 mL) was added and the mixture was stirred at room temperature overnight. The mixture was quenched by water and extracted with ethyl acetate. The organic layer was dried over sodium sulfate and evaporated. The residue obtained was purified by flash chromatography (silica gel, ethyl acetate/hexanes=1/4) to afford methyl 5-(1-(4-(trifluoromethyl)phenyl)piperidin-4-yloxy)pyrazine-2-carboxylate as a white solid (0.23 g, 25%). $^1$H-NMR (CD$_3$Cl, 300 MHz): δ 8.86 (m, 1H), 8.28 (m, 1H), 7.48 (m, 2H), 6.96 (m, 2H), 5.36 (m, 1H), 4.00 (s, 3H), 3.64 (m, 2H), 3.26 (m, 2H), 2.16 (m, 2H), 1.99 (m, 2H) ppm; MS (ESI): 382.6 (M+1).

Step 2

A mixture of methyl 5-(1-(4-(trifluoromethyl)phenyl)piperidin-4-yloxy)pyrazine-2-carboxylate (0.10 g, 0.26 mmol) and 2N aqueous sodium hydroxide (0.4 mL) in acetone (2 mL) was stirred at room temperature for 0.5 h. The reaction mixture was acidified by concentrated hydrochloric acid and concentrated under reduced pressure to afford 5-(1-(4-(trifluoromethyl)phenyl)piperidin-4-yloxy)pyrazine-2-carboxylic acid hydrochloric acid salt as an off-white solid (0.10 g, 96%) which was used next step without further purifications. MS (ESI): 368.4 (M+1).

Step 3

To a stirred mixture of 5-(1-(4-(trifluoromethyl)phenyl)piperidin-4-yloxy)pyrazine-2-carboxylic acid hydrochloric acid salt (0.10 g, 0.25 mmol) in anhydrous N,N-dimethylformamide (3 mL) was added triethylamine (0.56 g, 0.55 mmol), 1-hydroxybenzotriazole hydrate (0.04 g, 0.3 mmol), 1-(3-dimethylaminopropyl)-3-ethylcarbodiimide hydrochloride (0.06 g, 0.3 mmol), and tert-butyl 4-aminopiperidine-1-carboxylate (0.06 g, 0.3 mmol). The mixture was stirred at room temperature overnight and then concentrated under reduced pressure. The residue obtained was purified by flash chromatography (silica gel, ethyl acetate/hexanes=1/1) to afford tert-butyl 4-(5-(1-(4-(trifluoromethyl)phenyl)piperidin-4-yloxy)pyrazine-2-carboxamido)piperidine-1-carboxylate (compound 19) as a white solid (0.06 g, 44%). $^1$H-NMR (CDC$_3$, 300 MHz): δ 8.89 (m, 1H), 8.06 (m, 1H), 7.50 (m, 3H), 6.96 (m, 2H), 5.33 (m, 1H), 4.10 (m, 3H), 3.64 (m, 2H), 3.25 (m, 2H), 2.95 (m, 2H), 2.15 (m, 2H), 1.97 (m, 4H), 1.56 (m, 2H), 1.47 (s, 9H) ppm; MS (ESI): 550.7 (M+1).

(b) Synthetic Example: Compounds 20-22

Step 1

A mixture of tert-butyl 4-(5-(1-(4-(trifluoromethyl)phenyl)piperidin-4-yloxy)pyrazine-2-carboxamido)piperidine-1-carboxylate (0.06 g, 0.11 mmol) and 4N hydrochloric acid in dioxane (1 mL) was stirred at room temperature for 0.5 h. The reaction mixture was concentrated and washed with diethyl ether (2×1 mL) and then dried under reduced pressure to afford N-(piperidin-4-yl)-5-(1-(4-(trifluoromethyl)phenyl)piperidin-4-yloxy)pyrazine-2-carboxamide dihydrochloride salt (compound 20) as a brown solid (0.56 g, 99%). $^1$H NMR (CD$_3$OD, 300 MHz) δ 8.80 (s, 1H), 8.25 (s, 5H), 7.59 (m, 2H), 7.28 (m, 2H), 5.44 (m, 1H), 4.18 (m, 1H), 3.55 (m, 4H), 3.77 (m, 2H), 3.42 (m, 4H), 3.15 (m, 2H), 2.07 (m, 8H) ppm; MS (ES) 450.5 (M+1).

Step 2

To a stirred mixture of N-(piperidin-4-yl)-5-(1-(4-(trifluoromethyl)phenyl)piperidin-4-yloxy)pyrazine-2-carboxamide dihydrochloride salt (0.03 g, 0.05 mmol) in anhydrous N,N-dimethylformamide (0.5 mL) at room temperature was added the appropriately-substituted benzyl bromide (0.06 mmol) (0.06 mmol) and N,N-diisopropylethylamine (0.03 g, 0.22 mmol). The resulting mixture was stirred at room temperature overnight. After this time the mixture was concentrated under reduced pressure and the resulting residue was purified by flash chromatography (silica gel, methylene chloride/methanol/30% ammonium hydroxide) to afford compounds 21-22 in solid form.

N-(1-(Pyridin-4-ylmethyl)piperidin-4-yl)-5-(1-(4-(trifluoromethyl)phenyl)piperidin-4-yloxy)pyrazine-2-carboxamide (compound 21): $^1$H-NMR (CDC$_3$, 300 MHz): δ 8.87 (m, 1H), 8.56 (m, 1H), 8.06 (m, 1H), 7.49 (m, 3H), 7.31 (m, 2H), 6.95 (m, 2H), 5.33 (m, 1H), 4.03 (m, 3H), 3.58 (m, 4H), 3.25 (m, 2H), 2.87 (m, 2H), 2.35-1.69 (m, 10H) ppm; MS (ESI): 541.8 (M+1).

N-(1-(4-Cyanobenzyl)piperidin-4-yl)-5-(1-(4-(trifluoromethyl)phenyl)piperidin-4-yloxy)pyrazine-2-carboxamide (compound 22): $^1$H-NMR (CDC$_3$, 300 MHz): δ 8.89 (m, 1H), 8.06 (m, 1H), 7.61 (m, 2H), 7.48 (m, 5H), 6.96 (m, 2H), 5.34 (m, 1H), 4.00 (m, 1H), 3.62 (m, 4H), 3.24 (m, 2H), 2.80 (m, 2H), 2.19 (m, 4H), 1.99 (m, 4H), 1.63 (m, 2H) ppm; MS (ESI): 565.9 (M+1).

(c) Increase in AMPK Activity

Compounds 19-22 were assayed for their ability to activate AMPK using an enzyme-linked immunosorbent assay. The EC$_{50}$ values for AMPK activation for compounds 19-22 are presented in Table 5 below, in which "A" is less than 0.1 μM; "B" is 0.1-1 μM; "C" is 1-10 μM; "D" is 10-100 μM and "F" is >100 μM:

TABLE 5

| Cpd No. | AMPK EC$_{50}$ |
|---|---|
| 19 | C |
| 20 | F |
| 21 | A |
| 22 | A |

Example 5 a) Synthetic Example: N-(1-(4-cyanobenzyl)piperidin-4-yl)-2-(1-(4-(trifluoromethyl)phenyl)piperidin-4-yloxy)thiazole-5-carboxamide (compound 23)

Step 1

To a stirred mixture of 2-bromothiazole-5-carboxylic acid (500 mg, 2.4 mmol) in anhydrous N,N-dimethylformamide (5 mL) was added triethylamine (1.1 mL, 7.92 mmol), HATU (1 g, 2.64 mmol), and 4-((4-aminopiperidin-1-yl)methyl)benzonitrile (762 mg, 2.64 mmol). The mixture was stirred at room temperature overnight and then poured into water. The resulting solids were collected by filtration and purified by column chromatography to yield 972 mg (100%) of 2-bromo-N-(1-(4-cyanobenzyl)piperidin-4-yl)thiazole-5-carboxamide as a yellow solid. LCMS (m/z): 406 (MH$^+$).

Step 2

To a stirred solution of 1-(4-(trifluromethyl)benzyl)piperidin-4-ol (121 mg, 0.493 mmol) in N,N-dimethylformamide (5 mL) at room temperature was slowly added sodium hydride (30 mg, 0.741 mmol). 2-Bromo-N-(1-(4-cyanobenzyl)piperidin-4-yl)thiazole-5-carboxamide (100 mg, 0.247 mmol) was added to the reaction mixture, which was stirred at 80° C. overnight and then poured into ice-water. The residue was purified by flash chromatography (silica gel, 2% methanol in methylene chloride) to afford N-(1-(4-cyanobenzyl)piperidin-4-yl)-2-(1-(4-(trifluoromethyl)phenyl)piperidin-4-yloxy)thiazole-5-carboxamide (compound 23) as a yellow solid (30 mg, 21%). $^1$H-NMR (CDC$_3$, 300 MHz): δ 7.61(m, 2H), 7.499-7.425 (m, 5H), 6.93 (d, 2H), 6.98 (d, 2H), 5.64 (d, 1H), 5.207 (m, 1H), 3.935 (m, 1H), 3.589 (m, 2H), 3.561 (s, 2H), 3.249 (m, 2H), 2.821(m, 2H), 2.196 (m, 4H), 2.028 (m, 4H), 1.587(m, 2H); LCMS: MS (m/z): 570 (MH$^+$).

(b) Synthetic Example: Compounds 24-25

Compounds 24 and 25 were prepared using procedures analogous to those described in Example 5(a).

N-(1-(4-Cyanobenzyl)piperidin-4-yl)-2-(1-(4-cyanophenyl)piperidin-4-yloxy)thiazole-5-carboxamide (compound 24): $^1$H-NMR (CDC$_3$, 300 MHz): δ 7.61 (m, 2H), 7.499-7.425 (m, 5H), 6.880 (d, 2H), 5.66 (d, 1H), 5.2031 (m, 1H), 3.935 (m, 1H), 3.589 (m, 2H), 3.555 (s, 2H), 3.321 (m, 2H), 2.821(m, 2H), 2.187 (m, 4H), 2.015 (m, 4H), 1.566(m, 2H); LCMS: MS (m/z): 527 (MH').

N-(1-(4-Cyanobenzyl)piperidin-4-yl)-2-(1-(4-(trifluoromethyl)benzyl)piperidin-4-yloxy)thiazole-5-carboxamide (compound 25): $^1$H-NMR (CDC$_3$, 300 MHz): δ 7.570(m, 4H), 7.419-7.471 (m, 5H), 5.66 (d, 1H), 5.103 (m, 1H), 3.935 (m, 1H), 3.71 (m, 1H), 3.565 (m, 4H), 2.76 (m, 4H), 2.29(m, 2H), 2.18 (m, 2H), 2.015 (m, 4H), 1.566(m, 4H); LCMS: MS (m/z): 584 (MH$^+$).

tert-Butyl 4-(5-(1-(4-cyanobenzyl)piperidin-4-ylcarbamoyl)thiazol-2-yloxy)piperidine-1-carboxylate (compound 26): $^1$H NMR (DMSO-d$_6$) δ 8.26 (d, J=7.4 Hz, 1H), 7.82 (s, 1H), 7.78 (d, J=7.4 Hz, 2H), 7.71 (d, J=7.7 Hz, 2H), 5.15-5.05 (m, 1H), 3.68-3.58 (m, 2H), 3.56 (s, 2H), 3.24-3.12 (m, 2H), 2.82-2.72 (m, 3H), 2.10-1.94 (m, 4H), 1.82-1.72 (m, 2H), 1.69-1.46 (m, 4H), 1.40 (s, 9H). MS (M+H)'=526.

(c) Increase in AMPK Activity

Compounds 23-26 were assayed for their ability to activate AMPK using an enzyme-linked immunosorbent assay. The EC$_{50}$ values for AMPK activation for compounds 23-26 are presented in Table 6 below, in which "A" is less than 0.1 μM; "B" is 0.1-1 μM; "C" is 1-10 μM; "D" is 10-100 μM and "F" is >100 μM:

TABLE 6

| Cpd No. | AMPK EC$_{50}$ |
|---|---|
| 23 | A |
| 24 | A |
| 25 | A |
| 26 | C |

Example 6

(a) Synthetic Example: N-(1-(4-cyanobenzyl)piperidin-4-yl)-4-(1-(4-ethoxybenzyl)piperidine-4-carbonyl)benzamide (compound 27)

Step 1

To a stirred mixture of 4-(methoxycarbonyl)benzoic acid (1 g, 5.55 mmol) in anhydrous N,N-dimethylformamide (5 mL) was added triethylamine (2.6 ml, 18.32 mmol), HATU (2.32 g, 6.11 mmol), and 4((4-aminopiperidin-1-yl)methyl)benzonitrile as its HCl salt (1.6 g, 5.55 mmol). The mixture was stirred at room temperature overnight and then poured into water. The resulting solids were collected by filtration, purified by column chromatography to yield 0.91 g (44%) of methyl 4-(1-(4-cyanobenzyl)piperidin-4-ylcarbamoyl)benzoate as a white solid. LCMS (m/z): 379 (MH$^+$).

Step 2

Methyl 4-(1-(4-cyanobenzyl)piperidin-4-ylcarbamoyl) benzoate (900 mg, 2.38 mmol) and lithium hydroxide (600 mg, 14.28 mmol) was added to MeOH/THF/H$_2$O(2/1/1, 20 mL), and the mixture was stirred overnight, then acidified with 2M hydrochloric acid (10 mL) to pH 5. A white solid separated, and was collected by filtration and washed with water. The combined filtrate and washings were acidified by adding further 2M hydrochloric acid to pH 1 and the solution was extracted three times with ethyl acetate. The combined organic extracts were washed with brine, dried with magnesium sulphate and evaporated to give 4-(1-(4-cyanobenzyl) piperidin-4-ylcarbamoyl)benzoic acid (0.718 g, 83%). LCMS (m/z): 364 (MH$^+$).

Step 3

To a stirred mixture of 4-(1-(4-cyanobenzyl)piperidin-4-ylcarbamoyl)benzoic acid (100 mg, 0.275 mmol) in anhydrous N,N-dimethylformamide (3 mL) was added triethylamine (84 μl, 0.825 mmol), HATU (115 mg, 0.3 mmol), and 4-(4-ethoxybenzyl)piperidine (61 mg, 0.275 mmol). The mixture was stirred at room temperature overnight and then poured into water. The resulting solids were collected by filtration, purified by column chromatography to yield 0.7 g (55%) of N-(1-(4-cyanobenzyl)piperidin-4-yl)-4-(1-(4-ethoxybenzyl)piperidine-4-carbonyl)benzamide (compound 27) as an offwhite solid. $^1$H-NMR (CDC$_3$, 300 MHz): δ 7.761 (d, 2H), 7.600 (m, 2H), 7.434 (m, 4H), 7.022 (d, 2H), 6.812 (d, 2H), 6.022 (d, 1H), 4.658(m, 1H), 3.994 (dd, 2H), 3.569 (m, 3H), 2.885 (m, 4H), 2.505(m, 2H), 2.227 (m, 2H), 2.049 (m, 2H), 1.639(m, 6H), 1.405(m, 3H); LCMS (m/z): 565 (MH$^+$).

(b) Synthetic Example: Compounds 28-33

Compounds 28-31 were prepared using procedures analogous to those described in Example 6(a).

4-(4-(4-Chlorobenzyl)piperazine-1-carbonyl)-N-(1-(4-cyanobenzyl)piperidin-4-yl)benzamide (compound 28): $^1$H-NMR (CDC$_3$, 300 MHz): δ 7.8(d, 2H), 7.6 (d, 2H), 7.43 (m, 4H), 7.22 (m, 4H), 6.0 (d, 1H), 4.01 (m, 1H), 3.89 (m, 2H), 3.563 (s, 2H), 3.496 (s, 2H), 3.39(m, 2H), 2.82 (m, 2H), 2.5 (m, 2H), 2.36(m, 2H), 2.21(m, 4H), 2.01 (m, 2H); LCMS (m/z): 565 (MH$^+$).

4-(4-(4-Chlorophenyl)piperazine-1-carbonyl)-N-(1-(4-cyanobenzyl)piperidin-4-yl)benzamide (compound 29): $^1$H-NMR (CDC$_3$, 300 MHz): δ 7.79(d, 2H), 7.600 (d, 2H), 7.434 (m, 4H), 7.21 (d, 2H), 6.83 (d, 2H), 5.98 (d, 1H), 4.05(m, 1H), 3.9 (m, 2H), 3.565 (s, 2H), 3.12 (m, 4H), 2.81 (m, 2H), 2.21 (m, 4H), 2.04 (m, 4H); LCMS (m/z): 542 (MH$^+$).

N-(1-(4-Cyanobenzyl)piperidin-4-yl)-4-(4-(5-(trifluoromethyl)pyridin-2-yl)piperazine-1-carbonyl)benzamide (compound 30): $^1$H-NMR (CDC$_3$, 300 MHz): δ 8.396 (s, 1H), 7.8 (d, 2H), 7.65 (m, 2H), 7.621 (d, 2H), 7.47 (dd, 4H), 6.57 (d, 1H), 4.05 (m, 1H), 3.90 (m, 2H), 3.69 (m, 4H), 2.85 (m, 2H), 2.24 (m, 4H), 2.06 (m, 4H); LCMS (m/z): 577 (MH$^+$).

N$^1$-(1-(4-Cyanobenzyl)piperidin-4-yl)-N$^4$-(1-(4-(trifluoromethyl)benzyl)piperidin-4-yl)terephthalamide (compound 31): $^1$H-NMR (CDC$_3$, 300 MHz): δ 7.783(m, 4H), 7.585 (m, 4H), 7.434 (m, 4H), 7.44 (d, 4H), 6.0 (m, 2H), 4.1 (m, 2H), 3.6(m, 4H), 2.854 (m, 4H), 2.23 (m, 8H), 2.05 (m, 4H); LCMS (m/z): 604 (MH$^+$).

N$^1$-(1-(4-Cyanobenzyl)piperidin-4-yl)-N$^4$-(1-phenylpiperidin-4-yl)terephthalamide (compound 32): MS (m/z): 522 (MH$^+$).

N$^1$-(1-Benzylpiperidin-4-yl)-N$^4$-(1-(4-cyanobenzyl)piperidin-4-yl)terephthalamide (compound 33): MS (m/z): 536 (MH$^+$).

(c) Increase in AMPK Activity

Compounds 27-33 were assayed for their ability to activate AMPK using an enzyme-linked immunosorbent assay. The EC$_{50}$ values for AMPK activation for compounds 27-33 are presented in Table 7 below, in which "A" is less than 0.1 μM; "B" is 0.1-1 μM; "C" is 1-10 μM; and "D" is 10-100 μM:

TABLE 7

| Cpd No. | AMPK EC$_{50}$ |
| --- | --- |
| 27 | A |
| 28 | A |
| 29 | D |
| 30 | A |
| 31 | A |
| 32 | D |
| 33 | D |

Example 7 a) Synthetic Example: 2-(4-cyanobenzyl)-N-(1-(4-cyanobenzyl)piperidin-4-yl)-1,2,3,4-tetrahydroisoquinoline-7-carboxamide (compound 37)

Step 1

A solution of 7-cyano-1,2,3,4-tetrahydroisoquinoline (5 g, 31.6 mmol) in methanol (150 mL) was saturated with HCl gas (bubbled HCl gas into solution for 15 min at room temperature) and placed in a sealed tube. The resulting reaction mixture was heated at 65° C. for 17 h, concentrated to dryness and partitioned between 5% sodium bicarbonate solution (200 mL) and dichloromethane (50 mL). The layers were separated and the aqueous layer was extracted with dichloromethane (3×25 mL). The combined organic layer was dried (MgSO$_4$), filtered and concentrated to provide methyl 1,2,3,4-tetrahydroisoquinoline-7-carboxylate hydrochloride as a pale brown oily residue (4.5 g, 63%). $^1$H NMR (CDC$_3$) δ 7.82 (1H, dd, J=8.0, 1.7 Hz); 7.74 (1H, d, J=1.4 Hz); 7.18 (1H, d, J=8.0 Hz); 4.16 (2H, br s); 3.92 (3H, s); 3.27 (2H, br s); 2.97 (2H, br s). MS (M+H)$^+$=192.

Step 2

Sodium triacetoxyborohydride (2.2 g, 10.4 mmol) was added to a solution of methyl 1,2,3,4-tetrahydroisoquinoline-7-carboxylate hydrochloride (1.0 g, 4.4 mmol) and 4-cyanobenzaldehyde (0.83 g, 6.3 mmol) in dichloromethane (10 mL). The resulting reaction mixture was allowed to stir at room temperature overnight, poured over saturated sodium bicarbonate solution (75 mL) and extracted with dichloromethane (3×30 mL). The combined organic layer was washed with water (2×30 mL), dried (MgSO$_4$), filtered and concentrated to give a foamy residue. Column chromatography (30% ethyl acetate/hexanes) provided methyl 2-(4-cyanobenzyl)-1,2,3,4-tetrahydroisoquinoline-7-carboxylate as a white crystalline solid upon trituration with ethyl ether (1.30 g, 97%). $^1$H NMR (CDC$_3$) δ 7.85 (1H, d, J=7.7 Hz); 7.72-7.58 (5H, m); 7.23 (1H, d, J=8.0 Hz); 4.00-3.98 (2H, m); 3.92 (3H, s); 3.83 (2H, br s); 3.08 (2H, br s); 2.97 (2H, br s). MS (M+H)$^+$=307.

Step 3

A solution of methyl 2-(4-cyanobenzyl)-1,2,3,4-tetrahydroisoquinoline-7-carboxylate (1.26 g, 4.1 mmol) and lithium hydroxide hydrate (1.04 g, 24.8 mmol) in THF/MeOH/H$_2$O (2:1:1, 48 mL) was allowed to stir at room temperature until all the starting material disappeared (overnight). The resulting cloudy reaction mixture was then concentrated to give a yellow foamy residue. Trituration with 10% HCl solution provided 2-(4-cyanobenzyl)-1,2,3,4-tetrahydroisoquinoline-7-carboxylic acid hydrochloride as a white crystalline solid upon filtration and drying under vacuum (1.06 g, 78%). $^1$H NMR (DMSO-d$_6$) δ 11.52 (1H, br s); 7.97 (2H, d, J=8.3 Hz); 7.87 (2H, d, J=8.0 Hz); 7.79 (2H, d, J=9.4 Hz); 7.35 (1H, d, J=8.0 Hz); 4.55 (2H, br s); 4.36 (2H, br s); 3.65 (1H, br s); 3.31 (2H, d, J=9.9 Hz); 3.12 (1H, t, J=13.5 Hz). MS (M+H)$^+$=293.

Step 4

To a solution of 2-(4-cyanobenzyl)-1,2,3,4-tetrahydroisoquinoline-7-carboxylic acid hydrochloride (50 mg, 0.17 mmol) in DMF (2 mL), HATU (78 mg, 0.21 mmol), 4-amino-1-(4-cyanobenzyl)piperidine dihydrochloride (52 mg, 0.18 mmol) and triethylamine (125 uL, 91 mg, 0.9 mmol) were added. The resulting reaction mixture was allowed to stir at room temperature overnight and poured into saturated sodium bicarbonate solution (30 mL) to give a white precipitate which was filtered and dried under vacuum. The resulting solid was triturated with ethyl ether to provide 2-(4-cyanobenzyl)-N-(1-(4-cyanobenzyl)piperidin-4-yl)-1,2,3,4-tetrahydroisoquinoline-7-carboxamide (compound 37) as a white crystalline solid (69 mg, 82%). $^1$H NMR (DMSO-d$_6$): δ 8.08 (1H, d, J=7.7 Hz); 7.79 (4H, dd, J=8.5, 6.9 Hz); 7.60-7.54 (3H, m); 7.49 (3H, d, J=8.8 Hz); 7.16 (1H, d, J=8.3 Hz); 3.78-3.66 (3H, m); 3.55 (4H, br s); 2.86 (2H, t, J=5.2 Hz); 2.82-2.66 (4H, m); 2.04 (2H, t, J=11.3 Hz); 1.75 (2H, d, J=11.3 Hz); 1.55 (2H, q, J=11.8 Hz). MS (M+H)'=490.

(b) Synthetic Example: Compounds 34-36 and 38-39.

Compounds 34-36 and 38-39 were prepared using procedures analogous to those described in Example 7(a).

N-(1-(4-Cyanobenzyl)piperidin-4-yl)-2-(4-fluorobenzyl)-1,2,3,4-tetrahydroisoquinoline-7-carboxamide (compound 34): $^1$H NMR (DMSO-d$_6$): δ 8.08 (d, J=7.7 Hz, 1H), 7.78 (d, J=8.3 Hz, 2H), 7.57 (d, J=8.0 Hz, 1H), 7.49 (d, J=8.3 Hz, 3H), 7.41-7.36 (m, 2H), 7.18-7.12 (m, 3H), 3.78-3.68 (m, 1H), 3.64 (s, 2H), 3.53 (d, J=7.7 Hz, 4H), 2.89-2.65 (m, 6H), 2.04 (t, J=10.6 Hz, 2H), 1.74 (d, J=12.1 Hz, 2H), 1.54 (q, J=11.6 Hz, 2H). MS (M+H)$^+$=483.

2-(4-Fluorobenzyl)-N-(1-(pyridin-3-ylmethyl)piperidin-4-yl)-1,2,3,4-tetrahydroisoquinoline-7-carboxamide (compound 35): $^1$H NMR (DMSO-d$_6$): δ 8.47-8.44 (m, 2H), 8.08 (d, J=7.7 Hz, 1H), 7.68 (d, J=7.7 Hz, 1H), 7.57 (d, J=7.7 Hz, 1H), 7.47 (s, 1H), 7.40-7.32 (m, 3H), 7.18-7.12 (m, 3H), 3.78-3.68 (m, 1H), 3.64 (s, 2H), 3.50 (d, J=9.9 Hz, 4H), 2.89-2.64 (m, 6H), 2.02 (t, J=11.1 Hz, 2H), 1.74 (d, J=11.8 Hz, 2H), 1.55 (q, J=12.0 Hz, 2H). MS (M+H)$^+$=459.

2-(4-Fluorobenzyl)-N-(1-(4-(trifluoromethyl)benzyl)piperidin-4-yl)-1,2,3,4-tetrahydroisoquinoline-7-carboxamide (compound 36): $^1$H NMR (DMSO-d$_6$): δ 8.09 (d, J=7.7 Hz, 1H), 7.67 (d, J=8.3 Hz, 2H), 7.57 (d, J=8.0 Hz, 1H), 7.52 (d, J=7.7 Hz, 2H), 7.47 (s, 1H), 7.41-7.36 (m, 2H), 7.18-7.12 (m, 3H), 3.78-3.68 (m, 1H), 3.64 (s, 2H), 3.54 (d, J=8.5 Hz, 4H), 2.89-2.74 (m, 4H), 2.73-2.64 (m, 2H), 2.04 (t, J=11.1 Hz, 2H), 1.75 (d, J=12.4 Hz, 2H), 1.55 (q, J=10.6 Hz, 2H). MS (M+H)$^+$=526.

2-(4-Cyanobenzyl)-N-(1-(pyridin-3-ylmethyl)piperidin-4-yl)-1,2,3,4-tetrahydroisoquinoline-7-carboxamide (compound 38): White crystalline solid (58 mg, 73%). $^1$H NMR (DMSO-d$_6$): δ 8.68-8.65 (2H, m); 8.45 (1H, d, J=7.2 Hz); 7.99-7.93 (3H, m); 7.74 (3H, d, J=8.0 Hz); 7.64 (1H, s); 7.55-7.51 (1H, dd, J=7.7, 4.7 Hz); 7.32 (1H, d, J=8.0 Hz); 4.54 (3H, br s); 4.35 (2H, br s); 4.31 (2H, br s); 4.06-3.9 (1H, m); 3.43 (3H, d, J=11.3 Hz); 3.13 (4H, br s); 2.01 (2H, d, J=12.4 Hz); 1.75 (2H, q, J=11.7 Hz). MS (M+H)$^+$=466.

2-(4-Cyanobenzyl)-N-(1-(4-(trifluoromethyl)benzyl)piperidin-4-yl)-1,2,3,4-tetrahydroisoquinoline-7-carboxamide (compound 39): White crystalline solid (47 mg, 52%). $^1$H NMR (DMSO-d$_6$): δ 8.09 (1H, d, J=8.0 Hz); 7.81 (2H, d, J=8.3 Hz); 7.68 (2H, d, J=8.0 Hz); 7.60-7.44 (6H, m); 7.16 (1H, d, J=8.0 Hz); 3.78-3.66 (3H, m); 3.56 (4H, br s); 2.91-2.66 (6H, m); 2.07 (2H, m); 1.75 (2H, d, J=11.0 Hz); 1.57 (2H, q, J=11.7 Hz). MS (M+H)$^+$=533.

c) Synthetic Example: N-(1-(4-cyanobenzyl)piperidin-4-yl)-2-(4-fluorobenzyl)-1,2,3,4-tetrahydroisoquinoline-7-carboxamide (compound 40

Step 1

Methyl 2-(4-fluorobenzyl)-1,2,3,4-tetrahydroisoquinoline-7-carboxylate was prepared as described in step 2 of Example 7(a), above, using 4-fluorobenzaldehyde in place of 4-cyanobenzaldehyde. Column chromatography (20→30% ethyl acetate/hexanes) provided the compound as an off-white crystalline solid (1.26 g, 81%). $^1$H NMR (CDCl$_3$) δ 7.84 (1H, d, J=7.7 Hz); 7.71 (1H, s); 7.47 (2H, br s); 7.22 (1H, d, J=8.0 Hz); 7.08 (2H, t, J=8.5 Hz); 4.00-3.94 (2H, m); 3.91 (3H, s); 3.86 (2H, br s); 3.09 (2H, br s); 2.98 (2H, br s). MS (M+H)$^+$=300.

Step 2

2-(4-Fluorobenzyl)-1,2,3,4-tetrahydroisoquinoline-7-carboxylic acid hydrochloride was prepared from methyl 2-(4-fluorobenzyl)-1,2,3,4-tetrahydroisoquinoline-7-carboxylate as described in step 3 of Example 7(a), above. The compound was obtained as a white crystalline solid was upon filtration and drying under vacuum (1.20 g, 90%). $^1$H NMR (DMSO-d$_6$) δ 11.06 (1H, br s); 7.81-7.79 (2H, m); 7.68 (2H, dd, J=8.3, 5.5 Hz); 7.36-7.29 (3H, m); 4.45 (2H, br s); 4.38-4.34 (2H, m); 3.64 (2H, br s); 3.14 (2H, app t, J=14.9, 9.6 Hz). MS (M+H)$^+$=286.

Step 3

N-(1-(4-Cyanobenzyl)piperidin-4-yl)-2-(4-fluorobenzyl)-1,2,3,4-tetrahydroisoquinoline-7-carboxamide (compound 40) was prepared from methyl 2-(4-fluorobenzyl)-1,2,3,4-tetrahydroisoquinoline-7-carboxylate as described in step 4 of Example 7(a) above to yield the compound as a tan crystalline solid (70 mg, 83%). $^1$H NMR (DMSO-d$_6$): δ 8.08 (1H, d, J=7.7 Hz); 7.78 (2H, d, J=8.3 Hz); 7.57 (1H, d, J=8.0 Hz); 7.49 (3H, d, J=8.3 Hz); 7.41-7.36 (2H, m); 7.18-7.12 (3H, m); 3.78-3.68 (1H, m); 3.64 (2H, s); 3.53 (4H, d, J=7.7 Hz); 2.89-2.65 (6H, m); 2.04 (2H, t, J=10.6 Hz); 1.74 (2H, d, J=12.1 Hz); 1.54 (2H, q, J=11.6 Hz). MS (M+H)'=483.

(d) Synthetic Example: Compounds 41-42.

Compounds 41-42 were prepared using procedures analogous to those described in Example 7(c).

2-(4-Fluorobenzyl)-N-(1-(pyridine-3-ylmethyl)piperidin-4-yl)-1,2,3,4-tetrahydroisoquinoline-7-carboxamide (compound 41): Tan crystalline solid (40 mg, 50%). $^1$H NMR (DMSO-d$_6$): δ 8.47-8.44 (2H, m); 8.08 (1H, d, J=7.7 Hz); 7.68 (1H, d, J=7.7 Hz); 7.57 (1H, d, J=7.7 Hz); 7.47 (1H, s); 7.40-7.32 (3H, m); 7.18-7.12 (3H, m); 3.78-3.68 (1H, m); 3.64 (2H, s); 3.50 (4H, d, J=9.9 Hz); 2.89-2.64 (6H, m); 2.02 (2H, t, J=11.1 Hz); 1.74 (2H, d, J=11.8 Hz); 1.55 (2H, q, J=12.0 Hz). MS (M+H)$^+$=459.

2-(4-Fluorobenzyl)-N-(1-(4-(trifluoromethyl)benzyl)piperidin-4-yl)-1,2,3,4-tetrahydroisoquinoline-7-carboxamide (compound 42): White crystalline solid (55 mg, 60%). $^1$H NMR (DMSO-d$_6$): δ 8.09 (1H, d, J=7.7 Hz); 7.67 (2H, d, J=8.3 Hz); 7.57 (1H, d, J=8.0 Hz); 7.52 (2H, d, J=7.7 Hz); 7.47 (1H, s); 7.41-7.36 (2H, m); 7.18-7.12 (3H, m); 3.78-3.68 (1H, m); 3.64 (2H, s); 3.54 (4H, d, J=8.5 Hz); 2.89-2.74 (4H, m); 2.73-2.64 (2H, m); 2.04 (2H, t, J=11.1 Hz); 1.75 (2H, d, J=12.4 Hz); 1.55 (2H, q, J=10.6 Hz). MS (M+H)$^+$=526.

(e) Increase in AMPK Activity

Compounds 34-42 were assayed for their ability to activate AMPK using an enzyme-linked immunosorbent assay. The EC$_{50}$ values for AMPK activation for compounds 34-42 are presented in Table 8 below, in which "A" is less than 0.1 μM; "B" is 0.1-1 μM; "C" is 1-10 μM; and "D" is 10-100 μM:

TABLE 8

| Cpd No. | AMPK EC$_{50}$ |
|---|---|
| 34 | A |
| 35 | C |
| 36 | B |
| 37 | A |
| 38 | A |
| 39 | C |
| 40 | A |
| 41 | C |
| 42 | B |

What is claimed is:
1. A compound having the structural formula

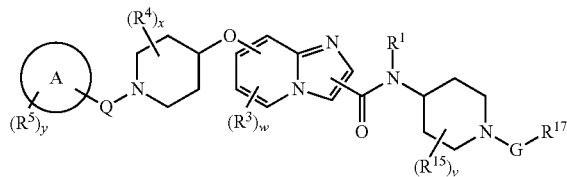

or a pharmaceutically acceptable salt or N-oxide thereof, wherein

R$^1$ is H, —(C$_1$-C$_4$ alkyl), —C(O)—(C$_1$-C$_4$ alkyl) or —C(O)O—(C$_1$-C$_4$ alkyl);

each R$^{15}$ is independently selected from —(C$_1$-C$_3$ alkyl), —(C$_1$-C$_3$ haloalkyl), —(C$_0$-C$_3$ alkyl)-L-R$^7$, —(C$_0$-C$_3$ alkyl)-NR$^8$R$^9$, —(C$_0$-C$_3$ alkyl)-OR$^{10}$, —(C$_0$-C$_3$ alkyl)-C(O)R$^{10}$, —(C$_0$-C$_3$ alkyl)-S(O)$_{0-2}$R$^{10}$, -halogen, —NO$_2$ and —CN and two R$^{15}$ on the same carbon optionally combine to form oxo;

v is 0, 1, 2, 3 or 4;

G is —S(O)$_2$—, L, or —(C$_0$-C$_3$ alkyl)-, in which each carbon of the —(C$_0$-C$_3$ alkyl)- is optionally and independently substituted with one or two R$^{16}$;

R$^{17}$ is aryl or heteroaryl, optionally substituted with 1, 2 or 3 substituents independently selected from —(C$_1$-C$_3$ alkyl), —(C$_1$-C$_3$ haloalkyl), —(C$_0$-C$_3$ alkyl)-L-R$^7$, —(C$_0$-C$_3$ alkyl)-NR$^8$R$^9$, —(C$_0$-C$_3$ alkyl)-OR$^{10}$, —(C$_0$-C$_3$ alkyl)-C(O)R$^{10}$, —(C$_0$-C$_3$ alkyl)-S(O)$_{0-2}$R$^{10}$, -halogen, —NO$_2$ and —CN;

each R$^3$ is independently selected from —(C$_1$-C$_3$ alkyl), —(C$_1$-C$_3$ haloalkyl), —(C$_0$-C$_3$ alkyl)-L-R$^7$, —(C$_0$-C$_3$ alkyl)-NR$^8$R$^9$, —(C$_0$-C$_3$ alkyl)-OR$^{10}$, —(C$_0$-C$_3$ alkyl)-C(O)R$^{10}$, —(C$_0$-C$_3$ alkyl)-S(O)$_{0-2}$R$^{10}$, -halogen, —NO$_2$ and —CN;

w is 0, 1, 2 or 3;

each R$^4$ is independently selected from —(C$_1$-C$_3$ alkyl), —(C$_1$-C$_3$ haloalkyl), —(C$_0$-C$_3$ alkyl)-L-R$^7$, —(C$_0$-C$_3$ alkyl)-NR$^8$R$^9$, —(C$_0$-C$_3$ alkyl)-OR$^{10}$, —(C$_0$-C$_3$ alkyl)-C(O)R$^{10}$, —(C$_0$-C$_3$ alkyl)-S(O)$_{0-2}$R$^{10}$, -halogen, —NO$_2$ and —CN, and two R$^4$ groups optionally combine to form an oxo;

x is 0, 1, 2, 3 or 4;

Q is —S(O)$_2$—, L, or —(C$_0$-C$_3$ alkyl)-, in which each carbon of the —(C$_0$-C$_3$ alkyl)- is optionally and independently substituted with one or two R$^{16}$;

the ring denoted by "A" is heteroaryl or aryl;

each R$^5$ is independently selected from —(C$_1$-C$_3$ alkyl), —(C$_1$-C$_3$ haloalkyl), —(C$_0$-C$_3$ alkyl)-L-R$^7$, —(C$_0$-C$_3$ alkyl)-NR$^8$R$^9$, —(C$_0$-C$_3$ alkyl)-OR$^{10}$, —(C$_0$-C$_3$ alkyl)-C(O)R$^{10}$, —(C$_0$-C$_3$ alkyl)-S(O)$_{0-2}$R$^{10}$, -halogen, —NO$_2$ and —CN;

y is 0, 1, 2, 3 or 4;

in which each L is independently selected from —NR$^9$C(O)O—, —OC(O)NR$^9$—, —NR$^9$C(O)—NR$^9$—, —NR$^9$C(O)S—, —SC(O)NR$^9$—, —NR$^9$C(O)—, —C(O)—NR$^9$—, —NR$^9$C(S)O—, —OC(S)NR$^9$—, —NR$^9$C(S)—NR$^9$—, —NR$^9$C(S)S—, —SC(S)NR$^9$—, —NR$^9$C(S)—, —C(S)NR$^9$—, —SC(O)NR$^9$—, —NR$^9$C(S)—, —S(O)$_{0-2}$—, —C(O)O, —OC(O)—, —C(S)O—, —OC(S)—, —C(O)S—, —SC(O)—, —C(S)S—, —SC(S)—, —OC(O)O—, —SC(O)O—, —OC(O)S—, —SC(S)O—, —OC(S)S—, —NR$^9$SO$_2$—, —SO$_2$NR$^9$— and —NR$^9$SO$_2$NR$^9$—, each R$^7$, R$^8$ and R$^{10}$ is independently selected from H, —(C$_1$-C$_2$ alkyl), —(C$_1$-C$_2$ haloalkyl), —(C$_0$-C$_2$ alkyl)-L-(C$_0$-C$_2$ alkyl), —(C$_0$-C$_2$ alkyl)-NR$^9$(C$_0$-C$_2$ alkyl), —(C$_0$-C$_2$ alkyl)-O—(C$_0$-C$_2$ alkyl), —(C$_0$-C$_2$ alkyl)-C(O)—(C$_0$-C$_2$ alkyl) and —(C$_0$-C$_2$ alkyl)-S(O)$_{0-2}$—(C$_0$-C$_2$ alkyl), each R$^9$ is independently selected from —H, —(C$_1$-C$_4$ alkyl), —C(O)—(C$_1$-C$_4$ alkyl) and —C(O)O—(C$_1$-C$_4$ alkyl), and each R$^{16}$ is independently selected from —(C$_1$-C$_3$ alkyl), —(C$_1$-C$_3$ haloalkyl), —(C$_0$-C$_3$ alkyl)-L-R$^7$, —(C$_0$-C$_3$ alkyl)-NR$^8$R$^9$, —(C$_0$-C$_3$ alkyl)-OR$^{10}$, —(C$_0$-C$_3$ alkyl)-C(O)R$^{10}$, —(C$_0$-C$_3$ alkyl)-S(O)$_{0-2}$R$^{10}$, -halogen, —NO$_2$ and —CN, and two R$^{16}$ on the same carbon optionally combine to form an oxo.

2. A compound according to claim 1, wherein R$^1$ is H.

3. A compound according to claim 1, wherein G is —CH$_2$—, —CH(CH$_3$)—, —C(O)—, —S(O)$_2$— or —C(O)—NH—.

4. A compound according to claim 1, wherein G is —CH$_2$— or —C(O)—.

5. A compound according to claim 1, wherein v is 0.

6. A compound according to claim 1, wherein R$^{17}$ is phenyl optionally substituted with 1, 2 or 3 substituents independently selected from —(C$_1$-C$_3$ alkyl), —(C$_1$-C$_3$ haloalkyl), —(C$_0$-C$_3$ alkyl)-L-R$^7$, —(C$_0$-C$_3$ alkyl)-NR$^8$R$^9$, —(C$_0$-C$_3$ alkyl)-OR$^{10}$, —(C$_0$-C$_3$ alkyl)-C(O)R$^{10}$, —(C$_0$-C$_3$ alkyl)-S(O)$_{0-2}$R$^{10}$, -halogen, —NO$_2$ and —CN.

7. A compound according to claim 1, wherein v is 0.

8. A compound according to claim 1, wherein x is 0.

9. A compound according to claim 1, wherein w is 0, x is 0 and v is 0.

10. A compound according to claim 1, wherein Q is a single bond, —CH$_2$—, —CH(CH$_3$)—, —C(O)— or —S(O)$_2$—.

11. A compound according to claim 1, wherein Q is a single bond, —$CH_2$—, —$CH(CH_3)$—, —C(O)— or —$S(O)_2$— and G is —$CH_2$—, —$CH(CH_3)$—, —C(O)—, —$S(O)_2$— or —C(O)—NH—.

12. A compound according to claim 1, wherein the ring system denoted by "A" is a monocyclic aryl or heteroaryl.

13. A compound according to claim 1, having the structural formula

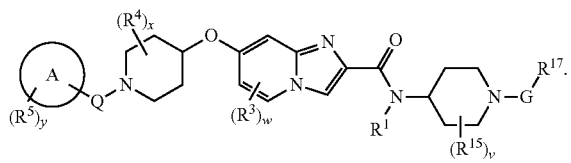

14. A compound according to claim 13, wherein
$R^1$ is H, —($C_1$-$C_4$ alkyl), —C(O) —($C_1$-$C_4$ alkyl) or —C(O)O—($C_1$-$C_4$ alkyl);
each $R^{15}$ is independently selected from —($C_1$-$C_3$ alkyl), —($C_1$-$C_3$ haloalkyl), —($C_0$-$C_3$ alkyl)-L-$R^7$, —($C_0$-$C_3$ alkyl)-$NR^8R^9$, —($C_0$-$C_3$ alkyl)-$OR^{10}$, —($C_0$-$C_3$ alkyl)-C(O)$R^{10}$, —($C_0$-$C_3$ alkyl)-$S(O)_{0-2}R^{10}$, -halogen, —$NO_2$ and —CN and two $R^{15}$ on the same carbon optionally combine to form oxo;
v is 0, 1 or 2;
G is —$CH_2$—, —$CH(CH_3)$—, —C(O)—, —$S(O)_2$— or —C(O)—NH —;
$R^{17}$ is aryl or heteroaryl, optionally substituted with 1, 2 or 3 substituents independently selected from —($C_1$-$C_3$ alkyl), —($C_1$-$C_3$ haloalkyl), —($C_0$-$C_3$ alkyl)-L-$R^7$, —($C_0$-$C_3$ alkyl)-$NR^8R^9$, —($C_0$-$C_3$ alkyl)-$OR^{10}$, —($C_0$-$C_3$ alkyl)-C(O)$R^{10}$, —($C_0$-$C_3$ alkyl)-$S(O)_{0-2}R^{10}$, -halogen, —$NO_2$ and —CN;
each $R^3$ is independently selected from —($C_1$-$C_3$ alkyl), —($C_1$-$C_3$ haloalkyl), —($C_0$-$C_3$ alkyl)-L-$R^7$, —($C_0$-$C_3$ alkyl)-$NR^8R^9$, —($C_0$-$C_3$ alkyl)-$OR^{10}$, —($C_0$-$C_3$ alkyl)-C(O)$R^{10}$, —($C_0$-$C_3$ alkyl)-$S(O)_{0-2}R^{10}$, -halogen, —$NO_2$ and —CN,
w is 0, 1 or 2;
each $R^4$ is independently selected from —($C_1$-$C_3$ alkyl), —($C_1$-$C_3$ haloalkyl), —($C_0$-$C_3$ alkyl)-L-$R^7$, —($C_0$-$C_3$ alkyl)-$NR^8R^9$, —($C_0$-$C_3$ alkyl)-$OR^{10}$, —($C_0$-$C_3$ alkyl)-C(O)$R^{10}$, —($C_0$-$C_3$ alkyl)-$S(O)_{0-2}R^{10}$, -halogen, —$NO_2$ and —CN, and two $R^4$ groups combine to form an oxo;
x is 0, 1 or 2;
Q is a single bond, —$CH_2$—, —$CH(CH_3)$—, —C(0)—or —$S(O)_2$—;
the ring denoted by "A" is monocyclic heteroaryl or aryl;
each $R^5$ is independently selected from —($C_1$-$C_3$ alkyl), —($C_1$-$C_3$ haloalkyl), —($C_0$-$C_3$ alkyl)-L-$R^7$, —($C_0$-$C_3$ alkyl)-$NR^8R^9$, —($C_0$-$C_3$ alkyl)-$OR^{10}$, —($C_0$-$C_3$ alkyl)-C(O)$R^{10}$, —($C_0$-$C_3$ alkyl)-$S(O)_{0-2}R^{10}$, -halogen, —$NO_2$ and —CN; and
y is 0, 1 or 2;
in which
each L is independently selected from —$NR^9C(O)O$—, —$OC(O)NR^9$—, —$NR^9C(O)$—$NR^9$—, —$NR^9C(O)S$—, —$SC(O)NR^9$—, —$NR^9C(O)$—, —C(O)—$NR^9$—, —$NR^9C(S)O$—, —$OC(S)NR^9$—, —$NR^9C(S)$—$NR^9$—, —$NR^9C(S)S$—, —$SC(S)NR^9$—, —$NR^9C(S)$—, —$C(S)NR^9$—, —$SC(O)NR^9$—, —$NR^9C(S)$—, —$S(O)_{0-2}$—, —C(O)O, —OC(O)—, —C(S)O—, —OC(S)—, —C(O)S —, —SC(O)—, —C(S)S —, —SC(S) —, —OC(O)O —, —SC(O)O —, —OC(O)S —, —SC(S)O —, —OC(S)S —, —$NR^9SO_2$—, —$SO_2NR^9$—and —$NR^9SO_2NR^9$—,
each $R^7$, $R^8$ and $R^{10}$is independently selected from H, —($C_1$-$C_2$ alkyl), —($C_1$-$C_2$ haloalkyl), —($C_0$-$C_2$ alkyl)-L-($C_0$-$C_2$ alkyl), —($C_0$-$C_2$ alkyl)-$NR^9$($C_0$-$C_2$ alkyl), —($C_0$-$C_2$ alkyl)-O-($C_0$-$C_2$ alkyl), —($C_0$-$C_2$ alkyl)-C(O) —($C_0$-$C_2$ alkyl) and —($C_0$-$C_2$ alkyl)-$S(O)_{0-2}$—($C_0$-$C_2$ alkyl), and
each $R^9$ is independently selected from —H, —($C_1$-$C_4$ alkyl), —C(O)—($C_1$-$C_4$ alkyl) and —C(O)O —($C_1$-$C_4$ alkyl).

15. A compound according to claim 14, wherein x is 0.

16. A compound according to claim 15, wherein v is 0.

17. A compound according to claim 16, wherein w is 0.

18. A compound according to claim 13, wherein
$R^1$ is H;
v is 0,
G is —C(O)— or —$CH_2$—;
w is 0;
x is 0;
Q is a single bond or —$CH_2$—; and
the ring denoted by "A" is phenyl or monocyclic heteroaryl.

19. A compound according to claim 18, wherein $R^{17}$ is aryl or heteroaryl substituted with 1, 2 or 3 substituents independently selected from halo, cyano, —($C_1$-$C_3$ haloalkyl), —O—($C_1$-$C_2$ haloalkyl), —($C_1$-$C_3$ alkyl), —O—($C_1$-$C_2$ alkyl), —C(O)—($C_0$-$C_2$ alkyl), —C(O)O—($C_0$-$C_2$ alkyl), —C(O)N($C_0$-$C_2$ alkyl)($C_0$-$C_4$ alkyl) and $NO_2$.

20. A compound according to claim 18, wherein each $R^5$ is independently selected from halo, cyano, —($C_1$-$C_3$ haloalkyl), —O—($C_1$-$C_2$ haloalkyl), —($C_1$-$C_3$ alkyl), —O—($C_1$-$C_2$ alkyl), —C(O)—($C_0$-$C_2$ alkyl), —C(O)O—($C_0$-$C_2$ alkyl), —C(O)N($C_0$-$C_2$ alkyl)($C_0$-$C_4$ alkyl) and $NO_2$.

21. A compound according to claim 18, wherein
$R^{17}$ is phenyl or monocyclic heteroaryl substituted with 1, 2 or 3 substituents independently selected from halo, cyano, —($C_1$-$C_3$ haloalkyl), —O—($C_1$-$C_2$ haloalkyl), —($C_1$-$C_3$ alkyl), —O—($C_1$-$C_2$ alkyl), —C(O)—($C_0$-$C_2$ alkyl), —C(O)O —($C_0$-$C_2$ alkyl), —C(O)N($C_0$-$C_2$ alkyl)($C_0$-$C_4$ alkyl) and $NO_2$; and
each $R^5$ is independently selected from halo, cyano, —($C_1$-$C_3$ haloalkyl), —O—($C_1$-$C_2$ haloalkyl), —($C_1$-$C_3$ alkyl), —O—($C_1$-$C_2$ alkyl), —C(O)—($C_0$-$C_2$ alkyl), —C(O)O—($C_0$-$C_2$ alkyl), —C(O)N($C_0$-$C_2$ alkyl)($C_0$-$C_4$ alkyl) and $NO_2$.

22. A compound according to claim 21 wherein $R^{17}$ is phenyl substituted with 1, 2 or 3 substituents independently selected from halo, cyano, —($C_1$-$C_3$ haloalkyl), —O—($C_1$-$C_2$ haloalkyl), —($C_1$-$C_3$ alkyl), —O—($C_1$-$C_2$ alkyl), —C(O)—($C_0$-$C_2$ alkyl), —C(O)O—($C_0$-$C_2$ alkyl), —C(O)N ($C_0$-$C_2$ alkyl)($C_0$-$C_4$ alkyl) and $NO_2$.

23. A compound according to claim 22, wherein the ring denoted by "A" is phenyl.

24. A compound according to claim 21, wherein the ring denoted by "A" is phenyl.

25. A compound according to claim 18, wherein
the ring denoted by "A" is phenyl; and
$R^{17}$ is phenyl substituted with 1, 2 or 3 substituents independently selected from halo, cyano, —($C_1$-$C_3$ haloalkyl), —O—($C_1$-$C_2$ haloalkyl), —($C_1$-$C_3$ alkyl), —O—($C_1$-$C_2$ alkyl), —C(O)—($C_0$-$C_2$ alkyl), —C(O)O—($C_0$-$C_2$ alkyl), —C(O)N($C_0$-$C_2$ alkyl)($C_0$-$C_4$ alkyl) and $NO_2$.

26. A compound according to claim 1, having the structural formula

[Chemical structure diagram showing a compound with substituents $(R^5)_y$, ring A, Q, piperidine with $(R^4)_x$, O linker, imidazo[1,2-a]pyridine core with $(R^3)_w$, carboxamide with $R^1$, piperidine with $(R^{15})_v$, N—G, and $R^{17}$]

27. A compound according to claim 1, wherein $R^{17}$ is aryl or heteroaryl substituted with 1, 2 or 3 substituents independently selected from halo, cyano, —($C_1$-$C_3$ haloalkyl), —O—($C_1$-$C_2$ haloalkyl), —($C_1$-$C_3$ alkyl), —O—($C_1$-$C_2$ alkyl), —C(O)—($C_0$-$C_2$ alkyl), —C(O)O—($C_0$-$C_2$ alkyl), —C(O)N($C_0$-$C_2$ alkyl)($C_0$-$C_4$ alkyl) and $NO_2$.

28. A compound according to claim 1, wherein each $R^5$ is independently selected from halo, cyano, —($C_1$-$C_3$ haloalkyl), —O—($C_1$-$C_2$ haloalkyl), —($C_1$-$C_3$ alkyl), —O—($C_1$-$C_2$ alkyl), —C(O)—($C_0$-$C_2$ alkyl), —C(O)O—($C_0$-$C_2$ alkyl), —C(O)N($C_0$-$C_2$ alkyl)($C_0$-$C_4$ alkyl) and $NO_2$.

29. A compound according to claim 1, wherein
$R^1$ is H;
v is 0,
G is —C(O)— or —$CH_2$—;
w is 0;
x is 0;
Q is a single bond or —$CH_2$—; and
the ring denoted by "A" is phenyl or monocyclic heteroaryl.

30. A compound according to claim 29, wherein $R^{17}$ is phenyl or monocyclic heteroaryl substituted with 1, 2 or 3 substituents independently selected from halo, cyano, —($C_1$-$C_3$ haloalkyl), —O—($C_1$-$C_2$ haloalkyl), —($C_1$-$C_3$ alkyl), —O—($C_1$-$C_2$ alkyl), —C(O)—($C_0$-$C_2$ alkyl), —C(O)O—($C_0$-$C_2$ alkyl), —C(O)N($C_0$-$C_2$ alkyl)($C_0$-$C_4$ alkyl) and $NO_2$.

31. A compound according to claim 29, wherein each $R^5$ is independently selected from halo, cyano, —($C_1$-$C_3$ haloalkyl), —O—($C_1$-$C_2$ haloalkyl), —($C_1$-$C_3$ alkyl), —O—($C_1$-$C_2$ alkyl), —C(O)—($C_0$-$C_2$ alkyl), —C(O)O—($C_0$-$C_2$ alkyl), —C(O)N($C_0$-$C_2$ alkyl)($C_0$-$C_4$ alkyl) and $NO_2$.

32. A compound according to claim 29, wherein
$R^{17}$ is phenyl or monocyclic heteroaryl substituted with 1, 2 or 3 substituents independently selected from halo, cyano, —($C_1$-$C_3$ haloalkyl), —O—($C_1$-$C_2$ haloalkyl), —($C_1$-$C_3$ alkyl), —O—($C_1$-$C_2$ alkyl), —C(O)—($C_0$-$C_2$ alkyl), —C(O)O—($C_0$-$C_2$ alkyl), —C(O)N($C_0$-$C_2$ alkyl)($C_0$-$C_4$ alkyl) and $NO_2$; and
each $R^5$ is independently selected from halo, cyano, —($C_1$-$C_3$ haloalkyl), —O—($C_1$-$C_2$ haloalkyl), —($C_1$-$C_3$ alkyl), —O—($C_1$-$C_2$ alkyl), —C(O)—($C_0$-$C_2$ alkyl), —C(O)O —($C_0$-$C_2$ alkyl), —C(O)N($C_0$-$C_2$ alkyl)($C_0$-$C_4$ alkyl) and $NO_2$.

33. A compound according to claim 32 wherein $R^{17}$ is phenyl substituted with 1, 2 or 3 substituents independently selected from halo, cyano, —($C_1$-$C_3$ haloalkyl), —O—($C_1$-$C_2$ haloalkyl), —($C_1$-$C_3$ alkyl), —O—($C_1$-$C_2$ alkyl), —C(O)—($C_0$-$C_2$ alkyl), —C(O)O—($C_0$-$C_2$ alkyl), —C(O)N($C_0$-$C_2$ alkyl)($C_0$-$C_4$ alkyl) and $NO_2$.

34. A compound according to claim 33, wherein the ring denoted by "A" is phenyl.

35. A compound according to claim 32, wherein the ring denoted by "A" is phenyl.

36. A compound according to claim 29, wherein
the ring denoted by "A" is phenyl; and
$R^{17}$ is phenyl substituted with 1, 2 or 3 substituents independently selected from halo, cyano, —($C_1$-$C_3$ haloalkyl), —O—($C_1$-$C_2$ haloalkyl), —($C_1$-$C_3$ alkyl), —O—($C_1$-$C_2$ alkyl), —C(O)—($C_0$-$C_2$ alkyl), —C(O)O—($C_0$-$C_2$ alkyl), —C(O)N($C_0$-$C_2$ alkyl)($C_0$-$C_4$ alkyl) and $NO_2$.

37. A compound according to claim 1, wherein the compound is
N-(1-(pyridin-4-ylmethyl)piperidin-4-yl)-7-(1-(4-(trifluoromethyl)phenyl)piperidin-4-yloxy)imidazo[1,2-a]pyridine-2-carboxamide; or
N-(1-(4-cyanobenzyl)piperidin-4-yl)-7-(1-(4-(trifluoromethyl)phenyl)piperidin-4-yloxy)imidazo[1,2-a]pyridine-2-carboxamide,
or a pharmaceutically acceptable salt or N-oxide thereof.

38. A pharmaceutical composition comprising:
at least one pharmaceutically acceptable carrier, diluent or excipient; and
a compound according to claim 1 or a pharmaceutically acceptable salt or N-oxide thereof.

39. A method for activating the AMPK pathway in subject, the method comprising
administering to the subject an effective amount of a compound according to claim 1, or a pharmaceutically acceptable salt or N-oxide thereof.

40. A method for treating type II diabetes in a subject, the method comprising
administering to the subject an effective amount of a compound according to claim 1, or a pharmaceutically acceptable salt or N-oxide thereof.

41. A method for reducing triglyceride levels in a subject, the method comprising
administering to the subject an effective amount of a compound according to claim 1, or a pharmaceutically acceptable salt or N-oxide thereof.

42. A method for increasing insulin sensitivity of a subject, the method comprising
administering to the subject an effective amount of a compound according to claim 1, or a pharmaceutically acceptable salt or N-oxide thereof.

43. A method for treating atherosclerosis in subject, the method comprising
administering to the subject an effective amount of a compound according to claim 1, or a pharmaceutically acceptable salt or N-oxide thereof.

* * * * *